(12) United States Patent
Lee et al.

(10) Patent No.: US 11,026,979 B2
(45) Date of Patent: *Jun. 8, 2021

(54) HUMAN HEPATOCYTES AND USES THEREOF

(71) Applicant: ACCELERATED BIOSCIENCES CORP., Carlsbad, CA (US)

(72) Inventors: Jau-Nan Lee, Kaohsiung (TW); Tony Tung-Yin Lee, Yakima, WA (US); Yuta Lee, Kaohsiung (TW); Eing-Mei Tsai, Kaohsiung (TW)

(73) Assignee: ACCELERATED BIOSCIENCES CORP., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/937,777

(22) Filed: Jul. 24, 2020

(65) Prior Publication Data

US 2020/0345788 A1    Nov. 5, 2020

Related U.S. Application Data

(60) Continuation of application No. 15/705,587, filed on Sep. 15, 2017, now Pat. No. 10,765,704, which is a division of application No. 14/952,023, filed on Nov. 25, 2015, now Pat. No. 9,808,490.

(60) Provisional application No. 62/085,185, filed on Nov. 26, 2014.

(51) Int. Cl.
*A61K 35/407* (2015.01)
*C12N 5/071* (2010.01)
*A61P 35/00* (2006.01)

(52) U.S. Cl.
CPC ............ *A61K 35/407* (2013.01); *A61P 35/00* (2018.01); *C12N 5/067* (2013.01); *C12N 5/0671* (2013.01); *C12N 2501/115* (2013.01); *C12N 2501/12* (2013.01); *C12N 2501/155* (2013.01); *C12N 2501/20* (2013.01); *C12N 2501/237* (2013.01); *C12N 2501/39* (2013.01); *C12N 2501/40* (2013.01); *C12N 2501/65* (2013.01); *C12N 2506/025* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,112,757 A | 5/1992 | Guguen-Guillouzo et al. |
| 5,384,261 A | 1/1995 | Winkler et al. |
| 5,445,934 A | 8/1995 | Fodor et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,854,033 A | 12/1998 | Lizardi |
| 5,874,219 A | 2/1999 | Rava et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,330,349 B1 | 12/2001 | Hays et al. |
| 6,344,316 B1 | 2/2002 | Lockhart et al. |
| 6,630,349 B1 | 10/2003 | Janet et al. |
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,642,091 B2 | 1/2010 | Lee et al. |
| 7,695,963 B2 | 4/2010 | Agulnick et al. |
| 7,695,965 B2 | 4/2010 | Martinson et al. |
| 7,704,738 B2 | 4/2010 | D'Amour et al. |
| 7,892,534 B2 | 2/2011 | Lee et al. |
| 8,071,562 B2 | 12/2011 | Bader et al. |
| 8,148,151 B2 | 4/2012 | Zhao et al. |
| 8,163,553 B2 | 4/2012 | Lee et al. |
| 8,247,229 B2 | 8/2012 | Odorico et al. |
| 8,497,120 B2 | 7/2013 | Lee et al. |
| 8,557,580 B2 | 10/2013 | Daigh et al. |
| 8,691,274 B2 | 4/2014 | Xu et al. |
| 8,691,974 B2 | 4/2014 | Gatenholm et al. |
| 9,149,952 B2 | 10/2015 | Murphy et al. |
| 9,335,322 B2 | 5/2016 | Lee et al. |
| 9,808,490 B2 | 11/2017 | Lee et al. |
| 9,927,426 B2 | 3/2018 | Lee et al. |
| 2003/0104616 A1 | 6/2003 | Parikh et al. |

(Continued)

FOREIGN PATENT DOCUMENTS

| | | |
|---|---|---|
| CN | 1435187 A | 8/2003 |
| CN | 1461340 A | 12/2003 |

(Continued)

OTHER PUBLICATIONS

Bedossa et al, Hepatology, 1995, 21:760-766. (Year: 1995).*
Bissell et al, J Clin Invest, 1995, 96:447-455. (Year: 1995).*
Gressner et al, J Hepatology, 1997, 26:1079-1092. (Year: 1997).*
Milani et al, Am J Pathol, 1991, 139(6):1221-1229. (Year: 1991).*
Adjaye, et al. Primary differentiation in the human blastocyst: comparative molecular portraits of inner cell mass and trophectoderm cells. Stem Cells. Nov.-Dec. 2005;23(10):1514-25. Epub Aug. 4, 2005.
Alexiou, et al. miRGen 2.0: a database of microRNA genomic information and regulation. Nucleic Acids Res. Jan. 2010;38(Database issue):D137-41. doi: 10.1093/nar/gkp888. Epub Oct. 22, 2009.
Ameri, et al. FGF2 specifies hESC-derived definitive endoderm into foregut/midgut cell lineages in a concentration-dependent manner. Stem Cells. Jan. 2010;28(1):45-56. doi: 10.1002/stem.249.

(Continued)

*Primary Examiner* — Allison M Fox
(74) *Attorney, Agent, or Firm* — Wilson Sonsini Goodrich & Rosati

(57) ABSTRACT

Disclosed herein are human hepatocytes for example isolated human hepatic progenitor cells, artificial tissue or organ thereof, and kits or compositions thereof. Also disclosed herein are various methods of using a human hepatocyte disclosed herein.

17 Claims, 45 Drawing Sheets

Specification includes a Sequence Listing.

(56) References Cited

U.S. PATENT DOCUMENTS

| | | |
|---|---|---|
| 2004/0072288 A1 | 4/2004 | Collas et al. |
| 2006/0062769 A1 | 3/2006 | Habener et al. |
| 2006/0211110 A1 | 9/2006 | Lee et al. |
| 2007/0026405 A1 | 2/2007 | Alitalo et al. |
| 2007/0128174 A1 | 6/2007 | Kleinsek et al. |
| 2009/0087417 A1 | 4/2009 | Arenas et al. |
| 2009/0208466 A1 | 8/2009 | Yoo et al. |
| 2009/0263361 A1 | 10/2009 | Lee et al. |
| 2011/0136162 A1 | 6/2011 | Sun et al. |
| 2011/0165682 A1 | 7/2011 | Lee et al. |
| 2011/0188728 A1 | 8/2011 | Sammak et al. |
| 2011/0250688 A1 | 10/2011 | Hasan |
| 2012/0089238 A1 | 4/2012 | Kang et al. |
| 2012/0135878 A1 | 5/2012 | Lee et al. |
| 2012/0148550 A1 | 6/2012 | Brodie et al. |
| 2012/0190078 A1 | 7/2012 | Gatenholm et al. |
| 2012/0190730 A1 | 7/2012 | Michael |
| 2012/0277111 A1 | 11/2012 | Crabtree et al. |
| 2012/0328579 A1 | 12/2012 | Lee et al. |
| 2013/0004469 A1 | 1/2013 | Glazier et al. |
| 2013/0017564 A1 | 1/2013 | Guillemot et al. |
| 2013/0028872 A1 | 1/2013 | Bone et al. |
| 2013/0164339 A1 | 6/2013 | Murphy et al. |
| 2013/0259836 A1 | 10/2013 | Lee et al. |
| 2013/0304233 A1 | 11/2013 | Dean et al. |
| 2013/0337458 A1 | 12/2013 | Lee et al. |
| 2014/0012407 A1 | 1/2014 | Murphy et al. |
| 2014/0052285 A1 | 2/2014 | Butcher et al. |
| 2014/0093932 A1 | 4/2014 | Murphy et al. |
| 2014/0099709 A1 | 4/2014 | Presnell et al. |
| 2014/0170118 A1 | 6/2014 | Lee et al. |
| 2016/0051592 A1 | 2/2016 | Lee et al. |

FOREIGN PATENT DOCUMENTS

| | | |
|---|---|---|
| CN | 101497872 A | 8/2009 |
| EP | 2679669 A1 | 1/2014 |
| JP | 2006511206 A | 4/2006 |
| JP | 2009533056 A | 9/2009 |
| JP | 2010534065 A | 11/2010 |
| WO | WO-0228997 A2 | 4/2002 |
| WO | WO-2005030961 A1 | 4/2005 |
| WO | WO-2006091766 A2 | 8/2006 |
| WO | WO-2008002662 A2 | 1/2008 |
| WO | WO-2009086333 A2 | 7/2009 |
| WO | WO-2010096496 A2 | 8/2010 |
| WO | WO-2011050476 A1 | 5/2011 |
| WO | WO-2011054100 A1 | 5/2011 |
| WO | WO-2012068170 A2 | 5/2012 |
| WO | WO-2012104731 A2 | 8/2012 |
| WO | WO-2012122105 A1 | 9/2012 |
| WO | WO-2013040087 A2 | 3/2013 |
| WO | WO 13/087843 * | 6/2013 ............ C12N 5/071 |
| WO | WO-2013181375 A1 | 12/2013 |
| WO | WO-2013189521 A1 | 12/2013 |
| WO | WO-2014039427 A1 | 3/2014 |
| WO | WO-2014085493 A1 | 6/2014 |
| WO | WO-2014130770 A1 | 8/2014 |
| WO | WO-2016/086132 A1 | 6/2016 |

OTHER PUBLICATIONS

Anderson. Human gene therapy. Science. May 8, 1992;256(5058):808-13.
Anneren, et al. The Srs family of tyrosine kinases is important for embryonic stem cell self-renewal. J Biol Chem. Jul. 23, 2004;279(30):31590-8. Epub May 17, 2004.
Arnit, et al. Clonally Derived Human Embryonic Stem Cell Lines Maintain Pluripotency and Proliferative Potential for Prolonged Periods of Culture, Developmental Biology 227,271-278 (2000).
Bain, et al. Embryonic stem cells express neuronal properties in vitro. Dev. Biol. 1995; 168:342-357.
"Barany. Genetic disease detection and DNA amplification using cloned thermostable ligase. Proc Natl Acad Sci U S A. Jan. 1, 1991;88(1):189-93."
Baroukh, et al. MicroRNA-124a regulates Foxa2 expression and intracellular signaling in pancreatic beta-cell lines. J Biol Chem. Jul. 6, 2007;282(27):19575-88. Epub Apr. 26, 2007.
Barral, et al. Roles of molecular chaperones in protein misfolding diseases. Seminars in Cell & Developmental Biology. 2004; 15:17-29.
Bavaresco, et al. The role of ecto-5'-nucleotidase/CD73 in glioma cell line proliferation. Mol Cell Biochem. Dec. 2008;319(1-2):61-8. Epub Jul. 18, 2008.
Bernardo, et al. Biphasic induction of Pdx1 in mouse and human embryonic stem cells can mimic development of pancreatic beta-cells. Stem Cells. Feb. 2009;27(2):341-51. doi: 10.1634/stemcells. 2008-0310.
Bi, et al. Pre-activation of retinoid signaling facilitates neuronal differentiation of mesenchymal stem cells. Dev Growth Differ. Jun. 2010;52(5):419-31. doi: 10.1111/j.1440-169X.2010.01182.x.
Bjorklund, et al. Embryonic stem cells develop into functional dopaminergic neurons after transplantation in a Parkinson rat model. Proc Natl Acad Sci U S A. Feb. 19, 2002;99(4):2344-9. Epub Jan. 8, 2002.
Boiani, et al. Regulatory networks in embryo-derived pluripotent stem cells. Nature Rev. Mol. Cell Biol. 2005; 6:872-884.
Borowiak. The new generation of beta-cells: replication, stem cell differentiation, and the role of small molecules. Rev Diabet Stud. 2010 Summer;7(2):93-104. doi: 10.1900/RDS.2010.7.93. Epub Aug. 10, 2010.
Burlison, et al. Pdx-1 and Ptf1a concurrently determine fate specification of pancreatic multipotent progenitor cells. Dev Biol. Apr. 1, 2008;316(1):74-86. doi: 10.1016/j.ydbio.2008.01.011. Epub Jan. 26, 2008.
Caroline Creput, "Human leukocyte antigen-G (HLA-G) expression in biliary epithelial cells is associated with allograft acceptance in liver-kidney transplantation", Journal of Hepatology, 2003, vol. 39, issue 4, pp. 587-594.
Cavaleri, et al. Nanog: a new recruit to the embryonic stem cell orchestra. Cell. 2003; 113:551-552.
Chai, et al. FGF Is an Essential Regulator of the Fifth Cell Division in Preimplantation Mouse Embryos, Development Biology, vol. 198, pp. 105-115 (1998).
Chambers, et al. Functional expression cloning of Nanog, a pluripotency sustaining factor in embryonic stem cells. Cell. 2003; 113:643-655.
Chambers, et al. Self-renewal of teratocarcinoma and embryonic stem cells. Oncogene. 2004; 23:7150-7160.
Chen, et al. Expression of leukemia inhibitory factor and its receptor is not altered in the decidua and chorionic villi of human anembryonic pregnancy. Hum Reprod. Jul. 2004;19(7):1647-54. Epub Jun. 4, 2004.
Chen, et al. Promotion of feeder-independent self-renewal of embryonic stem cells by retinol (vitamin A). Stem Cells. Jul. 2008;26(7):1858-64. Epub Apr. 24, 2008.
Cheng, et al. Human Adult Marrow Cells Support Prolonged Expansion of Human Embryonic Stem Cells in Culture, Stem Cells, vol. 21 pp. 131-142 (2003).
Chenn et al. Regulation of cerebral cortical size by control of cell cycle exit in neural precursors. Science 297:365-369 (2002).
Chiba, et al. Noggin and basic FGF were implicated in forebrain fate and caudal fate, respectively, of the neural tube-like structures emerging in mouse ES cell culture. Exp Brain Res. May 2005;163(1):86-99. Epub Feb. 10, 2005.
Choi, et al. Efficient drug screening and gene correction for treating liver disease using patient-specific stem cells. Hepatology. Jun. 2013;57(6):2458-68. doi: 10.1002/hep.26237.
Copp, A.J. Interaction between inner cell mass and trophectoderm of the mouse blastocyst, J. Embryol. Exp. Morph., vol. 51, pp. 109-120 (1979).
International Preliminary Report on Patentability dated Nov. 23, 2007 in connection with PCT/US2006/006512.
International Search Report dated Nov. 23, 2007 in connection with PCT/US2006/006512.

(56) References Cited

OTHER PUBLICATIONS

Written Opinion dated Nov. 23, 2007 in connection with PCT/US2006/006512.
Coutinho, et al. An Evolving Hierarchical Family Classification for Glycosyltransferases. J. Mol. Biol. 2003; 328:307-317.
Cunliffe, et al. Switching on the notochord. Genes Dev. Jul. 1, 1999;13(13):1643-6.
D'Amour, et al. Efficient differentiation of human embryonic stem cells to definitive endoderm. Nat Biotechnol. Dec. 2005;23(12):1534-41. Epub Oct. 28, 2005.
D'Amour, et al. Production of pancreatic hormone-expressing endocrine cells from human embryonic stem cells. Nat Biotechnol. Nov. 2006;24(11):1392-401. Epub Oct. 19, 2006.
De Rave et al, The optimal timing of liver transplantation in patients with chroniccholestatic liver disease, Transplant International, 2005, vol. 18, pp. 937-940.
Dunnett, et al. Cell therapy in Parkinson's disease—stop or go? Nat. Rev. Neurosci. 2001; 2:365-369.
Edghill, et al. Hepatocyte nuclear factor-1 beta mutations cause neonatal diabetes and intrauterine growth retardation: support for a critical role of HNF-1beta in human pancreatic development. Diabet Med. Dec. 2006;23(12):1301-6.
EP15864195.1 Exteded European Search Report dated Jul. 16, 2018.
Episkopou. SOX2 functions in adult neural stem cells. Trends Neurosci. May 2005;28(5):219-21.
European search report and opinion dated Mar. 24, 2014 for EP Application No. 11842036.3.
F. J. Souto et al., "Liver HLA-G expression is associated with multiple clinical and histopathological forms of chronic hepatitis B virus infection", Journal of Viral Hepat., 2011, vol. 18, No. 2, pp. 102-105.
Freed, et al. Transplantation of embryonic dopamine neurons for severe Parkinson's disease. N. Engl. J. Med. 2001; 344:710-719.
Furuyama, et al. Continuous cell supply from a Sox9-expressing progenitor zone in adult liver, exocrine pancreas and intestine. Nat Genet. Jan. 2011;43(1):34-41. doi: 10.1038/ng.722. Epub Nov. 28, 2010.
Gage, et al. Neural stem cells: generating and regenerating the brain. Neuron. Oct. 30, 2013;80(3):588-601. doi: 10.1016/j.neuron.2013.10.037.
Gerami-Naini, et al. Trophoblast Differentiation in Embryoid Bodies Derived from Human Embryonic Stem Cells, Endocrinology, vol. 145(4) p. 1517-1524 (2004).
Goncalves, et al. Sequential RARbeta and alpha signalling in vivo can induce adult forebrain neural progenitor cells to differentiate into neurons through Shh and FGF signalling pathways. Dev Biol. Feb. 15, 2009;326(2):305-13. doi: 10.1016/j.ydbio.2008.11.018. Epub Dec. 7, 2008.
Goncalves, et al. Timing of the retinoid-signalling pathway determines the expression of neuronal markers in neural progenitor cells. Dev Biol. Feb. 1, 2005;278(1):60-70.
Gotz. Glial cells generate neurons—master control within CNS regions: developmental perspectives on neural stem cells. Neuroscientist. 2003; 9:379-97.
Gradwohl, et al. neurogenin3 is required for the development of the four endocrine cell lineages of the pancreas. Proc Natl Acad Sci U S A. Feb. 15, 2000;97(4):1607-11.
Graphin-Botton, et al. Key events of pancreas formation are triggered in gut endoderm by ectopic expression of pancreatic regulatory genes. Genes Dev. Feb. 15, 2001;15(4):444-54.
Guatelli et al. Isothermal, in vitro amplification of nucleic acids by a multienzyme reaction modeled after retroviral replication. PNAS USA 87(5):1874-1878 (1990).
"Guha, et al. Hepatocyte-based gene therapy. J Hepatobiliary Pancreat Surg. 2001;8(1):51-7."
Haimovici, et al. Effects of growth factors and growth factor-extracellular matrix interactions on mouse trophoblast outgrowth in vitro. Biol Reprod. Jul. 1993;49(1):124-30.

Hart, et al. Mixl1 is required for axial mesendoderm morphogenesis and patterning in the murine embryo. Development. Aug. 2002;129(15):3597-608.
He, et al. Lymphoid enhancer factor 1-mediated Wnt signaling promotes the initiation of trophoblast lineage differentiation in mouse embryonic stem cells. Stem Cells. Apr. 2008;26(4):842-9. Epub Jan. 10, 2008.
Hochedlinger, et al. Nuclear transplantation, embryonic stem cells, and the potential for cell therapy. N. Engl J Med. Jul. 17, 2003;349(3):275-86.
Hori, et al. Neural progenitor cells lack immunogenicity and resist destruction as allografts. Stem Cells. 2003;21(4):405-16.
Hu, et al. In vitro culture of isolated primary hepatocytes and stem cell-derived hepatocyte-like cells for liver regeneration. Protein & cell 6.8 (2015): 562-574.
Iancu, et al. Behavioral characterization of a unilateral 6-OHDA-lesion model of Parkinson's disease in mice, Behavioural Brain Research, vol. 162 pp. 1-10 (2005).
Ilancheran, et al. Human fetal membranes: a source of stem cells for tissue regeneration and repair? Placenta. Jan. 2009;30(1):2-10. Epub Nov. 7, 2008.
International Preliminary Report on Patentability dated May 30, 2017 in connection with PCT/US2015/062674.
International search report and written opinion dated Mar. 13, 2013 for PCT/US2013/072073.
International search report and written opinion dated Mar. 15, 2016 for PCT Application No. PCTUS2015-062674.
International search report and written opinion dated May 3, 2012 for PCT/US2011/060868.
Izzi, et al. Foxh1 recruits Gsc to negatively regulate Mixl1 expression during early mouse development. EMBO J. Jul. 11, 2007;26(13):3132-43. Epub Jun. 14, 2007.
Jacobs, et al. Retinoic acid is required early during adult neurogenesis in the dentate gyrus. Proc Natl Acad Sci USA. Mar. 7, 2006;103(10):3902-7. Epub Feb. 27, 2006.
Jiang, et al. In vitro derivation of functional insulin-producing cells from human embryonic stem cells. Cell Res. Apr. 2007;17(4):333-44.
Kehler, et al. Oct4 is required for primordial germ cell survival, European Molecular Biology Organization reports, vol. 5 No. 1 1, pp. 1078-1083 (2004).
Keltz, et al. Modulation of leukemia inhibitory factor gene expression and protein biosynthesis in the human fallopian tube. Am J Obstet Gynecol. Dec. 1996;175(6):1611-9.
Kennea, et al. Neural stem cells. J Pathol. Jul. 2002;197(4):536-50.
Kim, et al. Dopamine neurons derived from embryonic stem cells function in an animal model of Parkinson's disease. Nature. Jul. 4, 2002;418(6893):50-6. Epub Jun. 20, 2002.
Kimura, et al. Conditional loss of PTEN leads to testicular teratoma and enhances embryonic germ cell production. Development. 2003; 130:1691-1700.
Kornblum, et al. Introduction to neural stem cells. Stroke. Feb. 2007;38(2 Suppl):810-6.
Kroon, et al. Pancreatic endoderm derived from human embryonic stem cells generates glucose-responsive insulin-secreting cells in vivo. Nat Biotechnol. Apr. 2008;26(4):443-52. doi: 10.1038/nbt1393. Epub Feb. 20, 2008.
K.S. Shin et al., "Culture and in vitro hepatogenic differentiation of placenta-derived stem cells, using placental extract as an alternative to serum", Cell Proliferation, 2010, vol. 43, issue 5, pp. 435-444.
Kuckenberg, et al. Lineage conversion of murine extraembryonic trophoblast stem cells to pluripotent stem cells. Mol Cell Biol. Apr. 2011;31(8):1748-56. doi: 10.1128/MCB.01047-10. Epub Feb. 7, 2011.
Kunath, et al. Trophoblast Stem Cells, Stem Cell Biology, pp. 267-287, (2001).
Kurie, et al. Retinoic acid stimulates the protein kinase C pathway before activation of its beta-nuclear receptor during human teratocarcinoma differentiation. Biochim Biophys Acta. 1993; 1179(2):203-7.

(56) References Cited

OTHER PUBLICATIONS

"Kwoh, et al. Transcription-based amplification system and detection of amplified human immunodeficiency virus type 1 with a bead-based sandwich hybridization format. Proc Natl Acad Sci U S A. Feb. 1989;86(4):1173-7."
Lee, et al. Ectopic pregnancy-derived human trophoblastic stem cells regenerate dopaminergic nigrostriatal pathway to treat parkinsonian rats. PLoS One. 2012;7(12):e52491. doi: 10.1371/journal.pone.0052491. Epub Dec. 21, 2012.
Li, et al. Human embryonic stem cells possess immune-privileged properties. Stem Cells. 2004; 22:448-456.
Li, et al. Specification of motoneurons from human embryonic stem cells. Nat Biotechnol. Feb. 2005;23(2):215-21. Epub Jan. 30, 2005.
Liew. Generation of insulin-producing cells from pluripotent stem cells: from the selection of cell sources to the optimization of protocols. Rev Diabet Stud. 2010 Summer;7(2):82-92. doi: 10.1900/RDS.2010.7.82. Epub Aug. 10, 2010.
Lim, et al. Enforced expression of Mixl1 during mouse ES cell differentiation suppresses hematopoietic mesoderm and promotes endoderm formation. Stem Cells. Feb. 2009;27(2):363-74. doi: 10.1634/stemcells.2008-1008.
Lindvall, et al. Stem cell therapy for human neurodegenerative disorders—how to make it work. Nat Med. Jul. 2004;10 Suppl:S42-50.
Lindvall, et al. Stem cells for the treatment of neurological disorders. Nature. 2006; 441:1094-1096.
Liu, et al. In vivo liver regeneration potential of human induced pluripotent stem cells from diverse origins. Sci Transl Med. May 11, 2011;3(82):82ra39. doi: 10.1126/scitranslmed.3002376.
"Lizardi, et al. Exponential amplification of recombinant-RNA hybridization probes. Nature Biotechnology 6.10 (1988): 1197-1202."
Long et al, The correlation of hepatocytenuclear factor 4 alpha and 3 beta with hepatitis B virus replication in the liver of chronic hepatitis B patients, J Viral Hepatitis, 2009, vol. 16, pp. 537-546.
Lovis, et al. Regulation of the expression of components of the exocytotic machinery of insulin-secreting cells by microRNAs. Biol Chem. Mar. 2008;389(3):305-12. doi: 10.1515/BC.2008.026.
Lu, et al. All-trans retinoic acid promotes neural lineage entry by pluripotent embryonic stem cells via multiple pathways. BMC Cell Biol. 2009; 10:57.
Maden. Retinoic acid in the development, regeneration and maintenance of the nervous system. Nat. Rev. Neuroscience. 2007; 8:755-765.
Makeyev, et al. The MicroRNA miR-124 promotes neuronal differentiation by triggering brain-specific alternative pre-mRNA splicing. Mol Cell. Aug. 3, 2007;27(3):435-48.
Marson et al. Connecting microRNA genes to the core transcriptional regulatory circuitry of embryonic stem cells. Cell 134:521-533 (2008).
Martin-Ibanez, et al. Interplay of leukemia inhibitory factor and retinoic acid on neural differentiation of mouse embryonic stem cells. J. Neuron. Res. 2007; 85:2686-2710.
Miller. Human gene therapy comes of age. Nature. Jun. 11, 1992;357(6378):455-60.
Mohn, et al. Mouse Mix gene is activated early during differentiation of ES and F9 stem cells and induces endoderm in frog embryos. Dev Dyn. Mar. 2003;226(3):446-59.
Mulligan. The basic science of gene therapy. Science 260(5110):926-932 (1993).
Myers, et al. Functional characterization of the brain-specific FGF-1 promoter, FGF-1.B. J. Biol. Chem. 1995; 270:8257-8266.
Napoli, et al. Microglial clearance function in health and disease. Neuroscience. Feb. 6, 2009;158(3):1030-8. Epub Jul. 1, 2008.
Nichols, et al. Formation of Pluripotent Stem Cells in the Mammalian Embryo Depends on the POU Transcription Factor Oct 4, Cell, vol. 95, pp. 379-391 (1998).
Niwa. Development. How is pluripotency determined and maintained? Development. Feb. 2007;134(4):635-46. Epub Jan. 10, 2007.
Niwa, et al. Interaction between Oct3/4 and Cdx2 determines trophectoderm differentiation. Cell. Dec. 2, 2005;123(5):917-29.
Notice of allowance dated May 9, 2013 for U.S. Appl. No. 13/415,595.
Notice of allowance dated Jul. 17, 2015 for U.S. Appl. No. 13/909,469.
Notice of allowance dated Jul. 24, 2017 for U.S. Appl. No. 14/952,023.
Notice of allowance dated Sep. 21, 2009 for U.S. Appl. No. 11/361,588.
Notice of allowance dated Oct. 7, 2010 for U.S. Appl. No. 12/405,112.
Notice of allowance dated Dec. 8, 2017 for U.S. Appl. No. 14/840,970.
Notice of allowance dated Dec. 22, 2011 for U.S. Appl. No. 12/972,237.
Office action dated Jan. 8, 2016 for U.S. Appl. No. 13/296,876.
Office action dated Mar. 3, 2014 for U.S. Appl. No. 13/909,469.
Office action dated Mar. 9, 2017 for U.S. Appl. No. 14/840,970.
Office action dated Mar. 11, 2015 for U.S. Appl. No. 13/296,876.
Office action dated Jul. 30, 2014 for U.S. Appl. No. 13/296,876.
Office action dated Aug. 4, 2014 for U.S. Appl. No. 13/909,469.
Office action dated Aug. 11, 2017 for U.S. Appl. No. 14/840,970.
Office action dated Aug. 18, 2009 for U.S. Appl. No. 11/361,588.
Office action dated Oct. 8, 2015 for U.S. Appl. No. 14/090,804.
Office action dated Nov. 25, 2008 for U.S. Appl. No. 11/361,588.
Office action dated Dec. 18, 2012 for U.S. Appl. No. 13/415,595.
Offield, et al. PDX-1 is required for pancreatic outgrowth and differentiation of the rostral duodenum. Development. Mar. 1996;122(3):983-95.
Okano, et al. Neural stem cells: involvement in adult neurogenesis and CNS repair. Phil. Trans. R. Soc. B. 2008; 363:2111-2122. doi:10.1098/rstb.2008.2264.
Panicker, et al. Stem cells and neurogenesis. Stem Cell Biology. 2001; 399-438.
Parolini, et al. Concise review: isolation and characterization of cells from human term placenta: outcome of the first international Workshop on Placenta Derived Stem Cells. Stem Cells. Feb. 2008;26(2):300-11. Epub Nov. 1, 2007.
Parolini, O, et al., Human Placenta: a source of progenitor/stem cells. Journal fuer reproduktionsmedizin und endokrinol, krause & pachernegg GMBH, Jan. 1, 2006; 3(2):117-126.
Pauli, et al. Non-coding RNAs as regulators of embryogenesis. Nat Rev Genet. Feb. 2011;12(2):136-49. doi: 10.1038/nrg2904.
Pereira, et al. Brachyury and related Tbx proteins interact with the Mixl1 homeodomain protein and negatively regulate Mixl1 transcriptional activity. PLoS One. 2011;6(12):e28394. doi: 10.1371/journal.pone.0028394. Epub Dec. 2, 2011.
Pereira, et al. The Mix family of homeobox genes—key regulators of mesendoderm formation during vertebrate development. Dev Biol. Jul. 15, 2012;367(2):163-77. doi: 10.1016/j.ydbio.2012.04.033. Epub May 8, 2012.
Phillips, et al. Cdx2 as a marker of epithelial intestinal differentiation in the esophagus. Am J Surg Pathol. Nov. 2003;27(11):1442-7.
Portmann-Lanz, et al. Placental mesenchymal stem cells as potential autologous graft for pre- and perinatal neuroregeneration. Am J Obstet Gynecol. Mar. 2006;194(3):664-73.
Qi, et al. BMP4 supports self-renewal of embryonic stem cells by inhibiting mitogen-activated protein kinase pathways. Proc Natl Acad Sci U S A. Apr. 20, 2004;101(16):6027-32. Epub Apr. 9, 2004.
Qureshi, et al. Anti-DNA antibodies cross-reacting with laminin inhibit trophoblast attachment and migration: implications for recurrent pregnancy loss in SLE patients. Am J Reprod Immunol. Sep. 2000;44(3):136-42.
Rajasethupathy, et al. Characterization of small RNAs in Aplysia reveals a role for miR-124 in constraining synaptic plasticity through CREB. Neuron. Sep. 24, 2009;63(6):803-17. doi: 10.1016/j.neuron.2009.05.029.
Reubinoff, et al. Neural progenitors from human embryonic stem cells. Nat. Biotech. 2001; 19:1134-1140.
Roelandt, et al. Human embryonic and rat adult stem cells with primitive endoderm-like phenotype can be fated to definitive endoderm, and finally hepatocyte-like cells. PLoS One. Aug. 11, 2010;5(8):e12101. doi: 10.1371/journal.pone.0012101.
Roger Barker (2013) "Stem cell therapies and neurological disorders of the brain: what is the truth'?", Eurostemcell, http://www.eurostemcell.org/roger-barker, 5 pages long, downloaded Mar. 3, 2017.

(56) References Cited

OTHER PUBLICATIONS

Rossant, et al. Effect of culture conditions on diploid to giant-cell transformation in postimplantation mouse trophoblast, J. Embryol. exp. Morph., vol. 62, pp. 217-227 (1981).
Rossant, J. Stem Cells from the Mammalian Blastocyst, Stem Cells, vol. 19, pp. 477-482 (2001).
Roy, et al. Functional engraftment of human ES cell-derived dopaminergic neurons enriched by coculture with telomerase-immortalized midbrain astrocytes. Nat Med. Nov. 2006;12(11):1259-68. Epub Oct. 22, 2006.
Schisler, et al. Stimulation of human and rat islet beta-cell proliferation with retention of function by the homeodomain transcription factor Nkx6.1. Mol Cell Biol. May 2008;28(10):3465-76. doi: 10.1128/MCB.01791-07. Epub Mar. 17, 2008.
Schulz, et al. Human embryonic stem cells as models for trophoblast differentiation. Placenta. Mar. 2008;29 Suppl A:S10-6.
Schwartz, et al. Differentiation of Neural Lineage Cells from Human Pluripotent Stem Cells. Methods. Jun. 2008; 45(2):142-158. doi:10.1016/j.ymeth.2008.03.007.
Schwartz, et al. Multipotent adult progenitor cells from bone marrow differentiate into functional hepatocyte-like cells. J Clin Invest. May 2002;109(10):1291-302.
Schwartz, et al. Pluripotent stem cell-derived hepatocyte-like cells. Biotechnology advances 32.2 (2014): 504-513.
Seaberg, et al. Stem and progenitor cells: the premature desertion of rigorous definitions. Trends Neurosci. Mar. 2003;26(3):125-31.
Seymour, et al. SOX9 is required for maintenance of the pancreatic progenitor cell pool. Proc Natl Acad Sci U S A. Feb. 6, 2007;104(6):1865-70. Epub Jan. 31, 2007.
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Shin, et al., Culture and in vitro hepatogenic differentiation of placenta-derived stem cells, using placental extract as an alternative to serum. Cell proliferation, Oct. 2010; 43(5): 435-444.
Shiraki, et al. Guided differentiation of embryonic stem cells into Pdx1-expressing regional-specific definitive endoderm. Stem Cells. Apr. 2008;26(4):874-85. doi: 10.1634/stemcells.2007-0608. Epub Jan. 31, 2008.
Silva, et al. Capturing pluripotency. Cell. Feb. 22, 2008;132(4):532-6. doi: 10.1016/j.cell.2008.02.006.
Singh, et al. Identification of human brain tumour initiating cells. Nature. 2004; 432:396-401.
Smith, et al. Inhibition of pluripotential embryonic stem cell differentiation by purified polypeptides. Nature. 1998; 336:688-690.
Smith, et al. Placental involvement in congenital neuroblastoma. J. Clin. Pathol. 1981; 34:785-789.
Sneddon, et al. Self-renewal of embryonic-stem-cell-derived progenitors by organ-matched mesenchyme. Nature. Nov. 29, 2012;491(7426):765-8. doi: 10.1038/nature11463. Epub Oct. 7, 2012.
Song, et al. Astroglia induce neurogenesis from adult neural stem cells. Nature. 2002; 417:39-44.
Souto, et al., Liver HLA-G expression is associated with multiple clinical and histopathological forms of chronic hepatitis B virus infection. Journal of Viral hepatitis, 2011;18:102-105.
Spence, et al. Sox17 regulates organ lineage segregation of ventral foregut progenitor cells. Dev Cell. Jul. 2009;17(1):62-74. doi: 10.1016/j.devcel.2009.05.012.
Surani, et al. Genetic and epigenetic regulators of pluripotency. Cell. 2007; 128:747-762.
Swijenburg, et al. Immunosuppressive therapy mitigates immunological rejection of human embryonic stem cell xenografts. Proc Natl Acad Sci U S A. Sep. 2, 2008;105(35):12991-6. Epub Aug. 26, 2008.

Takara Bio Inc "ProductInformation: Stem 121". Retrieved from internet Apr. 11, 2019.
Tam, et al. Early endoderm development in vertebrates: lineage differentiation and morphogenetic function. Curr Opin Genet Dev. Aug. 2003;13(4):393-400.
Tam, et al. Sequential allocation and global pattern of movement of the definitive endoderm in the mouse embryo during gastrulation. Development. Jan. 2007;134(2):251-60. Epub Dec. 6, 2006.
Taupin. Adult neural stem cells: The promise of the future. Neuropsychiatric Disease and Treatment 2007:3(6) 753-760.
Tee, et al. Immunogenicity and immunomodulatory properties of hepatocyte-like cells derived from human amniotic epithelial cells. Curr Stem Cell Res Ther. Jan. 2013;8(1):91-9.
Thomson, et al. EmbryonicStem Cell Lines Derived from Human Blastocysts, Science, vol. 282 pp. 1145-1147 (1998).
Torres, et al. Nanog maintains pluripotency of mouse embryonic stem cells by inhibiting NFkappaB and cooperating with Stat3. Nat Cell Biol. Feb. 2008;10(2):194-201. Epub Jan. 27, 2008.
Tropepe. Direct neural fate specification from embryonic stem cells: a primitive mammalian neural stem cell stage acquired through a default mechanism. Neuron. 2001; 30:65-78.
Tsai, et al. Involvement of replicative polymerases, Tel1p, Mec1p, Cdc13p, and the Ku complex in telomere-telomere recombination. Mol. Cell. Biol. 2002; 22:5679-5687.
Tsai, et al. The ubiquitin ligase gp78 promotes sarcoma metastasis by targeting KAI1 for degradation. Nat. Med. 2007; 13:1504-1509.
Van Brunt. Molecular farming: Transgenic animals as bio-reactors. Biotechnology 6(10):1149-1154 (1988).
Von Gunten, et al. Sialic acid binding immunoglobulin-like lectins may regulate innate immune responses by modulating the life span of granulocytes. FASEB J. Apr. 2006;20(6):601-5.
Wagner, et al. Induction of a midbrain dopaminergic phenotype in Nurr1-overexpressing neural stem cells by type 1 astrocytes. Nat. Biotechnol. 1999; 17:653-659.
Wanggren, et al. Leukaemia inhibitory factor receptor and gp130 in the human Fallopian tube and endometrium before and after mifepristone treatment and in the human preimplantation embryo. Mol Hum Reprod. Jun. 2007;13(6):391-7. Epub Apr. 12, 2007.
Wells, et al. Vertebrate endoderm development. Annu Rev Cell Dev Biol. 1999;15:393-410.
Wichterle et al., Directed Differentiation of Embryonic Stem Cells into Motor Neurons. Cell 110 (2002): 385-397.
Wilcox. Insulin and insulin resistance. Clin Biochem Rev. May 2005;26(2):19-39.
Williams, et al. Myeloid leukemia inhibitory factor maintains the developmental potential of embryonic stem cells. Nature. 1998; 336:684-687.
Wu, et al. Suppression of hydroxyl radical formation and protection of nigral neurons by l-deprenyl (selegiline). Ann. N.Y. Acad. Sci. 1996; 786:379-389.
Xi, et al. A poised chromatin platform for TGF-β access to master regulators. Cell. Dec. 23, 2011;147(7):1511-24. doi: 10.1016/j.cell.2011.11.032.
Xu, et al. Activin, BMP and FGF pathways cooperate to promote endoderm and pancreatic lineage cell differentiation from human embryonic stem cells. Mech Dev. Sep.-Dec. 2011;128(7-10):412-27. doi: 10.1016/j.mod.2011.08.001. Epub Aug. 10, 2011.
Xu, et al. BMP4 initiates human embryonic stem cell differentiation to trophoblast. Nat Biotechnol. Dec. 2002;20(12):1261-4.
Xu, R. In vitro induction of trophoblast from human embryonic stem cells. Methods Mol Med. 2006;121:189-202.
Yamanaka, et al. Cell and molecular regulation of the mouse blastocyst. Dev Dyn. Sep. 2006;235(9):2301-14.
Yan, et al. Retinoic acid promotes differentiation of trophoblast stem cells to a giant cell fate. Dev. Biol. 2001; 235:422-432.
Ying, et al. BMP induction of Id proteins suppresses differentiation and sustains embryonic stem cell self-renewal in collaboration with STAT3. Cell. 2003; 115:281-292.
Yokoyama, et al. Involvement of Two Distinct N-Acetylglucosaminyltransferases and a Dual-Function Deacetylase in Neomycin Biosynthesis. ChemBioChem. 2008; 9:865-869.
Yu, et al. Progress towards gene therapy for HIV infection. Gene Ther. Jan. 1994;1(1):13-26. Abstract only.

(56) References Cited

OTHER PUBLICATIONS

Yu, et al. Stem cell sources and therapeutic approaches for central nervous system and neural retinal disorders. Neurosurg Focus. 2008 ; 24(3-4): E11. doi:10.3171/FOC/2008/24/3-4/E10.

Zhang, et al. (2016) "The Preclinical Research Progress of Stem Cells Therapy in Parkinson's Disease", BioMed Research International, vol. 2016, Article 5683097.

Zhang, et al. Induction of neuronal differentiation of adult human olfactory neuroepithelial-derived progenitors. Brain Res. Feb. 16, 2006;1073-1074:109-19. Epub Feb. 7, 2006.

Zhu, et al. Grafted neural stem cells migrate to substantia nigra and improve behavior in Parkinsonian rats. Neurosci Lett. Oct. 25, 2009;462(3):213-8. Epub Jul. 9, 2009.

* cited by examiner

FIG. 1A
(first column)
FIG. 1B
(middle column)
FIG. 1C
(right column)
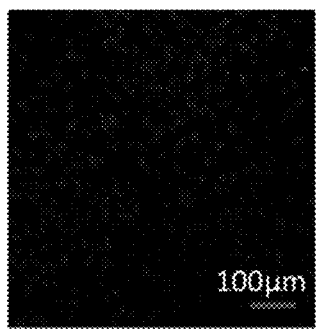
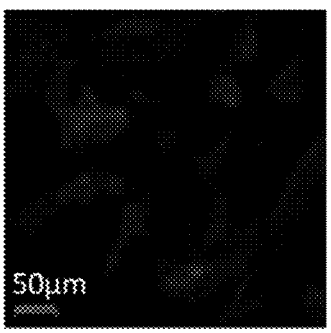
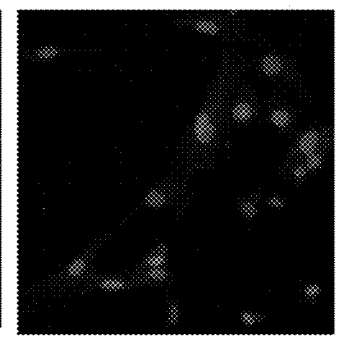
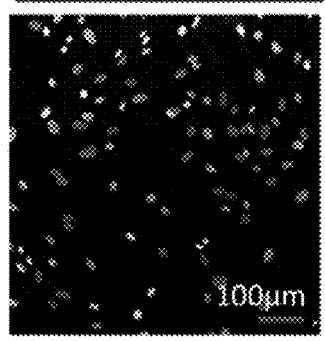
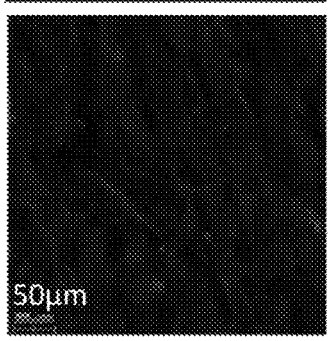
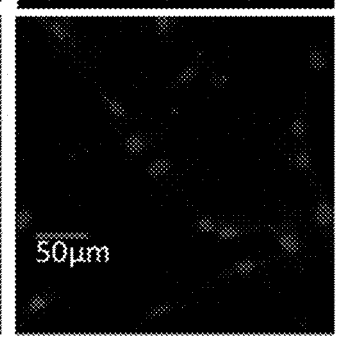

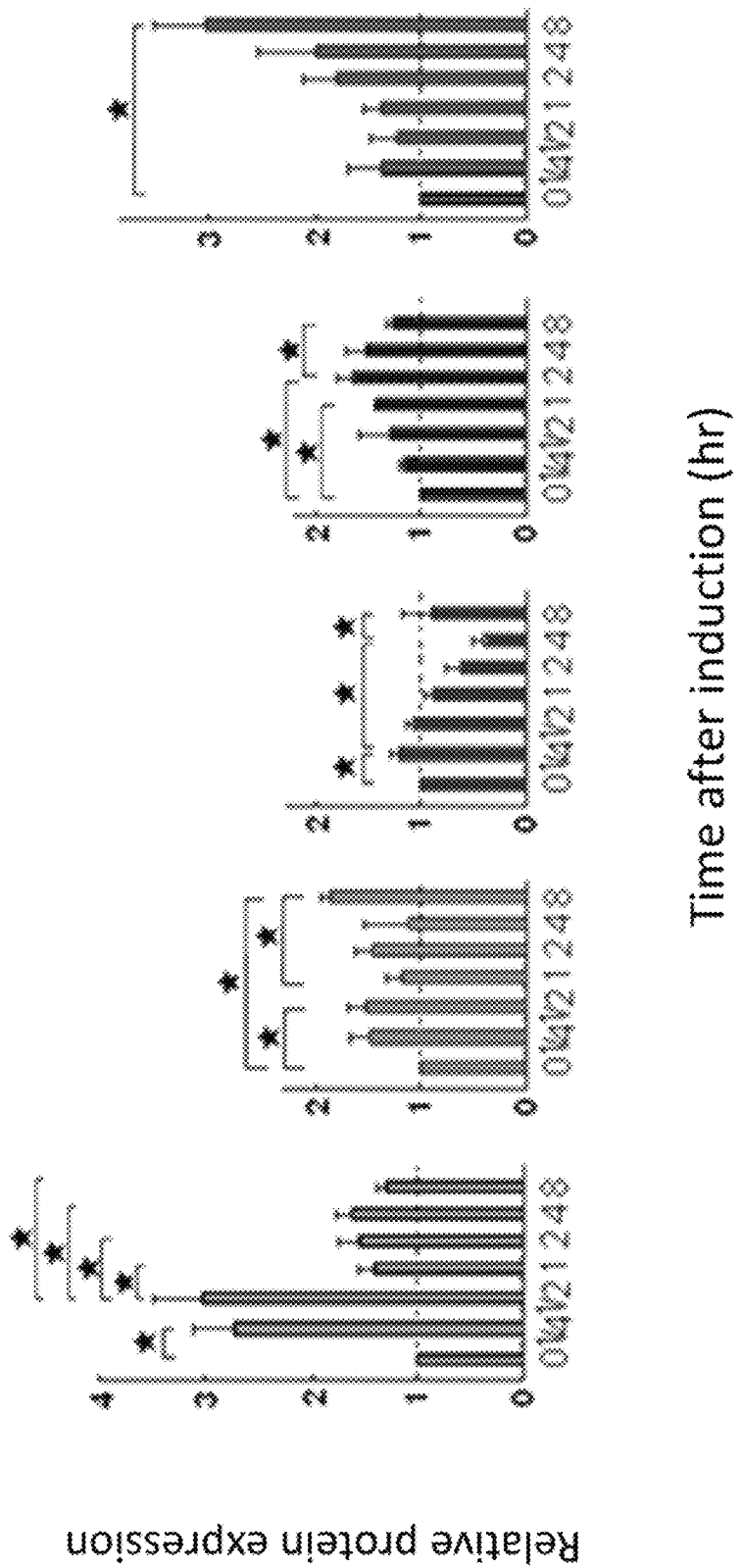

FIG. 2D
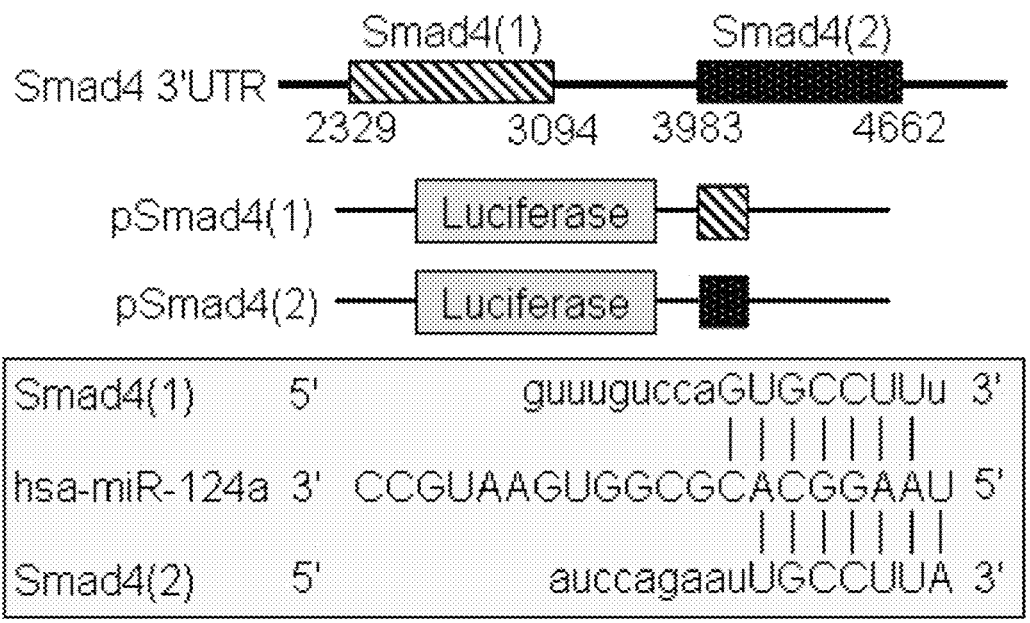
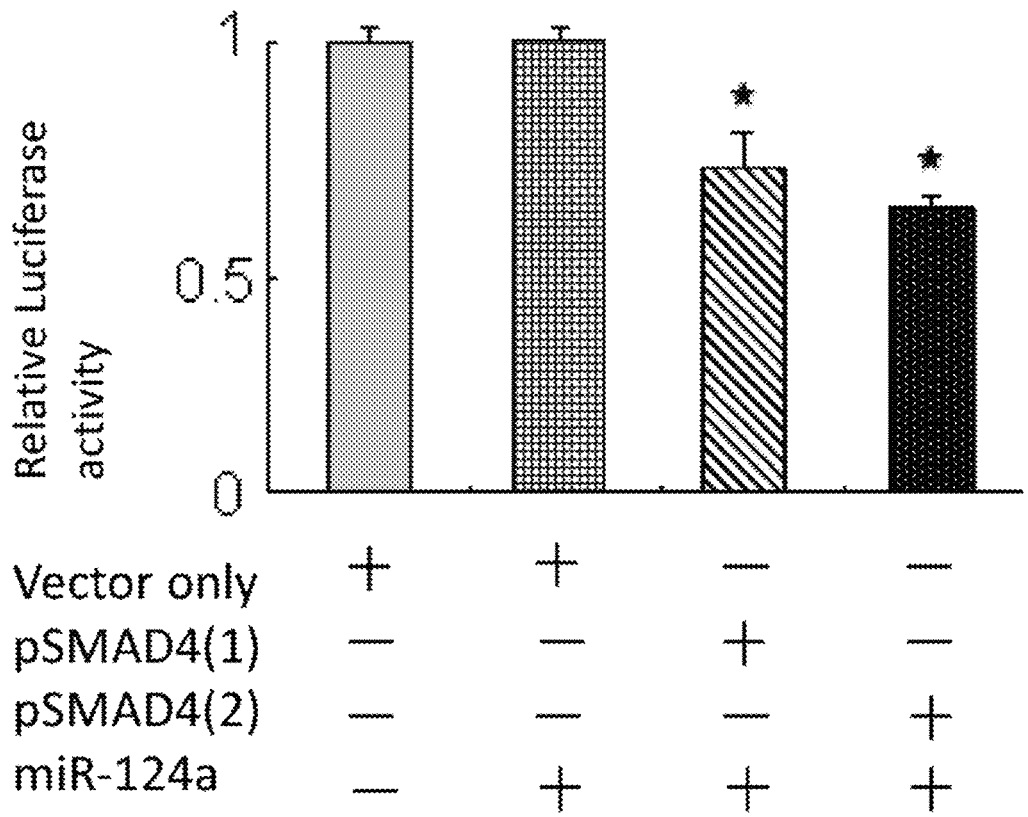

Oil-red-O

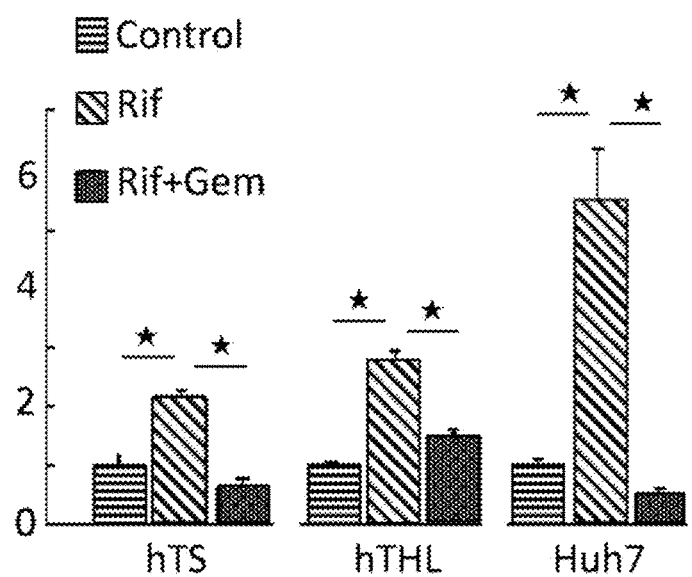
FIG. 5C CYP2C8
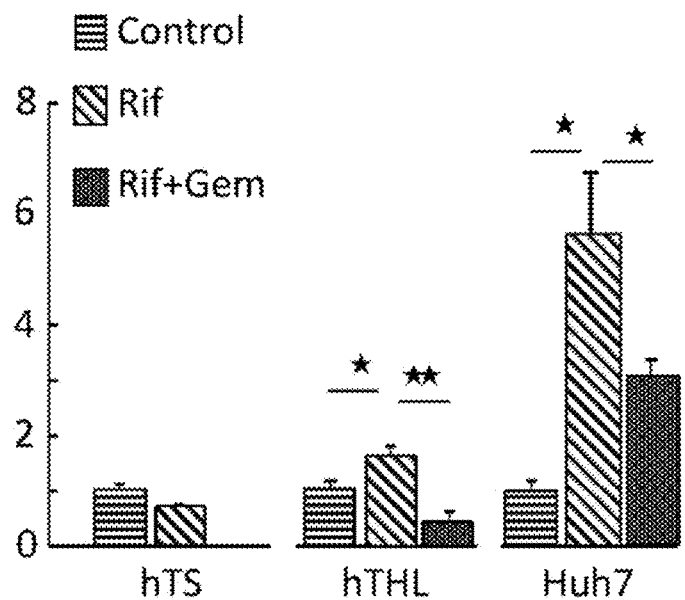
FIG. 5D CYP2C9

CYP2C19

CYP2D6

CYP2E1

CYP3A4

FIG. 6

| Function \ Stage | Gene | Primitive cells (< 8 hr) | Hepatic endoderm lineages (8 hr to day-1) | Hepatoblasts (day 2-4) | Fetal and adult hepatocyte-like cells (≥ day-4) |
|---|---|---|---|---|---|
| DE | CXCR4 | +++ | + | | + |
| DE | FOXA2 | ++++ | + | | + |
| DE | SOX17 | ++++ | ++ | | + |
| DE | HHEX | ++ | + | + | +++ |
| Secretion of bile salts | BSEP | | + | ++ | ++++ |
| Thyroxin- and retinol-binding protein | TTR | | ++ | ++ | +++ |
| Proteins carrier synthesized in the liver | ALB | | ++ | ++ | +++ |
| Tyrosine catabolism | TAT | | ++ | ++ | +++ |
| Serine protease inhibitor | SERPINA1 | | ++ | ++ | +++ |
| Bile acid biosynthesis | CYP7A1 | | ++ | ++ | ++ |
| Enzyme of glucose homeostasis | G6PC | | + | + | +++ |
| Hepatobiliary excretion | ABCC2 | | + | + | +++ |
| Adipocyte differentiation | C/EBPβ | | + | + | +++ |
| Regulator of several hepatic genes | HNF1α | | + | + | +++ |
| Regulator of several hepatic genes | HNF4α | | + | + | +++ |
| Fetal α-fetoprotein precursor | AFP | | + | + | ++ * |
| IL-6-mediated barrier protection | CK8 | | + | + | ++ |
| Gluconeogenesis | PCK2 | | + | + | ++ |
| Drug and steroid metabolism (phase I) | CYP2B6 | | + | + | ++ |
| Liver glucagon synthase | GYS2 | | + | + | ++ |
| Hepatic transcriptional activator | HNF6 | | + | + | + |
| Enzyme of urea cycle | CPS1 | | + | + | + |
| Ethanol catabolism (phase I) | ADH1C | | + | | + |
| Hepatic gap junction | CX32 | | + | | + |
| Drug and steroid metabolism (phase I) | CYP3A4 | | + | | + |
| Hepatocyte migration | PROX1 | | + | | ? |
| Tryptophan metabolism | TDO2 | | + | + | |
| Cholesterol transport regulator | APOF | | + | + | |
| IL-6-mediated barrier protection | CK18 | | | + | |
| Organization of bile duct | CK19 | | | + | + |
| Pancreatic β-cell promoter, Lipid regulator | Betatrophin | | | + | + |

Denotation: blank indicating expression <2-fold, +: >2-fold, ++: >10-fold, +++: >100-fold, and ++++: >1,000-fold  *: only at fetal and post-natal stages

FIG. 13C

Fixed modifications: Carboxymethyl (C)
Variable modifications: Oxidation (M)
Cleavage by Trypsin: cuts C-term side of KR unless next residue is P
Sequence Coverage: 46%

Matched peptides shown in BOLD

```
  1  MALFVRLLAL  ALALALGPAA  TLAGPAKSPY  QLVLQHSRLR  GRQHGPNVCA
 51  VQKVIGTNRK  YFTNCKQWYQ  RKICGKSTVI  SYECCPGYEK  VPGEKGCPAA
101  LPLSNLYETL  GVVGSTTTQL  YTDRTEKLRP  EMEGPGSFTI  FAPSNEAWAS
151  LPAEVLDSLV  SNVNIELLNA  LRYHMVGRRV  LTDELKHGMT  LTSMYQNSNI
201  QIHHYPNGIV  TVNCARLLKA  DHHATNGVVH  LIDKVISTIT  NNIQQIIEIE
251  DTFETLRAAV  AASGLNTMLE  GNGQYTLLAP  TNEAFEKIPS  ETLNRILGDP
301  EALRDLLNNH  ILKSAMCAEA  IVAGLSVETL  EGTTLEVGCS  GDMLTINGKA
351  IISNKDILAT  NGVIHYIDEL  LIPDSAKTLF  ELAAESDVST  AIDLFRQAGL
401  GNHLSGSERL  TLLAPLNSVF  KDGTPPIDAH  TRNLLRNHII  KDQLASKYLY
451  HGQTLETLGG  KKLRVFVYRN  SLCIENSCIA  AHDKRGRYGT  LFTMDRVLTP
501  PMGTVMDVLK  GDNRFSMLVA  AIQSAGLTET  LNREGVYTVF  APTNEAFRAL
551  PPRERSRLLG  DAKELANILK  YHIGDEILVS  GGIGALVRLK  SLQGDKLEVS
601  LKNNVSVNK   EPVAEPDIMA  TNGVVHVITN  VLQPPANRPQ  ERGDELADSA
651  LEIFKQASAF  SRASQRSVRL  APVYQKLLER  MKH
```

FIG. 15A
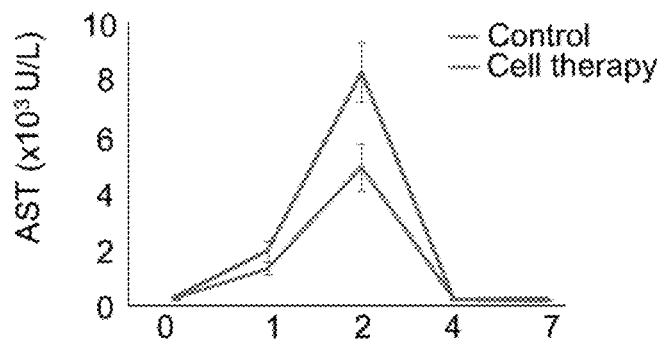
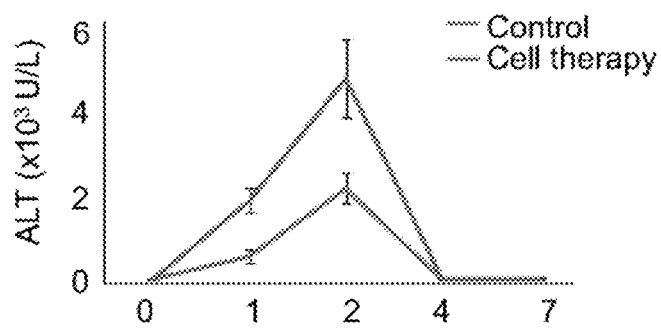
FIG. 15B
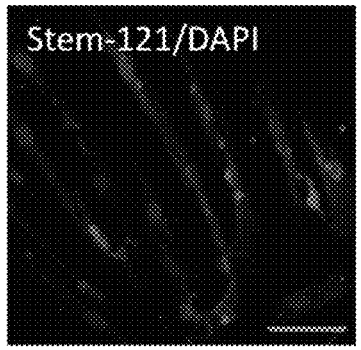
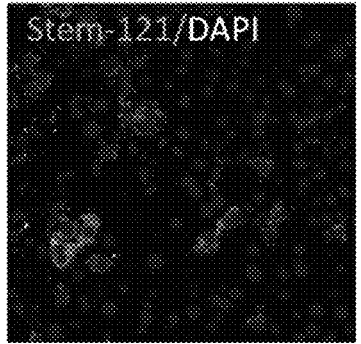
FIG. 15C
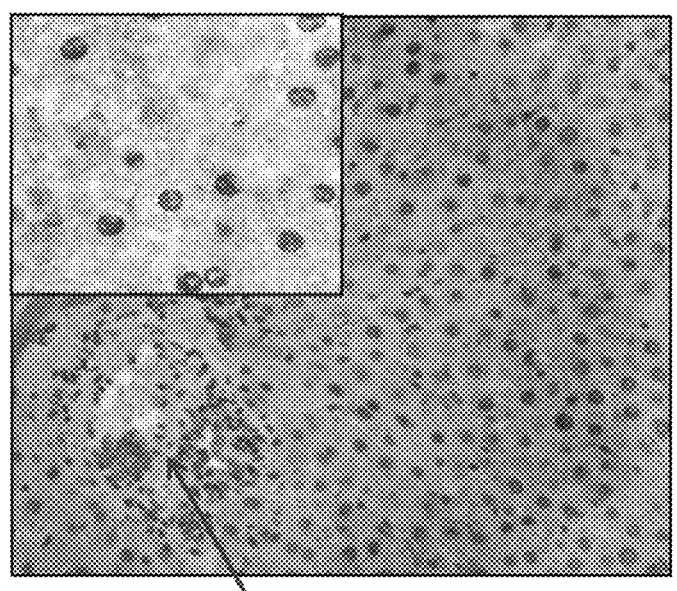

```
                              SEQUENCE LISTING

<160> NUMBER OF SEQ ID NOS: 117

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaattataag ctgtttgggt tgttggtct                                          29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaacaattgc ccccataatt tctgactgc                                          29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaattataac tcccaaagtg ctgggatta                                          29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaacaattgc tgcactgttc acaggagga                                          29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaattataac agttgtccca gtgctgcta                                          29

<210> SEQ ID NO 6
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
aaacaattga tgacttgccc aaaggtcac                                      29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaattataac ccacaactgg ggtaaaaga                                      29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaacaattgc tgtggaaggg gcaaagata                                      29

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acctgggtac tcccaatcct a                                              21

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgaagcgagg cgaccc                                                    16

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaaccctca gcgtctcagt                                                20

<210> SEQ ID NO 12
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 12
ctggtcgttt gttgtggctg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatacgccag tgacgaccag                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagccacttg ttgccaactc                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagccttggt gttgattgcc                                               20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caccaagcag gtcttcacct c                                             21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgacgatggg caatgacacg                                               20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gcttagcagc atgcaaaagg a                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcctctggga aaaccagtga                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggacctgcag gaagggatct                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acatccgggc ccaatatgac                                                20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agctgagcat gaaagctgcc t                                              21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tccgataact ggggtgacct                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gatgagcagc aaaggcaacc          20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcaacctcgt ctttaagtgg att          23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctgcaggaa tctgtcgttc          20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aatgactgga ctgtgtgggt a          21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taactccccc atggagtcgg          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actttagcga gtcagagccg          20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
aggcccatgc cacaaatca                                              19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acagtgaagg tcgactccg                                              19

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgggaactac ctgcatttgg a                                           21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccaagagaag ctaccaaagc c                                           21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cccctgggca aacctctact                                             20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agcaaatgac tttgaggttc ca                                          22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
```
gctccccaag gtgtgaatga                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tattcacagg gtcgttggct                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgtttccac agagcggcta                                              20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aacaagggac acaacgctga at                                           22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atggggcact gaaaaagact ga                                           22

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccttacacat acacaccctt tggaagt                                      27

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatggtcctg tgttcaccgt                                         20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttcatgcctt tctcagcagg                                         20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgaggtccag agatacatc                                          19

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctaagggaac gacactcatc ac                                      22

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acagagacca ccagcacaac t                                       21

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaagaaaagt cgcctcaac                                          19

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgctacttct gcgaaggcat                                         20

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cccctatttt ttcaaaaatg tctt                                              24

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acatctccct ccccagactc                                                   20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctgtcggctg agggtttcca t                                                 21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tctgcggctc tttggtttca                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcggctcttt ggtttcaagg                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cccgcagttc tcaaggacac                                                   20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ttgtagattg ctctctctcc tcc                                    23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
cccatcattg attcctggat                                        20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gtcagccctc cctgactgat                                        20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
actgactgga gctggtaggt                                        20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ccacgacttt cccagcatct                                        20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
agtagtgggc taagggcaca                                        20

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggaggagtag ccctcgg                                                    17

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgacttgcc cagcatcttg                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggccaacacc agggtttact                                                 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcacagcagt cagccatttc                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tctcgatgac gctgtggttg                                                 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agcccggaag catttcttga                                                 20

<210> SEQ ID NO 67

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctgacagtgc tcagctccaa                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
atcccatccc tcgtccttca                                                  20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tctggttgac cgtaactgcg                                                  20

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tccaagctgg ccttcagatt t                                                21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gatcttcctg tccctcgagc a                                                21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agacggcatt gtcgattcac t                                                21

<210> SEQ ID NO 73
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acagtagggt ccccaatgga                                               20

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtatacacct gctgtgccca t                                             21

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccccgaggat tgcctagatc at                                            22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caggacaagg ggtctgagga                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
atgtcgatgg acgtctcgtg                                               20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gatttaaagg caggcggcg                                                19

<210> SEQ ID NO 79
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 79
agcaacagag gatggatggc                                                     20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccgcacatac caggtttcca                                                     20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tcggtgcatc cgagaaacaa                                                     20

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgcctccaac tttattggtc ac                                                  22

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tctcctccat ttagcgcgtc                                                     20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ctcttgtagg cagttcgggg                                                     20

<210> SEQ ID NO 85
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 85
actaggatga gctgcaggga                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agaagccaac tctaacgcca                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccaggttcac atctcggact                                                    20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggaagagaaa caagggctga gt                                                 22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
agaggcgggg acactgaatg ac                                                 22

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agctcaatgc atgtacagaa tccccggtta                                         30

<210> SEQ ID NO 91
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 91
tcaactcctc cacaaggcag t                                              21

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ttgcacagtg aaacatagga                                                20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgtcatgtag cacagaagtg                                                20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ctcaccagga aagcaaagac ac                                             22

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atgagcgggg aatgacacag a                                              21

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aagaagtcct tgcgtgtcta                                                20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
tccgtgaggg aattcaaggc                                               20

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
attgatccca aagagaaaac cac                                           23

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tgctctgtgc tcagaagtgg                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gagtctgggg agggagatgt                                               20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tctgccttca gcacaagagg                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctgccttcag cacaagagga                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
agaagggagc caggcaagtc                                              20

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gtgaagcctt ggctagggg                                               19

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ttgggaggct gagatttgtc                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
catgtggatt tccagcctgc                                              20

<210> SEQ ID NO 107
<211> LENGTH: 12
<212> TYPE: DNA
<213> ORGANISM: Homo sapiens

<400> SEQUENCE: 107
ggtgacgtca gc                                                      12

<210> SEQ ID NO 108
<211> LENGTH: 11
<212> TYPE: DNA
<213> ORGANISM: Homo sapiens

<400> SEQUENCE: 108
acgccgtcat t                                                       11

<210> SEQ ID NO 109
<211> LENGTH: 12
<212> TYPE: DNA
<213> ORGANISM: Homo sapiens

<400> SEQUENCE: 109
ggtgacgtca cc                                                      12

<210> SEQ ID NO 110
<211> LENGTH: 17
<212> TYPE: RNA
<213> ORGANISM: Homo sapiens -continued

<400> SEQUENCE: 110
guuuguccag ugccuuu                                                      17

<210> SEQ ID NO 111
<211> LENGTH: 20
<212> TYPE: RNA
<213> ORGANISM: Homo sapiens

<400> SEQUENCE: 111
uaaggcacgc ggugaaugcc                                                   20

<210> SEQ ID NO 112
<211> LENGTH: 16
<212> TYPE: RNA
<213> ORGANISM: Homo sapiens

<400> SEQUENCE: 112
auccagaauu gccuua                                                       16

<210> SEQ ID NO 113
<211> LENGTH: 15
<212> TYPE: RNA
<213> ORGANISM: Homo sapiens

<400> SEQUENCE: 113
guuuggagug ccuuc                                                        15

<210> SEQ ID NO 114
<211> LENGTH: 15
<212> TYPE: RNA
<213> ORGANISM: Homo sapiens

<400> SEQUENCE: 114
uaaggcacgc gguga                                                        15

<210> SEQ ID NO 115
<211> LENGTH: 17
<212> TYPE: RNA
<213> ORGANISM: Homo sapiens

<400> SEQUENCE: 115
gggaguauuu gaacaca                                                      17

<210> SEQ ID NO 116
<211> LENGTH: 17
<212> TYPE: RNA
<213> ORGANISM: Homo sapiens

<400> SEQUENCE: 116
cguguucaca gcggacc                                                      17

<210> SEQ ID NO 117
<211> LENGTH: 683
<212> TYPE: PRT
<213> ORGANISM: Homo sapiens

<400> SEQUENCE: 117

Met Ala Leu Phe Val Arg Leu Leu Ala Leu Ala Leu Ala Leu
1               5                   10                  15

Gly Pro Ala Ala Thr Leu Ala Gly Pro Ala Lys Ser Pro Tyr Gln Leu
            20                  25                  30

```
Val Leu Gln His Ser Arg Leu Arg Gly Arg Gln His Gly Pro Asn Val
             35                  40                  45

Cys Ala Val Gln Lys Val Ile Gly Thr Asn Arg Lys Tyr Phe Thr Asn
 50                  55                  60

Cys Lys Gln Trp Tyr Gln Arg Lys Ile Cys Gly Lys Ser Thr Val Ile
 65                  70                  75                  80

Ser Tyr Glu Cys Cys Pro Gly Tyr Glu Lys Val Pro Gly Glu Lys Gly
                 85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
            115                 120                 125

Arg Pro Glu Met Glu Gly Pro Gly Ser Phe Thr Ile Phe Ala Pro Ser
130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
            195                 200                 205

Ile Val Thr Val Asn Cys Ala Arg Leu Leu Lys Ala Asp His His Ala
        210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
            275                 280                 285

Pro Ser Glu Thr Leu Asn Arg Ile Leu Gly Asp Pro Glu Ala Leu Arg
290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350

Ser Asn Lys Asp Ile Leu Ala Thr Asn Gly Val Ile His Tyr Ile Asp
            355                 360                 365

Glu Leu Leu Ile Pro Asp Ser Ala Lys Thr Leu Phe Glu Leu Ala Ala
370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
            435                 440                 445

Leu Tyr His Gly Gln Thr Leu Glu Thr Leu Gly Gly Lys Lys Leu Arg
```

-continued

```
                    450                 455                 460
Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
        515                 520                 525

Glu Thr Leu Asn Arg Glu Gly Val Tyr Thr Val Phe Ala Pro Thr Asn
    530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
            580                 585                 590

Gln Gly Asp Lys Leu Glu Val Ser Leu Lys Asn Asn Val Val Ser Val
        595                 600                 605

Asn Lys Glu Pro Val Ala Glu Pro Asp Ile Met Ala Thr Asn Gly Val
    610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
            660                 665                 670

Val Tyr Gln Lys Leu Leu Glu Arg Met Lys His
        675                 680
```

HUMAN HEPATOCYTES AND USES THEREOF

CROSS-REFERENCE

This application is a continuation of U.S. application Ser. No. 15/705,587, filed on Sep. 15, 2017, now U.S. Pat. No. 10,765,704, which is a divisional application of U.S. application Ser. No. 14/952,023, filed on Nov. 25, 2015, now U.S. Pat. No. 9,808,490, which claims the benefit of U.S. Provisional Application No. 62/085,185, filed on Nov. 26, 2014, each of which is incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 31, 2015, is named 44980-704.201_SL.txt and is 31,606 bytes in size.

INCORPORATION BY REFERENCE

All publications, patents, and patent applications disclosed herein are incorporated by reference to the same extent as if each individual publication, patent, or patent application was specifically and individually indicated to be incorporated by reference. In the event of a conflict between a term disclosed herein and a term in an incorporated reference, the term herein controls.

BRIEF SUMMARY

In one of many aspects, disclosed herein is a method of inducing a trophoblast stem (TS) cell to differentiate into an induced hepatocyte in vitro, comprising: contacting the trophoblast stem cell with a conditioned medium (e.g., for sufficient time) to induce differentiation of the trophoblast stem cell into an induced hepatocyte, wherein the condition medium comprises a fibroblast growth factor (FGF), a steroid, and a cytokine. In some embodiments, disclosed herein is a method of inducing a trophoblast stem (TS) cell to differentiate into an induced hepatocyte in vitro, which comprises (a) contacting the trophoblast stem cell in a conditioned medium comprising a fibroblast growth factor (FGF), a steroid, and a cytokine; and (b) incubating the cell for sufficient time to induce differentiation of the trophoblast stem cell into an induced hepatocyte. In some embodiments, the method further comprises contacting the trophoblast stem cell with the FGF prior to addition of the steroid and the cytokine to the conditioned medium. In some embodiments, the trophoblast stem cell is contacted with FGF for at least 2 hours, at least 4 hours, at least 6 hours, 8 hours, at least 12 hours, at least 16 hours, at least 20 hours, or at least 24 hours prior to addition of the steroid and the cytokine to the conditioned medium. In some embodiments, the method further comprises incubating the trophoblast stem cell for at least 1 day, at least 2 days, at least 3 days, at least 4 days, at least 5 days, at least 6 days, or at least 7 days. In some embodiments, the steroid and the cytokine are added simultaneously or sequentially into the conditioned medium.

In some embodiments, an induced hepatocyte herein is a hepatic progenitor cell. In some embodiments, FGF upregulates miRNA-124a in the TS cell. In some embodiments, elevated level of miRNA-124a initiates definitive endoderm (DE) specification in the TS cell. In some embodiments, the DE specification is associated with biomarkers comprising forkhead box protein A2 (FOXA2), SRY-box 17 (SOX17), Goosecoid (GSC), or Homeodomain protein MIXL1. In some embodiments, the DE specification is associated with elevated expression levels of SOX17, FOXA2, and GSC. In some embodiments, the elevated expression levels are increased protein expression levels. In some embodiments, the DE specification is associated with a decreased expression level of MIXL1. In some embodiments, the decreased expression level is a decreased protein expression levels. In some embodiments, the elevated protein expression levels of SOX17, FOXA2, and GSC and the decreased protein expression level of MIXL1 are relative to the protein expression levels of SOX17, FOXA2, GSC, and MIXL1 in an equivalent TS cell that has not undergone DE specification. In some embodiments, the DE specification is further associated with elevated expression levels of SOX2, NANOG, and OCT4. In some embodiments, elevated expression levels of SOX2, NANOG, and OCT4 are increased level of protein expressions. In some embodiments, elevated expression levels of SOX2, NANOG, and OCT4 are increased level of gene expressions. In some embodiments, the elevated expression levels of SOX2, NANOG, and OCT4 are relative to the expression levels of SOX2, NANOG, and OCT4 in an equivalent TS cell that has not undergone DE specification. In some embodiments, differentiation induced by a method herein comprises one or more of four stages: primitive streak to definitive endoderm (DE) stage, hepatic specified endoderm stage, hepatoblastic stage, and the fetal and adult hepatocyte cell stage. In some embodiments, one or more biomarkers selected from the group consisting of CXCR4, FOXA2, SOX17, HHEX, TTR, ALB, TAT, CYP7A1, BSEP, SERPINA1, G6PC, ABCC2, C/EBPβ, HNF1α, HNF4α, and any combination thereof express in one or more of the four stages. In some embodiments, one or more biomarkers selected from the group consisting of CXCR4, FOXA2, SOX17, HHEX, and any combination thereof, express at the primitive streak to DE stage. In some embodiments, an expression level of CXCR4, FOXA2, SOX17, and/or HHEX increases at the primitive streak to DE stage, relative to that before the primitive streak to DE stage. In some embodiments, the increased expression level is an increased level of gene expression. In some embodiments, the expression level of CXCR4, FOXA2, SOX17 and/or HHEX increases by about 1 fold and about 10,000 fold higher than that before the primitive streak to DE stage. In some embodiments, the expression level of CXCR4, FOXA2, SOX17 and/or HHEX increases by about 10 fold and about 1000 fold higher than that before the primitive streak to DE stage. In some embodiments, one or more biomarkers selected from the group consisting of SOX17, TTR, ALB, TAT, SERPINA1, CYP7A1, and any combination thereof express in the hepatic specified endoderm stage. In some embodiments, an expression level of SOX17, TTR, ALB, TAT, SERPINA1, and/or CYP7A1 increases at the hepatic specified endoderm stage, relative to that before the hepatic specified endoderm stage. In some embodiments, the increased expression level is an increased level of gene expression. In some embodiments, the expression level of SOX17, TTR, ALB, TAT, SERPINA1, and/or CYP7A1 increases by about 1 fold and about 1000 fold higher than that before the hepatic specified endoderm stage. In some embodiments, the expression level of SOX17, TTR, ALB, TAT, SERPINA1, and/or CYP7A1 increases by about 10 fold and about 100 fold higher than that before the hepatic specified endoderm stage. In some embodiments, one or more biomarkers selected from the group consisting of TTR, ALB, TAT, CYP7A1, SERPINA1, BSEP, and any combination thereof express at the hepatoblastic stage. In some embodiments, an expression level of TTR, ALB, TAT, CYP7A1, SERPINA1, and/or BSEP increases at the hepatoblastic stage, relative to that before the hepatoblastic stage. In some embodiments, the increased expression level is an increased level of gene expression. In some embodiments, the expression level of TTR, ALB, TAT, CYP7A1, SERPINA1, and/or BSEP increases by about 1 fold and about 1000 fold higher than that before the hepatoblastic stage. In some embodiments, the expression level of TTR, ALB, TAT, CYP7A1, SERPINA1, and/or BSEP increases by about 10 fold and about 100 fold higher than that before the hepatoblastic stage. In some embodiments, one or more biomarkers selected from the group consisting of HHEX, BSEP, TTR, ALB, TAT, SERPINA1, G6PC, ABCC2, C/EBPβ, HNF1α, HNF4α, and any combination thereof express at the fetal and adult hepatocyte-like cell stage. In some embodiments, an expression level of HHEX, BSEP, TTR, ALB, TAT, SERPINA1, G6PC, ABCC2, C/EBPβ, HNF1α, and/or HNF4α increases at the fetal and adult hepatocyte-like cell stage, relative to that before the fetal and adult hepatocyte-like cell stage. In some embodiments, the increased expression level is an increased level of gene expression. In some embodiments, the expression level of HHEX, BSEP, TTR, ALB, TAT, SERPINA1, G6PC, ABCC2, C/EBPβ, HNF1α, and/or HNF4α increases by about 10 fold and about 1000 fold higher than that before the fetal and adult hepatocyte cell stage. In some embodiments, the expression level of HHEX, BSEP, TTR, ALB, TAT, SERPINA1, G6PC, ABCC2, C/EBPβ, HNF1α, and/or HNF4α increases by at least 100 fold higher than that before the fetal and adult hepatocyte cell stage.

In some embodiments, a trophoblast stem cell herein is a human trophoblast stem cell. In some embodiments, the steroid is dexamethasone. In some embodiments, the cytokine is oncostatin M. In some embodiments, the oncostatin M is a human oncostatin M. In some embodiments, the human oncostatin M is a recombinant human oncostatin M. In some embodiments, the conditioned medium further comprises a bone morphogenetic protein (BMP). In some embodiments, the BMP is present in a concentration of about 1-100 ng/ml. In some embodiments, the BMP is present in a concentration of about 1-50 ng/ml, e.g., about 20 ng/ml. In some embodiments, the BMP is BMP1, BMP2, BMP3, BMP4, BMP5, BMP6, BMP7, BMP8a, BMP8b, BMP10, or BMP15. In some embodiments, the BMP is BMP4. In some embodiments, the conditioned medium further comprises a hepatic growth factor (HGF). In some embodiments, the HGF is present in a concentration of about: 0.1-50 ng/ml or 0.1-25 ng/ml, e.g., about 5 ng/ml.

In some embodiments, a hepatocyte disclosed herein is immune privileged. In some embodiments, the induced hepatocyte expresses TGFβ1. In some embodiments, the induced hepatocyte expresses TGFβ1, fibronectin, and collagen IV in extracellular matrix (ECM). In some embodiments, the induced hepatocyte expresses HLA-G. In some embodiments, the induced hepatocyte expresses HLA-G and stem-121. In some embodiments, the induced hepatocytes recruit CD4+Foxp3+ Treg cells. In some embodiments, the induced hepatocytes form tissue of a 3-dimensional structure. In some embodiments, the induced hepatocytes cluster or aggregate. In some embodiments, the induced hepatocytes form a crescent cell mass. In some embodiments, the induced hepatocytes comprise a peripheral compartment and a central compartment. In some embodiments, the induced hepatocytes distribute irregularly along ECM beyond basement membrane in the peripheral compartment. In some embodiments, the induced hepatocytes distribute from basal towards central areas in the central compartment. In some embodiments, the induced hepatocyte expresses one or more markers selected from the group consisting of TGFβ1, HLA-G, stem 121, C-kit, CK19, CK18, ALB, α-AFP, betatrophin, ADH1, APOF, CPS1, GATA4, CYP1A1, CYP2B6, ASGR1, CXCR4, BSEP, MRP2, Cx32, and any combination thereof. In some embodiments, the induced hepatocyte expresses one or more markers selected from the group consisting of TGFβ1, HLA-G, stem 121, C-kit, betatrophin, ADH1, APOF, CPS1, CYP2B6, ASGR1, CXCR4, Cx32, and any combination thereof. In some embodiments, the induced hepatocyte expresses one or more markers selected from the group consisting of CPS1, CYP2B6, and a combination thereof.

In one aspect, provided herein is an induced hepatocyte produced by any method disclosed herein. In another aspect, provided herein is an isolated induced hepatocyte derived from a trophoblast stem cell. In another aspect, provided herein is an isolated hepatocyte induced from a trophoblast stem cell. In some embodiments, the hepatocyte expresses one or more biomarkers selected from the group consisting of transforming growth factor beta 1 (TGFβ1), human leukocyte antigen G (HLA-G), cluster of differentiation 4 (CD4), forkhead box P3 (Foxp3), human cytoplasmic marker stem 121 (stem 121), mast/stem cell growth factor receptor C-kit (C-kit), betatrophin, apolipoprotein F (APOF), alcohol dehydrogenase-1 (ADH1), carbamoyl-phosphate synthase 1 (CPS1), GATA transcription factor 4 (GATA4), cytochrome P450 family 1 subfamily A polypeptide 1 (CYP1A1), cytochrome P450 2B6 (CYP2B6), asialoglycoprotein receptor 1 (ASGR1), C—X—C chemokine receptor type 4 (CXCR4), bile salt export pump (BSEP), multi-drug resistance protein-2 (MRP2), connexin 32 (CX32), forkhead box protein A2 (FOXA2), SRY-box 17 (SOX17), hexosaminidase A alpha polypeptide (HEXA), hematopoietically expressed homeobox (HHEX), transthyretin (TTR), albumin (ALB), tyrosine aminotransferase (TAT), cytochrome P450 7A1 (CYP7A1), glucose-6-phosphatase (G6PC), serpin peptidase inhibitor clade A (alpha-1 antiproteinase, antitrypsin) member 1 (SERPINA1), ATP-binding cassette sub-family C (ABCC2), CCAAT-enhancer-binding protein beta (C/EBPβ), hepatocyte nuclear factor 1-alpha (HNF1α), hepatocyte nuclear factor 4-alpha (HNF4α), alpha-1-fetoprotein (AFP), cytokeratin 8 (CK8), phosphoenolpyruvate carboxykinase 2 mitochondrial (PCK2), glycogen synthase 2 (GYS2), hepatocyte nuclear factor 6 (HNF6), alcohol dehydrogenase 1C (class I) gamma polypeptide (ADH1C), cytochrome P450 3A4 (CYP3A4), prospero homeobox 1 (PROX1), tryptophan 2,3-dioxygenase (TDO2), cytokeratin 18 (CK18), and cytokeratin 19 (CK19).

In some embodiments, a hepatocyte herein is a hepatic progenitor cell. In some embodiments, FGF upregulates miRNA-124a in the TS cell. In some embodiments, elevated level of miRNA-124a initiates definitive endoderm (DE) specification in the TS cell. In some embodiments, the DE specification is associated with biomarkers comprising forkhead box protein A2 (FOXA2), SRY-box 17 (SOX17), Goosecoid (GSC), or Homeodomain protein MIXL1. In some embodiments, the DE specification is associated with elevated expression levels of SOX17, FOXA2, and GSC. In some embodiments, the elevated expression levels are increased protein expression levels. In some embodiments, the DE specification is associated with a decreased expression level of MIXL1. In some embodiments, the decreased expression level is a decreased protein expression levels. In some embodiments, the elevated protein expression levels of SOX17, FOXA2, and GSC and the decreased protein expression level of MIXL1 are relative to the protein expression levels of SOX17, FOXA2, GSC, and MIXL1 in an equivalent TS cell that has not undergone DE specification. In some embodiments, the DE specification is further associated with elevated expression levels of SOX2, NANOG, and OCT4. In some embodiments, elevated expression levels of SOX2, NANOG, and OCT4 are increased level of protein expressions. In some embodiments, elevated expression levels of SOX2, NANOG, and OCT4 are increased level of gene expressions. In some embodiments, the elevated expression levels of SOX2, NANOG, and OCT4 are relative to the expression levels of SOX2, NANOG, and OCT4 in an equivalent TS cell that has not undergone DE specification. In some embodiments, a hepatocyte disclosed herein is at one of four stages: primitive streak to definitive endoderm (DE) stage, hepatic specified endoderm stage, hepatoblastic stage, and the fetal and adult hepatocyte cell stage. In some embodiments, one or more biomarkers selected from the group consisting of CXCR4, FOXA2, SOX17, HHEX, TTR, ALB, TAT, CYP7A1, BSEP, SERPINAL G6PC, ABCC2, C/EBPβ, HNF1α, HNF4α, and any combination thereof express in one or more of the four stages. In some embodiments, one or more biomarkers selected from the group consisting of CXCR4, FOXA2, SOX17, HHEX, and any combination thereof, express at the primitive streak to DE stage. In some embodiments, an expression level of CXCR4, FOXA2, SOX17, and/or HHEX increases at the primitive streak to DE stage, relative to that before the primitive streak to DE stage. In some embodiments, the increased expression level is an increased level of gene expression. In some embodiments, the expression level of CXCR4, FOXA2, SOX17 and/or HHEX increases by about 1 fold and about 10,000 fold higher than that before the primitive streak to DE stage. In some embodiments, the expression level of CXCR4, FOXA2, SOX17 and/or HHEX increases by about 10 fold and about 1000 fold higher than that before the primitive streak to DE stage. In some embodiments, one or more biomarkers selected from the group consisting of SOX17, TTR, ALB, TAT, SERPINAL CYP7A1, and any combination thereof express in the hepatic specified endoderm stage. In some embodiments, an expression level of SOX17, TTR, ALB, TAT, SERPINAL and/or CYP7A1 increases at the hepatic specified endoderm stage, relative to that before the hepatic specified endoderm stage. In some embodiments, the increased expression level is an increased level of gene expression. In some embodiments, the expression level of SOX17, TTR, ALB, TAT, SERPINAL and/or CYP7A1 increases by about 1 fold and about 1000 fold higher than that before the hepatic specified endoderm stage. In some embodiments, the expression level of SOX17, TTR, ALB, TAT, SERPINAL and/or CYP7A1 increases by about 10 fold and about 100 fold higher than that before the hepatic specified endoderm stage. In some embodiments, one or more biomarkers selected from the group consisting of TTR, ALB, TAT, CYP7A1, SERPINAL bile salts excretion pump (BSEP), and any combination thereof express at the hepatoblastic stage. In some embodiments, an expression level of TTR, ALB, TAT, CYP7A1, SERPINA1, and/or BSEP increases at the hepatoblastic stage, relative to that before the hepatoblastic stage. In some embodiments, the increased expression level is an increased level of gene expression. In some embodiments, the expression level of TTR, ALB, TAT, CYP7A1, SERPINAL and/or BSEP increases by about 1 fold and about 1000 fold higher than that before the hepatoblastic stage. In some embodiments, the expression level of TTR, ALB, TAT, CYP7A1, SERPINAL and/or BSEP increases by about 10 fold and about 100 fold higher than that before the hepatoblastic stage. In some embodiments, one or more biomarkers selected from the group consisting of HHEX, BSEP, TTR, ALB, TAT, SERPINAL G6PC, ABCC2, C/EBPβ, HNF1α, HNF4α, and any combination thereof express at the fetal and adult hepatocyte-like cell stage. In some embodiments, an expression level of HHEX, BSEP, TTR, ALB, TAT, SERPINA1, G6PC, ABCC2, C/EBPβ, HNF1α, and/or HNF4α increases at the fetal and adult hepatocyte-like cell stage, relative to that before the fetal and adult hepatocyte-like cell stage. In some embodiments, the increased expression level is an increased level of gene expression. In some embodiments, the expression level of HHEX, BSEP, TTR, ALB, TAT, SERPINAL G6PC, ABCC2, C/EBPβ, HNF1α, and/or HNF4α increases by about 10 fold and about 1000 fold higher than that before the fetal and adult hepatocyte cell stage. In some embodiments, the expression level of HHEX, BSEP, TTR, ALB, TAT, SERPINAL G6PC, ABCC2, C/EBPβ, HNF1α, and/or HNF4α increases by at least 100 fold higher than that before the fetal and adult hepatocyte cell stage. In some embodiments, the trophoblast stem cell is a human trophoblast stem cell.

In some embodiments, a hepatocyte herein is immune privileged. In some embodiments, the hepatocyte expresses TGFβ1. In some embodiments, the hepatocyte expresses TGFβ1, fibronectin, and collagen IV in extracellular matrix (ECM). In some embodiments, the hepatocyte expresses HLA-G. In some embodiments, the hepatocyte expresses HLA-G and stem-121. In some embodiments, the hepatocyte recruits $CD4^+Foxp3^+$ Treg cells. In some embodiments, the hepatocytes form tissue of a 3-dimensional structure. In some embodiments, the hepatocytes cluster or aggregate. In some embodiments, the hepatocytes form a crescent cell mass. In some embodiments, the hepatocytes comprise a peripheral compartment and a central compartment. In some embodiments, the hepatocytes distribute irregularly along ECM beyond basement membrane in the peripheral compartment. In some embodiments, the hepatocytes distribute from basal towards central areas in the central compartment. In some embodiments, the hepatocyte expresses one or more markers selected from the group consisting of TGFβ1, HLA-G, stem 121, C-kit, CK19, CK18, ALB, α-AFP, beta-trophin, ADH1, APOF, CPS1, GATA4, CYP1A1, CYP2B6, ASGR1, CXCR4, BSEP, MRP2, Cx32, and any combination thereof. In some embodiments, the hepatocyte expresses one or more markers selected from the group consisting of TGFβ1, HLA-G, stem 121, C-kit, betatrophin, ADH1, APOF, CPS1, CYP2B6, ASGR1, CXCR4, Cx32, and any combination thereof. In some embodiments, the hepatocyte expresses one or more markers selected from the group consisting of CPS1, CYP2B6, and a combination thereof. In some embodiments, the hepatocyte expresses one or more markers selected from the group consisting of stem 121, C-kit, CK19, CK18, and any combination thereof. In some embodiments, the hepatocyte expresses one or more markers selected from the group consisting of ALB, AFP, betatrophin, ADH1, APOF, CPS1, GATA4, CYP1A1, CYP2B6, and any combination thereof. In some embodiments, the hepatocyte expresses one or more markers selected from the group consisting of ASGR1, CXCR4, BSEP, MRP2, Cx32, and any combination thereof.

Also disclosed herein is a method of screening a therapeutic compound for use in treatment or prevention of a condition, comprising: contacting an isolated hepatocyte disclosed herein with the therapeutic compound; and detecting an expression level of a biomarker in the isolated hepatocyte. In some embodiments, the expression level of a biomarker in the isolated hepatocyte increases as compared to an equivalent isolated hepatocyte not contacted with the therapeutic compound. In some embodiments, the expression level of a biomarker in the isolated hepatocyte decreases as compared to an equivalent isolated hepatocyte not contacted with the therapeutic compound. In some embodiments, the expression level is a gene expression level. In some embodiments, the biomarker comprises CYP1A2, CYP2B6, CYP2C8, CYP2C9, CYP2D6, CYP2E1, CYP3A4, or CYP7A1. In some embodiments, the therapeutic compound is a small molecule drug, a peptide, or a protein. In some embodiments, the therapeutic compound is a synthetic chemical drug. In some embodiments, the condition is a liver failure. In some embodiments, the condition is a liver-associated disease or disorder. In some embodiments, the liver-associated disease or disorder comprises alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (optionally acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis, Wilson disease, or any combination thereof.

In one aspect, disclosed herein is a composition (e.g., pharmaceutical composition) comprising any hepatocyte disclosed herein.

In another aspect, disclosed herein is a method of treating a condition in a subject, comprising administering to a subject a pharmaceutical composition that comprises an isolated hepatocyte herein, in an amount effective for the hepatocytes to engraft to the subject (e.g., to the subject's liver). In some embodiments, the hepatocytes are administered in a pharmaceutically acceptable carrier. In some embodiments, the pharmaceutically acceptable carrier comprises a phosphate buffer saline. In some embodiments, the hepatocytes are administered in a suspension containing about $1\times10^6$ to about $100\times10^6$ cells per ml, about $1\times10^6$ to about $250\times10^6$ cells per ml, about $1\times10^6$ to about $500\times10^6$ cells per ml, or about $10\times10^6$ to about $40\times10^6$ cells per ml. In some embodiments, the hepatocytes are administered in a volume of about: 1-5 ml, 1-10 ml, 1-50 ml, 1-100 ml, or 10-150 ml. In some embodiments, the subject is a human. In some embodiments, the administering comprises an injection, e.g., intravenous injection. In some embodiments, the injection is administered at a hepatic vein. In some embodiments, the injection is administered at a hepatic artery. In some embodiments, the condition is a liver-associated disease or disorder. In some embodiments, the condition is a liver failure. In some embodiments, the liver-associated disease or disorder comprises alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (optionally, acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis, Wilson disease, or any combination thereof.

In another aspect, disclosed herein is a use of a composition comprising a hepatocyte herein for the production of therapeutic proteins. In some embodiments, the therapeutic proteins comprise major plasma proteins such as human serum albumin, soluble plasma fibronectin, α-fetoprotein, C-reactive protein, and several globulins; proteins involved in hemostasis and fibrinolysis such as coagulation factors involved in the coagulation cascade, α2-macroglobulin, α1-antitrypsin, antithrombin III, protein S, protein C, plasminogen, α2-antiplasmin, and complement component 3; carrier proteins such as albumin, ceruloplasmin, transcortin, haptoglobin, hemopexin, IGF binding protein, major urinary proteins, retinol binding protein, sex hormone-binding globulin, transthyretin, transferrin, and Vitamin D-binding protein; hormones such as insulin-like growth factor 1, thrombopoietin, hepcidin, and betatrophin; prohormones such as angiotensinogen; or apolipoproteins.

Also disclosed herein is a use of a composition comprising a hepatocyte herein for liver regeneration. In some embodiments, the liver regeneration is an ex vivo liver regeneration. In some embodiments, the ex vivo liver regeneration is a bioprinting method. In some embodiments, the bioprinting method is a 3 dimensional bioprinting method.

In one aspect, disclosed herein is a use of a composition comprising a hepatocyte herein for bioprinting. In some embodiments, the bioprinting is a 3 dimensional bioprinting.

Also disclosed herein is a use of the hepatocyte herein for tissue scaffold generation. In some embodiments, the tissue scaffold is a 3 dimensional tissue scaffold.

In one aspect, disclosed herein is a use of a composition comprising a hepatocyte herein for gene therapy. In some embodiments, the gene therapy is an ex vivo gene therapy.

In another aspect, disclosed herein is an artificial tissue generated from hepatocytes herein. In some embodiments, the tissue is three-dimensional. In some embodiments, the issue is vascularized.

Also disclosed herein is an artificial organ generated from hepatocytes herein.

In some embodiments, a hepatocyte, tissue, or organ disclosed herein produces AFP, ALB, alpha-1-antitrypsin, glucose, or glycogen. In some embodiments, the hepatocyte, tissue, or organ metabolizes a lipid, cholesterol, or carbohydrate. In some embodiments, the hepatocyte, tissue, or organ metabolizes a pharmaceutical drug or toxic substance. In some embodiments, the hepatocyte, tissue, or organ uptakes ammonia or bile acid.

In some embodiments, a hepatocyte herein has comparable phenotypic (e.g., immunophenotypic) properties as a primary hepatocyte. In some embodiments, a hepatocyte herein has comparable morphologic properties as a primary hepatocyte. In some embodiments, a hepatocyte herein has comparable functional properties as a primary hepatocyte.

In some embodiments, a hepatocyte, tissue, or organ disclosed herein has one or more functions of: synthesis of fatty acids, triglycerides, cholesterol, bile salts, or phospholipids; detoxification, modification, and excretion of exogenous or endogenous compounds (e.g., drug, insecticide, steroid, ammonia, heavy metal, or toxin); carbohydrate metabolism; synthesis of proteins (e.g., serum albumin, fibrinogen, lipoprotein, apoprotein, ceruloplasmin, transferrin, complement, or glycoprotein); protein storage; or formation or secretion of bile. In some instances, a hepatocyte can be a hepatic progenitor cell (e.g., hepatocyte-like cell) or a hepatocyte derived from a stem cell; a hepatic stem cell; or a primary hepatocyte (e.g., are or comparable to freshly isolated or uncultured, cryopreserved hepatocytes obtained from a liver).

In some embodiments, a trophoblast stem cell disclosed herein is derived from an ectopic pregnancy mass (e.g., tubal). In some embodiments, the method of isolating a trophoblast stem cell herein comprises the steps of: obtaining trophoblastic villi from an ectopic pregnancy mass (e.g., tubal); collecting cells from the trophoblastic villi; and culturing the collected cells in a culture medium to obtain the isolated trophoblast stem cell. In some embodiments, the method further comprises cutting the trophoblastic villi into pieces. In some embodiments, the method further comprises treating the trophoblastic villi with an enzyme. In some embodiments, the human trophoblast stem cell is genetically modified to introduce a mutation into the cell. In some embodiments, the pregnant mass is obtained in an unruptured manner. In some embodiments, the pregnant mass is at a gestational age of no older than 7 or 8 weeks. In some embodiments, the culture medium is free of a feeder layer. In some embodiments, the method further comprises the steps of: forming embryonic bodies (EBs) in the culture medium; treating the EBs with an enzyme; and collecting cells from the enzyme-treated EBs to obtain the isolated human trophoblast stem cell.

BRIEF DESCRIPTION OF THE DRAWINGS

FIGS. 1A to 1F illustrate immunoreactive markers of DE lineages. FIGS. 1A-1D show immunocytochemistry to detect FOXA2 and SOX17 (FIG. 1A), GSC (FIG. 1B), and MIXL1 (FIG. 1C) at 4 hr of bFGF induction compared to the control in hTS cells. FIG. 1D shows western blots in time course of DE-related transcription factors including GSC, Brachyury, MIXL1, SOX17, and FOXA2 at initial 8 hr of bFGF induction. Error bars indicate standard deviation (SD) of mean. N=3, *: $p<0.05$ as statistic significant. FIG. 1E shows colocalization of hepatocyte-associated markers showing AFP and albumin (upper panel) and ABCC2 and BSEP (lower panel) at day 4 after induction. FIG. 1F shows a two-step regimen for hepatocyte-like cell differentiation showing various hepatocyte-specific markers by Western blotting assay in hTS cells. α-tubulin as loading control.

FIGS. 2A to 2M illustrate regulatory Molecular Mechanisms for DE Specification. FIG. 2A indicates miR-124a analysis (ChIP-qPCR) which identifies that CREB1 targets at three sites of promoter of miR-124a mRNA (SEQ ID NOS 107-109, respectively, in order of appearance). A schematic drawing of the consensus miR-124a binding sites (upper panel). C: as no-antibody control. Error bars indicate SD of 3 replicates. FIG. 2B illustrates that knockdown of CREB1 reduces the bFGF-induced miR-124a expression by immunoblotting assay. Error bars indicate SD of 3 replicates. *: $p<0.05$. FIG. 2C shows bFGF induced expression of phosphor(p)-CREB1 and miRNA-124a during 8 hr induction by qPCR assay. Error bars indicate SD of 4 replicates. FIG. 2D shows ChIP-qPCR of Smad4 which identifies that miR-124a represses Smad4 expression via targeting two sites of the promoter by luciferase reporter assay (SEQ ID NOS 110-112, respectively, in order of appearance). The schematic drawing of the consensus miR-124a binding sites (upper panel). Empty vector as control; pSmad4 indicating Smad4 plasmid, Error bars indicate SD of 3 replicates. *: $p<0.05$. FIG. 2E shows the effects of bFGF, miR-124a, and anti-miR-124a antibody on the expression of DE-related transcription factors by Western blots. β-actin was used as loading control. FIG. 2F shows the knockdown of Smad4 using shRNAs represses expression of Smad4 and MIXL1 by Western blots. β-actin was used as loading control. FIG. 2G and FIG. 2H show ChIP-qPCR assays which identify the inhibitory GSK3β (SEQ ID NO: 113) by miR-124a (SEQ ID NO: 114) by luciferase report assays at 4 hr induction (FIG. 2G); while qPCR assay showed an inhibitory FOXA2 by β-catenin (FIG. 2H). A schematic drawing of the consensus miR-124a binding sites (G, upper panel). Empty vector as control; pGSK3β indicating GSK3β plasmid, Error bars indicate SD of 3 replicates. *: $p<0.05$. FIG. 2I shows ChIP-qPCR assay which identifies the inhibitory CDX2 (SEQ ID NO: 115) by miR-124a (SEQ ID NO: 116) by luciferase reporter assay. A schematic drawing of the consensus miR-124a binding sites (upper panel). Empty vector as control; pCDX2 indicating CDX2 plasmid, Error bars indicate SD of 3 replicates. *: $p<0.05$. FIG. 2J shows imaging which revealed a reciprocal inhibitory mechanism between CDX2 and OCT4 at 4 hr bFGF induction in hTS cells. FIG. 2K shows western blots in timeline of pluripotent transcription factors CDX2 and OCT4 (upper panel) as well as NANOG, and SOX2 (lower panel) during DE differentiation. Error bars indicate SD of 3 replicates. *: $p<0.05$. FIG. 2L shows ChIP-qPCR assay which identifies binding of OCT4 at the two sites of the promoter of SOX17 gene. Error bars indicate SD of 3 replicates. FIG. 2M shows a schematic illustration of bFGF induction in the differentiation of hTS cells towards DE lineages.

FIG. 3A shows morphological changes of cells the differentiation, forming a plate-like tissue structure at day 6-8 day of induction. FIG. 3B shows electron micrographs revealed the infrastructure: large cytoplasm/nucleus ratio, plenty of mitochondria (m), Golgi apparatus (Gi), well-organized endoplasmic reticulum (RER), the junctional complexes (white arrow) to form bile canaliculus lumen (Cn), and the junctional complexes (double arrows) seal off the space from the remaining extracellular space, lamelleted inculsion at cytoplasm, and desmosome junction (arrow). FIG. 3C shows immunohistochemistry of the hepatic plate-like tissue showing immunoreactive cell membrane markers of hepatocytes: CXCR4, CX32, BSEP, and MRP2 (ABCC2) and cytoplasmic markers: Betatrophin, HNF4α, Albumin, AFP, CYP2B6, APOF, CPS1, and ADH1.

FIG. 4A shows differentiated hepatocyte-like cells (4 days) exhibiting protein secreting capacity in the medium such as albumin and urea measured by an automatic analyzer (Hitachi 7080; Tokyo, Japan). Error bars indicate SD of 3 replicates. **: $p<0.01$. FIG. 4B and FIG. 4C show a LDL uptake assay which illustrates immunoreactive LDL receptor (LDLR,middle panel) and LDL staining (left panel) (FIG. 4B) and Oil-O-Red test showing fat droplets (FIG. 4C) in the differentiated hepatocyte-like cells. FIG. 4D shows glycogen storage test identifies the presence of glycogen in the cells by periodic acid-Schiff (PAS) staining evidenced by diastase to digest glycogen (upper pane) and confirmed by fluorescent PAS staining (lower panel) in the hepatocyte-like cells (left 3 panel) and the hepatic plate-like tissue (right panel).

FIGS. 5A to 5I illustrate a variety of CYP 450 enzyme activities in the differentiated hepatocyte-like cells. Phase I-II CYP450 enzyme activity is estimated by drug-drug interaction and detoxification tests (inducer, inhibitor), including CYP1A2 (FIG. 5A), CYP2B6 (FIG. 5B), CYP2C8 (FIG. 5C), CYP2C9 (FIG. 5D), CYP2C19 (FIG. 5E), CYP2D6 (FIG. 5F), CYP2E1 (FIG. 5G), CYP3A4 (FIG. 5H), and CYP 7A1 (FIG. 5I). Inducer and inhibitor used as (rifampin, Rif and ciprofloxacin, Cip), (phenobarbital, phen and Cip), (Rif and gemfibrozil, Gem), (Rif and Gem), (Rif and ticlopidine,Tico), (Rif as inducer only), (Rif as inducer only), (Rif, and itraconazole, Itra), and (THA, 2,4,6-trihydroxyacetophenone and CDCA, chenodeoxycholic acid), respectively. hTS indicating hTS cells, hTHL indicating human trophoblast-derived hepatocyte-like cells; and Huh7 indicating human hepatoma Huh7 cells.

FIG. 6 illustrates a table showing biomarker expression (e.g. mRNAs) during the different stages of a hepatocyte differentiation.

FIG. 8A illustrates that FGFR inhibitor (PD166866) blocks bFGF-induced PI3K with β-actin as a loading control. FIG. 8B illustrates that PI3K siRNA inhibits the expression of PI3K and p-AKT. Cells transfected with non-specific shRNA were used as control. β-actin was used as a loading control. FIG. 8C shows that siRNAs against AKT subunits inhibits the bFGF-induced expression of p-AKT and p-CREB1. Cells transfected with non-specific shRNA were used as control. β-actin was used as a loading control. FIG. 8D shows that AKT interacts directly to CREB1 by IP assay.

FIG. 11A discloses SEQ ID NOS 110-112, respectively, in order of appearance, and FIG. 11C discloses SEQ ID NOS 115-116, respectively, in order of appearance. (11D) β-catenin binds to the region (−2.1 kb) of promoter in Foxa2 gene over time by ChIP-qPCR assay. Error bars indicate SD of 3 replicates. (11E) Foxa2 targets the promoter of Betatrophin by ChIP assay, showing production of betatrophin at 12 hr induction (arrow). Input: whole cells as positive control. IgG as negative control. FIG. 11E discloses SEQ ID NOS 113-114, respectively, in order of appearance. (11F) Expression of various transcription factors in response to miR-124a and anti-miR-124a antibody at 4 hr of bFGF induction by Western blot analysis. β-actin: loading control. (11G) A reciprocal inhibitory function between Cdx2 (green) and Oct4 (red) at 4 hr of bFGF induction immunocytochemically. (11H) Oct4 binds to two regions (−1 and −1.8 kb) of promoter in Sox17 gene at 2 hr of bFGF induction by ChIP-qPCR assay. Error bars indicate SD of 3 replicates. (11I) Schematic illustration of molecular regulation in DE differentiation of hTS cells. (11J) Smad4 shRNAs inhibit expression of Mixl1 by immunoblotting assay. (11K) Expression of Oct4, Cdx2, Nanog, and Sox2 in time course during DE formation. Data indicating mean±SD, n=3, *: p<0.05.

FIGS. 13A, 13B, and 13C illustrate secretomics in hepatocyte-like cell culture medium. (13A) Proteomic analysis of culture medium before cell culture (as control, left panel) and after 5-day cell culture (right panel) revealing a new formation of protein (designated as No. 413, circle). (13B) No immunoreactive TGFβ1, collagen IV (COL4), and fibronectin (FN) expressed in hTS cells before induction (upper panels) and after induction for 5-days, coexpression of them distribute as columnar ECMs between hepatocyte-like cells in 3-D structure (lower panels). (13C) Mascot MS/MS ions search system analysis 20151001_LiP_413, transforming growth factor-beta-induced protein ig-h3 precursor [*Homo sapiens*] (SEQ ID NO: 117).

FIGS. 15A to 15F illustrate responsiveness of intravenous transplantation by hepatocyte-like cells (15A) Serum levels of AST and ALT are higher in cell therapy group (CCl4+ cells; n=8) than control group ($CCl_4$ only; n=8) over time. Data represent mean±s.e.m., Student test: *: p<0.01. (15B) Expression of immunoreactive stem-121 in hTS cells (upper) and in hepatocyte-like cells resided in liver tissues (lower). (15C) Stem-121-positive hepatocytes in the $CCl_4$-damaged liver tissues expressing characteristics of cellular degeneration (insert). PT indicating portal triad. (15D) Coexpression of immunoreactive Stem-121 and HLA-G in the implanted hepatocyte-like cells. Bar scale: 20 µm. (15E, 15F) Distribution of immunoreactive $CD4^+Foxp3^+$ Treg cells among the CCl4-damaged hepatocytes immunocytochemistry (15E) and immunoreactive $CD4^+$ cells (red) around a central vein immunohistochemistry (15F).

DETAILED DESCRIPTION

Figure 1E:
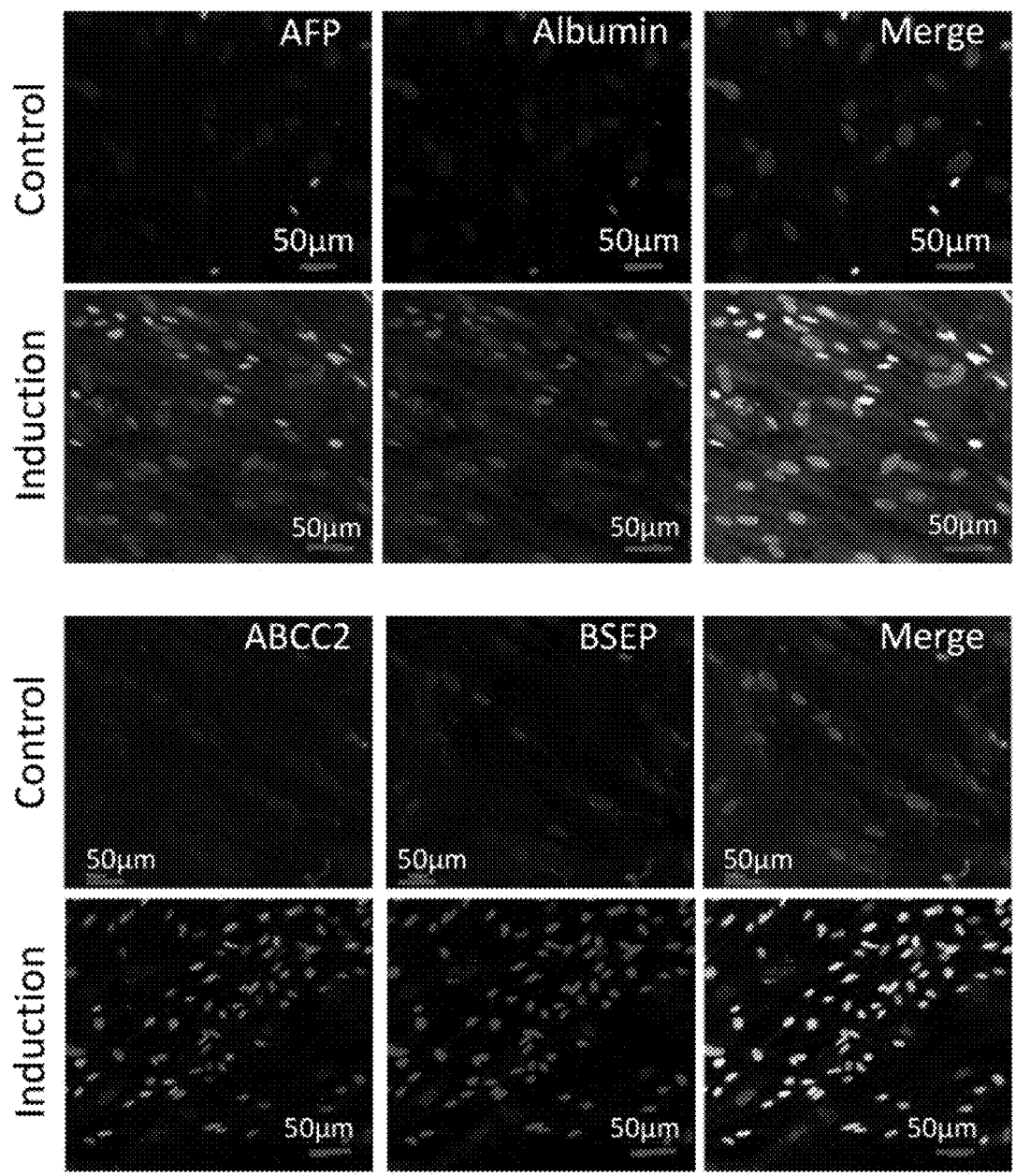

Disclosed herein are methods, compositions, cells, manufacture process, and kits for generating an induced hepatocyte from a trophoblast stem cell. In some embodiments, described herein is a method of inducing a trophoblast stem (TS) cell to differentiate into an induced hepatocyte in vitro, that comprises (a) contacting the trophoblast stem cell in a conditioned medium comprising a fibroblast growth factor (FGF), a steroid, and a cytokine; and (b) incubating the cell for sufficient time to induce differentiation of the trophoblast stem cell into an induced hepatocyte.

Also described herein is an isolated induced hepatocyte derived from a trophoblast stem cell, wherein the isolated induced hepatocyte comprises an elevated level of expression of one or more biomarkers comprising C—X—C chemokine receptor type 4 (CXCR4), Forkhead box protein A2 (FOXA2), SRY-box 17 (SOX17), hexosaminidase A (alpha polypeptide) (HHEX), bile salt export pump (BSEP), transthyretin (TTR), albumin (ALB), tyrosine aminotransferase (TAT), cytochrome P450 7A1 (CYP7A1), glucose-6-phosphatase (G6PC), serpin peptidase inhibitor clade A (alpha-1 antiproteinase, antitrypsin) member 1 (SERPINA1), ATP-binding cassette sub-family C (ABCC2), CCAAT-enhancer-binding protein beta (C/EBPβ), hepatocyte nuclear factor 1-alpha (HNF1α), hepatocyte nuclear factor 4-alpha (HNF4α), alpha-1-fetoprotein (AFP), keratin 8 (KRT8), phosphoenolpyruvate carboxykinase 2 mitochondrial (PCK2), cytochrome P450 2B6 (CYP2B6), glycogen synthase 2 (GYS2), hepatocyte nuclear factor 6 (HNF6), carbamoyl-phosphate synthase 1 mitochondrial (CPS1), alcohol dehydrogenase 1C (class I) gamma polypeptide (ADH1C), connexin 32 (CX32), cytochrome P450 3A4 (CYP3A4), prospero homeobox 1 (PROX1), tryptophan 2,3-dioxygenase (TDO2), apolipoprotein F (APOF), keratin 18 (KRT18), keratin 19 (KRT19), or chromosome 19 open reading frame 80 (angiopoietin-like protein 8, hepatocellular carcinoma-associated gene TD26, lipasin) (Betatrophin).

Further described herein is a method of screening a compound for use in treatment or prevention of a disease or disorder, which comprises (a) contacting an isolated induced hepatocyte herein with the compound; and (b) detecting the expression level of a biomarker in the isolated induced hepatocyte.

Described herein, in addition, are compositions (e.g. pharmaceutical compositions) that comprises an isolated induced hepatocyte disclosed herein, manufacture process for generating a composition (e.g. pharmaceutical composition) that comprises an isolated induced hepatocyte disclosed herein, and methods of treating a disease or disorder (e.g. a liver-associated disease or disorder) with an isolated induced hepatocyte disclosed herein or a composition that comprises an isolated induced hepatocyte disclosed herein.

In some aspects, disclosed herein is a highly efficient generation of hepatocyte-like cells from ectopic pregnancy-derived human trophoblast (hTS) stem cells, exhibiting molecular, genetic, and biological characteristics resemblance to primary hepatocytes in liver development. In some embodiments, disclosed herein is a mechanism of microRNA-124a controlling definitive endoderm formation during differentiation. In some embodiments, hepatocyte-like cells can construct a 3-D liver plate-like structure in cell culture, expressing HLA-G and secreting TGFβ1 to maintain $CD4^+Foxp3^+$ Treg cells in liver tissues for immune tolerance after intravenous implantation. In some embodiments, the cells herein assist and promote liver regeneration in rat model of $CCl_4$-induced acute liver failure. In some embodiments, hTS cell-derived hepatocyte-like cells herein can be applied in the urgent management of liver failure or in regenerative medicine. In some embodiments, disclosed herein is efficient two-step differentiation of hTS cells to functional hepatocytes within a week (e.g., 4-6 days). In some embodiments, miR-124a controls DE formation during hepatogenesis. In some embodiments, disclosed herein are hepatocyte-like cells that construct 3-D tissue structure with biological functions mimicking primary hepatocytes.

In some aspects, disclosed herein is intravenous infusion of hepatocyte-like cells can homed to the $CCl_4$-damaged liver tissues to promote liver regeneration in rat animal model. In some embodiments, disclosed herein are both hTS cells and its derivative hepatocyte-like cells express HLA-G to obtain immune tolerance after transplantation. In some embodiments, disclosed herein are homing hepatocyte-like cells secret TGFβ1 to assist the construction of new ECMs after injury via the formation of fibronectin and collagen. In some embodiments, Hepatocyte-like cell-secreted TGFβ1 resulting in the bone marrow's fibrocytes migration to liver, activates hepatic stellate cells for liver regeneration and maintains $CD4^+Foxp3^+$ Treg cells in liver tissues for immune tolerance. In some embodiments, basic fibroblast growth factor (bFGF) alone induces activation of microRNA (miRNA)-124a to consequently control the DE specification in early differentiation. In some embodiments, with certain conditions, DE gives rise to hepatic endoderm followed by hepatoblasts and eventually differentiates to fetal/adult hepatocyte-like cells, bearing similar genetic, molecular and biological characteristics to primary human hepatocytes.

In some aspects, hepatocyte-like cells enable to build a three-dimensional (3-D) tissue structure in vitro and intravenous infusion of such cells results in hepatic homing and protects the liver from damage. In some embodiments, a tissue-culture media composition used herein comprises about serum and culture medium. In some embodiments, the culture medium is Synthetic Oviductal Fluid (SOF), Modified Eagle's Medium (MEM), Dulbecco's Modified Eagle's Medium (DMEM), RPMI 1640, F-12, IMDM, Alpha Medium, or McCoy's Medium. In some embodiments, the serum is allogeneic serum, autologous serum, or xenogeneic serum. In some embodiments, hTS cells are cultured with a combination of fibroblast growth factor (e.g., bFGF), steroid (e.g., dexamethasone), cytokine (e.g., oncoststin M), bone morphogenetic protein (e.g., BMP4), and hepatic growth factor (HGF) after DE formation (e.g., 8 hr). In some embodiments, the resulting cells form dispersed fibroblast-like cells. In some embodiments, the resulting cells gradually aggregate to form a crescent cell mass. In some embodiments, two distinct peripheral and central compartments construct a 3-dimensional (3D) tissue structure. In some embodiments, in the peripheral part, numerous clustered small cells distribute irregularly among the extracellular matrix (ECM) beyond the basement membrane. In some embodiments, cells have condensed nuclei, frequently eccentric located, and abundant granular and vacuoles in the eosinophilic cytoplasm similar to the embryonic stem/progenitor cells. In some embodiments, in the central part, many independent columnar ECMs, by cell linings at both sides, distribute from the basal towards the central areas. These cells contain abundant eosinophilic cytoplasm and disperse chromatin in the single round nucleus with one or two prominent nucleoli mimicking the phenotypic hepatocytes. In some embodiments, several binucleate cells can form, similar to hepatic plates in human liver.

In some embodiments, the hepatocyte or hepatocyte-like cells herein exhibit specific marker(s) of: i) human cytoplasmic marker stem 121™ for human cells, mast/stem cell growth factor receptor C-kit for liver intrinsic stem cells, CK19 for cholangiocytes, and CK18 for hepatocytes; and ii) albumin (ALB), α-fetoprotein (AFP), Betatrophin, ADH1, APOF, CPS1, GATA4, CYP1A1, and CYP2B6 in the cytoplasm for hepatocytes immunohistochemically. In some embodiments, a subset of surface markers including ASGR1, CXCR4, BSEP, MRP2, and Cx32 construct a polygonal cell shape similar to the primary human hepatocyte, e.g., a similar ultrastructure to primary hepatocyte, including a large cytoplasm to nucleus ratio, plenty of mitochondoria, well-organized endoplasmic reticulum, tight junction, numerous lipid vacuoles, glycogen storage, enlarged lumen of the bile canaliculus with junctional complexes, and multiplex ECMs.

Among 9 newly upregulated, secreted proteins in the cell-cultured medium, protein (no. 413) significantly predicts, by 46% of peptide sequences matched, to be the transforming growth factor-β(TGF-β)-induced protein ig-h3 precursor (TGFβ1) by Mascot MS/MS ions search system (ESI-QUAD-TOF, Bruker Impact HD, Matrix Science, USA). TGFβ1 is a major fibrogenic, multifunctional cytokine, acting as both autocrine and paracrine manner to enhance fibronectin and collagen formation in hepatic stellate cells (HSCs). In some embodiments, TGFβ1 is expressed in ECM. In some embodiments, TGFβ1, fibronectin, and collagen IV are co-expressed in the ECMs. In some embodiments, TGFβ1, fibronectin, and collagen IV constitute, at least partly, the scaffold of ECMs in the 3-D tissue structure of hepatocyte-like cells that may support proliferation and differentiation of hepatocytes in the hepatic plates.

In some aspects, hepatocyte-like cells can be efficiently generated from pluripotent hTS cells through a series of cellular processes, including the primitive streak, DE formation, hepatic endoderm, hepatoblasts, and ultimately hepatocyte-like cells. The onset of primitive streak differentiation can be verified at the initial induction (e.g., 30 min) by upregulation of GSC, Brachyury, and Mixl1. The immediately decreased Mixl1 can perform an impact on the endoderm potential of the mesendoderm progenitors. Moreover, Sox7-expressing cells can be originally present at the extra-embryonic endoderm but not at the DE lineages. As development progresses, the apparent upregulation of Sox17 and Foxa2 as well as downregulation of Mixl1 can define the formation of DE, in which Oct4 play a main role in the maintenance of pluripotency distinct from Nanog in the hES cell- or iPS cell-derived DE.

In some aspects, a transient elevation of miR-124a can negatively modulate multiple gene expressions post-transcriptionally via binding to the targeted mRNAs, typically in the 3'UTR to control DE specification. There can be presence of functionally silenced miR-124a in the early hepatic differentiation. Wherein, the downregulated miR-124a after peaking at 4 hr induction bears a resemblance to the scenario when cell migration begins in gastrulation to form three embryonic germ layers in hES cells.

In some aspects, the initiation of hepatic lineage differentiation following DE specification can be achieved by a combination of bFGF, dexamethasone, oncoststin M, BMP4, and HGF The stage-specific gene profiles can indicate a committed step in the hepatic specified endoderm (Table 3, second column). For example, expression of α-fetoprotein (AFP) expression suggests the initial differentiation of hepatic endoderm and both C/EBPβ and Hnf4α control initial liver-specific activity in the urea cycle. Expression of α-1-antitrypsin (SERPINA1) can protect cells from damage and promotes metabolic activity of enzymes such as CYP7A1, CYP3A4, and CYP2B6. These facts represent that hepatic endoderm is capable of metabolism of cholesterol, drug, and toxin at the early differentiation. Since Sox17 directly induces zinc finger protein 202 (ZFP202) to suppress the master hepatic gene regulator Hnf4α, thereby, withdrawal of Sox17 facilitated the initiation of Hnf4α expression after DE stage, which, in turn, to characterize the specification of hepatic progenitor cells, controlling hepatocyte cell fate. A sustained Foxa2 can be responsible for the consequent expressions of albumin, AFP, mitochondrial protein TAT, and betatrophin; while betatrophin expression reflects the early capacity in the promotion of 0 cell proliferation and lipid metabolism at the early hepatic differentiation.

In some aspects, as differentiation proceeds, numerous hepatic markers begin to emerge, including PROX1, G6PC, Hnf1α, ABCC2, and TDO2 as well as cytokeratins such as CK8, CK18, and CK19. PROX1, for example, is required for hepatoblastic migration and its ablation in hepatoblasts causes defective hepatocyte specification and promotes biliary cell commitment. CK8 is an intermediate filament protein to polymerize with CK18 forming a component of the epithelial cytoskeleton and acts as a plasminogen receptor. Hepatoblasts in between 2 and 4 days differentiation can express cholangiocyte marker CK19 and hepatic progenitor markers CK8 and CK18 (Table 3), mimicking the bipotential capacity in differentiation to biliary epithelial cells and hepatocytes, respectively. Expression of the hepatocyte-enriched transcription factor cluster, including Foxa2, Hnf1α, Hnf4α, and Hnf6, can represent a milestone of the hepatoblastic differentiation, directing the parenchymal hepatoblasts into hepatocytes and promoting hepatocyte maturation. For metabolism, expression of hepatobiliary excretion transporter MRP2 (ABCC2) and hepatic gap junction protein Cx32 can facilitate the transport of various molecules across cellular membranes. An upregulation of HHEX, however, can implicate the presence of hematopoietic capacity in the hepatoblasts.

In some aspects, implanted hTS cell-derived hepatocyte-like cells can survive to reach a subject's liver after intravenous transplantation. In some embodiments, the cells herein have a homing instinct. In some embodiments, these cells can express HLA-G, a nonclassical HLA class I molecule, which, membrane-bound or soluble, strongly acts on different immune cell types (NK, T, B, monocytes/dendritic cells) to inhibit both innate and adaptive immunity through the interaction with the inhibitory receptors that are expressed at the surface of immune cells. Additionally, these hepatocyte-like cells can enable to recruit $CD4^+Foxp3^+$ regulatory T (Treg) cell population postimplantation, contributing to the generation of an immunosuppressive environment by the inhibition of proinflammatory T cells and the induction of T cells with a regulatory. In some embodiments, hTS cell-derived hepatocyte-like cells possess immune privilege.

In some aspects, provided herein are compositions and methods for transplanting hepatocyte or hepatocyte-like cells to subjects. In some embodiments, the subject is injected by hTS cell-derived hepatocytes (e.g., intravenously, intramuscularly, transdermally, endoscopic retrograde injection, or intraperitoneally). In some embodiments, the subject is not treated with an immunosuppressive agent prior to the transplanting. In some embodiments, the method further comprises treating the patient with an immunosuppressive agent, e.g., FK-506, cyclosporin, or GAD65 antibodies.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range, e.g., ±15% of a referenced numeral value. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

Overview

Liver possesses a dynamic range of functions including detoxification, protein synthesis, protein storage, and production of biochemical components necessary for digestion. It comprises two major types of cells, parenchymal and non-parenchymal cells. Parenchymal cells make up about 80% of the liver volume and are also referred to as hepatocytes. Non-parenchymal cells contribute to about 6.5% of liver volume, but constitute to about 40% of the total number of liver cells. In some instances, non-parenchymal cells comprise sinusoidal hepatic endothelial cells, Kupffer cells, and hepatic stellate cells.

Hepatocytes

Hepatocytes, or parenchymal cells, are responsible for the function of the liver. In some instances, hepatocytes are involved in protein synthesis, protein storage, synthesis of cholesterol, bile salts and phospholipids, formation and secretion of bile, carbohydrate metabolism, and detoxification, modification, and excretion of exogenous and endogenous substances.

In some instances, proteins synthesized from the hepatocytes include major plasma proteins such as human serum albumin, soluble plasma fibronectin, α-fetoprotein, C-reactive protein, and several globulins; proteins involved in hemostasis and fibrinolysis such as coagulation factors involved in the coagulation cascade, a2-macroglobulin, α1-antitrypsin, antithrombin III, protein S, protein C, plasminogen, a2-antiplasmin, and complement component 3; carrier proteins such as albumin, ceruloplasmin, transcortin, haptoglobin, hemopexin, IGF binding rotein, major urinary proteins, retinol binding protein, sex hormone-binding globulin, transthyretin, transferrin, and Vitamin D-binding protein; hormones such as insulin-like growth factor 1, thrombopoietin, hepcidin, and betatrophin; prohormones such as angiotensinogen; and apolipoproteins.

In addition to formation, breakdown, and interconversion of carbohydrates, in some instances, carbohydrate metabolism also involves gluconeogenesis, glycogenolysis, and glycogenesis. Gluconeogenesis is the synthesis of glucose from certain amino acids, lactate or glycerol. Glycogenolysis is the breakdown of glycogen into glucose. Glycogenesis is the formation of glycogen from glucose.

In some instances, lipid metabolism within hepatocytes includes cholesterol synthesis and lipogenesis, the production of triglycerides or fats.

In some cases, after injuries such as tissue damage or tissue loss, hepatocytes can re-enter the cell cycle leading to proliferation and subsequent regeneration of the injured portion, such as the damaged or lost tissue. In some instances after the removal of liver tissue, the remaining hepatocytes undergo at least one, two, three, or more rounds of DNA synthesis leading to regeneration of the lost tissue mass.

In some embodiments, hepatocytes are utilized for pharmaceutical research. In some embodiments, these researches include drug metabolism, enzyme induction, hepatotoxicity, hepatocyte regeneration, and transplantation.

The term hepatocyte refers to a hepatic cell or hepatic progenitor cell that has one or more functions of: synthesis of fatty acids, triglycerides, cholesterol, bile salts, or phospholipids; detoxification, modification, and excretion of exogenous or endogenous compounds (e.g., drug, insecticide, steroid, ammonia, heavy metal, or toxin); carbohydrate metabolism; synthesis of proteins (e.g., serum albumin, fibrinogen, lipoprotein, apoprotein, ceruloplasmin, transferrin, complement, or glycoprotein); protein storage; or formation or secretion of bile. In some instances, a hepatocyte can be a hepatic progenitor cell (e.g., hepatocyte-like cell) or a hepatocyte derived from a stem cell; a hepatic stem cell; or a primary hepatocyte (e.g., are or comparable to freshly isolated or uncultured, cryopreserved hepatocytes obtained from a liver).

In some embodiments, a hepatic stem cell is a small epithelial cell adhesion molecule-expressing (EpCAM-expressing) cell that constitutes about 0.5%-2.5% of the liver parenchyma. In some embodiments, the stems cell includes, but is not limited to, embryonic stem cell, adult stem cell, inducible pluripotent stem (iPS) cell, parthenogenetic stem cells, or trophoblast stem cell. In some embodiments, the stem cell is a human stem cell. In some embodiments, the stem cell is a trophoblast stem cell. In some embodiments, the trophoblast stem cell is a human trophoblast stem cell. In some embodiments, the human trophoblast stem cell is an ectopic pregnancy-derived human trophoblast stem cell. In some instances, a hepatocyte derived from a stem cell is also referred to as an induced hepatocyte. In some embodiments, an induced hepatocyte is derived from a human trophoblast stem cell. In some embodiments, an induced hepatocyte is derived from an ectopic pregnancy-derived human trophoblast stem cell. In some embodiments, an induced hepatocyte comprises a trophoblast stem cell undergoing the process of differentiation into a hepatocyte, and a differentiated trophoblast stem cell. In some embodiments, a trophoblast stem cell undergoing the process of differentiation into a hepatocyte is also referred to as an immature induced hepatocyte. In some embodiments, a differentiated trophoblast stem cell is also referred to as a mature induced hepatocyte.

In some embodiments, an induced hepatocyte functions similarly to a primary hepatocyte. In some embodiments, an induced hepatocyte comprises cellular functions exhibited by a primary hepatocyte. In some embodiments, an induced hepatocyte participates in cellular functions such as for example protein synthesis, protein storage, synthesis of cholesterol, bile salts and phospholipids, formation and secretion of bile, carbohydrate metabolism, and detoxification, modification, and excretion of exogenous and endogenous substances, which are observed in a primary hepatocyte. In some embodiments, hepatocytes herein express a subset of surface markers including ASGR1, CXCR4, BSEP, MRP2, and Cx32 and construct a polygonal cell shape similar to the primary human hepatocyte, e.g., a similar ultrastructure to primary hepatocyte, including a large cytoplasm to nucleus ratio, plenty of mitochondoria, well-organized endoplasmic reticulum, tight junction, numerous lipid vacuoles, glycogen storage, enlarged lumen of the bile canaliculus with junctional complexes, and multiplex ECMs.

In some instances, proteins synthesized from an induced hepatocyte include major plasma proteins such as human serum albumin, soluble plasma fibronectin, α-fetoprotein, C-reactive protein, and several globulins; proteins involved in hemostasis and fibrinolysis such as coagulation factors involved in the coagulation cascade, α2-macroglobulin, α1-antitrypsin, antithrombin III, protein S, protein C, plasminogen, α2-antiplasmin, and complement component 3; carrier proteins such as albumin, ceruloplasmin, transcortin, haptoglobin, hemopexin, IGF binding rotein, major urinary proteins, retinol binding protein, sex hormone-binding globulin, transthyretin, transferrin, and Vitamin D-binding protein; hormones such as insulin-like growth factor 1, thrombopoietin, hepcidin, and betatrophin; prohormones such as angiotensinogen; and apolipoproteins.

In some embodiments, carbohydrate metabolism such as the formation, breakdown, and interconversion of carbohydrates, gluconeogenesis, glycogenolysis, glycogenesis, lipid metabolism including cholesterol synthesis, and lipogenesis, the production of triglycerides or fats, are observed in an induced hepatocyte.

In some embodiments, an induced hepatocyte comprises similar ultrastructure, or the cellular makeup, as a primary hepatocyte. In some instances, this is achieved through comparison based on transmission electron microscopy images.

In some embodiments, an induced hepatocyte is utilized for pharmaceutical research, such as drug metabolism, enzyme induction, hepatotoxicity, hepatocyte regeneration, and transplantation.

Trophoblast Stem Cells (hTS Cells)

Trophoblast stem cells (TS cells) are precursors of differentiated placenta cells. In some instances, a TS cell is derived from a blastocyst polar trophectoderm (TE) or an extraembryonic ectoderm (ExE) cell. In some cases, TS is capable of indefinite proliferation in vitro in an undifferentiated state, and is capable of maintaining the potential multilineage differentiation capabilities in vitro. In some instances, a TS cell is a mammalian TS cell. Exemplary mammals include mouse, rat, rabbit, sheep, cow, cat, dog, monkey, ferret, bat, kangaroo, seals, dolphin, and human. In some embodiments, a TS cell is a human TS (hTS) cell.

In some instances, TS cells are obtained from fallopian tubes. Fallopian tubes are the site of fertilization and the common site of ectopic pregnancies, in which biological events such as the distinction between inner cell mass (ICM) and trophectoderm and the switch from totipotency to pluripotency with major epigenetic changes take place. In some instances, these observations provide support for fallopian tubes as a niche reservoir for harvesting blastocyst-associated stem cells at the preimplantation stage. Blastocyst is an early-stage preimplantation embryo, and comprises ICM which subsequently forms into the embryo, and an outer layer termed trophoblast which gives rise to the placenta.

In some embodiments, a TS cell is a stem cell used for generation of a progenitor cell such as for example a hepatocyte. In some embodiments, a TS cell is derived from ectopic pregnancy. In some embodiments, the TS cell is a human TS cell. In one embodiment, the human TS cell derived from ectopic pregnancies does not involve the destruction of a human embryo. In another embodiment, the human TS cell derived from ectopic pregnancies does not involve the destruction of a viable human embryo. In another embodiment, the human TS cell is derived from trophoblast tissue associated with non-viable ectopic pregnancies. In another embodiment, the ectopic pregnancy cannot be saved. In another embodiment, the ectopic pregnancy would not lead to a viable human embryo. In another embodiment, the ectopic pregnancy threatens the life of the mother. In another embodiment, the ectopic pregnancy is tubal, abdominal, ovarian or cervical.

During normal blastocyst development, ICM contact per se or its derived diffusible 'inducer' triggers a high rate of cell proliferation in the polar trophectoderm, leading to cell movement toward the mural region throughout the blastocyst stage and can continue even after the distinction of the trophectoderm from the ICM. The mural trophectoderm cells overlaying the ICM are able to retain a 'cell memory' of ICM. At the beginning of the implantation, the mural cells opposite the ICM cease division because of the mechanical constraints from the uterine endometrium. However, in an ectopic pregnancy in which the embryo is located within the fallopian tube, constraints do not exist in the fallopian tubes which result in continuing division of polar trophectoderm cells to form extraembryonic ectoderm (ExE) in the stagnated blastocyst. In some instances, the ExE-derived TS cells exist for up to 20 days in a proliferation state. As such, until clinical intervention occurs, the cellular processes can yield an indefinite number of hTS cells in the preimplantation embryos and such cells can retain cell memory from ICM.

In some instances, TS cells possess specific genes of ICM (e.g. OCT4, NANOG, SOX2, FGF4) and trophectoderm (e.g. CDX2, Fgfr-2, Eomes, BMP4), and express components of the three primary germ layers, mesoderm, ectoderm, and endoderm. In some instances, TS cells express embryonic stem (e.g. human embryonic stem) cell-related surface markers such as specific stage embryonic antigen (SSEA)-1, -3 and -4 and mesenchymal stem cell-related markers (CD 44, CD90, CK7 and Vimentin). In other instances, hematopoietic stem cell markers (CD34, CD45, a6-integrin, E-cadherin, and L-selectin) are not expressed.

Methods of Preparation of Induced Hepatocytes

Disclosed herein, in certain embodiments, is a method of inducing a trophoblast stem (TS) cell to differentiate into an induced hepatocyte in vitro, which comprises contacting the trophoblast stem cell in a conditioned medium comprising a fibroblast growth factor (FGF), a steroid, and a cytokine; and incubating the cell for a sufficient time to induce differentiation of the trophoblast stem cell into an induced hepatocyte. In some embodiments, the TS cell is a human TS (hTS) cell. In some embodiments, the FGF, the steroid, and the cytokine are human FGF, human steroid, and human cytokine.

In some embodiments, fibroblast growth factors (FGFs) are a family of growth factors involved in angiogenesis, wound healing, embryonic development, and cellular proliferation and differentiation processes. In some instances, FGFs are heparin-binding proteins and interacts with heparin sulfate proteoglycans. In some instances, there are 22 members of the FGF family. Exemplary FGFs include: FGF1, FGF2 (also known as basic FGF or bFGF or FGF-β), FGF3, FGF4, FGF5, FGF6, FGF7, FGF8, FGF9, FGF10, FGF11, FGF12, FGF13, FGF14, FGF16, FGF17, FGF18, FGF15/19, FGF20, FGF21, FGF22, and FGF23. In some embodiments, the fibroblast growth factor is basic fibroblast growth factor (bFGF, also known as FGF2 or FGF-β). In some embodiments, the bFGF is a human bFGF. In some embodiments, the human bFGF is a recombinant human bFGF, or a fragment thereof.

In some embodiments, FGF is introduced into the cultured medium at a concentration of between about 0.001 and about 5000 ng/mL, about 0.01 and about 500 ng/mL, about 0.1 and about 100 ng/mL, or about 1 and about 50 ng/mL.

In some instances, FGF is introduced into the cultured medium at a concentration of at least 0.001, 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or more. In some embodiments, FGF is introduced into the cultured medium at a concentration of at most 0.001, 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or less.

In some embodiments, bFGF is introduced into the cultured medium at a concentration of between about 0.001 and about 5000 ng/mL, about 0.01 and about 500 ng/mL, about 0.1 and about 100 ng/mL, or about 1 and about 50 ng/mL.

In some instances, FGF is introduced into the cultured medium at a concentration of at least 0.001, 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or more. In some embodiments, bFGF is introduced into the cultured medium at a concentration of at most 0.001, 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or less.

In some embodiments, a fibroblast growth factor is introduced into the cultured medium comprising hTS cells to initiate hTS cell differentiation event. In some embodiments, the fibroblast growth factor is bFGF. In some embodiments, a steroid and a cytokine are introduced into the cultured medium after the addition of FGF (e.g. bFGF).

In some embodiments, a steroid is a chemical involved in a wide range of physiological processes such as stress response, immune response, regulation of inflammation, carbohydrate metabolism, protein catabolism, blood electrolyte levels, and behaviors. In some instances, steroids also include steroid hormones, such as glucocorticoids, mineralocorticoids, androgens, estrogens, and progestogens. In some embodiments, steroids include, but are not limited to, hydrocortisone types such as hydrocortisone, hydrocortisone acetate, cortisone acetate, tixocortol pivalate, prednisolone, methylprednisolone, and prednisone; acetonides such as triamcinolone acetonide, triamcinolone alcohol, mometasone, amcinonide, budesonide, desonide, fluocinonide, fluocinolone acetonide, and halcinonide; betamethasone types such as betamethasone, betamethasone sodium phosphate, dexamethasone, dexamethasone sodium phosphate, and fluocortolone; halogenated such as hydrocortisone-17-valerate, halometasone, alclometsone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate; labile prodrug esters such as hydrocortisone-17-butyrate, hydrocortisone-17-aceponate, hydrocortisone-17-buteprate, ciclesonide, and prednicarbate. In some embodiments, a steroid is a naturally derived or chemically modified steroid. In some embodiments, a steroid is dexamethasone, betamethasone, prednisolone, methylprednisolone, triamcinolone acetonide, triamcinolone alcohol, or hydrocortisone. In some embodiments, a steroid is dexamethasone. As used herein, the term "dexamethasone" refers to dexamethasone and its derivatives. In some embodiments, dexamethasone is utilized for directing an hTS cell to differentiate into hepatic lineage. In some embodiments, dexamethasone is utilized in combination with another agent for directing an hTS cell to differentiate into hepatic lineage. In some embodiments, the another agent is a cytokine.

In some embodiments, a steroid is introduced into the cultured medium at a concentration of between about 0.001 and about 100 μM, about 0.005 and about 5 μM, about 0.01 and about 1 μM, or about 0.05 and about 0.5 μM.

In some instances, a steroid is introduced into the cultured medium at a concentration of at least 0.001, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.7, 0.8, 0.9, 1, 1.5, 2, 3, 4, 5, 6, 7, 8, 9, 10 μM, or more. In some embodiments, a steroid is introduced into the cultured medium at a concentration of at most 0.001, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.7, 0.8, 0.9, 1, 1.5, 2, 3, 4, 5, 6, 7, 8, 9, 10 μM, or less.

In some embodiments, dexamethasone is introduced into the cultured medium at a concentration of between about 0.001 and about 100 µM, about 0.005 and about 5 µM, about 0.01 and about 1 µM, or about 0.05 and about 0.5 µM.

In some embodiments, dexamethasone is introduced into the cultured medium at a concentration of at least 0.001, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.7, 0.8, 0.9, 1, 1.5, 2, 3, 4, 5, 6, 7, 8, 9, 10 µM, or more. In some embodiments, dexamethasone is introduced into the cultured medium at a concentration of at most 0.001, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.7, 0.8, 0.9, 1, 1.5, 2, 3, 4, 5, 6, 7, 8, 9, 10 µM, or less.

In some embodiments, a cytokine is a category of small proteins between about 5-20 dKa that are involved in cell signaling. In some instances, cytokines include chemokines, interferons, interleukins, and tumor necrosis factors. Chemokines can play a role as a chemoattractant to guide the migration of cells, and can be classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

Interleukins are expressed by leukocytes or white blood cells and they promote the development and differentiation of T and B lymphocytes and hematopoietic cells. Exemplary interleukins include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

In some embodiments, dexamethasone is utilized in combination with a cytokine for directing an hTS cell to differentiate into hepatic lineage. In some instances, the cytokine is a chemokine, an interferon, an interleukins, or a tumor necrosis factor. In some instances, the cytokine is an interleukin. In some embodiments, dexamethasone is utilized in combination with an interleukin for directing an hTS cell to differentiate into hepatic lineage. In some embodiments, the interleukin is IL-6. In some instances, IL-6 is further grouped with additional cytokines based on its interaction through the Gp130 receptor sub-unit. In some instances, additional members of the IL-6 group include oncostatin M (OSM), IL-11, Ciliary neurotropic factor (CNTF), Cardiotrophin-1 (CT-1), Cardiotrophin-like cytokine (CLC), and Leukaemia inhibitory factor (LIF). In some embodiments, dexamethasone is utilized in combination with IL-6 for directing an hTS cell to differentiate into hepatic lineage. In some embodiments, dexamethasone is utilized in combination with a member of the IL-6 group for directing an hTS cell to differentiate into hepatic lineage. In some embodiments, dexamethasone is utilized in combination with OSM, IL-11, CNTF, CT-1, CLC, or LIF for directing an hTS cell to differentiate into hepatic lineage. In some embodiments, dexamethasone is utilized in combination with OSM for directing an hTS cell to differentiate into hepatic lineage. In some embodiments, the IL-6 group of cytokines is human IL-6 cytokines or their fragments thereof. In some embodiments, OSM is a human OSM. In some embodiments, the human OSM is a recombinant human OSM, or its fragments thereof.

In some embodiments, a cytokine is introduced into the cultured medium at a concentration of between about 0.001 and about 5000 ng/mL, about 0.01 and about 500 ng/mL, about 0.1 and about 100 ng/mL, or about 1 and about 50 ng/mL.

In some embodiments, a cytokine is introduced into the cultured medium at a concentration of at least 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or more. In some embodiments, a cytokine is introduced into the cultured medium at a concentration of at most 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or less.

In some embodiments, OSM is introduced into the cultured medium at a concentration of between about 0.001 and about 5000 ng/mL, about 0.01 and about 500 ng/mL, about 0.1 and about 100 ng/mL, or about 1 and about 50 ng/mL.

In some embodiments, OSM is introduced into the cultured medium at a concentration of at least 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or more. In some embodiments, OSM is introduced into the cultured medium at a concentration of at most 0.01, 0.1, 0.5, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 100, 200, 300, 400, 500, 1000 ng/mL or less.

In some embodiments, a fibroblast growth factor (e.g. bFGF) modulates the expression of a biomarker within an hTS cell. In some embodiments, the biomarker is a microRNA (miR). In some embodiments, the biomarker is miRNA-124a. In some embodiments, the fibroblast growth factor is bFGF. In some embodiments, bFGF upregulates or activates miRNA-124a. In some embodiments, bFGF downregulates miRNA-124a.

In some embodiments, the expression level of miRNA-124a in a bFGF treated trophoblast stem cell is compared to the expression level of miRNA-124a in an untreated trophoblast stem cell. In some embodiments, the expression level of miRNA-124a is at least 1, 2, 3, 4, 5, 6, 7, 8, 9, 10, 20, 30, 40, 50, 100, 1000 fold, or more in a bFGF treated trophoblast stem cell relative to the expression level of miRNA-124a in an untreated trophoblast stem cell. In some embodiments, the expression level of miRNA-124a is at most 1, 2, 3, 4, 5, 6, 7, 8, 9, 10, 20, 30, 40, 50, 100, 1000 fold, or less in a bFGF treated trophoblast stem cell relative to the expression level of miRNA-124a in an untreated trophoblast stem cell.

In some embodiments, activation or upregulation of miRNA-124a initiates definitive endoderm (DE) specification in the trophoblast stem cell. In some embodiments, the DE specification occurs between about 0.1 and about 96 hours, about 0.5 and about 36 hours, about 1 and about 24 hours, about 2 and about 18 hours, about 4 and about 12 hours, or about 6 and about 10 hours.

In some embodiments, the DE specification occurs at least 0.1, 0.5, 1, 2, 3, 4, 5, 6, 7, 8, 9, 10, 11, 12, 13, 14, 15, 16, 17, 18, 19, 20, 21, 22, 23, 24, 36, 48, 72 hours, or more after induction with bFGF. In some embodiments, the DE specification occurs at most 0.1, 0.5, 1, 2, 3, 4, 5, 6, 7, 8, 9, 10, 11, 12, 13, 14, 15, 16, 17, 18, 19, 20, 21, 22, 23, 24, 36, 48, 72 hours, or less after induction with bFGF. In some embodiments, the DE specification occurs about 1, 2, 3, 4, 5, 6, 7, 8, 9, 10, 11, 12, 13, 14, 15, 16, 17, or 18 hours post induction with bFGF. In some embodiments, the DE specification occurs about 6, 7, 8, 9, or 10 hours post induction with bFGF.

In some embodiments, the DE specification is associated with a set of biomarkers. In some embodiments, the biomarkers include forkhead box protein A2 (FOXA2), SRY-box 17 (SOX17), Goosecoid (GSC), Homeodomain protein MIXL1, SRY-box 2 (SOX2), transcription factor NANOG, and OCT4. In some embodiments, the DE specification is characterized by an elevated expression of biomarkers selected from forkhead box protein A2 (FOXA2), SRY-box 17 (SOX17), Goosecoid (GSC), Homeodomain protein MIXL1, SRY-box 2 (SOX2), transcription factor NANOG, and OCT4. In some embodiments, the DE specification is characterized by an elevated expression of biomarkers selected from forkhead box protein A2 (FOXA2), SRY-box 17 (SOX17), Goosecoid (GSC), SRY-box 2 (SOX2), transcription factor NANOG, and OCT4. In some embodiments, the DE specification is characterized by a decreased expression of biomarkers selected from forkhead box protein A2 (FOXA2), SRY-box 17 (SOX17), Goosecoid (GSC), Homeodomain protein MIXL1, SRY-box 2 (SOX2), transcription factor NANOG, and OCT4. In some embodiments, the DE specification is characterized by a decreased expression of Homeodomain protein MIXL1.

In some embodiments, the expression levels of FOXA2, SOX17, GSC, MIXL1, SOX2, NANOG, and OCT4 in a bFGF induced trophoblast stem cell are compared to the expression levels of FOXA2, SOX17, GSC, MIXL1, SOX2, NANOG, and OCT4 in an uninduced trophoblast stem cell. In some embodiments, the elevated expression level is an increased protein expression level. In some embodiments, the protein expression levels of FOXA2, SOX17, GSC, MIXL1, SOX2, NANOG, and OCT4 are between about 1 and about 20,000 fold, about 2 and about 1000 fold, or about 10 and about 100 fold higher than the protein expression levels of FOXA2, SOX17, GSC, MIXL1, SOX2, NANOG, and OCT4 in an untreated trophoblast stem cell. In some embodiments, the protein expression levels of FOXA2, SOX17, GSC, MIXL1, SOX2, NANOG, and OCT4 are at least 1, 2, 3, 4, 5, 6, 7, 8, 9, 10, 20, 30, 40, 50, 100, 1000, 10,000 fold, or more in a bFGF treated trophoblast stem cell relative to the protein expression levels of FOXA2, SOX17, GSC, MIXL1, SOX2, NANOG, and OCT4 in an untreated trophoblast stem cell. In some embodiments, the protein expression levels of FOXA2, SOX17, GSC, MIXL1, SOX2, NANOG, and OCT4 are at most 1, 2, 3, 4, 5, 6, 7, 8, 9, 10, 20, 30, 40, 50, 100, 1000, 10,000 fold, or less in a bFGF treated trophoblast stem cell relative to the protein expression levels of FOXA2, SOX17, GSC, MIXL1, SOX2, NANOG, and OCT4 in an untreated trophoblast stem cell.

In some embodiments, the elevated expression is an increased gene expression level. In some embodiments, the gene expression levels of FOXA2, SOX17, GSC, MIXL1, SOX2, NANOG, and OCT4 are between about 1 and about 20,000 fold, about 2 and about 1000 fold, or about 10 and about 100 fold higher than the gene expression levels of FOXA2, SOX17, GSC, MIXL1, SOX2, NANOG, and OCT4 in an untreated trophoblast stem cell. In some embodiments, the gene expression levels of FOXA2, SOX17, GSC, MIXL1, SOX2, NANOG, and OCT4 are at least 1, 2, 3, 4, 5, 6, 7, 8, 9, 10, 20, 30, 40, 50, 100, 1000, 10,000 fold, or more in a bFGF treated trophoblast stem cell relative to the gene expression levels of FOXA2, SOX17, GSC, MIXL1, SOX2, NANOG, and OCT4 in an untreated trophoblast stem cell. In some embodiments, the gene expression levels of FOXA2, SOX17, GSC, MIXL1, SOX2, NANOG, and OCT4 are at most 1, 2, 3, 4, 5, 6, 7, 8, 9, 10, 20, 30, 40, 50, 100, 1000, 10,000 fold, or less in a bFGF treated trophoblast stem cell relative to the gene expression levels of FOXA2, SOX17, GSC, MIXL1, SOX2, NANOG, and OCT4 in an untreated trophoblast stem cell.

In some embodiments, a cocktail of a steroid and a cytokine is utilized to direct DE differentiation into hepatic lineage. In some embodiments, the cocktail comprise dexamethasone and oncostatin M is utilized to direct DE differentiation into hepatic lineage. In some embodiments, the cocktail is introduced into a cultured medium comprising hTS cells before, after, or simultaneously with the addition of bFGF. In some embodiments, the cocktail is introduced into a cultured medium comprising hTS cells between about 0.5 and about 96 hours, about 1 and about 48 hours, about 2 and about 36 hours, about 3 and about 24 hours, about 4 and about 12 hours, or about 6 and about 10 hours.

In some embodiments, the cocktail is introduced into a cultured medium comprising hTS cells at least 0.5, 1, 2, 3, 4, 5, 6, 7, 8, 9, 10, 11, 12, 13, 14, 15, 16, 17, 18, 19, 20, 21, 22, 23, 24, 36, 48, 60, 72 hours, or more after addition of bFGF. In some embodiments, the cocktail is introduced into a cultured medium comprising hTS cells at most 0.5, 1, 2, 3, 4, 5, 6, 7, 8, 9, 10, 11, 12, 13, 14, 15, 16, 17, 18, 19, 20, 21, 22, 23, 24, 36, 48, 60, 72 hours, or less after addition of bFGF. In some embodiments, the cocktail is introduced into a cultured medium comprising hTS cells about 4, 5, 6, 7, 8, 9, 10, 11, 12, 13, 14, 15, 16, 17, or 18 hours after addition of bFGF. In some embodiments, the cocktail is introduced into a cultured medium comprising hTS cells about 6, 7, 8, 9, 10, 11, or 12 hours after addition of bFGF.

In some embodiment, a hTS cell is incubated in a cultured medium comprising bFGF, dexamethasone and oncostatin M for between about 0.5 and about 100 days, about 1 and about 50 days, about 2 and about 30 days, about 3 and about 15 days, or about 4 and about 12 days.

In some embodiment, an hTS cell is incubated in a cultured medium comprising bFGF, dexamethasone and oncostatin M for at least 0.5 1, 2, 3, 4, 5, 6, 7, 8, 9, 10, 11, 12, 13, 14 days or more. In some embodiment, an hTS cell is incubated in a cultured medium comprising bFGF, dexamethasone and oncostatin M for at most 0.5 1, 2, 3, 4, 5, 6, 7, 8, 9, 10, 11, 12, 13, 14 days or less.

In some embodiments, the trophoblast stem cell is classified into four stages of hepatocyte-like cell development. In some embodiments, the four stages include primitive streak to DE stage, hepatic specified endoderm, hepatoblastic stage, and the fetal and adult hepatocyte-like cell stage. In some embodiments, each of the four stages are associated with a set of biomarkers comprising C—X—C chemokine receptor type 4 (CXCR4), Forkhead box protein A2 (FOXA2), SRY-box 17 (SOX17), hexosaminidase A (alpha polypeptide) (HHEX), bile salt export pump (BSEP), transthyretin (TTR), albumin (ALB), tyrosine aminotransferase (TAT), cytochrome P450 7A1 (CYP7A1), glucose-6-phosphatase (G6PC), serpin peptidase inhibitor clade A (alpha-1 antiproteinase, antitrypsin) member 1 (SERPINA1), ATP-binding cassette sub-family C (ABCC2), CCAAT-enhancer-binding protein beta (C/EBPβ), hepatocyte nuclear factor 1-alpha (HNF1α), hepatocyte nuclear factor 4-alpha (HNF4α), alpha-1-fetoprotein (AFP), keratin 8 (KRT8), phosphoenolpyruvate carboxykinase 2 mitochondrial (PCK2), cytochrome P450 2B6 (CYP2B6), glycogen synthase 2 (GYS2), hepatocyte nuclear factor 6 (HNF6), carbamoyl-phosphate synthase 1 mitochondrial (CPS1), alcohol dehydrogenase 1C (class I) gamma polypeptide (ADH1C), connexin 32 (CX32), cytochrome P450 3A4 (CYP3A4), prospero homeobox 1 (PROX1), tryptophan 2,3-dioxygenase (TDO2), apolipoprotein F (APOF), keratin 18 (KRT18), keratin 19 (KRT19), or chromosome 19 open reading frame 80 (angiopoietin-like protein 8, hepatocellular carcinoma-associated gene TD26, lipasin) (Betatrophin). In some embodiments, each of the four stages are associated with a set of biomarkers comprising CXCR4, FOXA2, SOX17, HHEX, TTR, ALB, TAT, CYP7A1, BSEP, SERPINA1, G6PC, ABCC2, C/EBPβ, HNF1α, or HNF4α.

In some instances, the primitive streak to DE stage is a stage in which an hTS cell that has not entered a hepatic differentiation stage or is about to enter a hepatic differentiation stage. In some embodiments, an hTS cell at the primitive streak to DE stage undergoes DE specification. In some instances after induction with a FGF (e.g. bFGF), a hTS cell remains in the primitive streak to DE stage for between about 0.1 and about 24 hours, about 0.5 and about 18 hours, or about 1 and about 12 hours. In some instances after induction with a FGF (e.g. bFGF), a hTS cell remains in the primitive streak to DE stage for at most 0.1, 0.5, 1, 2, 3, 4, 5, 6, 7, 8, 9, 10 hours or less. In some instances after induction with a FGF (e.g. bFGF), an hTS cell remains in the primitive streak to DE stage for at least 0.1, 0.5, 1, 2, 3, 4, 5, 6, 7, 8, 9, 10 hours or more.

In some instances, a hTS cell in the primitive streak to DE stage is characterized with a set of biomarkers selected from CXCR4, FOXA2, SOX17, HHEX, BSEP, TTR, ALB, TAT, CYP7A1, G6PC, SERPINA1, ABCC2, C/EBPβ, HNF1α, HNF4α, AFP, KRT8, PCK2, CYP2B6, GYS2, HNF6, CPS1, ADH1C, CX32, CYP3A4, PROX1, TDO2, APOF, KRT18, KRT19, and Betatrophin. In some embodiments, the primitive streak to DE stage is associated with a set of biomarkers selected from CXCR4, FOXA2, SOX17 and HHEX.

In some embodiments, the primitive streak to DE stage is associated with elevated expression levels of CXCR4, FOXA2, SOX17 and HHEX. In some embodiments, the elevated expression level is an increased protein expression level or an increased gene expression level. In some embodiments, the elevated expression level is an increased gene expression level. In some embodiments, the elevated gene expression levels of CXCR4, FOXA2, SOX17 and HHEX are relative to the gene expression levels of CXCR4, FOXA2, SOX17 and HHEX in an equivalent trophoblast stem cell which has not entered the primitive streak to DE stage. In some embodiments, the elevated gene expression levels of CXCR4, FOXA2, SOX17 and HHEX are between about 0.1 and about 10,000, about 1 and about 5000, or about 2 and about 1000. In some embodiments, the elevated gene expression levels of CXCR4, FOXA2, SOX17 and HHEX are at least 1, 2, 3, 4, 5, 6, 7, 8, 9, 10, 20, 30, 40, 50, 100, 1000, 5000 fold, or more relative to the gene expression levels of CXCR4, FOXA2, SOX17 and HHEX in an equivalent hTS cell which has not entered the primitive streak to DE stage. In some embodiments, the gene expression levels of CXCR4, FOXA2, SOX17 and HHEX are at most 1, 2, 3, 4, 5, 6, 7, 8, 9, 10, 20, 30, 40, 50, 100, 1000, 5000 fold, or less relative to the gene expression levels of CXCR4, FOXA2, SOX17 and HHEX in an equivalent hTS cell which has not entered the primitive streak to DE stage.

In some instances, the hepatic specified endoderm characterizes the first appearance of epithelium cells after hepatic specification. In some embodiments, the hepatic specified endoderm stage is initiated with the addition of a cocktail of steroid (e.g. dexamethasone) and cytokine (e.g. oncostatin M). In some instances, the cocktail of steroid (e.g. dexamethasone) and cytokine (e.g. oncostatin M) is added to the cultured medium at between about 1 and about 48 hours, about 2 and about 24 hours, about 3 and about 18 hours, or about 4 and about 12 hours. In some instances, the cocktail of steroid (e.g. dexamethasone) and cytokine (e.g. oncostatin M) is added to the cultured medium at least 1, 2, 3, 4, 5, 6, 7, 8, 9, 10, 11, 12, 13, 14, 15, 16 hours, or more post induction of a FGF (e.g. bFGF). In some instances, the cocktail of steroid (e.g. dexamethasone) and cytokine (e.g. oncostatin M) is added to the cultured medium at most 1, 2, 3, 4, 5, 6, 7, 8, 9, 10, 11, 12, 13, 14, 15, 16 hours, or less post induction of a FGF (e.g. bFGF).

In some cases after induction with the cocktail of steroid (e.g. dexamethasone) and cytokine (e.g. oncostatin M), a hTS cell remains in the hepatic specified endoderm stage for between about 1 and about 72 hours, about 2 and about 36 hours, about 3 and about 24 hours, or about 4 and about 12 hours. In some cases after induction with the cocktail of steroid (e.g. dexamethasone) and cytokine (e.g. oncostatin M), a hTS cell remains in the hepatic specified endoderm stage for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 hours, or more. In some cases after induction with the cocktail of steroid (e.g. dexamethasone) and cytokine (e.g. oncostatin M), a hTS cell remains in the hepatic specified endoderm stage for at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 hours, or less.

In some instances, a hTS cell in the hepatic specified endoderm stage is characterized with a set of biomarkers selected from CXCR4, FOXA2, SOX17, HHEX, BSEP, TTR, ALB, TAT, CYP7A1, G6PC, SERPINAL ABCC2, C/EBPβ, HNF1α, HNF4α, AFP, KRT8, PCK2, CYP2B6, GYS2, HNF6, CPS1, ADH1C, CX32, CYP3A4, PROX1, TDO2, APOF, KRT18, KRT19, and Betatrophin. In some embodiments, the hepatic specified endoderm is associated with a set of biomarkers selected from SOX17, TTR, ALB, TAT, and CYP7A1.

In some embodiments, the hepatic specified endoderm is associated with elevated expression levels of SOX17, TTR, ALB, TAT, and CYP7A1. In some embodiments, the elevated expression level is an increased protein expression level or an increased gene expression level. In some embodiments, the elevated expression level is an increased gene expression level. In some embodiments, the elevated gene expression levels of SOX17, TTR, ALB, TAT, and CYP7A1 are relative to the gene expression levels of SOX17, TTR, ALB, TAT, and CYP7A1 in an equivalent trophoblast stem cell which has not entered the hepatic specified endoderm stage. In some embodiments, the gene expression levels of SOX17, TTR, ALB, TAT, and CYP7A1 are between about 1 and about 10,000 fold, about 2 and about 1000 fold, or about 2 and about 100 fold. In some embodiments, the gene expression levels of SOX17, TTR, ALB, TAT, and CYP7A1 are at least 1, 2, 3, 4, 5, 6, 7, 8, 9, 10, 20, 30, 40, 50, 100, 1000, 5000 fold, or more relative to the gene expression levels of SOX17, TTR, ALB, TAT, and CYP7A1 in an equivalent trophoblast stem cell which has not entered the hepatic specified endoderm stage. In some embodiments, the gene expression levels of SOX17, TTR, ALB, TAT, and CYP7A1 are at most 1, 2, 3, 4, 5, 6, 7, 8, 9, 10, 20, 30, 40, 50, 100, 1000, 5000 fold, or less relative to the gene expression levels of SOX17, TTR, ALB, TAT, and CYP7A1 in an equivalent trophoblast stem cell which has not entered the hepatic specified endoderm stage.

In some embodiments, a hTS cell enters the hepatoblastic stage after between about 1 and about 36 hours, about 3 and about 24 hours, or about 6 and about 12 hours post addition of a cocktail of steroid (e.g. dexamethasone) and cytokine (e.g. oncostatin M). In some embodiments, a hTS cell enters the hepatoblastic stage after about 1, 2, 3, 4, 5, 6, 7, 8, 9, 10, 11, 12, 13, 14, 15, 16, 17, 18, 19, 20, 21, 22, 23, or 24 hours post addition of a cocktail of steroid (e.g. dexamethasone) and cytokine (e.g. oncostatin M).

In some embodiments, an hTS cell remains in the hepatoblastic stage for between about 1 and about 30 days, about 2 and about 12 days, or about 3 and about 7 days. In some embodiments, an hTS cell remains in the hepatoblastic stage for at most 1, 2, 3, 4, 5, 6, 7, 8 days or less. In some embodiments, an hTS cell remains in the hepatoblastic stage for at least 1, 2, 3, 4, 5, 6, 7, 8 days or more.

In some instances, a hTS cell in the hepatoblastic stage is characterized with a set of biomarkers selected from CXCR4, FOXA2, SOX17, HHEX, BSEP, TTR, ALB, TAT, CYP7A1, G6PC, SERPINA1, ABCC2, C/EBPβ, HNF1α, HNF4α, AFP, KRT8, PCK2, CYP2B6, GYS2, HNF6, CPS1, ADH1C, CX32, CYP3A4, PROX1, TDO2, APOF, KRT18, KRT19, and Betatrophin. In some embodiments, the hepatoblastic stage is associated with a set of biomarkers selected from TTR, ALB, TAT, CYP7A1, and BSEP.

In some embodiments, the hepatoblastic stage is associated with elevated expression levels of TTR, ALB, TAT, CYP7A1, and BSEP. In some embodiments, the elevated expression level is an increased protein expression level or an increased gene expression level. In some embodiments, the elevated expression level is an increased gene expression level. In some embodiments, the elevated gene expression levels of TTR, ALB, TAT, CYP7A1, and BSEP are relative to the gene expression levels of TTR, ALB, TAT, CYP7A1, and BSEP in an equivalent hTS cell which has not entered the hepatoblastic stage. In some embodiments, the gene expression levels of TTR, ALB, TAT, CYP7A1, and BSEP are between about 1 and about 10,000 fold, about 2 and about 1000 fold, or about 2 and about 100 fold.

In some embodiments, the gene expression levels of TTR, ALB, TAT, CYP7A1, and BSEP are at least 1, 2, 3, 4, 5, 6, 7, 8, 9, 10, 20, 30, 40, 50, 100, 200, 300, 400, 500, 1000, 5000 fold, or more relative to the gene expression levels of TTR, ALB, TAT, CYP7A1, and BSEP in an equivalent hTS cell which has not entered the hepatoblastic stage. In some embodiments, the gene expression levels of TTR, ALB, TAT, CYP7A1, and BSEP are at most 1, 2, 3, 4, 5, 6, 7, 8, 9, 10, 20, 30, 40, 50, 100, 200, 300, 400, 500, 1000, 5000 fold, or less relative to the gene expression levels of TTR, ALB, TAT, CYP7A1, and BSEP in an equivalent hTS cell which has not entered the hepatoblastic stage.

In some instances, a hTS cell enters the fetal and adult hepatocyte-like stage between about 1 and about 20 days, about 2 and about 10 days, or about 3 and about 6 days post addition of a cocktail of steroid (e.g. dexamethasone) and cytokine (e.g. oncostatin M). In some instances, an hTS cell enters the fetal and adult hepatocyte-like stage after about 1, 2, 3, 4, 5, or 6 days after post addition of a cocktail of steroid (e.g. dexamethasone) and cytokine (e.g. oncostatin M).

In some embodiments, an hTS cell remains in the fetal and adult hepatocyte-like stage for between about 1 and about 100 days, about 2 and about 50 days, about 3 and about 30 days, about 4 and about 12 days, or about 6 and about 10 days. In some embodiments, an hTS cell remains in the fetal and adult hepatocyte-like stage for at most 1, 2, 3, 4, 5, 6, 7, 8, 9, 10, 11, 12, 13, 14, 15, 20, 25, 30, 60 days or less. In some embodiments, an hTS cell remains in the fetal and adult hepatocyte-like stage for at least 1, 2, 3, 4, 5, 6, 7, 8, 9, 10, 11, 12, 13, 14, 15, 20, 25, 30, 60 days or more.

In some instances, a hTS cell in the fetal and adult hepatocyte-like stage is characterized with a set of biomarkers selected from CXCR4, FOXA2, SOX17, HHEX, BSEP, TTR, ALB, TAT, CYP7A1, G6PC, SERPINA1, ABCC2, C/EBPβ, HNF1α, HNF4α, AFP, KRT8, PCK2, CYP2B6, GYS2, HNF6, CPS1, ADH1C, CX32, CYP3A4, PROX1, TDO2, APOF, KRT18, KRT19, and Betatrophin. In some embodiments, the fetal and adult hepatocyte-like cell stage is associated with a set of biomarkers selected from HHEX, BSEP, TTR, ALB, TAT, SERPINA1, G6PC, ABCC2, C/EBPβ, HNF1α, and HNF4α.

In some embodiments, the fetal and adult hepatocyte-like cell stage is associated with elevated expression levels of HHEX, BSEP, TTR, ALB, TAT, SERPINA1, G6PC, ABCC2, C/EBPβ, HNF1α, and HNF4α. In some embodiments, the elevated expression level is an increased protein expression level or an increased gene expression level. In some embodiments, the elevated expression level is an increased gene expression level. In some embodiments, the elevated gene expression levels of HHEX, BSEP, TTR, ALB, TAT, SERPINA1, G6PC, ABCC2, C/EBPβ, HNF1α, and HNF4α are relative to the gene expression level of HHEX, BSEP, TTR, ALB, TAT, SERPINA1, G6PC, ABCC2, C/EBPβ, HNF1α, and HNF4α in an equivalent hTS cell which has not entered the fetal and adult hepatocyte-like cell stage. In some embodiments, the gene expression levels of HHEX, BSEP, TTR, ALB, TAT, SERPINA1, G6PC, ABCC2, C/EBPβ, HNF1α, and HNF4α are between about 1 and about 10,000 fold, about 2 and about 5000 fold, or about 2 and about 1000 fold.

In some embodiments, the gene expression levels of HHEX, BSEP, TTR, ALB, TAT, SERPINA1, G6PC, ABCC2, C/EBPβ, HNF1α, and HNF4α are at least 1, 2, 3, 4, 5, 6, 7, 8, 9, 10, 20, 30, 40, 50, 100, 1000, 5000 fold, or more relative to the gene expression levels of HHEX, BSEP, TTR, ALB, TAT, SERPINA1, G6PC, ABCC2, C/EBPβ, HNF1α, and HNF4α in an equivalent hTS cell which has not entered the fetal and adult hepatocyte-like cell stage. In some embodiments, the gene expression levels of HHEX, BSEP, TTR, ALB, TAT, SERPINA1, G6PC, ABCC2, C/EBPβ, HNF1α, and HNF4α are at most 1, 2, 3, 4, 5, 6, 7, 8, 9, 10, 20, 30, 40, 50, 100, 1000, 5000 fold, or less relative to the gene expression levels of HHEX, BSEP, TTR, ALB, TAT, SERPINA1, G6PC, ABCC2, C/EBPβ, HNF1α, and HNF4α in an equivalent hTS cell which has not entered the fetal and adult hepatocyte-like cell stage.

In some embodiments, a cell in the fetal and adult hepatocyte-like cell stage matures into an induced hepatocyte. In some embodiments, a cell in the fetal and adult hepatocyte-like cell stage is an induced hepatocyte. In some embodiments, the induced hepatocyte does not differentiate further. In some embodiments, the induced hepatocyte reaches a terminally differentiated stage. In some embodiments, the induced hepatocyte remains as a stable cell for up to 2, 3, 4, 5, 6, 7, 8, 9, 10, 12, 15, 18, 20, 25, 30, 35, 40, 45, 50, 55, 60, 70, 80, 90, 100 generations or more. In some embodiments, the induced hepatocyte remains as a stable cell for up to 7 days, 10 days, 14 days, 21 days, 30 days, 60 days, 3 months, 4 months, 5 months, 6 months, 7 months, 8 months, 9 months, 10 months, 11 months, 1 years, 2 years, or more.

Methods of Use

Described herein, in certain embodiments, are methods of utilizing induced hepatocytes for one or more uses. In some embodiments, induced hepatocytes are utilized for screening a compound for use in treatment or prevention of a disease or disorder. In some embodiments, the screening process involves one or more of studies of the compound, enzyme induction, and toxicity studies. In some embodiments, induced hepatocytes are administered for the treatment of a liver injury, such as a damage or loss of liver tissue due to a liver-associated disease or disorder. In other embodiments, induced hepatocytes are utilized for the production of therapeutic proteins (e.g. hormones), cytokines, cholesterols, carbohydrates, bile, or a combination thereof. In other embodiments, induced hepatocytes are utilized for liver regeneration. In additional embodiments, induced hepatocytes are utilized as a source for gene therapy.

Induced Hepatocytes for Screening a Compound

In some embodiments, induced hepatocytes are utilized for screening a compound for use in treatment or prevention of a disease or disorder. In some embodiments, the method comprises contacting an isolated induced hepatocyte with a compound. In some embodiments, the method comprises contacting an isolated primary hepatocyte with the compound. In other embodiments, the method further comprises detecting a change in the activity of at least one biomarker (e.g. gene, transcript or protein) in the induced hepatocytes. In other embodiments, the method further comprises detecting a change in the level of at least one biomarker (e.g. gene, transcript or protein) in primary hepatocytes. In some embodiments, a change in the level of at least one biomarker is a change in the gene expression level of at least one biomarker. In some embodiments, the biomarker comprises a member of the cytochrome P450 superfamily. In some embodiments, the biomarker comprises cytochrome P450 families: CYP1, CYP2, CYP3, CYP4, CYP5, CYP7, CYP8, CYP11, CYP17, CYP19, CYP20, CYP21, CYP24, CYP26, CYP27, CYP39, CYP46, CYP51, and their respective subfamily members. In some embodiments, the biomarker comprises CYP1A2, CYP2B6, CYP2C8, CYP2C9, CYP2D6, CYP2E1, CYP3A4, or CYP7A1.

In some embodiments, a compound (e.g. a drug) is metabolized through the liver. In some instances, the liver's primary mechanism for metabolizing the compound (e.g. drug) is the P450 cytochrome system of enzymes. In some instances, the rate of metabolizing the compound is too quickly, it may decrease the compound's efficacy. Alternatively, if the rate of metabolizing the compound is too slow, it may allow toxicity to build up in the host cell. Therefore in some instances, the metabolism of a compound is evaluated, such as for example, its toxicity.

In some instances, the compound acts as an inducer or an inhibitor toward a member of the cytochrome P450 family of enzymes. In some cases, the compound is an inducer toward a member of the cytochrome P450 family of enzymes. In some instances, an inducer initiates or enhances the expression level of an enzyme, such as a member of the cytochrome P450 family of enzymes. In some instances, an inducer initiates or enhances the gene expression level of a member of the cytochrome P450 family of enzymes. In some instances, an inducer initiates or enhances the protein expression level of a member of the cytochrome P450 family of enzymes. In some cases, the compound is an inhibitor toward a member of the cytochrome P450 family of enzymes. In some instances, an inhibitor inhibits, decreases, or interferes with the expression level of an enzyme, such as a member of the cytochrome P450 family of enzymes. In some instances, an inhibitor inhibits, decreases, or interferes with the gene expression level of a member of the cytochrome P450 family of enzymes. In some instances, an inhibitor inhibits, decreases, or interferes with the protein expression level of a member of the cytochrome P450 family of enzymes. In some instances, the expression level of the enzyme, such as a member of the cytochrome P450 family of enzymes, is compared to a control expression level of the enzyme. In some embodiments, the control expression level of the enzyme is the expression level of the enzyme uninduced by the compound.

In some instances after contacting an isolated induced hepatocyte with a compound, a change in the gene expression of a member of the cytochrome P450 superfamily is detected. In some cases, the gene expression level of a biomarker from a member of the cytochrome P450 superfamily from an isolated induced hepatocyte that have been contacted with a compound is compared to the gene expression level of a biomarker from the cytochrome P450 superfamily of an equivalent isolated induced hepatocyte not contacted with the compound or compared with a primary hepatocyte.

In some instances after contacting an isolated induced hepatocyte with a compound, a change in the gene expression level of a biomarker selected from cytochrome P450 families: CYP1, CYP2, CYP3, CYP4, CYP5, CYP7, CYP8, CYP11, CYP17, CYP19, CYP20, CYP21, CYP24, CYP26, CYP27, CYP39, CYP46, CYP51, and their respective subfamily members is detected. In some cases, the gene expression level of a biomarker from the cytochrome P450 families: CYP1, CYP2, CYP3, CYP4, CYP5, CYP7, CYP8, CYP11, CYP17, CYP19, CYP20, CYP21, CYP24, CYP26, CYP27, CYP39, CYP46, CYP51, and their respective subfamily members from an isolated induced hepatocyte that have been contacted with a compound is compared to the gene expression level of a biomarker from the cytochrome P450 families: CYP1, CYP2, CYP3, CYP4, CYP5, CYP7, CYP8, CYP11, CYP17, CYP19, CYP20, CYP21, CYP24, CYP26, CYP27, CYP39, CYP46, CYP51, and their respective subfamily members of an equivalent isolated induced hepatocyte not contacted with the compound or compared with a primary hepatocyte.

In some instances after contacting an isolated induced hepatocyte with a compound, a change in the gene expression level of a biomarker selected from CYP1A2, CYP2B6, CYP2C8, CYP2C9, CYP2D6, CYP2E1, CYP3A4, and CYP7A1 is detected. In some cases, the gene expression level of a biomarker selected from CYP1A2, CYP2B6, CYP2C8, CYP2C9, CYP2D6, CYP2E1, CYP3A4, and CYP7A1 from an isolated induced hepatocyte that have been contacted with a compound is compared to the gene expression level of a biomarker selected from CYP1A2, CYP2B6, CYP2C8, CYP2C9, CYP2D6, CYP2E1, CYP3A4, and CYP7A1 of an equivalent isolated induced hepatocyte not contacted with the compound or compared with a primary hepatocyte.

In one embodiment, provided herein describes a method of screening a compound for the ability to induce changes in a cell. In one embodiment, the method comprises contacting an isolated induced hepatocyte with the compound. In another embodiment, the method comprises contacting an isolated primary hepatocyte with the compound. In another embodiment, the method further comprises detecting an induction of change (e.g. proliferation) of the induced hepatocyte such as during regeneration. In another embodiment, the method further comprises detecting an induction of change (e.g. proliferation) of the primary hepatocyte such as during regeneration.

Also provided herein a method of screening a compound for cellular toxicity or modulation of the cell, the method comprising contacting an induced hepatocyte with the compound. In another embodiment, the method further comprises determining any phenotypic or metabolic changes in the cell that result from contact with the compound, and correlating the change with cellular toxicity or any other change in cell function or biochemistry. In another embodiment, screening of pharmaceuticals, toxins, or potential modulators of differentiation is facilitated. These substances (e.g., pharmaceuticals, toxins, or potential modulators) can be added to the culture medium.

One embodiment provided herein described a method of screening proliferation factors, differentiation factors, and pharmaceuticals. In one embodiment, induced hepatocytes or primary hepatocytes are used to screen for factors (such as small molecule drugs, peptides, polynucleotides, and the like) or conditions (such as culture conditions or manipulation) that affect the characteristics of induced hepatocytes or primary hepatocytes in culture. In one embodiment, this system has the advantage of not being complicated by a secondary effect caused by perturbation of the feeder cells by the test compound. In another embodiment, growth affecting substances are tested. In another embodiment, the conditioned medium is withdrawn from the culture and a simpler medium is substituted. In another embodiment, different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cell according to the test protocol, and then determining whether the treated cell develops functional or phenotypic characteristics of a differentiated cell of a particular lineage.

In one embodiment, the induced hepatocyte or primary hepatocyte are used to screen potential modulators of cellular differentiation. For example, in one assay for screening modulators of cellular differentiation, the induced hepatocyte or primary hepatocyte can be cultured under serum free, or in the present of a modulator, as the situation requires, and the effect on differentiation can be detected. In another embodiment, the screening methods described herein can be used to study conditions associated with cellular development and screen for potential therapeutic or corrective drugs or modulators of the condition. For example, in one embodiment, the development of the induced hepatocyte or primary hepatocyte is compared with the development with cells having a disease or condition.

In one embodiment, biomarker such as gene and protein expression can be compared between different cell populations obtained from induced hepatocyte or primary hepatocyte, and used to identify and characterize factors upregulated or downregulated in the course of proliferation, and produce nucleotide copies of the affected genes.

In one embodiment, feeder-free induced hepatocyte or primary hepatocyte cultures can also be used for the testing of pharmaceutical compounds in drug research. Assessment of the activity of candidate pharmaceutical compounds generally involves combining the induced hepatocyte or primary hepatocyte with the candidate compound, determining any resulting change, and then correlating the effect of the compound with the observed change. In another embodiment, the screening is done, for example, either because the compound is designed to have a pharmacological effect on certain cell types, or because a compound designed to have effects elsewhere have unintended side effects. In another embodiment, two or more drugs are be tested in combination (by combining with the cells either simultaneously or sequentially), to detect possible drug-drug interaction effects. In another embodiment, compounds are screened initially for potential toxicity. In another embodiment, cytotoxicity is be determined by the effect on cell viability, survival, morphology, on the expression or release of certain markers, receptors or enzymes, on DNA synthesis or repair.

The terms "treating," "treatment," and the like are used herein to mean obtaining a desired pharmacologic and/or physiologic effect. In some embodiments, an individual (e.g., an individual suspected to be suffering from and/or genetically pre-disposed to a liver-associated disease or disorder is treated prophylactically with a preparation of induced hepatocyte described herein and such prophylactic treatment completely or partially prevents a liver-associated disease or disorder or sign or symptom thereof. In some embodiments, an individual is treated therapeutically (e.g., when an individual is suffering from a liver-associated disease or disorder), such therapeutic treatment causes a partial or complete cure for the disease or disorder and/or reverses an adverse effect attributable to the disease or disorder and/or stabilizes the disease or disorder and/or delays progression of the disease or disorder and/or causes regression of the disease or disorder.

Administration (e.g., transplantation) of induced hepatocyte to the area in need of treatment is achieved by, for example and not by way of limitation, local infusion during surgery, by injection, by means of a catheter, or by means of an implant, said implant being of a porous, non-porous, or gelatinous material, including membranes, such as sialastic membranes, or fibers.

"Transplanting" a composition into a mammal refers to introducing the composition into the body of the mammal by any method established in the art. The composition being introduced is the "transplant", and the mammal is the "recipient". The transplant and the recipient can be syngeneic, allogeneic or xenogeneic. Further, the transplantation can be an autologous transplantation.

An "effective amount" is an amount of a therapeutic agent sufficient to achieve the intended purpose. For example, an effective amount of induced hepatocytes is an amount sufficient, as the case can be, to result in an increase in primary hepatocyte number. An effective amount of a composition to treat or ameliorate a liver-associated disease or disorder is an amount of the composition sufficient to reduce or remove the symptoms of the liver-associated disease or disorder. The effective amount of a given therapeutic agent will vary with factors such as the nature of the agent, the route of administration, the size and species of the animal to receive the therapeutic agent, and the purpose of the administration.

Further provided herein in one embodiment are genetically modified induced hepatocytes. Manipulations modify various properties of the cell, e.g., render it more adapted or resistant to certain environmental conditions, and/or induce a production of one or more certain substances therefrom, which substances can, e.g., improve the viability of the cell. Such genetic alterations can be performed in order to make the cell more suitable for use in transplantation, for example, in order to avoid rejection thereof from the recipient (for reviews of gene therapy procedures, see Anderson, Science, 256:808; Mulligan, Science, 926; Miller, Nature, 357:455; Van Brunt, Biotechnology, 6(10):1149; and Yu et al., Gene Therapy, 1:13).

A "vector" refers to a recombinant DNA or RNA construct, such as a plasmid, a phage, recombinant virus, or other vector that, upon introduction into an appropriate host cell, results in a modification of a progenitor cell described herein. Appropriate expression vectors are well known to those with ordinary skill in the art and include those that are replicable in eukaryotic and/or prokaryotic cells and those that remain episomal or those that integrate into the host cell genome.

Construction of vectors is achieved using techniques described in, for example, as described in Sambrook et al., 1989. In one embodiment isolated plasmids or DNA fragments are cleaved, tailored, and relegated in the form desired to generate the plasmids. If desired, analysis to confirm correct sequences in the constructed plasmids is performed using any suitable method. Suitable methods for constructing expression vectors, preparing in vitro transcripts, introducing DNA into host cells, and performing analyses for assessing gene expression and function are known. Gene presence, amplification, and/or expression are measured in a sample directly, for example, by conventional Southern blotting, Northern blotting to quantitate the transcription of mRNA, dot blotting (DNA or RNA analysis), or in situ hybridization, using an appropriately labeled probe which can be based on a sequence provided herein.

As used herein, terms such as "transfection", "transformation", and the like are intended to indicate the transfer of nucleic acid to a cell or organism in functional form. Such terms include various means of transferring nucleic acids to cells, including transfection with CaPO4, electroporation, viral transduction, lipofection, delivery using liposomes, and/or other delivery vehicles.

Induced Hepatocytes for Treatment of a Disease or Disorder

In some embodiments, induced hepatocytes are administered for the treatment of a liver injury. In some embodiments, liver injury includes damaged or loss of liver tissue due to external factors, such as injury to the host, e.g. injury to an individual, or due to surgery. In some embodiments, liver injury includes damage or loss of liver tissue due to a liver-associated disease or disorder. In some embodiments, the liver-associated disease or disorder is an acute liver disease or disorder such as acute liver failure, or is a chronic liver disease or disorder such as cirrhosis. In some embodiments, the liver-associated disease or disorder is resulted from genetic factors, chemicals or pathogenic infections.

Exemplary liver-associated diseases or disorders include, but are not limited to, alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (e.g. acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis A, B, C, and Wilson disease.

In some embodiments, induced hepatocytes are administered for the treatment of an acute liver disease or disorder. In other embodiments, induced hepatocytes are administered for the treatment of a chronic liver disease or disorder. In some embodiments, induced hepatocytes are administered for the treatment of alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (e.g. acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis A, B, C, Wilson disease, or a combination thereof.

In some embodiments, induced hepatocytes are administered in combination with an additional therapeutic agent for the treatment of a liver-associated disease or disorder. In some embodiments, the additional therapeutic agent includes, but is not limited to, curcumin, resveratrol, thalidomide, cholestyramine (Questran), tacrolimus (PROGRAF), ursodiol (Actigall), interferons, diuretics such as loop diuretics, and liver transplantation.

In some embodiments, chemicals that are toxic to the liver results in chemical-induced liver disease. In some embodiments, chemicals that are toxic to the liver include drugs; consumables such as alcohols, food additives, or preservatives; and chemical and environmental toxins. In some instances, drugs that cause liver injury include, but are not limited to, acetaminophen, allopurinol, anabolic steroids, danazol, dantrolene, imipramine, isoniazid, methotrexate, methyldopa, nicotinic acid, nitrofurantoin, phenothiazines, phenytoin, salicylates, statins, terbinafine HCl, thiabendazole, thorotrast, tolbutamide, chlorpromazine/valproic acid, and chlorpropamide/erythro-mycin.

In some embodiments, pathogenic infections induce liver-associated diseases or disorders. In some embodiments, a pathogen is a virus, a bacterium, a fungus, or a parasite. In some embodiments, the pathogen is a virus. In some embodiments, a viral infection induces liver-associated diseases or disorders.

In some embodiments, a virus is a DNA virus or an RNA virus. In some instances, a DNA virus is a single-stranded (ss) DNA virus, a double-stranded (ds) DNA virus, or a DNA virus that contains both ss and ds DNA regions. In some cases, an RNA virus is a single-stranded (ss) RNA virus or a double-stranded (ds) RNA virus. Sometimes, a ssRNA virus is further classified into a positive-sense RNA virus or a negative-sense RNA virus.

In some instances, a dsDNA virus is from the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

In some instances, an ssDNA virus is from the family: Anelloviridae, Bacillariodnaviridae, Bidnaviridae, Circoviridae, Geminiviridae, Inoviridae, Microviridae, Nanoviridae, Parvoviridae, and Spiraviridae.

In some instances, a DNA virus that contains both ss and ds DNA regions is from the group of pleolipoviruses. In some cases, the pleolipoviruses include Haloarcula hispanica pleomorphic virus 1, Halogeometricum pleomorphic virus 1, Halorubrum pleomorphic virus 1, Halorubrum pleomorphic virus 2, Halorubrum pleomorphic virus 3, and Halorubrum pleomorphic virus 6.

In some instances, a dsRNA virus is from the family: Birnaviridae, Chrysoviridae, Cystoviridae, Endornaviridae, Hypoviridae, Megavirnaviridae, Partitiviridae, Picobirnaviridae, Reoviridae, Rotavirus and Totiviridae.

In some cases, a positive-sense ssRNA virus is from the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Narnaviridae, Nodaviridae, Permutotetraviridae, Picornaviridae, Potyviridae, Roniviridae, Secoviridae, Togaviridae, Tombusviridae, Tymoviridae, and Virgaviridae.

Sometimes, a negative-sense ssRNA virus is from the family: Bornaviridae, Filoviridae, Paramyxoviridae, Rhabdoviridae, Nyamiviridae, Arenaviridae, Bunyaviridae, Ophioviridae, and Orthomyxoviridae.

Exemplary virus includes, but is not limited to: Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

In some embodiments, a viral infection induces a liver-associated disease or disorder. In some embodiments, the viral infection is a hepatitis infection. In some embodiments, the virus is a hepatitis A virus, a hepatitis B virus, a hepatitis C virus, a hepatitis D virus, a hepatitis E virus, a hepatitis F virus, or a hepatitis G virus. In some embodiments, a viral infection that induces a liver-associated disease or disorder is caused by a hepatitis A virus, a hepatitis B virus, a hepatitis C virus, a hepatitis D virus, a hepatitis E virus, a hepatitis F virus, or a hepatitis G virus.

In some embodiments, liver injury arises as a consequence of an immune response to virus within the liver. In some instances, liver injury arises as part of a generalized host infection in which viruses target tissues other than the liver. Exemplary viruses those primary target is not liver include herpes viruses such as Epstein-Barr virus, cytomegalovirus (CMV) or herpes simplex virus; parvovirus; adenovirus; influenza viruses; lentivirus such as human immunodeficiency virus (HIV); and severe acute respiratory syndrome (SARS)-associated coronavirus. In some instances, viral infections described herein results in hepatitis.

In some embodiments, the pathogen is a bacterium. In some embodiments, a bacterial infection induces liver-associated diseases or disorders. Examples of bacteria include: *Helicobacter pyloris, Borelia burgdorferi, Legionella pneumophilia, Mycobacteria* spp. (e.g., *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic spp.), *Streptococcus pneumoniae*, pathogenic *Campylobacter* sp., *Enterococcus* sp., *Haemophilus influenzae, Bacillus anthracis, Corynebacterium diphtherias, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelli*.

In some embodiments, the pathogen is a fungus. In some embodiments, a fungal infection induces liver-associated diseases or disorders. Examples of fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

In some embodiments, the pathogen is a parasite. In some embodiments, a parasitic infection induces liver-associated diseases or disorders. Examples of parasite include: sarcodina (e.g. *Entamoeba*), mastigophora (e.g. *Giardia, Leishmania*), ciliophora (e.g. *Balantidium*), and sporozoa (e.g. *Plasmodium, Cryptosporidium*).

In some embodiments, induced hepatocytes are utilized for regeneration of a defect liver. In some instances, induced hepatocytes are introduced at the site of liver injury. In some cases, induced hepatocytes are introduced or transplanted as a cell suspension to the site of liver injury. In other cases, induced hepatocytes are introduced or transplanted as a tissue mass to the site of liver injury. In other instances, induced hepatocytes are utilized for regeneration of a defect liver ex vivo. In other instances, induced hepatocytes are utilized for ex vivo liver generation prior to transplantation into a site of liver injury.

In some embodiments, induced hepatocytes are formulated as a composition, such as a pharmaceutical composition, for treating a liver injury due to external factors, such as injury to the host, e.g. injury to an individual, or due to surgery.

In some embodiments, induced hepatocytes are formulated as a composition, such as a pharmaceutical composition, for treating a liver injury due to a liver-associated disease or disorder. In some embodiments, induced hepatocytes are formulated as a composition, such as a pharmaceutical composition, for treating alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (e.g. acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, *porphyria*, Reye's Syndrome, sarcoidosis, toxic hepatitis, type 1 glocogen storage disease, tyrosinemia, viral hepatitis A, B, C, Wilson disease, or a combination thereof.

In some embodiments, the composition comprising induced hepatocytes further comprises an additional therapeutic agent. In some embodiment, the additional therapeutic agent is a therapeutic agent for the treatment of a liver-associated disease or disorder. In some embodiments, the additional therapeutic agent includes, but is not limited to, curcumin, resveratrol, thalidomide, cholestyramine (Questran), tacrolimus (PROGRAF), ursodiol (Actigall), interferons, diuretics such as loop diuretics, and liver transplantation.

In some embodiments, the composition comprising induced hepatocytes are utilized at the site of liver injury for regeneration of the liver. In some embodiments, the composition comprising induced hepatocytes are introduced or transplanted as a cell suspension to the site of liver injury. In some embodiments, the composition comprising induced hepatocytes are introduced or transplanted as a tissue mass to the site of liver injury. In other embodiments, the composition comprising induced hepatocytes are utilized for regeneration of a defect liver ex vivo. In other embodiments, the composition comprising induced hepatocytes are utilized for ex vivo liver generation prior to transplantation into a site of liver injury.

Modes of administration of an isolated induced hepatocyte include, but are not limited to, systemic intravenous injection and injection directly to the intended site of activity (e.g., endoscopic retrograde injection). The preparation can be administered by any convenient route, for example, by infusion or bolus injection, and can be administered together with other biologically active agents. In some embodiments, the administration is systemic localized administration.

In some embodiments, a composition comprising induced hepatocytes is formulated as a pharmaceutical composition for intravenous administration to a mammal, including a human. In some embodiments, compositions for intravenous administration are solutions in sterile tonic aqueous buffer. Where necessary, the composition also includes a local anesthetic to ameliorate any pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients are mixed prior to administration.

In some embodiments, suitable pharmaceutical compositions comprise a therapeutically effective amount of the induced hepatocytes and a pharmaceutically acceptable carrier or excipient. Such a carrier includes, but is not limited to, saline, buffered saline, dextrose, water, and combinations thereof.

In some embodiments, the induced hepatocytes described herein are delivered to a targeted site (e.g., a defect section of the liver) by a delivery system suitable for targeting cells to a particular tissue. For example, the cells are encapsulated in a delivery vehicle that allows for the slow release of the cell(s) at the targeted site. The delivery vehicle is modified such that it is specifically targeted to a particular tissue. The surface of the targeted delivery system is modified in a variety of ways. In the case of a liposomal-targeted delivery system, lipid groups are incorporated into the lipid bilayer of the liposome in order to maintain the targeting ligand in stable association with the liposomal bilayer.

In other examples, a colloidal dispersion system is used. Colloidal dispersion systems include macromolecule complexes, nanocapsules, microspheres, beads, and lipid-based systems, including oil-in-water emulsions, micelles, mixed micelles, and liposomes.

The administration of induced hepatocytes described herein is optionally tailored to an individual, by: (1) increasing or decreasing the amount cells injected; (2) varying the number of injections; or (3) varying the method of delivery of the cells.

The induced hepatocyte preparation is used in an amount effective to promote engraftment of cells in the recipient. At the physician's discretion, the administration is adjusted to meet optimal efficacy and pharmacological dosing.

Induced Hepatocytes for Production of Therapeutic Proteins

In some embodiments, induced hepatocytes are utilized for the production of therapeutic proteins (e.g. hormones), cytokines, cholesterols, carbohydrates, bile, or a combination thereof. In some instances, induced hepatocytes are utilized for the production of therapeutic proteins. In some instances, the therapeutic proteins include full length proteins, domains or fragments thereof, or peptides. In some instances, the proteins, domains or fragments thereof, or peptides containing natural and/or unnatural amino acid residues. In some cases, the therapeutic proteins, their fragments thereof, or peptides, include, but are not limited to, major plasma proteins such as human serum albumin, soluble plasma fibronectin, α-fetoprotein, C-reactive protein, and several globulins; proteins involved in hemostasis and fibrinolysis such as coagulation factors involved in the coagulation cascade, α2-macroglobulin, α1-antitrypsin, antithrombin III, protein S, protein C, plasminogen, α2-antiplasmin, and complement component 3; carrier proteins such as albumin, ceruloplasmin, transcortin, haptoglobin, hemopexin, IGF binding rotein, major urinary proteins, retinol binding protein, sex hormone-binding globulin, transthyretin, transferrin, and Vitamin D-binding protein; hormones such as insulin-like growth factor 1, thrombopoietin, hepcidin, and betatrophin; prohormones such as angiotensinogen; and apolipoproteins. In some embodiments, induced hepatocytes are utilized for the production of hormones or its fragments thereof. In some embodiments, induced hepatocytes are utilized for the production of insulin-like growth factor 1, thrombopoietin, hepcidin, betatrophin, angiotensinogen, or their fragments thereof.

In some instances, induced hepatocytes are utilized for the production of cytokines. As described elsewhere herein, cytokines include chemokines, interferons, interleukins, and tumor necrosis factors. In some embodiments, cytokines are proinflammatory cytokines. In some embodiments, the cytokines include C—X—C and C—C subfamilies of chemokines: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some embodiments, the cytokines include growth related (GRO)-alpha, GRO-beta, GRO-gamma, epithelial neutrophile activating peptide-78 (ENA-78), RANTES, TNF-alpha, IL-1β, IL-6, IL-8, MCP-1, M-CSF, IFN-α, IFN-β, and cytokine-induced neutrophil chemoattractant (CINC). In some instances, induced hepatocytes are utilized for the production of one or more cytokines described herein. In some embodiments, induced hepatocytes are utilized for the production of cytokines including, but not limiting to: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, growth related (GRO)-alpha, GRO-beta, GRO-gamma, epithelial neutrophile activating peptide-78 (ENA-78), RANTES, TNF-alpha, IL-1β, IL-6, IL-8, MCP-1, M-CSF, IFN-α, IFN-β, and cytokine-induced neutrophil chemoattractant (CINC).

In some instances, induced hepatocytes are utilized for the production or process of cholesterol. As used herein, the term "cholesterol" includes cholesterol, its stereoisomers (e.g. nat-cholesterol, or ent-cholesterol), naturally occurring cholesterols, genetically modified cholesterol, or their fragments thereof. In some embodiments, induced hepatocytes are utilized for the production or process of nat-cholesterol or its fragments thereof. In some embodiments, induced hepatocytes are utilized for the production or process of ent-cholesterol or its fragments thereof.

In some instances, induced hepatocytes are utilized for the production or process of carbohydrates. In some instances, induced hepatocytes are utilized for the formation, breakdown or interconversion of carbohydrates, gluconeogenesis, glycogenolysis, glycogenesis, lipid metabolism including cholesterol synthesis as disclosed above, and lipogenesis.

In some instances, induced hepatocytes are utilized for the production of bile.

As used herein, an amino acid residue can refer to a molecule containing both an amino group and a carboxyl group. Suitable amino acids include, without limitation, both the D- and L-isomers of the naturally-occurring amino acids, as well as non-naturally occurring amino acids prepared by other metabolic routes. The term amino acid, as used herein, includes, without limitation, α-amino acids, natural amino acids, non-natural amino acids, and amino acid analogs.

The term "α-amino acid" can refer to a molecule containing both an amino group and a carboxyl group bound to a carbon which is designated the α-carbon.

The term "β-amino acid" can refer to a molecule containing both an amino group and a carboxyl group in a β configuration.

"Naturally occurring amino acid" can refer to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" refers to a molecule which is structurally similar to an amino acid and which can be substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids include, without limitation, p-acetylphenylalanine, m-acetylphenylalanine, p-(3-oxbutanoyl)-1-phenylalanine, p-(2-amino-3-hydroxyethyl)phenylalanine, p-isopropylthiocarbonyl-phenylalanine, p-ethylthiocarbonyl-phenylalanine, o-propargyloxyphenylalanine, p-azidophehylalanine, phenyl selenidylalanine, p-benzoyl-1-phenylalanine, or p-boronophenylalanine.

Induced Hepatocytes for Liver Regeneration

In other embodiments, induced hepatocytes are utilized for liver regeneration. In other embodiments, induced hepatocytes are utilized for ex-vivo liver regeneration. In some cases, the ex-vivo liver regeneration utilizes an ex vivo perfusion system. In some instances, the ex vivo perfusion system include ex vivo perfusion bioreactor system (e.g. a 3D perfusion bioreactor system). In some cases, the ex-vivo liver regeneration utilizes a bioprinting system. In some instances, the bioprinting system is a 3 dimensional (3D) bioprinting system. In some cases, the ex-vivo liver regeneration utilizes a 3D bioprinting system. In some embodiments, a 3D bioprinting system includes Organovo's NovoGEn MMX Bioprinter, EnvisionTEC's BioPlotter®, GeSims BioScaffolder 2.1, or regenHu's BioFactory®. In some embodiments, a 3D bioprinting system includes the 3D printing technology from OxSyBio.

In some embodiments, a 3D bioprinting system includes the system described in: U.S. Pat. Nos. 8,691,974, 8,691,274, US20140052285, US20140012407, US20140099709, US20140093932, US20130304233, US20130004469, US20130017564, US20130164339, US20120089238, US20110250688, US20090208466, EP2679669, WO2014039427, WO2013181375, WO2013040087, and WO2012122105.

In some embodiments, induced hepatocytes are utilized for liver regeneration using a perfusion system (e.g. an ex vivo perfusion system). In some embodiments, induced hepatocytes are utilized for liver regeneration using an ex vivo perfusion bioreactor system (e.g. a 3D perfusion bioreactor system). In some instances, induced hepatocytes are utilized for liver regeneration using a bioprinting system (e.g. a 3D bioprinting system). In some instances, induced hepatocytes are utilized for liver regeneration using Organovo's NovoGEn MMX Bioprinter, EnvisionTEC's BioPlotter®, GeSims BioScaffolder 2.1, or regenHu's BioFactory®. In some instances, induced hepatocytes are utilized for liver regeneration using the 3D printing technology from OxSyBio.

In some cases, induced hepatocytes are utilized for liver regeneration using a 3D bioprinting system described in: U.S. Pat. Nos. 8,691,974, 8,691,274, US20140052285, US20140012407, US20140099709, US20140093932, US20130304233, US20130004469, US20130017564, US20130164339, US20120089238, US20110250688, US20090208466, EP2679669, WO2014039427, WO2013181375, WO2013040087, or WO2012122105.

In some instances, induced hepatocytes are utilized for generation of tissue scaffolds through one or more of the methods described above. In some instances, the tissue scaffold is a 2 dimensional (2D) tissue scaffold or a 3 dimensional (3D) tissue scaffold. In some instances, the tissue scaffold is a 3D tissue scaffold. In some instances, induced hepatocytes are utilized for generation of 3D tissue scaffolds. In some embodiments, the 3D-scaffold is pre-coated with one or more extracellular matrix components, e.g., gelatin, laminin, fibronectin, collagen, polylysine, vitronectin, hyaluronic acid, hyaluronan hydrogels, silk fibroin, chitosan or a composite of any of the aforementioned. In some embodiments, the cells are seeded at higher density on the 3D scaffolds than on the 2D cultures, such as threefold higher or fivefold higher or tenfold higher. In some embodiments, the cells are seeded in the presence of cell survival factor, such as an inhibitor of ROCK Rho kinase.

In some aspects, a biocompatible substrate is used to generate the tissue herein, e.g., culturing cells under a culture medium on a three dimensional biocompatible substrate. In some embodiments, the biocompatible substrate comprises a polymeric substrate. In some embodiments, the biocompatible substrate is biodegradable. In some embodiments, the polymeric substrate comprises poly(caprolactone) (PCL). In some embodiments, the polymeric substrate is selected from the group consisting of polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, teflon RTM, nylon silicon, poly(styrene-block-butadiene), polynorbornene, hydrogels, metallic alloys and oligo(ε-caprolactone)diol. In some embodiments, the biocompatible substrate comprises a synthetic polymer. According to some embodiments of the invention, the biocompatible substrate comprises a natural polymer. In some embodiments, the biodegradable substrate is selected from the group consisting of poly(caprolactone) (PCL), polyglycolic acid, poly (DL-lactic-coglycolic acid), cat gut sutures, cotton, cellulose, gelatin, dextran, alginate, fibronectin, laminin, collagen, hyaluronic acid, polyhydroxyalkanoate, poly 4 hydroxybutirate (P4HB) and polygluconic acid (PGA).

Induced Hepatocytes as a Source for Gene Therapy

In additional embodiments, induced hepatocytes are utilized as a source for gene therapy. In some instances, the gene therapy is an ex vivo gene therapy. In some instances, induced hepatocytes are utilized as a therapeutic agent for gene therapy treatment of a liver-associated disease or disorder. In some instances, the gene therapy treatment is an induced hepatocyte-based gene therapy. In some instances, the induced hepatocyte-based gene therapy is utilized such as for example replacing defective or missing gene products, preventing allograft rejection, repopulating host liver, aid in generating xenogeneic hepatocytes, or tailored for patient-specific liver treatment or regeneration.

As described elsewhere herein, a liver-associated disease or disorder includes alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (e.g. acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis A, B, C, and Wilson disease.

In some instances, induced hepatocytes are utilized as a therapeutic agent for gene therapy treatment of alagille syndrome, alpha 1 anti-trypsin deficiency, autoimmune hepatitis, benign liver tumors, biliary atresia, cirrhosis, cystic disease of the liver, fatty liver disease including alcohol-related liver disease and non-alcohol fatty liver disease (NAFLD), galactosemia, gallstones, Gilbert's Syndrome, hemochromatosis, liver cysts, liver cancer, liver disease in pregnancy (e.g. acute fatty liver of pregnancy, intrahepatic cholestasis of pregnancy, preeclampsia, or HELLP Syndrome (hemolysis, elevated liver tests, low platelets)), neonatal hepatitis, primary billary cirrhosis, primary sclerosing cholangitis, porphyria, Reye's Syndrome, sarcoidosis, toxic hepatitis, type 1 glocogen storage disease, tyrosinemia, viral hepatitis A, B, C, Wilson disease, or a combination thereof.

In some instances, genes are transferred into induced hepatocytes via viral or nonviral means. In some instances, viral means include vectors such as from murine leukemia retroviruses and lentiviruses, adenoassociated virus, T-antigen-deleted SV40 virus, neurotropic viruses such as Herpes simplex virus, episomal viruses and hybrid viruses such as adenoassociated viruses. In some instances, nonviral means include lipoplexes, polyplexes, dendrimers, inorganic nanoparticles, or hybrid vectors such as virosomes, which are a combination of liposomes with an inactivated virus such as HIV or influenza virus. In some instances, additional non-viral means include injection of naked DNA, electroporation, gene gun, sonoporation, or magnetofection. Methods of gene transfer by viral or nonviral means are well known in the art and are described for example, in Guha et al. "Hepatocyte-based gene therapy," *J Hepatobillary Pancreat Surg.* 8(1):51-57 (2001).

As used herein, a gene can contain at least two nucleotides linked together. In some instances, a nucleic acid described herein can contain phosphodiester bonds, natural nucleic acids, or unnatural nucleic acids. A natural nucleic acid include both deoxyribonucleic acid (DNA) and robonucleic acid (RNA) and is known by the one letter abbreviations A, T, G, C, and U. Exemplary unnatural nucleic acids include, without limitation, diaminopurine, isoguanine, isocytosine, 2-amino-6-(2-thienyl)purine, pyrrole-2-carbaldehyde, 2,6-bis(ethylthiomethyl)pyridine, pyridine-2,6-dicarboxamide, 4-methylbenzimidazole, 2,3-difluorotoluene, d5SICS, and dNaM.

Diagnostic Methods

Methods for determining the expression or presence of biomarkers described supra are well known in the art, and can be measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

By "detecting expression" or detecting "expression levels" is intended for determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In some embodiments, the expression or presence of a biomarker described herein is determined at a nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of a biomarker is carried out through gel electrophoresis. In one embodiment, the determination is carried out through transfer to a membrane and hybridization with a specific probe.

In other embodiments, the determining the expression or presence of a biomarker is carried out by a diagnostic imaging technique.

In still other embodiments, the determining the expression or presence of a biomarker is carried out by a detectable solid substrate. In one embodiment, the detectable solid substrate is paramagnetic nanoparticles functionalized with antibodies.

In some embodiments, the expression or presence of a biomarker is at an RNA (e.g. mRNA) level. In some embodiments, techniques that detect RNA (e.g. mRNA) level include, but are not limited to, Southern or Northern analyses, polymerase chain reaction analyses and probe arrays.

One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker described herein. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In some embodiments, biomarker expression is assessed by quantitative fluorogenic RT-PCR (i.e., the TaqMan® System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In some embodiments, microarrays are used to determine expression or presence of one or more biomarkers. Nucleic acid microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

In some embodiments, the expression or presence of a biomarker described herein is determined at a protein level, using, for example, antibodies that are directed against specific biomarker proteins. These antibodies are used in various methods such as Western blot, ELISA, multiplexing technologies, immunoprecipitation, or immunohistochemistry techniques. In some embodiments, detection of biomarkers is accomplished by ELISA. In some embodiments, detection of biomarkers is accomplished by electrochemiluminescence (ECL).

Any means for specifically identifying and quantifying a biomarker in the biological sample is contemplated. Thus, in some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression or presence of one or more biomarkers or other proteins of interest within a biological sample is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of use.

For example, the container(s) include hTS cells, optionally in a composition as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1

Cell Culture and Differentiation

Undifferentiated hTS cells were maintained in α-MEM (Gibco) supplemented with 10% (v/v) fetal bovine serum (SAFC Biosciences). Cultures were manually passaged at a 1:3-1:6 split ratio every 2-3 days. Differentiation of DE was carried out by a conditioned α-MEM media containing 10% FBS, 1 mM 2-mercaptoethanol, 10 mM nicotinamide, and 10 ng/ml bFGF for 8 hr in 37° C., 5% $CO_2$ incubator. For hepatocytic differentiation, cultured medium was added with dexamethasone (0.1 µM, Sigma) and recombinant human oncostatin M (10 ng/ml, Excel-Biomedical Inc.) and incubated for an additional 4 days or 6 days.

The study was approved by the Institutional Review Board on Human Subjects Research and Ethics Committees, Kaohsiung Medical University Hospital. The hTS cells were obtained with informed consent.

Plasmids

MiR-124a precursor and anti-miR-124a were purchased from System Biosciences. Briefly, miR-124a precursor (60 pmol) or anti-miR-124a (60 pmol) was transfected to hTS cells in 12-well culture dishes using TransIT-LT1 transfection reagent (Minis, Madison, Wis.). Total RNAs were used for quantifying miR-124a at 36 hr after transfection. Small interfering RNA (siRNA) targeting PI3K (SASI_Hs01_00233971 and SASI_Hs01_00127787), AKT1 (SASI_Hs01_00205545), and AKT2 (SASI_Hs01_00035055) were purchased from Sigma. Short hairpin RNA (shRNA) targeting CREB1 (TRCN0000007310, TRCN0000226467 and TRCN0000226468), SMAD4 (TRCN0000010321, TRCN0000010323 and TRCN0000040032), AKT3 (TRCN0000001615 and TRCN0000001616), OCT4 (TRCN0000004879 and TRCN0000004882), CDX2 (TRCN0000013683 and TRCN0000013686), and control shRNA (shGFP; TRCN0000072178, TRCN0000072179 and TRCN0000072183) were purchased from National RNAi Core platform, Academia Sinica, Taiwan. Transfection was performed with siRNA or shRNA at 2 µg plus 4 µl transfection reagent.

Western Blot and Immunoprecipitation (IP)

For immunoblotting assay, cells were harvested into RIPA lysis solution (Millipore, Billerica, Mass.) supplemented with protease and phosphatase inhibitors (Roche). After electrophoresis of 30 µg lysates on polyacrylamide gels, electroblotting onto PDVF membranes (Millipore) was performed. After blocked by 5% non-fat milk in PBS at room temperature (1 hr), target protein was detected by using primary antibody. All membranes were incubated with chemiluminescent (Millipore) and imaging was captured by the ChemiDoc XRS system (Bio-RAD). Antibodies used were listed in Table 1. Data were analyzed by AlphaEaseFC (version 4.0.0) system. For IP assay, Cell lysates of bFGF-treated hTS cells were collected. By incubation with protein G-agarose (Millipore) for 30 min, total protein (100 µg) was treated with specific primary antibody overnight listed in Table 1. After treating with protein G-agarose beads (2 hr), sample was washed three times with RIPA lysis buffer (Millipore), following by adding with protein loading dye and boiled for 5 min. The sample was resolved by 8% SDS-PAGE and subjected to immunoblotting analysis.

mRNA, miRNA, and Chromatin Immunoprecipitation (CHIP)-qPCR Assays

For mRNA expression, RNA was isolated from hTS cells in triplicate or quintuple samples using TRIZOL reagent (Invitrogen) with DNAase I on-column digestion (Qiagen, Valencia, Calif.). Total RNA (500 ng) was used for reverse transcription with iScript cDNA synthesis kit (Bio-Rad). Real-time polymerase chain reaction (qPCR) was carried out in duplicate using $\frac{1}{40}^{th}$ of the cDNA per reaction and 400 nM forward and reverse primers. Comparative real-time PCR was carried out at least triplicate using the Power SYBR® Master Mix (Applied BioSystems) with the 7500 Real-Time PCR System (Applied Biosystems). All genes were normalized to the GAPDH expression and were normalized to the expression of undifferentiated hTS cells using the ΔΔCt method. Primer sequences used in this study are illustrated in Table 2.

For miRNA analysis, 25 ng of total RNA was reverse-transcribed using the TaqMan MicroRNA Reverse Transcription Kit (Applied Biosystems). qPCR was carried out at least triplicate using the TaqMan Universal PCR Master Mix (Applied Biosystems) with the 7500 Real-Time PCR System (Applied Biosystems) including no-template controls, using specific primers for miR-124a or RNU6B (Applied Biosystems). U6 snRNA (RNU6B; Applied Biosystems) served as an endogenous control.

For ChIP assay, hTS cell samples of indicated time in induction were fixed with a final concentration of 1% formaldehyde. After incubation at room temperature (10 min), the reaction was stopped by adding glycine (125 mM). ChIP assay was performed using a protocol associated with the ChIP assay kit (Upstate Biotechnology). After extensive washing, ChIPed DNA was eluted from the beads and analyzed by qPCR.

Luciferase Reporter Assay

To prepare the luciferase-3' UTR reporter plasmids, 3'UTR fragments from genomic DNA extract of hTS cells were amplified. The 3' UTR PCR fragment was cloned into the pGL4.51 vector (Promega, Madison, Wis.) downstream of the luciferase gene by using PsiI and MfeI (Thermo Scientific, Rockford, Ill.). Primers for 3' UTR reporter construct were listed as followings: For CDX2 3' UTR region: forward, 5'-aaattataagctgtttgggttgttggtct-3' (SEQ ID NO: 1) and reverse, 5'-aaacaattgcccccataatttctgactgc-3 (SEQ ID NO: 2); For SMAD4 3' UTR region 1: forward, 5'-aaattataactcccaaagtgctgggatta-3' (SEQ ID NO: 3) and reverse, 5'-aaacaattgctgcactgttcacaggagga-3 (SEQ ID NO: 4); For SMAD4 3' UTR region 2: forward, 5'-aaattataacagttgtcccagtgctgcta-3' (SEQ ID NO: 5) and reverse, 5'-aaacaattgatgacttgcccaaaggtcac-3 (SEQ ID NO: 6); For GSK3β3' UTR region: forward, 5'-aaattataacccacaactggggtaaaaga-3' (SEQ ID NO: 7) and reverse, 5'-aaacaattgctgtggaaggggcaaagata-3 (SEQ ID NO: 8).

For dual luciferase assays, firefly luciferase reporter (500 ng) or empty vector without any 3'UTR co-transfected with pGL4.74 and renilla luciferase plasmid (500 ng, Promega), and non-specific control miRNA (30 pmol) or miR-124a precursor (30 pmol; System Biosciences, Mountain View, Calif.) were co-transfected to hTS cells ($1.5 \times 10^4$ cells in each well) using TransIT®-LT1 transfection reagent (Minis Bio LLC, Madison, Wis.). After transfection (36 hr), the luciferase activity was analyzed by the dual luciferase reporter assay system (Promega) and the Centro LB 960 Microplate Luminometer (Berthold Technologies, Bad Wildbad, Germany). For evaluation, renilla luciferase value was first normalized to the firefly luciferase activity and the calculated activity of each 3'UTR reporter was further normalized to the control vector. Data represented as mean±SD, n=8, p<0.05 as statistic significance. Whole cell extracts prepared in the cell lysis buffer were subjected to immunoblotting with CDX2, SMAD4, GSK3β, and β-actin antibodies.

Immunofluorescence Staining

Slides with cell culture was fixed for 30 min at room temperature in 95% (v/v) ethanol, washed three times in PBS and incubated with blocking buffer PBS containing 0.1% (wt/v) Triton X-100 (Sigma) and 5% (v/v) normal donkey serum (Millipore) for 60 min. Primary and secondary antibodies were diluted in blocking buffer. Primary antibody was incubated. After incubation with specific primary antibody in PBS at 4° C. (24 hr) or room temperature (2 hr), appropriate fluorescein isothiocynate (FITC, Invitrogen) or Alexa Fluor 488, 594, and 647 (Invitrogen) or Dylight 488 and 594 (BioLegend) conjugated secondary antibody was added at room temperature (1 hr). After DAPI staining of nucleus (5 min), incubation with secondary antibody (1 hr) at room temperature, and washes, sample was mounted with 50% glycerol. Images were captured by confocal laser scanning microscopy (LSM700; Zeiss Z1 or Olympus FluoView 1000 confocal laser scanning microscope) or TissueFAXS system (TissueQnostics GmbH, Vienna, Austria). Data were analyzed by TissueQuest software.

Flow Cytometry

After transfection with non-specific shRNA or shRNAs against CDX2, OCT4, SOX2, and NANOG, cells ($5 \times 10^6$ cells/ml) were incubated with specific primary antibodies for 30 min as listed in Table 1. Followed by incubation with the appropriate fluorescent dye-conjugated primary antibody at adjusted dilution for 1 hr at 4° C., samples were washed and re-suspended in PBS. After passing through polystyrene round-bottom tube with cell strainer cap (BD Falcon), sample was subjected for flow cytometry (FACScan, BD Biosciences, San Jose, Calif.). Data were analyzed with Cell-Quest software (BD Biosciences).

Electron Microscopy

For transmission electron microscopy, the hTS cell-derived hepatocytes-like cells (at day 4 after induction) were fixed in 0.1 M sodium cacodylate buffer (pH 7.4) containing 3% wt/vol formaldehyde, 1.5% (wt/vol) glutaraldehyde and 2.5% (wt/vol) sucrose at room temperature (RT) for 1 hr or at 4° C. overnight. The samples were washed with 0.1 M sodium cacodylate buffer (pH 7.4) before and after osmication treatment (2 hr) at 4° C. in Palade's fixative containing 1% (vol/vol) $OsO_4$. After treated with tannic acid, stained with 1% uranyl acetate, and dehydrated through a graded series of ethanol solutions, sample was embedded in TABB epoxy resin (Agar Scientific Ltd.). Ultrathin sections were stained with uranyl acetate and lead citrate and analyzed by using JEM-2000 EXIT Transmission electron microscope (JEOL, Tokyo).

LDL Uptake Assay

LDL uptake was performed by using LDL Uptake Cell-Based Assay Kit as manufacturer's instruction (Cayman Chem Co. Ann Arbor, Mich.). Briefly, $5 \times 10^4$ cells were seeded at coverslip in each well of a 24-well plate. hTS cells (as control) and the differentiated hepatocyte-like cells (hHLCs) were fixed after 5 μg/ml LDL-DyLight™ 549 probe treatment (4 hr, 37° C.) and then stained for LDL receptor by rabbit anti-LDL and DyLight™ 488-conjugated Goat anti-rabbit antibody. Nuclei were visualized with DAPI. The final staining was observed by fluorescence microscopy.

Oil-O-Red Test

For detection of lipid accumulation, differentiated cells were fixed with 4% paraformaldehyde (20 min) at room temperature (RT) and washed with 60% isopropanol for 5 min. After incubation at RT (20 min) with a freshly prepared 60% Oil Red 0 solution (0.5 g Oil Red 0 in 100 ml isopropanol passed through a 0.22 μm filter before using, Sigma), cells were rinsed with 60% isopropanol and counterstained with Hematoxylin I (Thermo Scientific) for microscopy.

Glycogen Storage Test

For glycogen detection, differentiated cells were fixed by 4% paraformaldehyde. Fixed samples were permeabilized with 0.4% Triton X-100. Undifferentiated control cells were incubated with Diastase (1 mg/ml in PBS; Sigma) for 1 hr at 37° C. Cells were incubated with periodic acid (0.5 g dissolved in 100 ml distilled water) for 5 min at RT, washed with distilled water, and incubated with fresh prepared Schiff's reagent (15 min) and subjected for microscopy.

Albumin and Urea Assays

The concentrations of total protein, albumin, and urea in the culture medium of hTS cells were measured before and after induction by an automatic analyzer (Hitachi 7080; Tokyo, Japan).

Statistical Analysis

All of the experiments were conducted in triplicate and repeated two times as indicated. Data obtained from Western blots, qPCR, luciferase reporter assay, and flow cytometry were calculated by Student's t-test. p-value <0.05 was considered statistically significant.

A Cellular Process from hTS Cells to DE Lineages.

Figure 7:
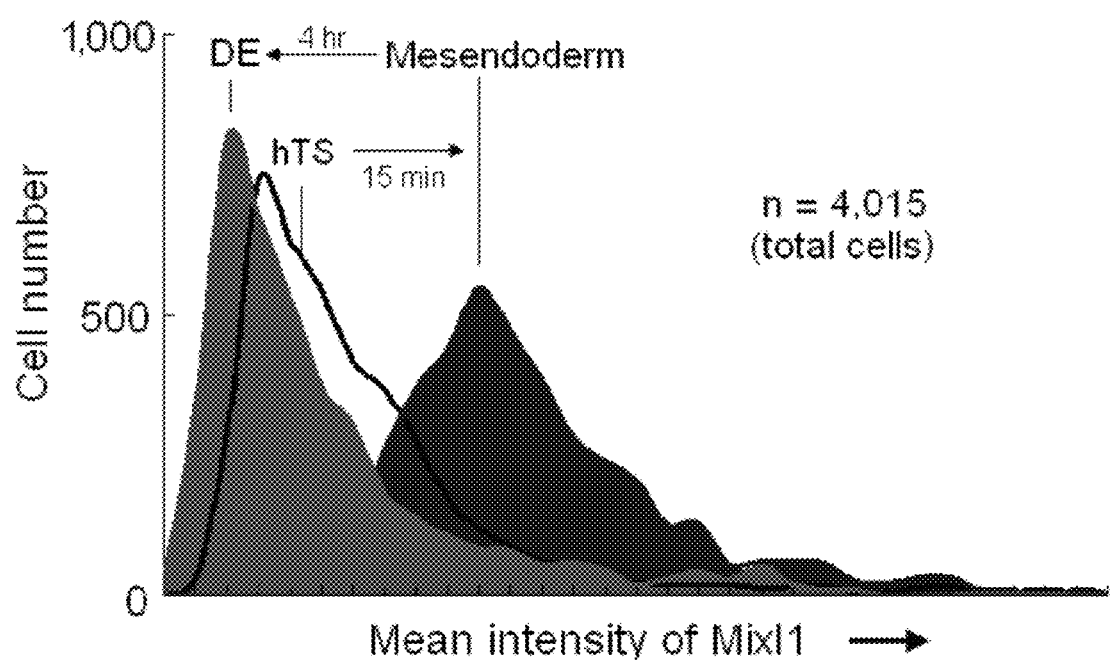
FIG. 7 illustrates the cellular processes of DE formation by TissueFAX analysis. bFGF (10 ng/mL) was used to induce differentiation of hTS cells to mesendoderm indicated by upregulation of MIXL1 (black). Subsequently, the mesendoderm differentiated into DE lineage at about 4 hours induction, expressing a downregulation of MIXL1 (grey). n indicates the total number of cells counted.

Differentiation of human pluripotent stem cells to hepatocyte-like cells, DE formation is the first step needed to be identified during the cell processes. It was found that in hTS cells, bFGF (10 ng/ml) enabled to efficiently yield DE at 8 hr induction, expressing specific biomarkers; forkhead box protein A2 (FOXA2) and SRY-box 17 (SOX17), Goosecoid (GSC), and Homeodomain protein MIXL1 by immunofluorescence microscopy (FIG. 1A-1C). Subsequently, a timeline expression of the DE-associated markers was established, including transcription factors: GSC, brachyury (T), MIXL1, SOX17, and FOXA2, upon bFGF induction by immunoblotting assays (FIG. 1D). It was found that levels of MIXL1, Brachyury, and GSC significantly elevated at the initial 15 min, suggesting a transition of primitive streak. These levels, however, declined after 30 min, implicating a migration from primitive streak to a nascent mesendoderm. Specifically, MIXL1 levels decreased from the peak (15 min) down to a nadir (~50% lower than the native one) at 4 hr and, henceforth, the levels returned to the original ones. This fact was supported by imaging study (FIG. 1C) and TissueFAX analysis (FIG. 7). These results suggested the cellular processes moving from the mesendoderm to the DE stage because: i) MIXL1 mRNA expression is absent from endoderm but confined to the mesoderm, and ii) loss of MIXL1 has an impact on the endoderm potential of the mesendoderm progenitors as MIXL1 is expressed specifically in the primitive streak. SOX17 levels upregulated to peak at 2 hr (1.5-fold) but downregulated at 8 hr; while a continually upregulated FOXA2 to the highest levels (3-fold) at 8 hr (FIG. 1D). However, there was a downregulation of GSC from 30 min to 1 hr but still sustained at a slightly higher than the original levels (FIG. 1D). To this end, these data suggest that bFGF (10 ng/ml) enables to induce transdifferentiation of hTS cells to DE lineages in a highly efficient manner by upregulating SOX17, FOXA2, and GSC, but downregulating MIXL1 at 8 hr induction. Wherefrom, DE gives rise to epithelial lining of the lungs, esophagus, stomach, and intestines, as well as endocrine glands such as the liver, pancreas, and thyroid.

Dexamethasone and SOX17 Driving Differentiation to Hepatic Fate by HNF4α Expression Hepatocyte nuclear factor 4 (HNF4) is an essential transcription factors for specification of human hepatic progenitor cells. Since dexamethasone (Dexa) induces HNF4α expression and cytokine oncostatin M (OSM) involves in the fetal liver development. It was found that by adding dexamethasone (0.1 μM) and oncoststin M (10 ng/ml) to the conditioned culture medium at 8 hr of induction resulted in the differentiation of hepatocyte-like cells, expressing hepatic markers after 4 days by immunostainings, for example, albumin, α-fetoprotein (AFP), biliary transport protein MRP2 (ABCC2), and bile salt export pump (B SEP) (FIG. 1E).

Figure 1F:
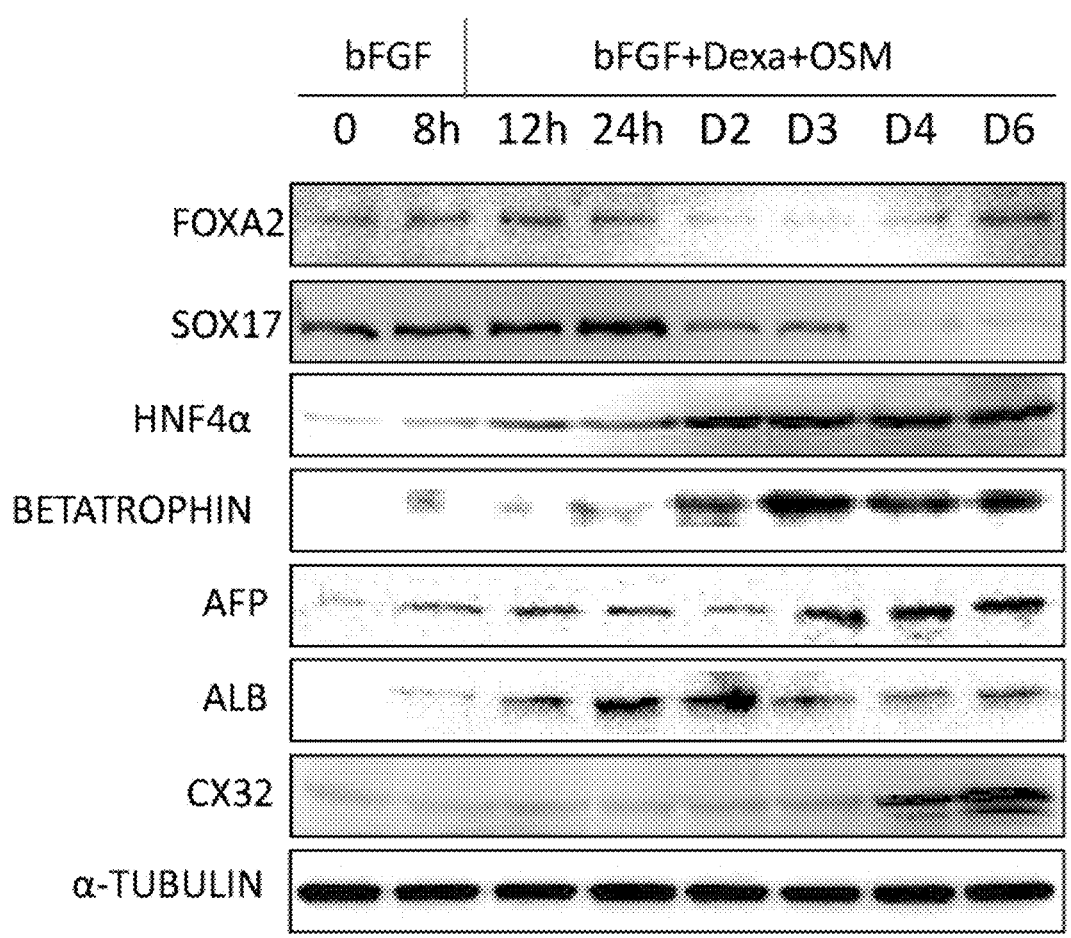

Subsequently, immunoblotting assays in time course revealed that both FOXA2 and SOX17 sustained at a higher level towards 24 hr, following a sudden declination at day 2 (FIG. 1F). Interestingly, SOX17 can directly activate zinc finger protein 202 (ZFP202) that suppresses HNF4α during endoderm differentiation. In DE stage, a significant reduction of SOX17 levels after peaking (2 hr) (FIG. 1D) that probably indirectly reduced the suppressive effect on HNF4α; thereby, facilitated the dexamethasone-induced HNF4α activation. As such a combinatory effect of bFGF, dexamethasone, and SOX17 withdrawal devotes the initiation of hepatic specified endoderm by HNF4α expression. Moreover, albumin expressed after 12 hr, supporting a differentiation to hepatic endodermal lineages (FIG. 1F). Consequently, active HNF4α may control morphological and functional differentiation of hepatocytes; thereby, the entrance of hepatoblastic stage can take place at day 2 of induction. The appearance of AFP at day 3 indicated a cell process of fetal immature hepatocytes. Interestingly, a peak level of betatrophin appeared at day 3, suggesting its involvement in the regulation of nutrition and lipid metabolism. Taken together, hTS cells can be efficiently differentiated to hepatocyte-like cells within week, mimicking cellular processes of primary hepatocytes in embryogenesis. Indeed, these findings suggest that this two-step regimen enables to generate hepatocyte-like cells from hTS cells distinct from the time-consuming protocols reported previously in hES cells and iPS cells.

Regulatory Mechanisms of miRNA-124a in DE Specification.

Figure 2A:
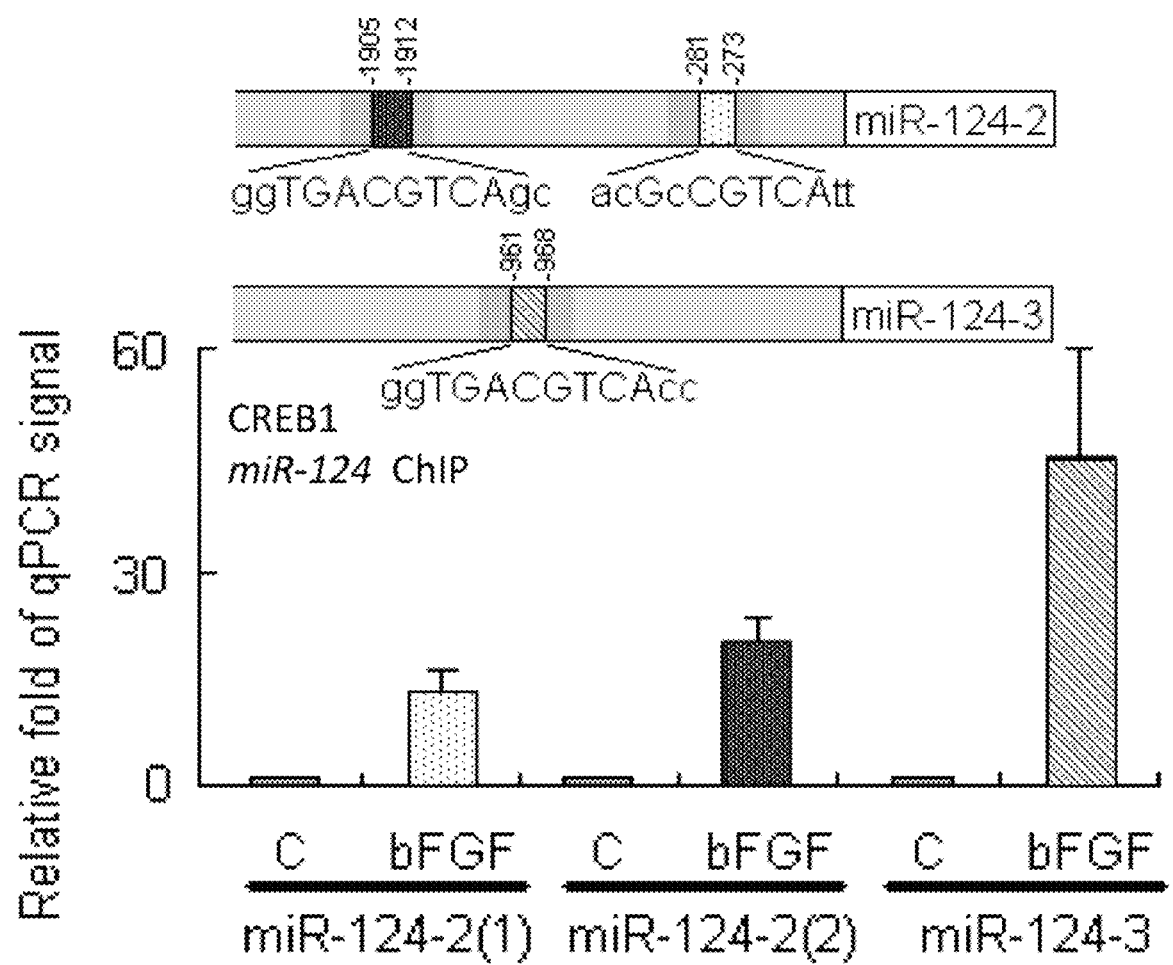
Figure 2B:
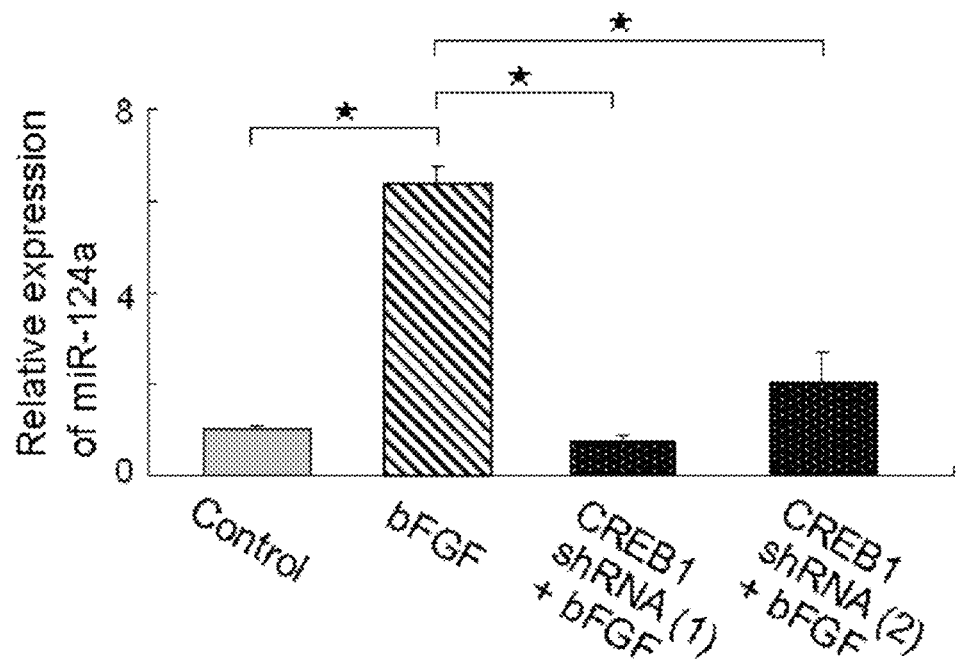
Figure 2C:
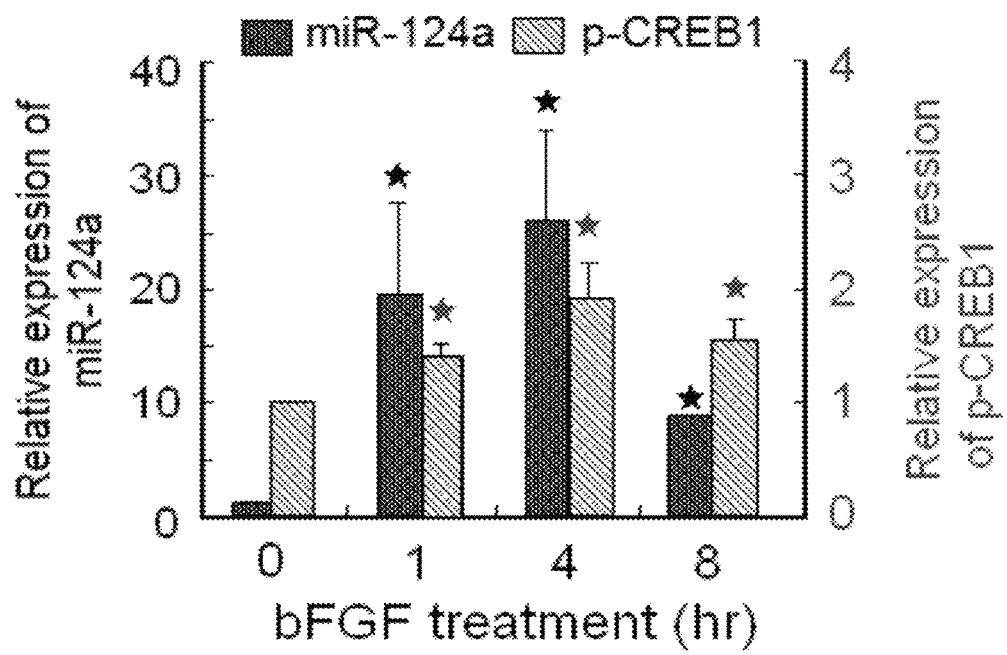

Understanding the molecular mechanisms of how bFGF induces DE formation are essential and required for further hepatic differentiation. bFGF enabled to induce the PI3K/AKT/CREB1 signaling pathway via its receptor FGFR1 (FIG. 8A-8D). Activation of CREB1 therefore allowed us to focus on the involvement of microRNAs (miRs), the small non-coding RNAs, because of two reasons: i) miR-124a enables to regulate FOXA2 in pancreatic β-cells, the hepatocyte counterpart of DE-derivation and ii) miR-124 binding to the site of CREB1 gene is conserved in the mammalian CREB1 3'UTR. Generally, miRs play as key regulators involved in various biological processes including the stem cell differentiation by inhibiting translation and/or to cause RNA degradation. To that, it was found that active CREB1 enabled to target at three sites of the promoter of miR-124a mRNA by ChIP-qPCR assay to promote miR-124a expression (FIG. 2A). This action was supported by knockdown of CREB1 that reduced miR-124a expression (FIG. 2B) and, also, a parallel correlation in expression by qPCR assay (FIG. 2B). Together, these results suggest that bFGF enables to induce the PI3K/AKT/CREB1 signaling pathway and, in turn, CREB1 promoted miR-124a expression peaking at 4 hr induction during DE stage.

Figure 2E:
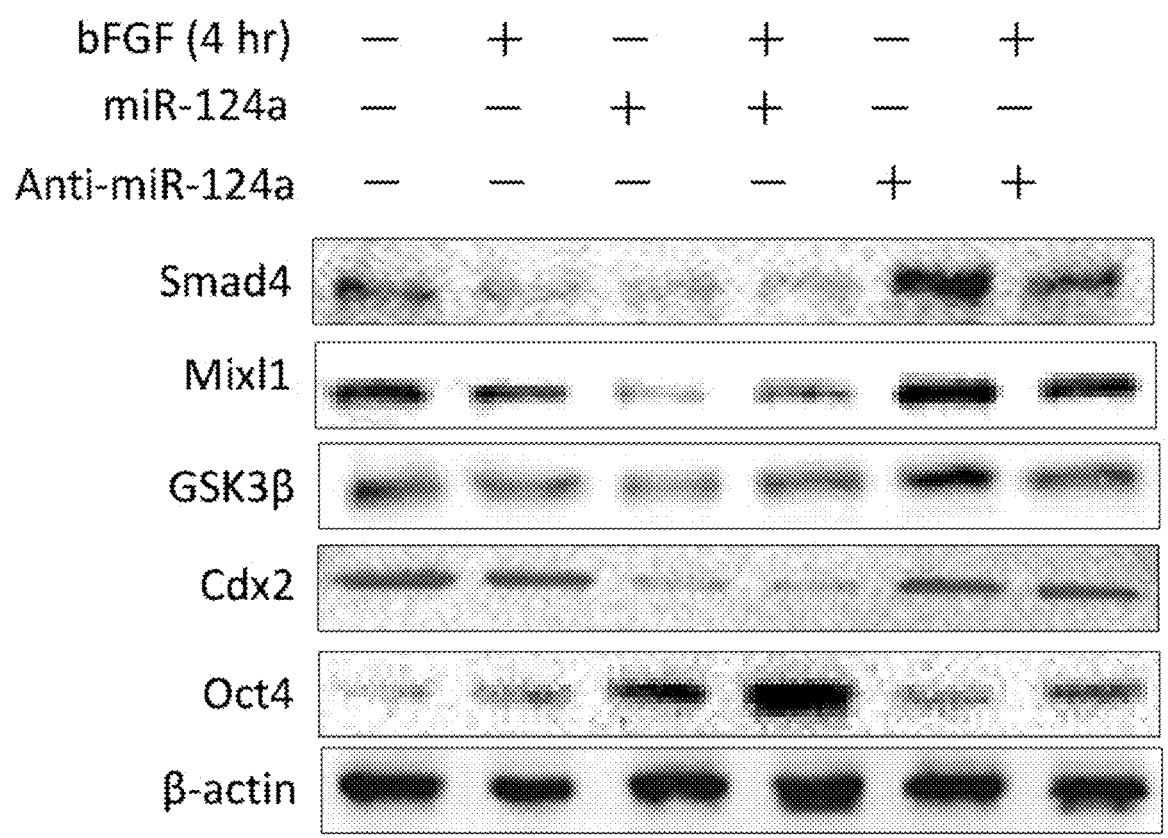
Figure 2F:
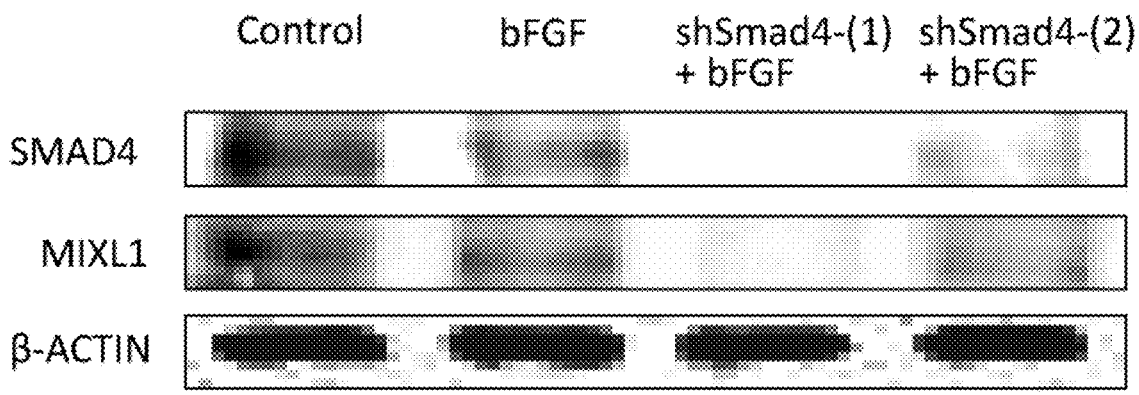
Figure 2G:
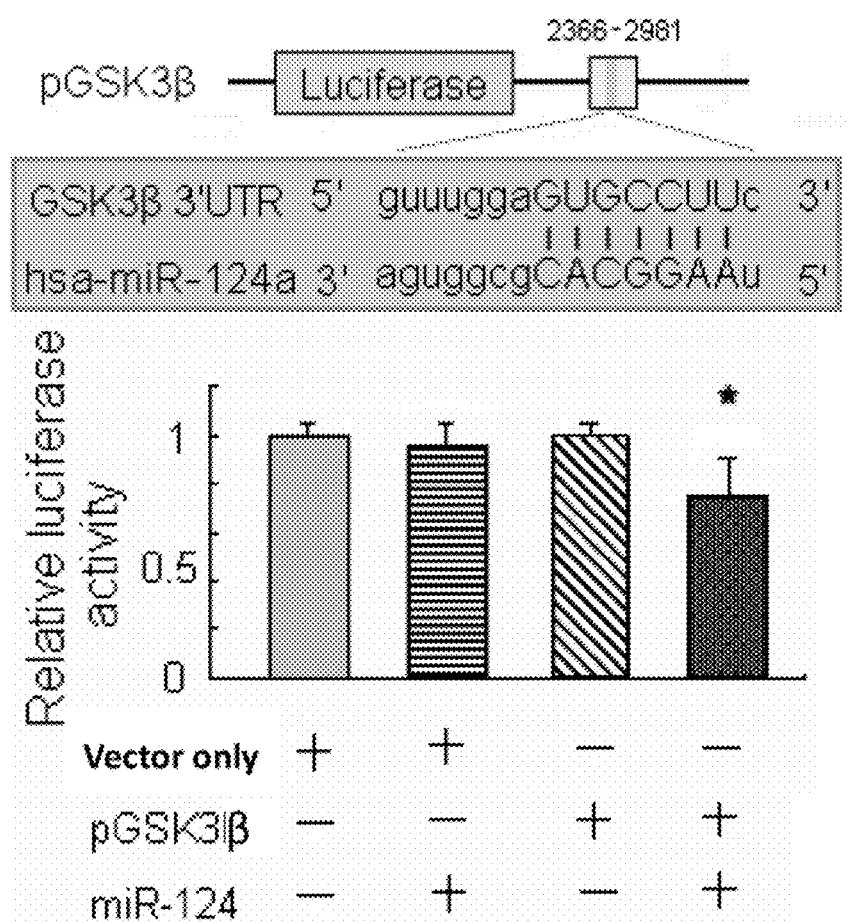
Figure 2H:
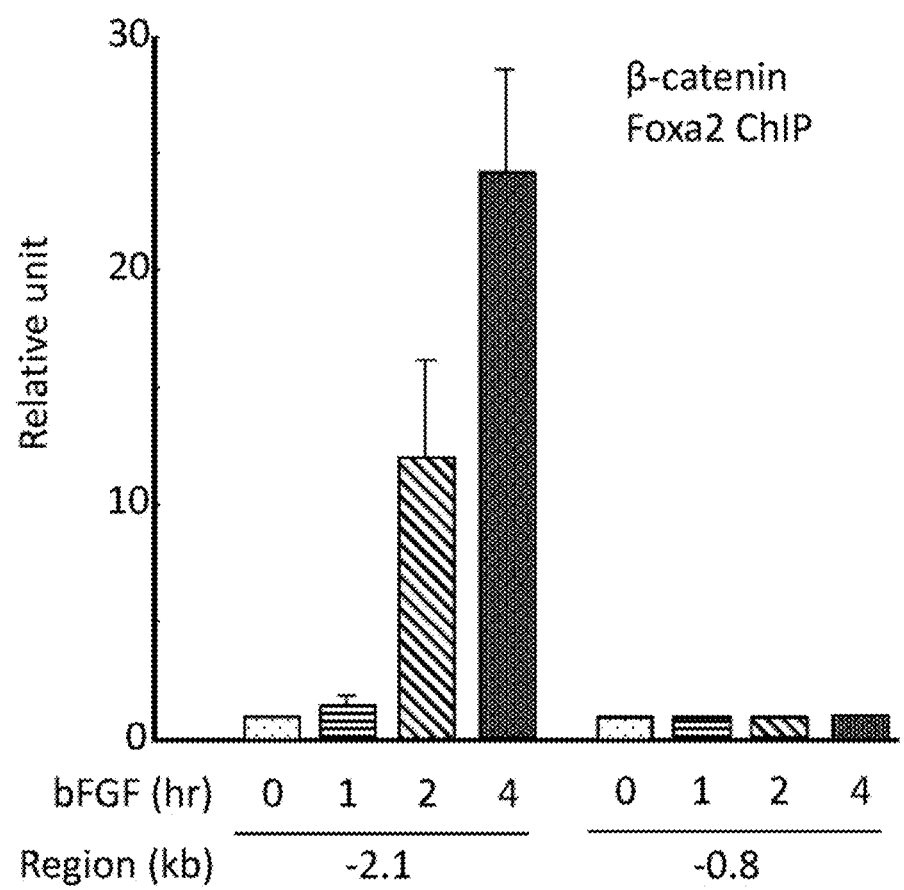

Notably, a correlative expression between the highest miR-14a and the lowest MIXL1 at 4 hr induction attracted us to examine whether there was a relationship between them. By sequence analysis and luciferase reporter assay, miR-124a enabled to target Smad4 messenger RNA (mSmad4) at two sites, resulting in the prevention of signal transduction protein Smad4 production evidenced by the luciferase reporter assay (FIG. 2D) and immunoblotting assay (FIG. 2E). Consistently, the inhibitory Smad4 of miR-124 caused a suppression of MIXL1, supported by knockdown of Smad4 (FIG. 2F). These data explained the downregulation of MIXL1 in DE stage, which was attributed to the activation of bFGF-induced miR-124a. Furthermore, miR-124a also enabled to play other roles, for example, it suppressed glycogen synthase kinase 3β (GSK3β) mRNA by luciferase reporter assay (FIG. 2G) that inhibited the production of GSK3β (FIG. 2E). This inhibitory GSK3β resulted in the nuclear translocation of its downstream substrate β-catenin. In the nucleus, β-catenin enabled to target the promoter of FOXA2 gene by ChIP-qPCR assay to produce FOXA2 (FIG. 2H). To this end, the expression of FOXA2 highlights the cell differentiation at DE stage.

Maintenance of Self-Renewal Characteristics by OCT4

Figure 2I:
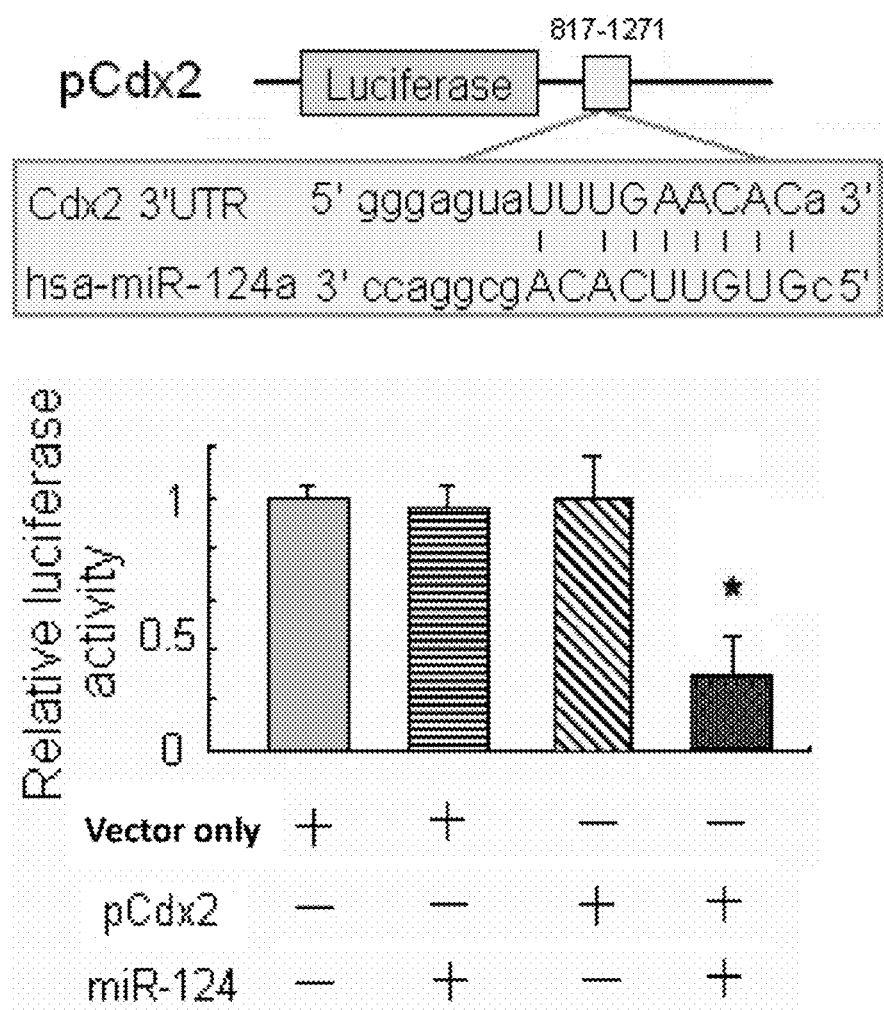
Figure 2J:
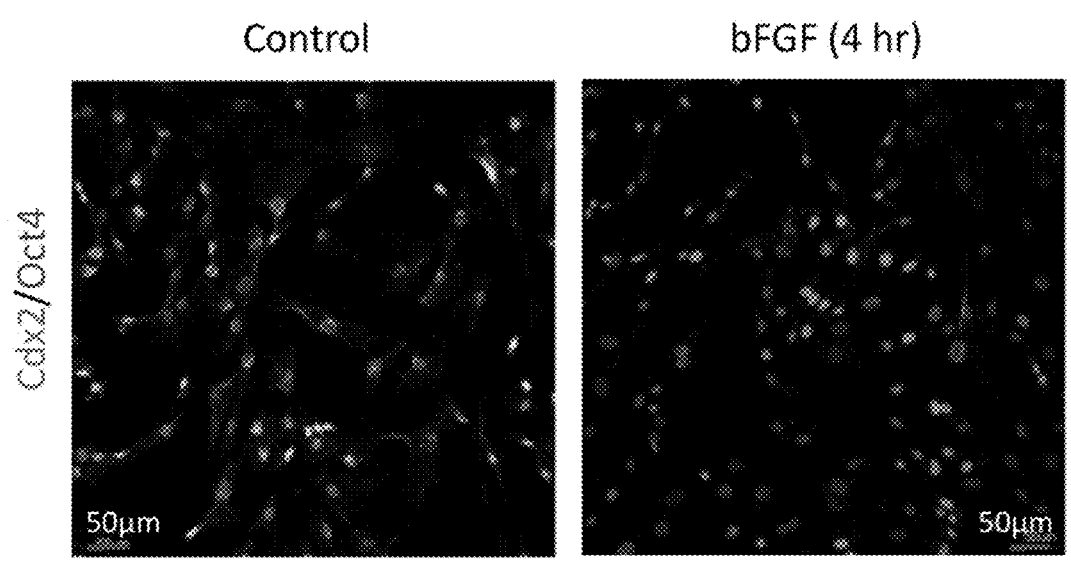
Figure 2K:
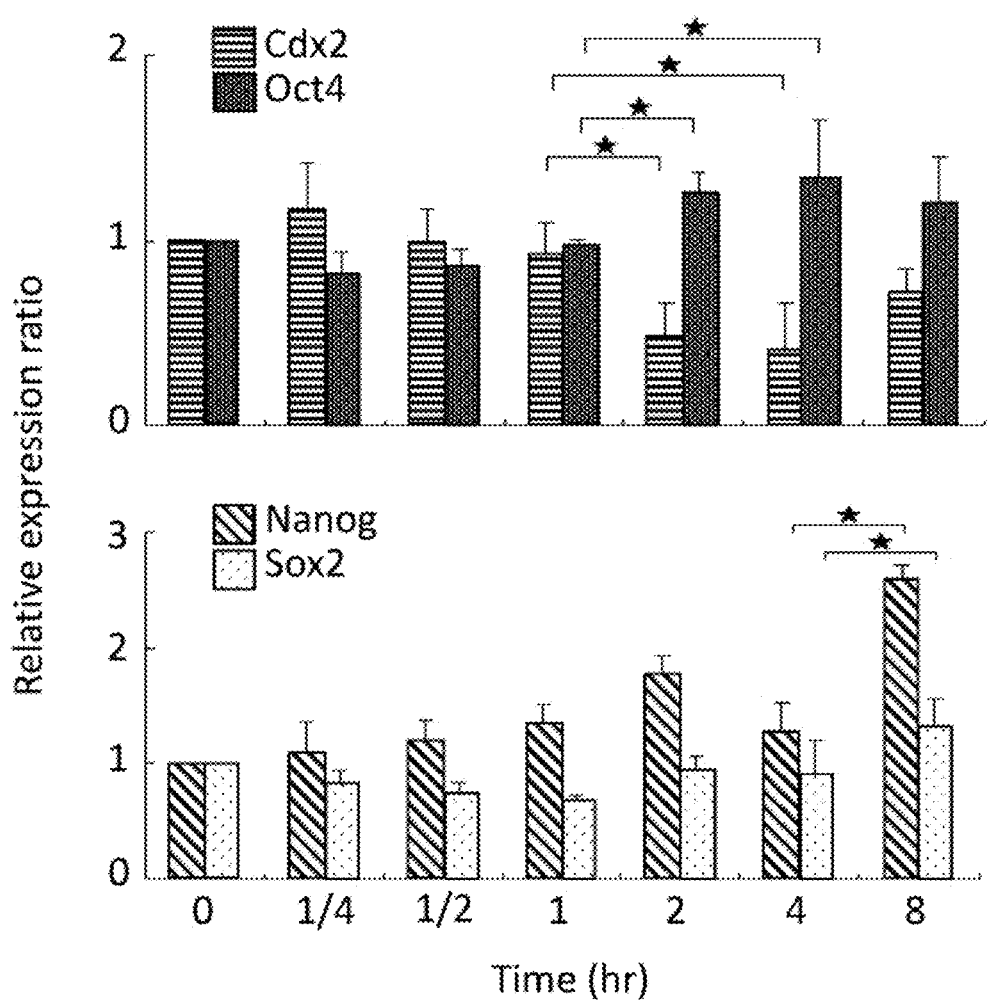
Figure 2L:
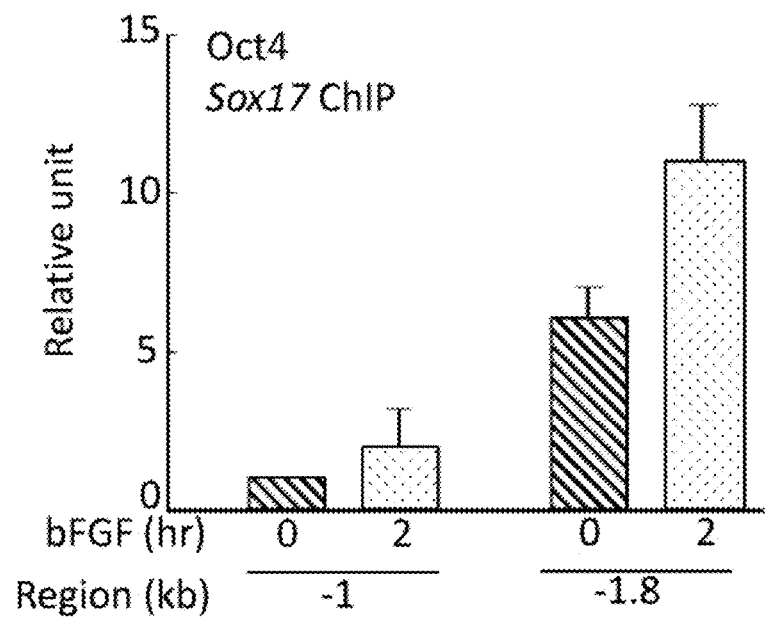
Figure 2M:
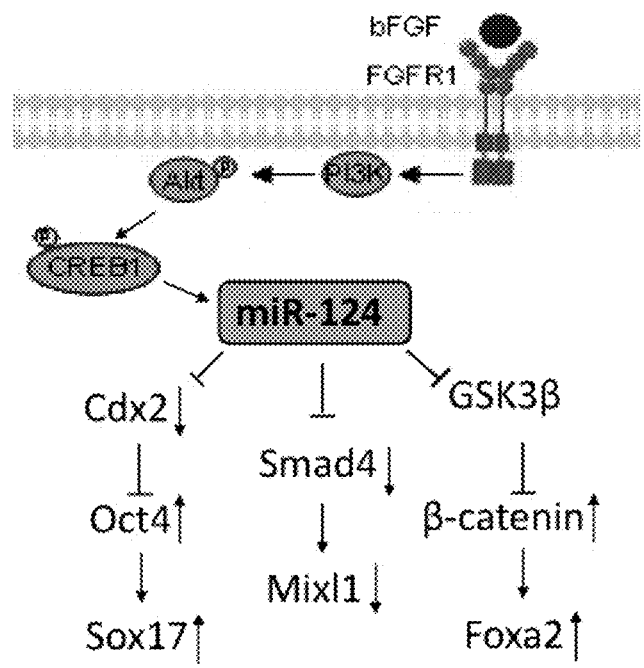

On the other hand, miR-124a also enabled to target CDX2 mRNA (FIG. 2I) to inhibit its translation that decreased CDX2 production of CDX2, a pluripotent transcription factor (FIG. 2E). This was supported by the presence of co-transfected miR-124a- and CDX2 plasmids (FIG. 2I). The inhibitory CDX2, however, led to an activation of pluripotent transcription factor OCT4 (FIG. 2E) via the reciprocal inhibitory relationship between OCT4 and CDX2. This function was reflected by the imaging study (FIG. 2J) and immunoblotting assay (FIG. 2K). OCT4 activation could be inhibited by anti-miR-124a antibody, linking miR-124a and OCT4 by immunoblotting assay (FIG. 2E). The gradual elevation of both pluripotent transcription factors NANOG and SOX2 towards 8 hr (FIG. 2K) suggested a supportive role in the maintenance of pluripotency of DE lineages compatible with that in hES cells. Therefore, these data suggest that OCT4 mainly maintains the self-renewal characteristics of DE, supported by other core pluripotency transcription factors NANOG and SOX2. Furthermore, the active OCT4 was capable of targeting at two sites of the promoter of SOX17 mRNA by ChIP-qPCR assay (FIG. 2L) that induced SOX17 expression peaking at 2 hr (FIG. 1C). SOX17 expression represents another milestone in DE identification. Taken together, these results demonstrate in hTS cells that bFGF-dependent miR-124a induces DE formation in a highly efficient manner (8 hr) distinct from the 3-day course in hES cells. A schematic regulatory molecular mechanism illustrates the DE specification through the miR-124a signaling to upregulate FOXA2, SOX17, and OCT4 but downregulate MIXL1; wherein OCT4 plays a main role in the maintenance of self-renewal of DE lineages (FIG. 2L).

Genetic Profiles Correspond with the Stage-Specific Phenotypes in Hepatic Development To subsequently direct DE differentiation into hepatic lineages, dexamethasone and oncostatin M were added after completion of DE stage at 8 hr. Given the advantages of qRT-PCR assay, the dynamic expression of hepatic development-associated 31 genes in a time course profile was explore to characterize mRNA fingerprint that could be used to follow the differentiation process. In all, the genetic profiles of each gene revealed a similar pattern with 4-5 peaks during 6-day induction. Based on the cellular processes of hepatic development in mouse model, the hTS cells treated with bFGF and the cocktail of dexamethasone and oncostatin M were classified based on their genetic expression profiles into four stages of cellular processes: primitive streak to DE (<8 hr), hepatic specified endoderm lineages (8 hr to day 1), hepatoblasts (day 2-4), and fetal and adult hepatocyte-like cells (day ≥day 4) (FIG. 9A-9F).

Therefore, these results revealed that i) at the stage of primitive streak to DE, four genes expressed predominantly (>10- to 1,000-fold), include CXCR4, FOXA2, SOX17, and HHEX; ii) at the hepatic specified endoderm, six genes expressed predominantly (between 10- and 100-fold), including SOX17 for liver bud formation and lipid metabolism, thyroxin- and retinol-binding protein TTR, proteins carrier albumin (ALB), tyrosine catabolism enzyme TAT, SERPINA1, and bile acid biosynthesis enzyme CYP7A1; iii) at the hepatoblastic stage, there were 6 genes expressed predominantly (between 10- and 100-fold), including TTR, ALB, TAT, CYP7A1, SERPINA1, and bile salts excretion pump BSEP; and iv) at the fetal and adult hepatocyte-like cell stage, there were 11 genes expressed prominently (>100-fold), including HHEX, BSEP, TTR, ALB, TAT, SERPINA1, glucose homeostasis enzyme G6PC, hepatobiliary excretion transporter MRP2 (ABCC2), immune and normal macrophage regulator C/EBPβ, and several hepatic gene regulators such as HNF4α and HNF1a. Furthermore, expression of α-fetoprotein (AFP) appeared at fetal stage (day 4 and day 5), but decreased after day 5 of adult hepatocyte-like cell stage (FIG. 6).

Hepatic Plate-Like Architecture Exhibits Signatures of Hepatocytes

Figure 3A:
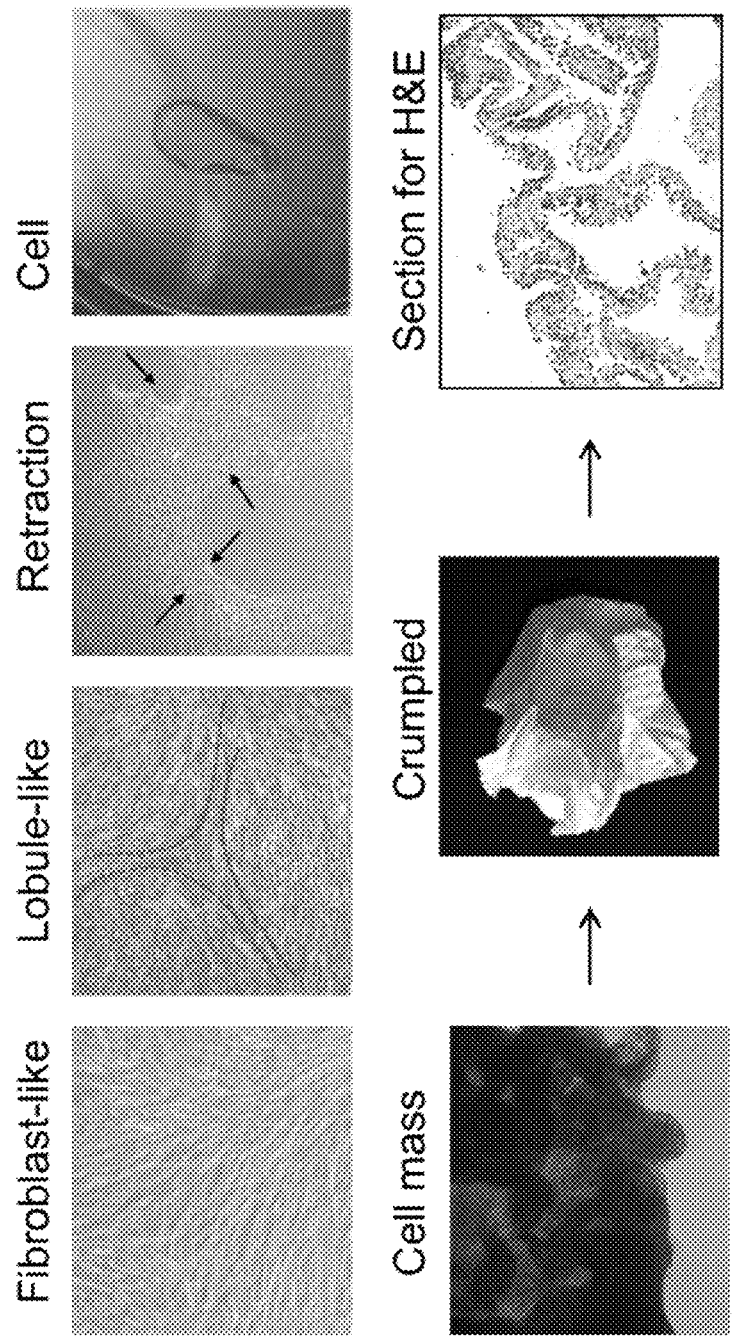
FIGS. 3A to 3C illustrate morphogenesis of hepatocyte-like cells.

In liver, hepatic plate system constitutes a unique tissue structure, composed of bile ducts and blood vessels surrounded by a sheath that is continuous with Glisson's capsule. To characterize the morphologic changes of hTS cell-derived hepatocyte-like cells during differentiation, it was found that cellular morphology changed from the initial fibroblast-like to a longer spindle feature in accompany with a trend to form lobular shape, showing numerous polygonal cells localized at the central areas at day 2 and day 3 (FIG. 3A). After day 4, however, cells might aggregate to form a plate-like mass and this phenomenon depended on the initial cell number cultured. The cell mass was then subjected to further examinations.

Figure 3B:
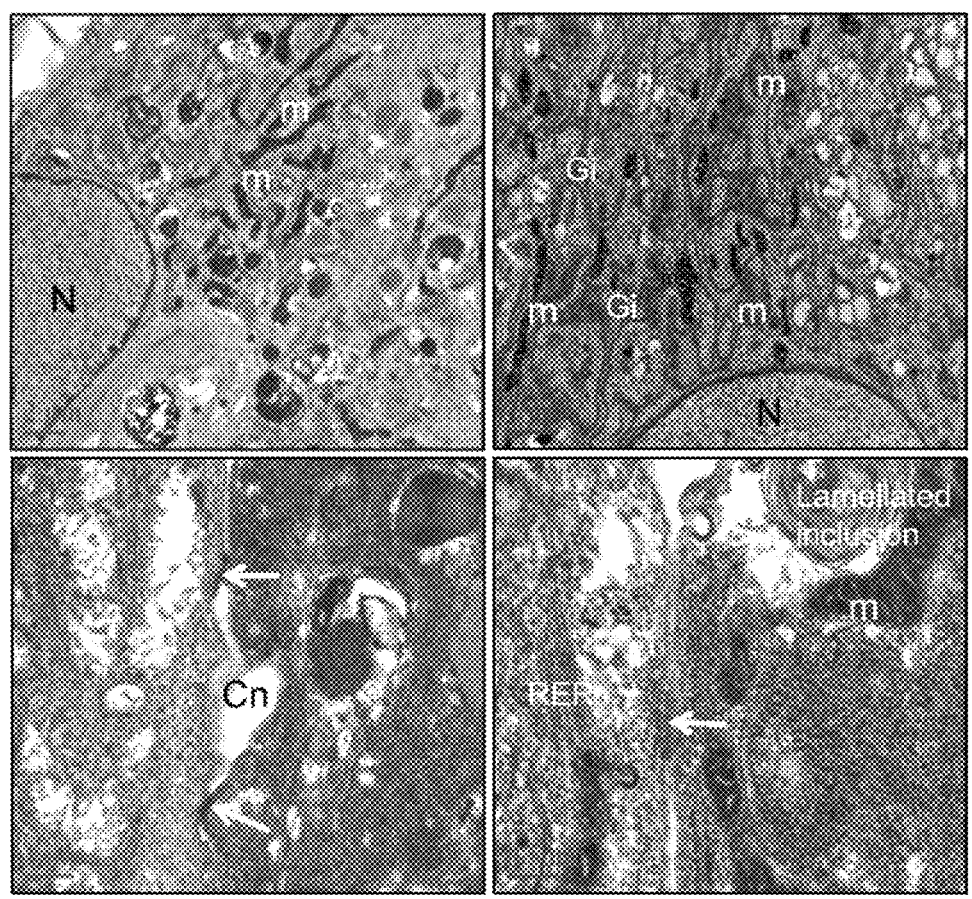
Figure 3C:
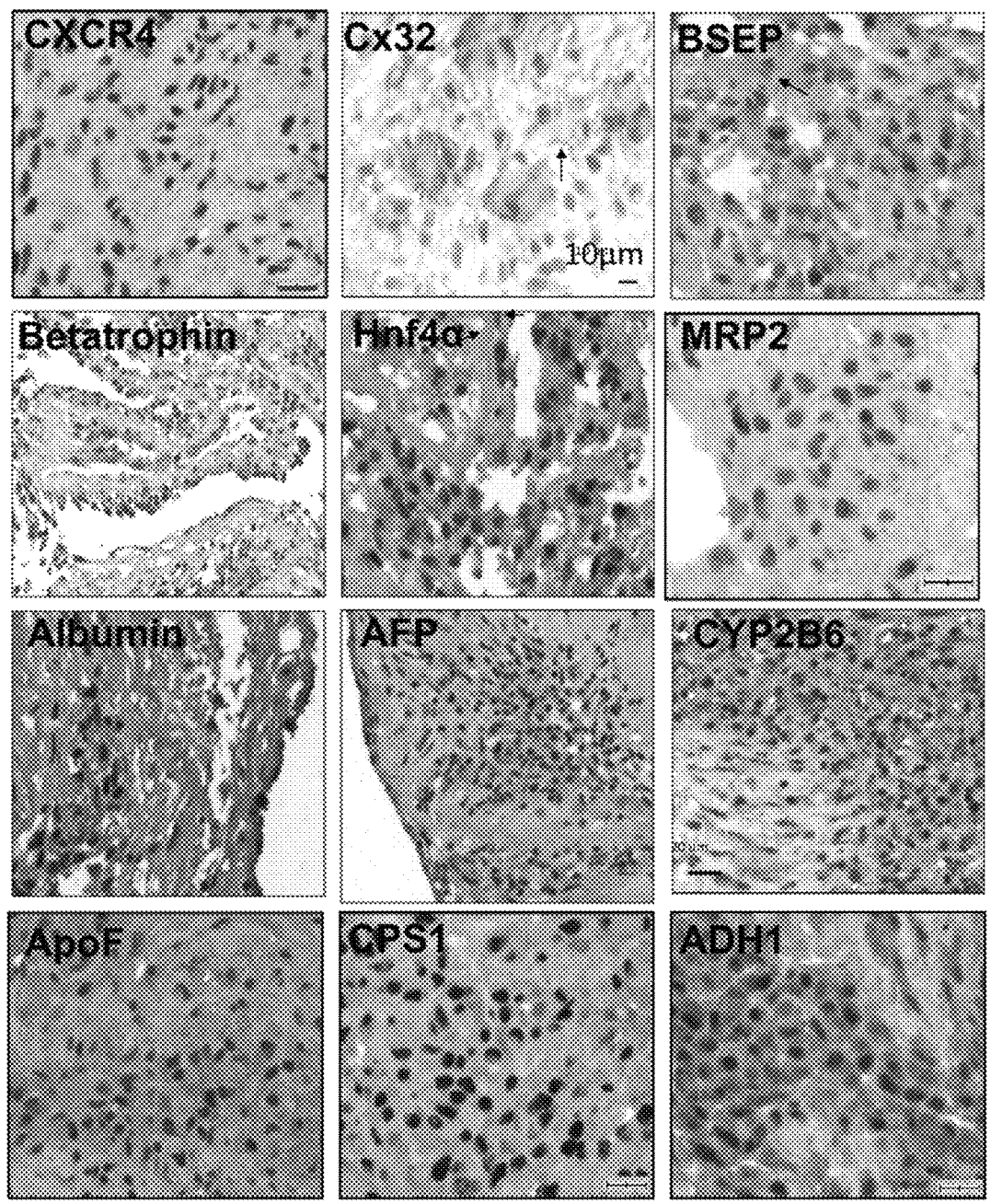

Histologically, most of the cellular arrangement appeared to be one cell or two cells thick eosinophilic cytoplasm to form a plate-like tissue; however, cells might aggregate together to form a cell mass (FIG. 3A). Immunohistochemically, these cells exhibited immunofluorescence stainings for Albumin, AFP, Betatrophin, HNF4α, APOF, CPS1, ADH1, and CYP2B6 in the cytoplasmic compartment; while a subset of cell membrane markers, including CXCR4, CX32, MRP2, and BSEP, making the cell in polygonal shape similar to the primary hepatocytes (FIG. 3B). Electron microscopy displayed ultrastructures similar to the primary hepatocyte, for example, large cytoplasm to nucleus ratio, plenty of mitochondoria, well-organized endoplasmic reticulum, desmosome junction, intact golgi apparatus, and specifically, the enlarged lumen of the canaliculus and the junctional complexes (FIG. 3C). Moreover, immunocytofluoresence imaging revealed a colocalization of AFP and Albumin as well as ABCC2 (MRP2) and BSEP (FIG. 1E). To this end, it was demonstrated that these hepatocyte-like cells possess hepatic characteristics of either cellular components or infrastructures that resemble to the primary hepatocytes.

Hepatocyte-Like Cells Function as Primary Hepatocytes In Vitro and In Vivo

Figure 4A:
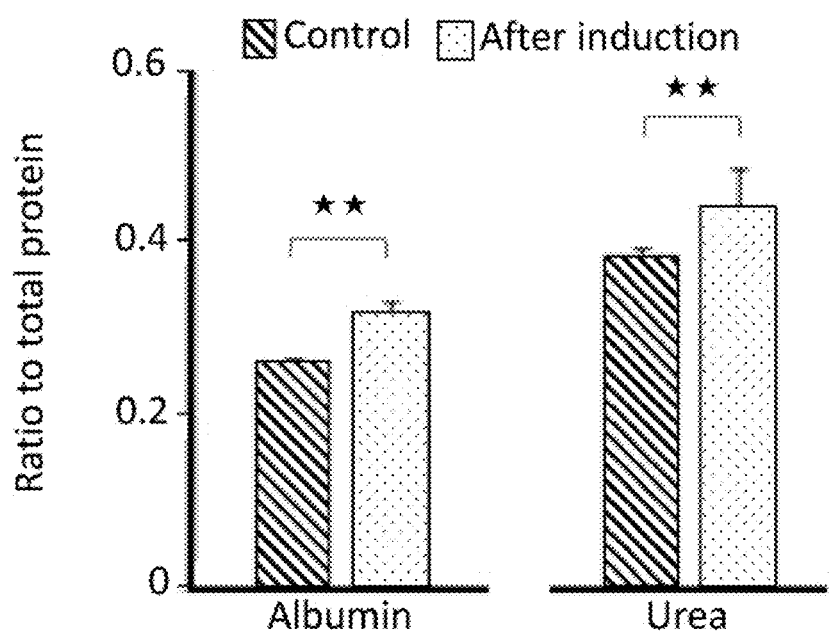
FIGS. 4A to 4D illustrate liver functions of the differentiated hepatocyte-like cells.
Figure 4B:
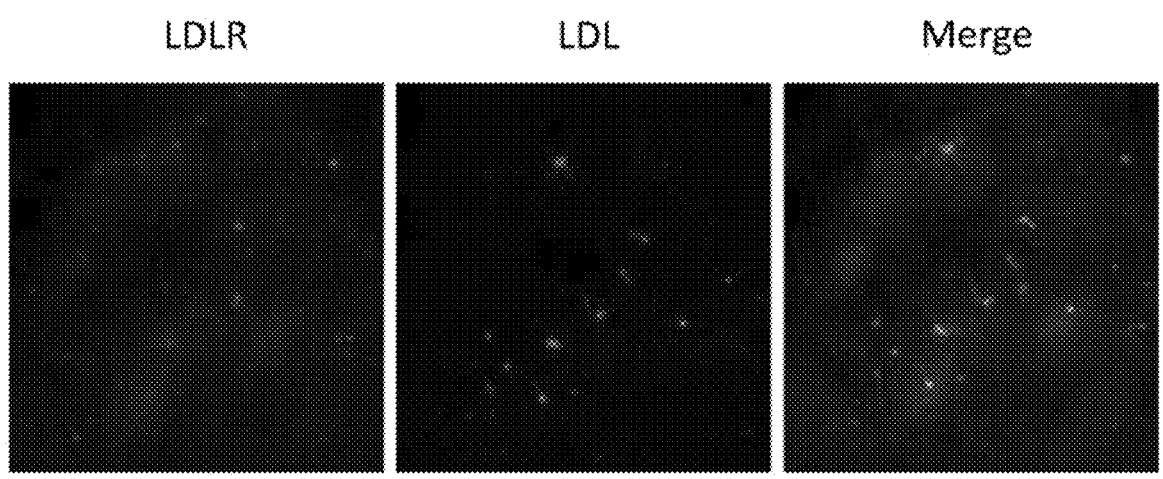
Figure 4C:
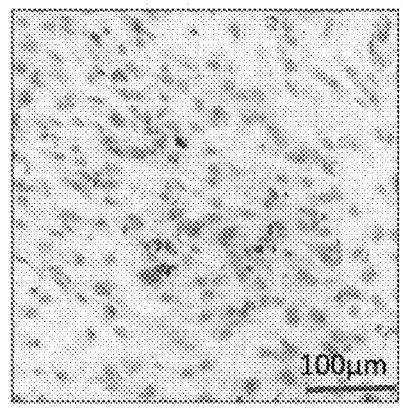
Figure 4D:
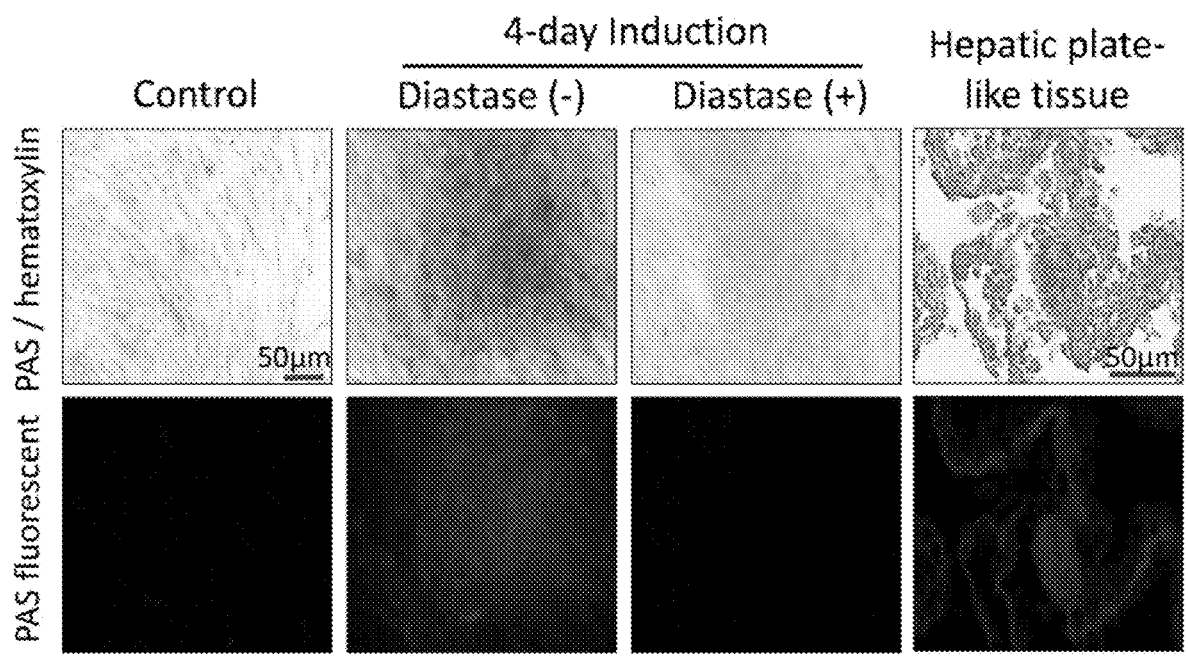
Figure 5A:
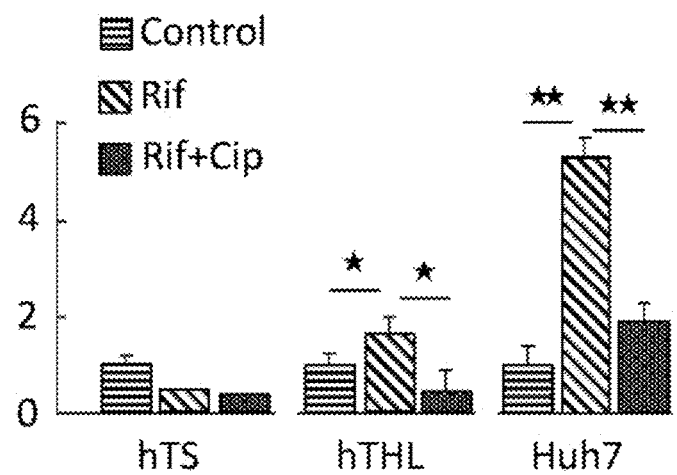
Figure 5B:
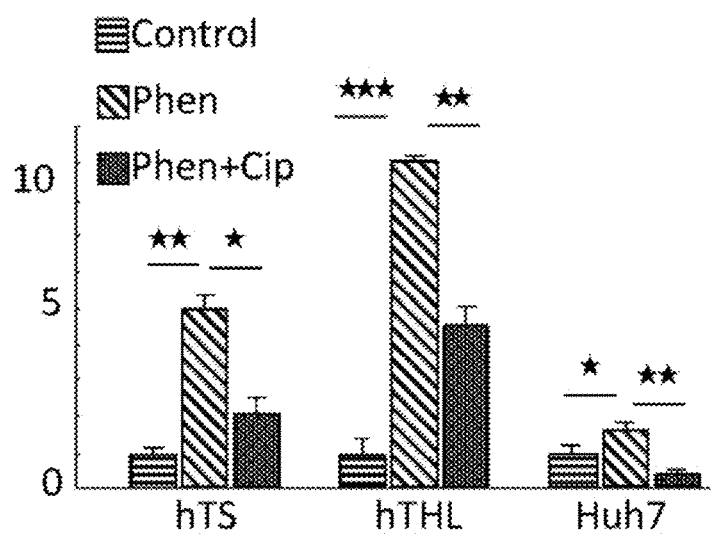
Figure 5E:
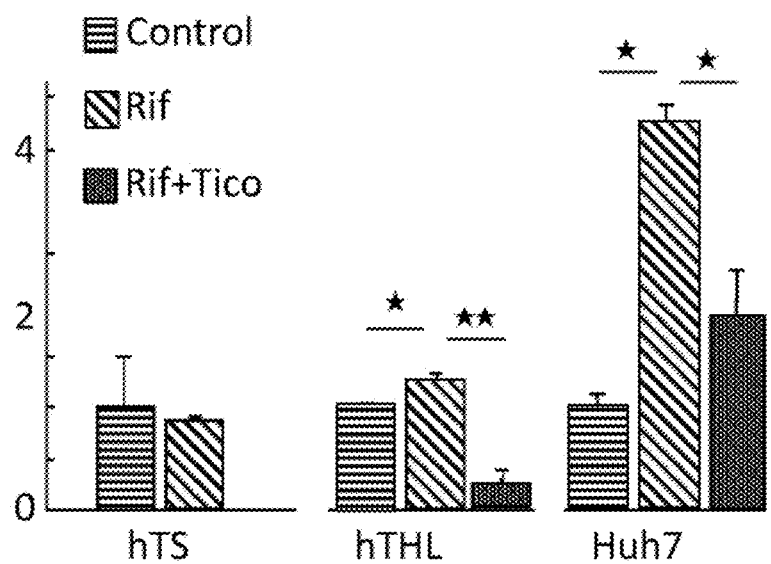
Figure 5F:
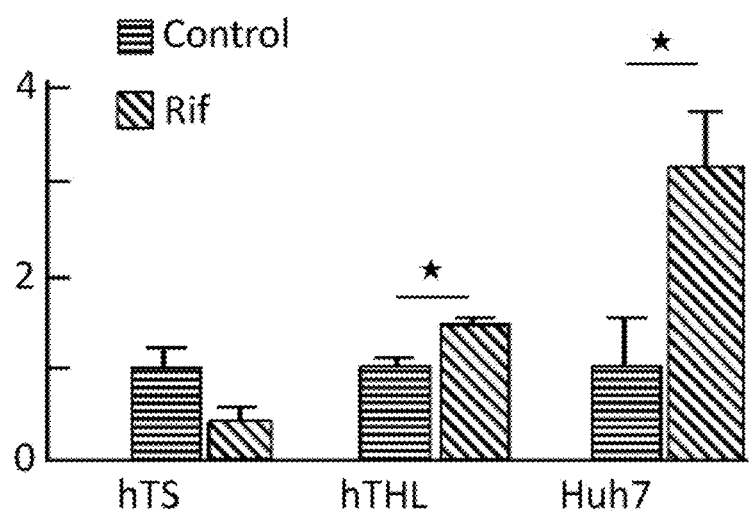
Figure 5G:
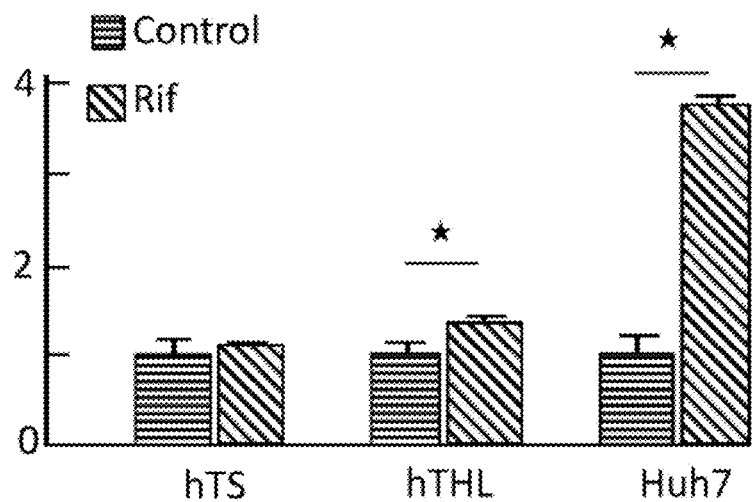
Figure 5H:
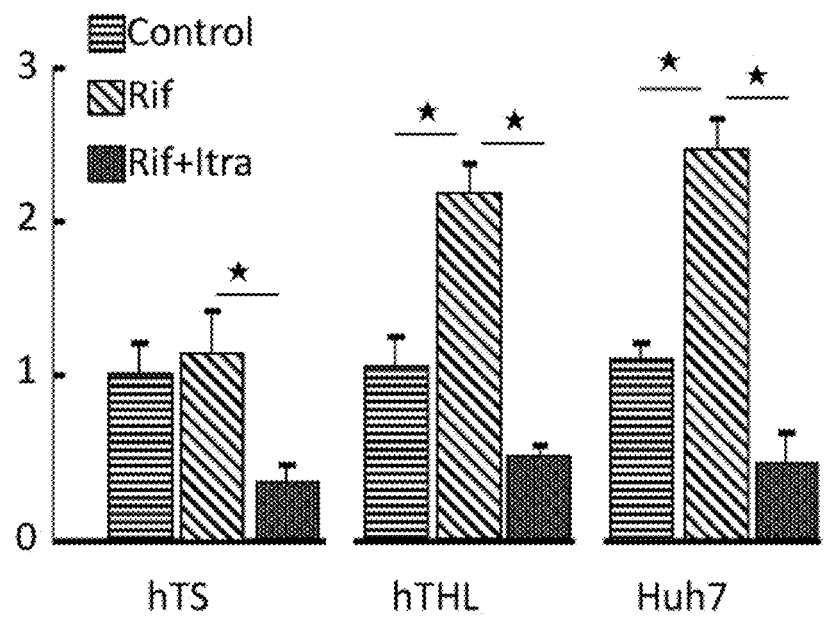
Figure 5I:
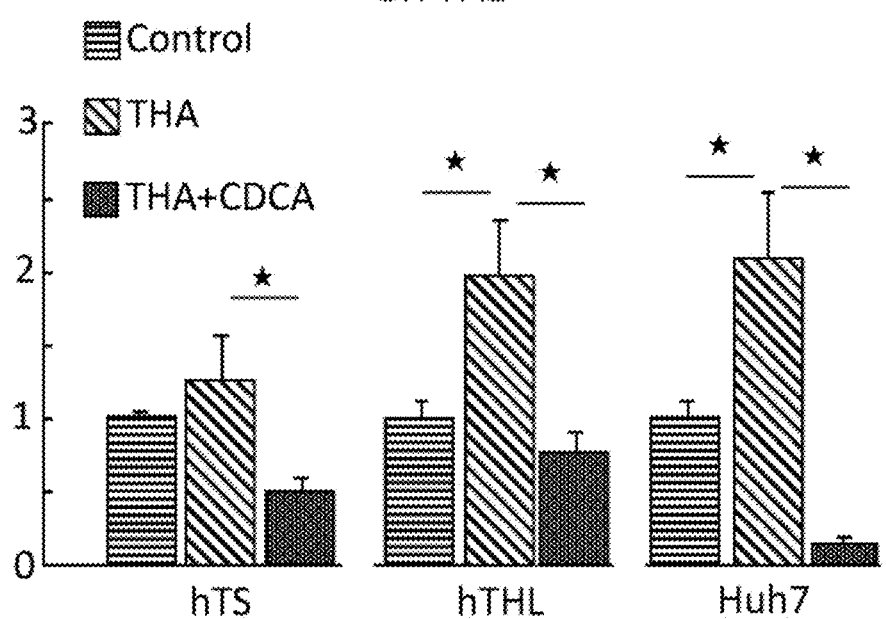

The liver is the most important organ responsible for many specific functions in metabolisms such as albumin synthesis, ureagenesis, glycogenesis, and detoxification. To examine whether these hepatocyte-like cells are able to function similar to the primary hepatocytes, the secreting capability of albumin and urea in the cells were investigated. Culture medium at day 4 induction was harvested and subjected to the ELISA analysis. The results revealed that both albumin and urea levels were significantly increased, suggesting their capabilities to produce secreting albumin and urea in the culture medium (FIG. 4A). Next, glycogen storage capacity test revealed a positive periodic acid-Schiff (PAS) staining after diastase digestion treatment in both cellular phase or hepatic plate-like tissue (FIG. 4B). This action was further confirmed by the PAS fluorescence emission for both immunocytochemistry and immunohistochemistry (FIG. 4B). In addition, LDL uptake assay revealed that the ability of LDL uptake of cells initiated at the immature hepatocytes of day 4 induction (FIG. 4C). Oil-O-Red staining revealed the presence of lipid droplets, suggesting somehow the degree of adipogenesis (FIG. 4D). Furthermore, it was examined whether the hepatocyte-like cells possess the capacity of drug metabolism and detoxification in vitro by using cytochromes P450 (CYPs) enzymes as target by qPCR analysis. The results revealed that the hepatocyte-like cells significantly expressed activities of CYP1A2, CYP2B6, CYP2C8, CYP2C9, CYP2D6, CYP2E1, CYP3A4, and CYP7A1 in responsive to metabolize specific drugs (FIG. 5A-5I), suggesting that these hepatocyte-like cells can be used for drug screening and discovery similar to primary hepatocytes. For example, a liver enzyme-inducer rifampin can promote CYP3A4 activity to increase the metabolic rate of drug and inhibition of CYP3A4 is a major cause of drug-drug interactions (DDI), which have been widely used in the clinical settings. Furthermore, it has been shown that phloracetophenone (2,4,6-trihydroxyacetophenone, THA)

promotes both CYP7A1 activity and mRNA expression to reduce both plasma cholesterol and triglyceride in hypercholesterolemic hamsters and THA antagonized the inhibitory regulation of chenodeoxycholic acid (CDCA) on CYP7A1 mRNA expression. To that, it was shown that in the hepatocyte-like cells, rifampin-induced CYP3A4 was able to be reduced by its inhibitor itraconazole (FIG. 5H), while THA induced elevation of CYP7A1 mRNA was reduced by CDCA (FIG. 5I). From the pharmacological point of view, for example, bile acid binding resins are indicated for the treatment of elevated plasma low-density lipoprotein cholesterol concentrations, however, resin therapy is hazardous. Therefore, new drugs have been designed by approaching the regulation of CYP7A1 to reduce plasma cholesterol and be based on the confirmation of CYP7A1 position as a focus for innovative pharmacological intervention.

Basic FGF Induced Activation of PI3K/AKT/CREB1 Signaling Pathway in hTS Cells

Figure 8A:
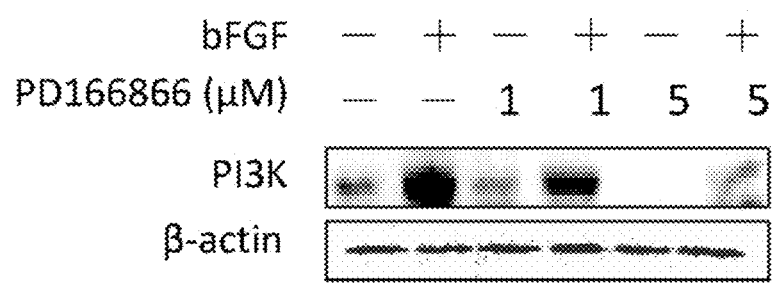
FIG. 8A to FIG. 8D illustrate expression level analysis of biomarkers described herein.
Figure 8B:
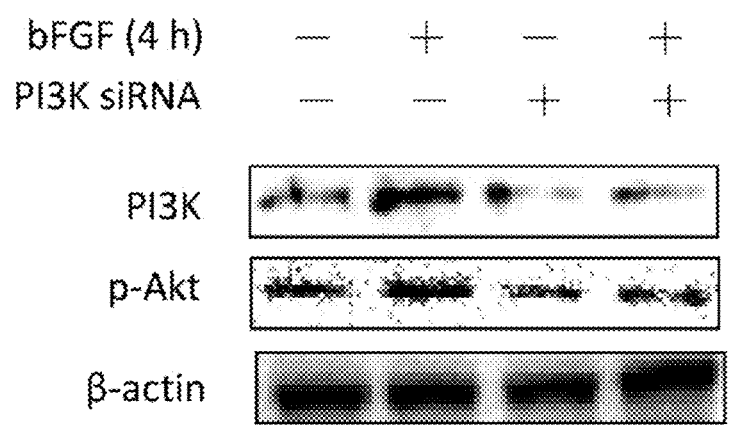
Figure 8C:
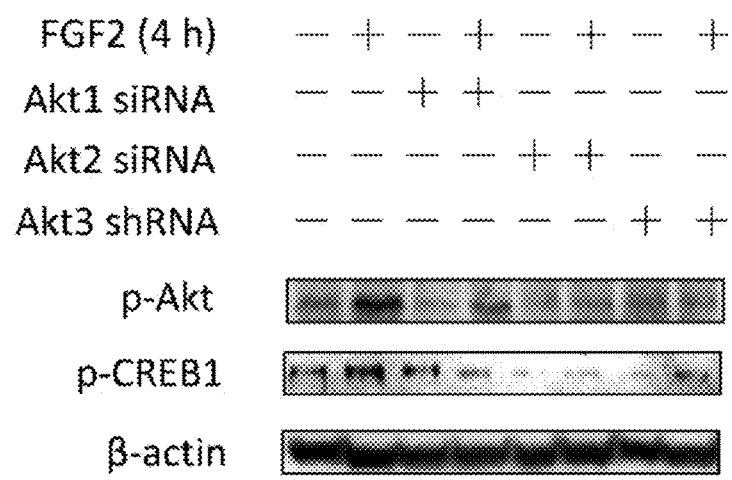
Figure 8D:
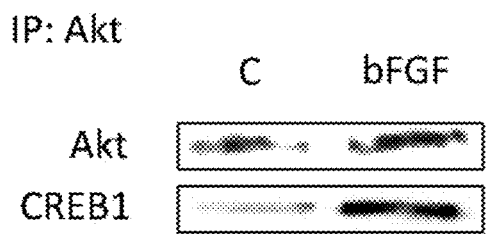
Figure 9A:
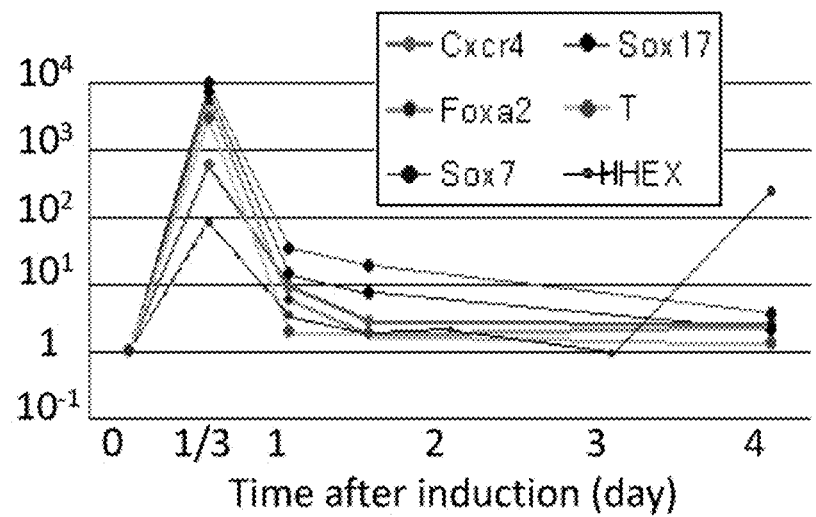
FIG. 9A to FIG. 9F illustrate the genetic fluctuation profiles of hepatic development-associated 31 genes after induction by qPCR analysis in hTS cells.
Figure 9B:
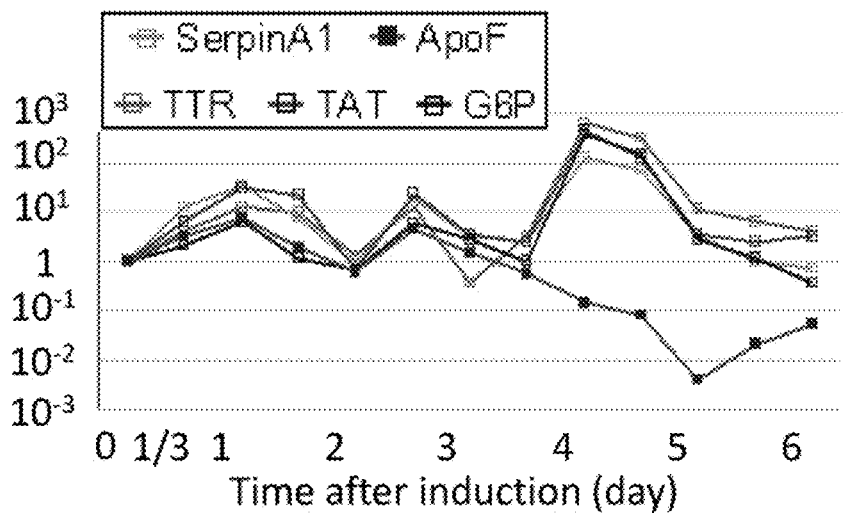
Figure 9C:
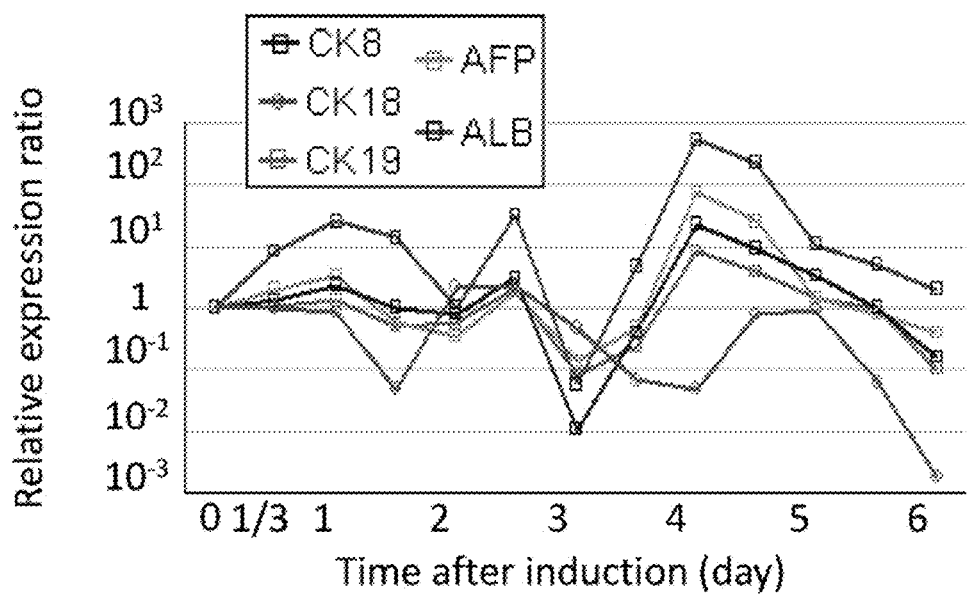
Figure 9D:
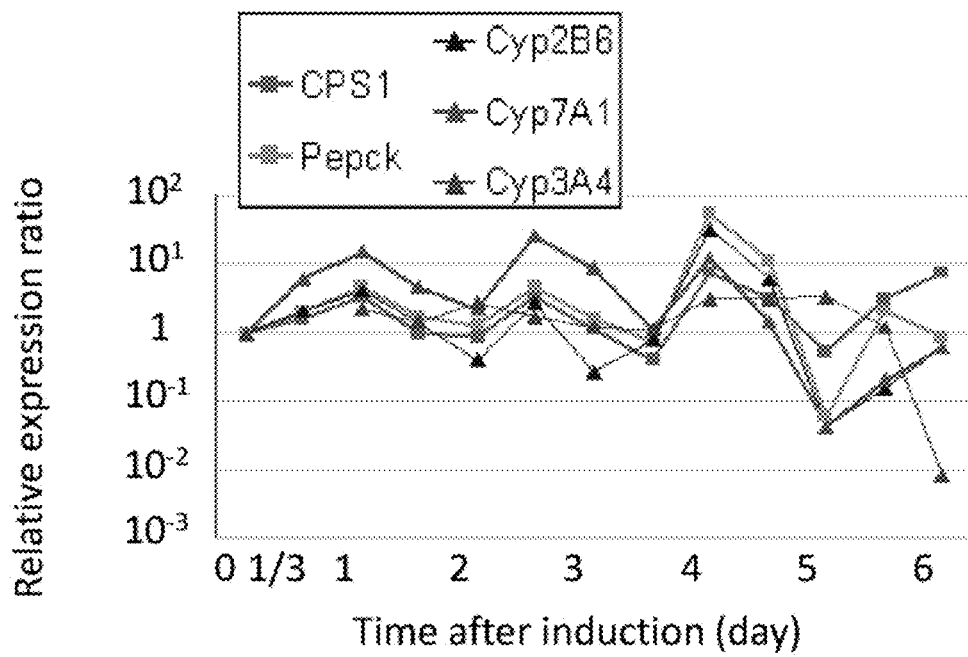
Figure 9E:
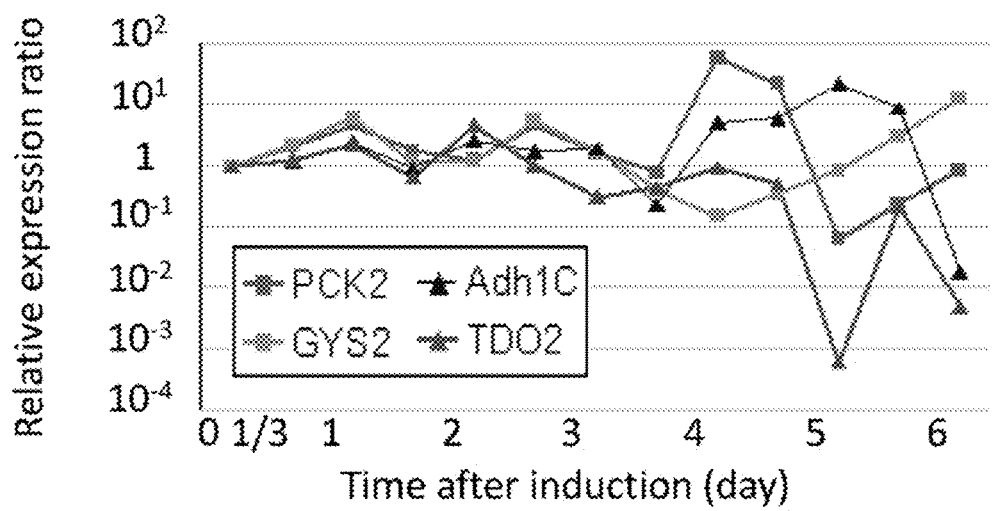
Figure 9F:
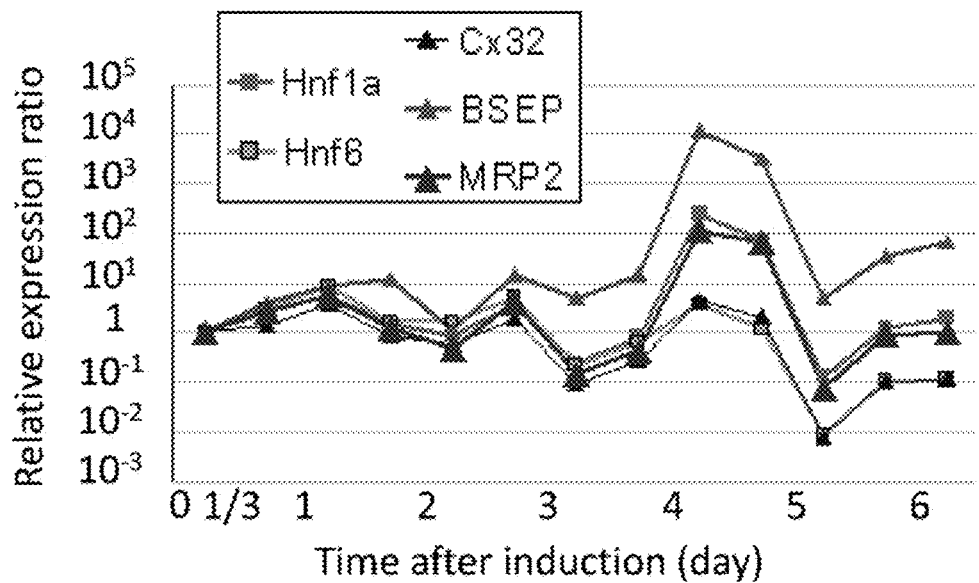

The hTS cells were treated with bFGF (10 ng/ml) in the conditioned medium, and it was shown that FGF receptor (FGFR) inhibitor PD166866 could block the bFGF-induced activation of phosphatidylinositol 3-kinase (PI3K) by immunoblotting assay (FIG. 8A), suggesting that the inhibitory effect was through the FGFR at the cell membrane. As a result, the downstream effector AKT was phosphorylated evidenced by using PI3K siRNA (FIG. 8B). To clarify which protein kinase B (AKT) subunit was activated, specific siRNA against three AKT subunits: AKT1, AKT2, and AKT3 were examined by immunoblotting assay. The result showed that only AKT1 phosphorylated and activated its downstream effector cAMP response element-binding protein 1 (CREB1) (FIG. 8C). This function was further confirmed by immunoprecipitation (IP) assay (FIG. 8D). Taken together, this indicates that bFGF induces activation of the PI3K/AKT1/CREB1 signaling pathway at 4 hr induction.

Example 2

Experimental Procedures
Cell Culture and Differentiation

This study was approved by the Institutional Review Board on Human Subjects Research and Ethics Committees (KMUHIRB-20140071). The hTS cells were obtained with informed consent as described previously (Lee et al., 2012, PLoS ONE 7, e52491) and maintained in α-MEM (Gibco) medium supplemented with 10% (v/v) fetal bovine serum (FBS; SAFC Biosciences) at 37° C. in humidified air containing 5% $CO_2$. For DE differentiation, cells were carried out by a conditioned α-MEM media containing 10% FBS, 2-mercaptoethanol (1 mM), nicotinamide (10 mM), and bFGF (10 ng/ml) for 8 hr, according to the empirical studies (data not shown). For hepatocyte differentiation after DE formation at 8 hr, cell culture was changed to medium containing bFGF (10 ng/ml), dexamethasone (0.1 Sigma), recombinant human oncostatin M (10 ng/ml, Excel-Biomedical Inc.), BMP4 (20 ng/ml), and HGF (5 ng/ml). Cells were harvested at 4-7 days for assay as indicated. Determination of stage-specific differentiation of lineages depends on the hepatic cell-associated markers in liver development.

Animal Study

Adult male Sprague-Dawley rats (300-350 g) were housed in a 12 hr light/12 hr dark cycle with ad libitum access to food and water. Experimental studies were approved by Institutional Animal Ethical Committee (IAEC) of Kaohsiung Medical University (IACUC-96009). For experiments, rats were anesthetized with chloral hydrate 25% (500 mg/kg) via intraperitoneal injection. Rats were divided into two groups: the sham operation as control (n=8) and the other as study group (n=8). Intravenous blood (0.5 ml) was obtained as baseline before experiment and both groups were injected intraperitoneally with CCl4 (1 ml/kg: 1:1 v/v in corn oil) after 12 hr. Immediately, study group was injected by hTS cell-derived hepatocytes ($1\times10^6$ cells/200 µl culture medium) from the tail vein and sham group was given PBS solution only. Serum sample was taken at baseline, cell injection point, 24 hr, 48 hr, and 72 hr and subjected for liver function tests, namely, aspartate aminotransferase (AST or formerly called SGOT), alanine aminotransferase (ALT or formerly called SGPT), and alkaline phosphatase (ALP), serum bilirubin. All rats were sacrificed at day 4 to obtained liver and lung organs for histopathological studies.

mRNA, miRNA, Chromatin Immunoprecipitation (ChIP)-qPCR, and mRNA Microarray

Methods were performed as described previously (Lee et al., 2012, PLoS ONE 7, e52491). For mRNA expression, RNA was isolated from hTS cells in triplicate or quintuple samples using TRIZOL reagent (Invitrogen) with DNAase I on-column digestion (Qiagen, Valencia, Calif.) according to manufacturer's instruction. Total RNA (500 ng) was used for reverse transcription with iScript cDNA synthesis kit (Bio-Rad). Real-time polymerase chain reaction (qPCR) carried out in duplicate using $\frac{1}{40}^{th}$ of the cDNA per reaction and 400 nM forward and reverse primers. Comparative real-time PCR was carried out at least triplicate using the Power SYBR® Master Mix (Applied BioSystems) with the 7500 Real-Time PCR System (Applied Biosystems). All genes were normalized to the GAPDH expression and were normalized to the expression of undifferentiated hTS cells using the ΔΔCt method unless stated otherwise. Primer sequences used in this study can be found in Table 5.

For miRNA analysis, 25 ng of total RNA was reverse-transcribed using the TaqMan MicroRNA Reverse Transcription Kit (Applied Biosystems). qPCR was carried out at least triplicate using the TaqMan Universal PCR Master Mix (Applied Biosystems) with the 7500 Real-Time PCR System (Applied Biosystems) including no-template controls, using specific primers for miR-124a or RNU6B (Applied Biosystems). U6 snRNA (RNU6B; Applied Biosystems) served as an endogenous control.

For ChIP assay, hTS cell samples of indicated time in induction were fixed with a final concentration of 1% formaldehyde. After incubation at room temperature (10 min), the reaction was stopped by adding glycine (125 mM). ChIP assay was performed using a protocol associated with the ChIP assay kit (Upstate Biotechnology). After extensive washing, ChIPed DNA was eluted from the beads and analyzed by qPCR.

Luciferase Reporter Assay

To prepare the luciferase-3' UTR reporter plasmids, amplified were 3'UTR fragments from genomic DNA extract of hTS cells. The 3' UTR PCR fragment was cloned into the pGL4.51 vector (Promega, Madison, Wis.) downstream of the luciferase gene by using PsiI and MfeI (Thermo Scientific, Rockford, Ill.). Primers for 3' UTR reporter construct were listed as followings:

```
For Cdx2 3' UTR region:
forward,
                                    (SEQ ID NO: 1)
5'-aaattataagctgtttgggttgttggtct-3'
and reverse,
```

-continued

For Smad4 3' UTR region 1:
forward,
(SEQ ID NO: 3)
5'-aaattataactcccaaagtgctgggatta-3'
and reverse,
(SEQ ID NO: 4)
5'-aaacaattgctgcactgttcacaggagga-3;

For Smad4 3' UTR region 2:
forward,
(SEQ ID NO: 5)
5'-aaattataacagttgtcccagtgctgcta-3'
and reverse,
(SEQ ID NO: 6)
5'-aaacaattgatgacttgcccaaaggtcac-3;

For GSK3β 3' UTR region:
forward,
(SEQ ID NO: 7)
5'-aaattataacccacaactggggtaaaaga-3'
and reverse,
(SEQ ID NO: 8)
5'-aaacaattgctgtggaaggggcaaagata-3.

(SEQ ID NO: 2)
5'-aaacaattgcccccataatttctgactgc-3;

For dual luciferase assays, firefly luciferase reporter (500 ng) or empty vector without any 3'UTR co-transfected with pGL4.74 and renilla luciferase plasmid (500 ng, Promega), and non-specific control miRNA (30 pmol) or miR-124a precursor (30 pmol; System Biosciences, Mountain View, Calif.) were co-transfected to hTS cells ($1.5 \times 10^4$ cells in each well) using TransIT®-LT1 transfection reagent (Minis Bio LLC, Madison, Wis.). After transfection (36 hr), the luciferase activity was analyzed by the dual luciferase reporter assay system (Promega) and the Centro LB 960 Microplate Luminometer (Berthold Technologies, Bad Wildbad, Germany). For evaluation, renilla luciferase value was first normalized to the firefly luciferase activity and the calculated activity of each 3'UTR reporter was further normalized to the control vector. Data represented as mean±SD, n=8, p<0.05 as statistic significance. Whole cell extracts prepared in the cell lysis buffer were subjected to immunoblotting with Cdx2, Smad4, GSK3β, and β-actin antibodies.

Plasmids

MiR-124a precursor and anti-miR-124a were purchased from System Biosciences. Briefly, miR-124a precursor (60 pmol) or anti-miR-124a (60 pmol) was transfected to hTS cells in 12-well culture dishes using TransIT-LT1 transfection reagent (Minis, Madison, Wis.). Total RNAs were used for quantifying miR-124a at 36 hr after transfection. Small interfering RNA (siRNA) targeting PI3K (SASI_Hs01_00233971 and SASI_Hs01_00127787), Akt1 (SASI_Hs01_00205545), and Akt2 (SASI_Hs01_00035055) were purchased from Sigma. Short hairpin RNA (shRNA) targeting CREB1 (TRCN0000007310, TRCN0000226467 and TRCN0000226468), Smad4 (TRCN0000010321, TRCN0000010323 and TRCN0000040032), Akt3 (TRCN0000001615 and TRCN0000001616), Oct4 (TRCN0000004879 and TRCN0000004882), Cdx2 (TRCN0000013683 and TRCN0000013686), and control shRNA (shGFP; TRCN0000072178, TRCN0000072179 and TRCN0000072183) were purchased from National RNAi Core platform, Academia *Sinica*, Taiwan. Transfection was performed with siRNA or shRNA at 2 μg plus 4 μl transfection reagent.

LDL Uptake Assay

LDL uptake was performed by using LDL Uptake Cell-Based Assay Kit as manufacturer's instruction (Cayman Chem Co. Ann Arbor, Mich.). Briefly, $5 \times 10^4$ cells were seeded at coverslip in each well of a 24-well plate. hTS cells (as control) and the differentiated hepatocyte-like cells (hHLCs) were fixed after 5 μg/ml LDL-DyLight™ 549 probe treatment (4 hr, 37° C.) and then stained for LDL receptor by rabbit anti-LDL and DyLight™ 488-conjugated Goat anti-rabbit antibody. Nuclei were visualized with DAPI. The final staining was observed by fluorescence microscopy.

Oil-O-Red Test

For detection of lipid accumulation, differentiated cells were fixed with 4% paraformaldehyde (20 min) at RT and washed with 60% isopropanol for 5 min. After incubation at RT (20 min) with a freshly prepared 60% Oil Red O solution (0.5 g Oil Red O in 100 ml isopropanol passed through a 0.22 μm filter before using, Sigma), cells were rinsed with 60% isopropanol and counterstained with Hematoxylin I (Thermo Scientific) for microscopy.

Glycogen Storage Test

For glycogen detection, differentiated cells were fixed by 4% paraformaldehyde. Fixed samples were permeabilized with 0.4% Triton X-100. Undifferentiated control cells were incubated with Diastase (1 mg/ml in PBS; Sigma) for 1 hr at 37° C. Cells were incubated with periodic acid (0.5 g dissolved in 100 ml distilled water) for 5 min at RT, washed with distilled water, and incubated with fresh prepared Schiff's reagent (15 min) and subjected for microscopy.

Biochemical Parameter Tests

All biochemical parameters of liver function including albumin, urea, aspartate aminotransferase (AST), and alanine aminotransferase (ALT) were measured by using autoanalyzer (Hitachi 7080, Japan).

Functional Cytochrome p450 Assay

To test the activity of CYP enzyme induction in hTS cell-derived hepatocyte-like cells, cells were treated with reagents for 24 hr, for example, for CYP1A2 test, used were rifampicin (25 μM)/rifampicin+ciprofloxacin (1 μM); for CYP2B6 test by phenobarbital (100 μM)/phenobarbital+ clopidogrel (25 μM), for CYP3A4 by rifampicin (25 μM)/ rifampicin+itraconazole (25 μM), for CYP7A1 by 2,4,6-trihydroxyacetophenone (THA, 1 μM)/THA+CDCA (25 μM), for CYP2C8 and CYP2C9 by rifampicin (25 μM)/ rifampicin+gemfibrozil (25 μM) and for CYP2C19 by rifampicin (25 μM)/rifampicin+ticlopidine (25 μM). Huh-7 cells were used as positive control.

Immunocytochemistry and Immunohistochemistry

Methods were performed as described previously (Lee et al., 2012, PLoS ONE 7, e52491). Briefly, slides with cell culture was fixed for 30 min at room temperature in 95% (v/v) ethanol, washed three times in PBS and incubated with blocking buffer PBS containing 0.1% (wt/v) Triton X-100 (Sigma) and 5% (v/v) normal donkey serum (Millipore) for 60 min. Primary and secondary antibodies were diluted in blocking buffer. Primary antibody was incubated. After incubation with specific primary antibody in PBS at 4° C. (24 hr) or room temperature (2 hr), appropriate fluorescein isothiocynate (FITC, Invitrogen) or Alexa Fluor 488, 594, and 647 (Invitrogen) or Dylight 488 and 594 (BioLegend) conjugated secondary antibody was added at room temperature (1 hr). After DAPI staining of nucleus (5 min), incubation with secondary antibody (1 hr) at room temperature, and washes, sample was mounted with 50% glycerol. Images were captured by confocal laser scanning microscopy (LSM700; Zeiss Z1 or Olympus FluoView 1000 confocal laser scanning microscope) or TissueFAXS system (TissueQnostics GmbH, Vienna, Austria). Data were analyzed by TissueQuest software.

Electron Microscopy

For transmission electron microscopy, methods were performed as described previously (Lee et al., 2012, PLoS ONE 7, e52491). Briefly, the hTS cell-derived hepatocytes-like cells (at day 4 induction) were fixed in 0.1 M sodium cacodylate buffer (pH 7.4) containing 3% wt/vol formaldehyde, 1.5% (wt/vol) glutaraldehyde and 2.5% (wt/vol) sucrose at RT for 1 hr or at 4° C. overnight. The samples were washed with 0.1 M sodium cacodylate buffer (pH 7.4) before and after osmication treatment (2 hr) at 4° C. in Palade's fixative containing 1% (vol/vol) $OsO_4$. After treated with tannic acid, stained with 1% uranyl acetate, and dehydrated through a graded series of ethanol solutions, sample was embedded in TABB epoxy resin (Agar Scientific Ltd.). Ultrathin sections were stained with uranyl acetate and lead citrate and analyzed by using JEM-2000 EXII Transmission electron microscope (JEOL, Tokyo).

Immunoblotting and Immunoprecipitation (IP)

Methods were performed as described previously (Lee et al., 2012, PLoS ONE 7, e52491). For immunoblotting assay, cells were harvested into RIPA lysis solution (Millipore, Billerica, Mass.) supplemented with protease and phosphatase inhibitors (Roche). After electrophoresis of 30 μg lysates on polyacrylamide gels, electroblotting onto PDVF membranes (Millipore) was performed. After blocked by 5% non-fat milk in PBS at room temperature (1 hr), target protein was detected by using primary antibody. All membranes were incubated with chemiluminescent (Millipore) and imaging was captured by the ChemiDoc XRS system (Bio-RAD). Antibodies used were listed in Table 4. Data were analyzed by AlphaEaseFC (version 4.0.0) system. For IP assay, Cell lysates of bFGF-treated hTS cells were collected. By incubation with protein G-agarose (Millipore) for 30 min, total protein (100 μg) was treated with specific primary antibody overnight listed in Table 4. After treating with protein G-agarose beads (2 hr), sample was washed three times with RIPA lysis buffer (Millipore), following by adding with protein loading dye and boiled for 5 min. The sample was resolved by 8% SDS-PAGE and subjected to immunoblotting analysis.

Sample Preparation for 2-Dimensional Gel Electrophoresis (2-DE)

Two samples were obtained: cell culture medium (5-days, as study group) and pure culture medium (as control group). Samples were prepared as described previously (Chou et al., 2015). Briefly, samples (0.1 ml) were incubated with 1 ml ice-cold acetone containing 11% trichloroacetic acid (TCA, w/v) and 20 mM DTT for 30 min at −20° C. After centrifugation (12,000 rpm, 10 min, 4° C.), the protein pellet was washed twice with 1 ml cold acetone containing 20 mM DTT, followed by air-dry to remove the acetone. Then, appropriate rehydration buffer (7 M urea, 2 M thiourea, 2% CHAPS, 0.5% IPG buffer, 20 mM DTT) was added and the concentrated sample was measured by the Bradford method. For 2-DE analysis, a total of 150 μg protein was incubated with buffer containing 5 M urea, 2 M thiourea, 3% w/v CHAPS, 1% immobilized pH gradient (IPG) with a nonlinear pH of 3-10, 100 mM DeStreak reagent, and a trace of bromophenol blue. After a series of treating processes, the sample was cup-loaded near the anode of the IPG strips using the Ettan IPGphor cup-loading (Amersham Biosciences) and protein focusing was achieved using the IEF parameters according to the manufacturer's protocol. After first dimensional electrophoresis, isoelectric focusing IPG strips was shaked in a conditioned equilibration buffer containing 1% w/v DTT (15 min), and followed by the same solution containing 2.5% w/v iodoacetamide (15 min). The strip was transferred on top of the 12% SDS-polyacrylamide gel (PAGE). The second dimension separation was performed by a constant 75 V (30 min) and 100 V (16 hr). The 2-DE gel was silver-stained and detected with the Typhoon 9410 scanner (Amersham Biosciences) The spots were compared and quantified by using the Image Master 2D Platinum system. (Amersham Biosciences).

Electrospray Ionization-Quadrupole-Time of Flight Tandem Mass Spectrometry (ESI-Q-TOF-MS/MS) for Protein Identification and Quantitation To identify the 2D gel protein observed, the samples were digested by trypsin, followed by subjecting to the nanoflow liquid chromatography and Waters-Micromass ESI-Q-TOF for protein identification (Waters, Manchester, UK) as described previously (Chou et al., 2015). To obtain the corresponding peak lists, the MS/MS spectra of individual fragments of each of the precursors were processed by MassLynx 4.0 software (Manchester, UK) and the peak list files were uploaded to an in-house Mascot server for protein identification.

Statistical Analysis

All of the experiments were conducted in triplicate and repeated two times as indicated. Data obtained from Western blots, qPCR, luciferase reporter assay, and flow cytometry were calculated by Student's t-test. In animal study, paired ANOVA test was use statistically. p-value <0.05 was considered statistically significant.

Results 1) bFGF Alone Induces DE Differentiation in hTS Cells

Figure 10A:
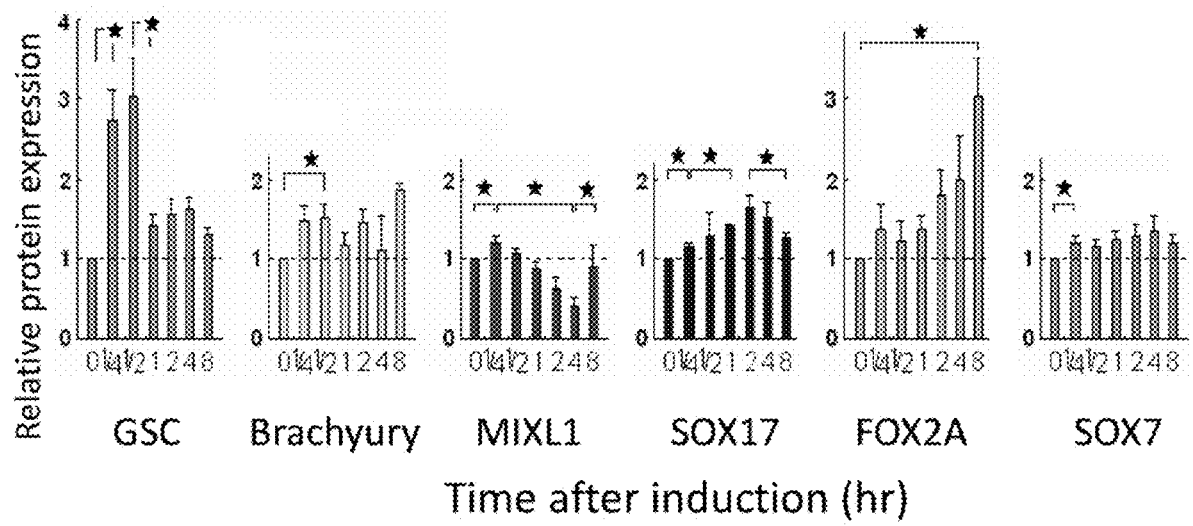
FIGS. 10A to 10D and 10E to 10J illustrate immunoreactive markers during DE formation. (10A) Western blot analysis in time course of representative markers of primitive streak and DE markers at the initial induction (8 hr). Data indicating mean±SD, n=3, *: p<0.05 as statistic significant. (10B) immunocytochemistry of Foxa2 and Sox17 (left panel), Gsc (middle panel), and Mixl1 (right panel) at 4 hr of bFGF induction. (10C) Identification of CREB1 in targeting at three sites of promoter (SEQ ID NOS 107-109, respectively, in order of appearance) (upper panel) in miR-124a to increase its levels by ChIP-qPCR. C: as control. Data representing mean±SD, n=3, *: p<0.05 as statistic significant. (10D) bFGF induces a parallel expression between phosph(p)-CREB1 and miRNA-124a by qPCR assay. Data indicating mean±SD, n=4, *: p<0.05 as statistic significant. (10E) A shifting mean Mixl1 intensity in cells within 4 hr induction by TissueFAX analysis. Blank area as control, blue area as mesendoderm stage, red area as DE stage. (10F) FGFR inhibitor (PD 166866) blocks the bFGF-induced PI3K by Western blotting. β-actin was used as loading control. (10G) PI3K siRNA inhibits expression of PI3K and p-Akt. Cells transfected with non-specific shRNA are used as control. β-actin was used as loading control. (10H) siRNAs against Akt subunits inhibits the bFGF-induced expressions of p-Akt and p-CREB1. Cells transfected with non-specific shRNA were used as control. β-actin was used as loading control. (10I) Akt interacts directly to CREB1 by IP assay. (10J) bFGF-induced miR-124a is inhibited by using CREB1 shRNAs. Data representing mean±SD, n=3, *: p<0.05 as statistic significant.
Figure 10B:
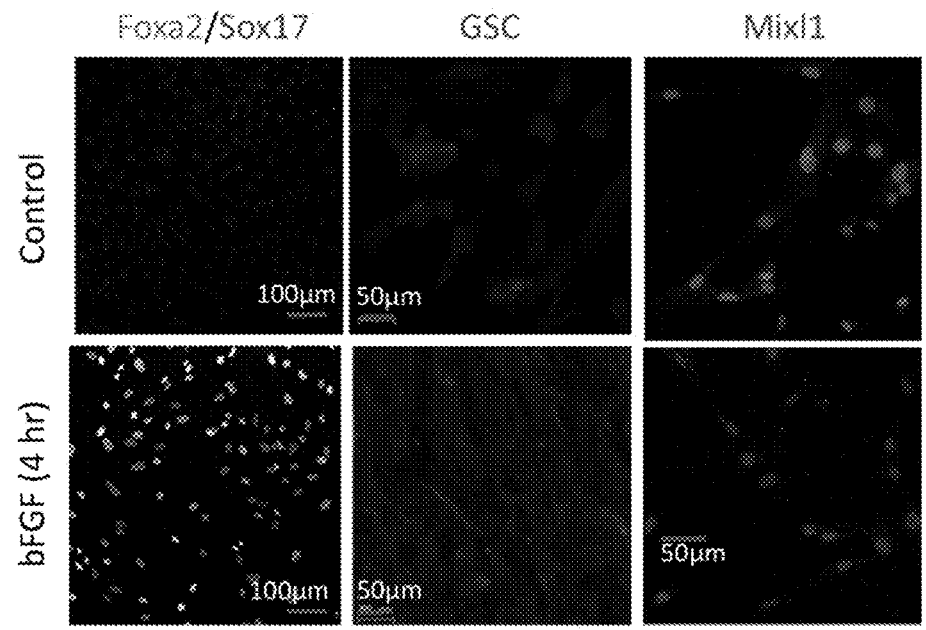
Figure 10C:
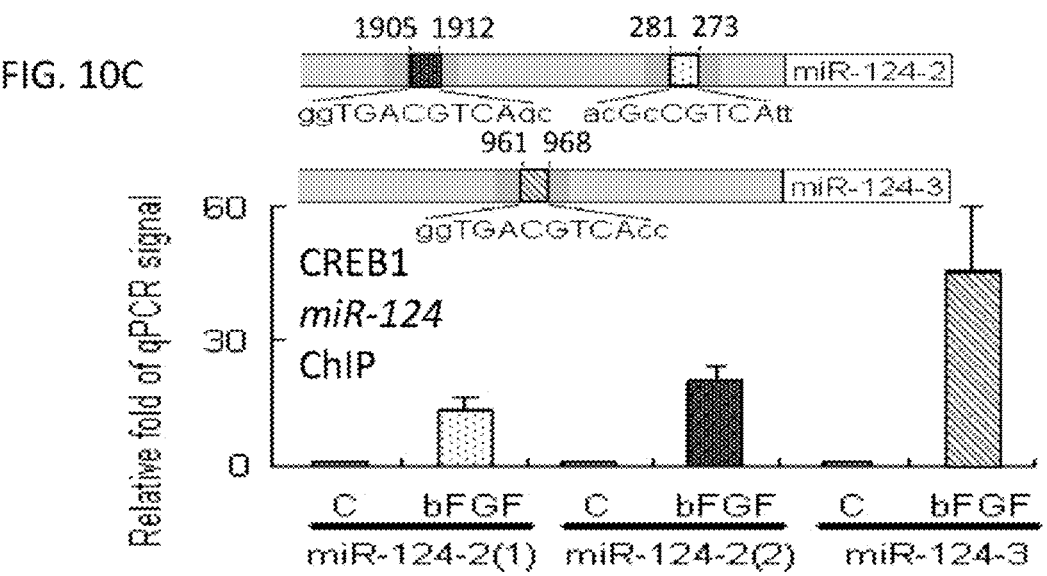
Figure 10D:
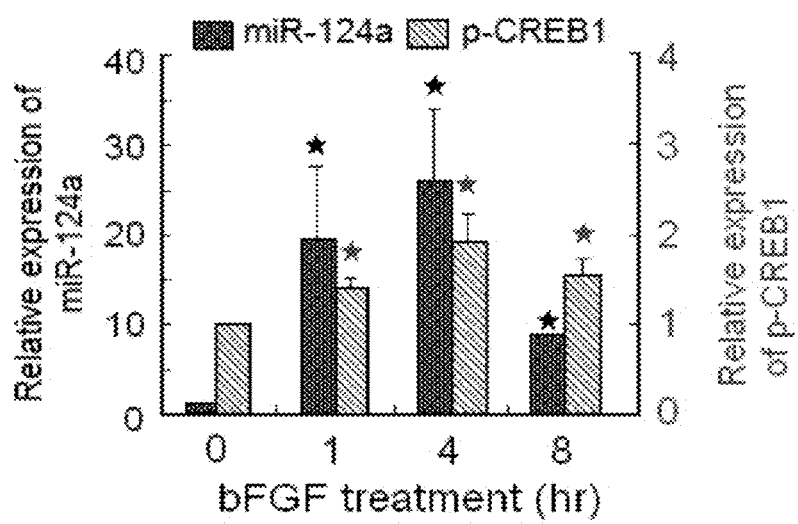
Figure 10E:
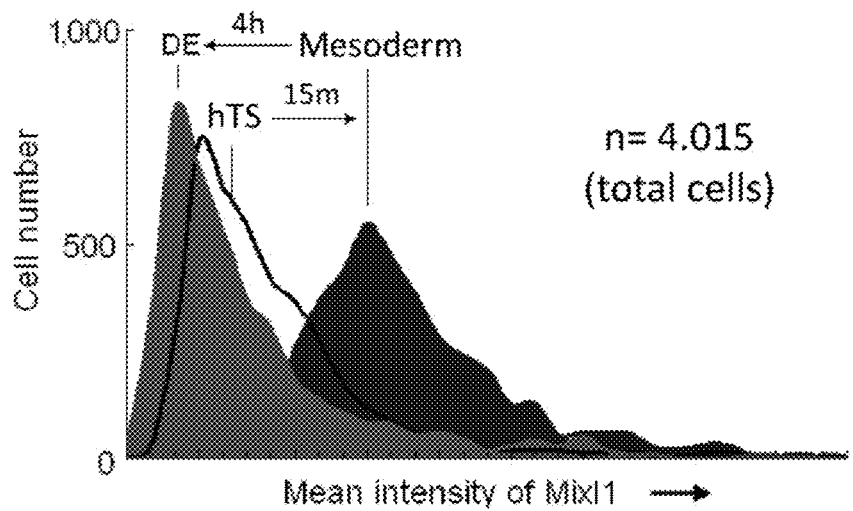

The path from stem cells to hepatic lineages composes of a progressive series of cellular processes, particularly including the required and essential step in DE formation. hTS cells were treated with bFGF (10 ng/ml) initially and measured the levels of DE-associated markers over time by immunoblotting assay. The results showed that at the initial 15 min of induction, transcription factors such as goosecoid (Gsc), Brachyury (T), homeodomain protein Mixl1 (Mixl1), SRY-box 17 (Sox17), forkhead box protein A2 (Foxa2, also known as Hnf3β), and the primitive endoderm marker Sox7 were significantly upregulated, peaking in between 30 min and 1 hr (FIG. 10A). These data implicated a fast transition from hTS cells to the nascent mesendoderm mediating primitive streak stage compatible with the liver development in early embryogenesis. Henceforth, Sox17 levels continually elevated to 4 hr and declined; whilst Foxa2 and Brachyury elevated to 8 hr but Sox7 expression became nascent after 15 min of induction. Notably, intensity of Mixl1 downregulated from the peak (15 min) to a nadir at 4 hr (~50% lower than the native one) and returned to the original levels at 8 hr measured by TissueFAX analysis (FIG. 10E). Their changes in expression were also demonstrated by immunofluoresence imagings (FIG. 10B). These results indicate that bFGF alone enables to rapidly differentiate hTS cells to DE stage through primitive streak and mesendoderm mimicking the embryonic liver development.

Figure 10F:
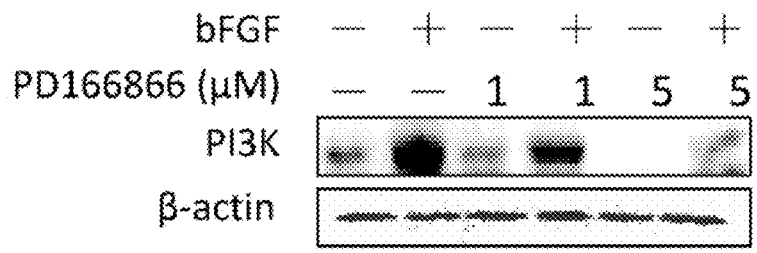
Figure 10G:
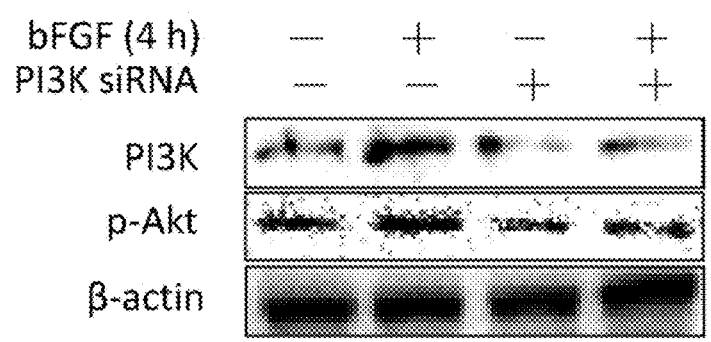
Figure 10H:
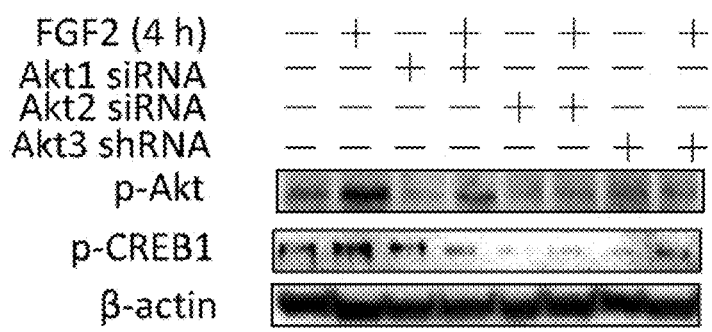
Figure 10I:
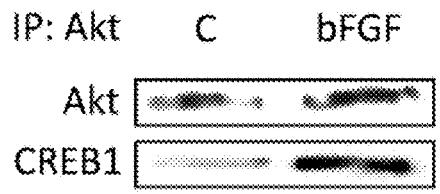
Figure 10J:
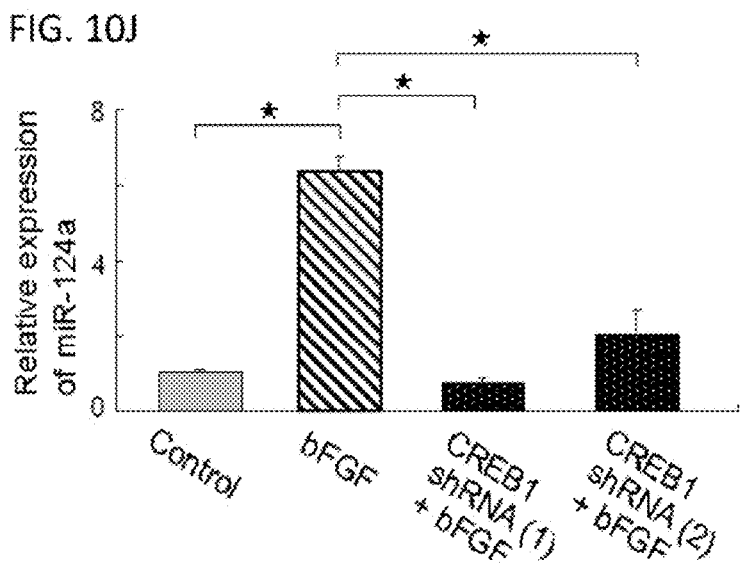

2) PI3K/Akt/CREB1 Signaling Pathway Promotes MiR-124a Expression bFGF enabled to induce the PI3K/Akt/CREB1 signaling pathway via its receptor FGFR1 in hTS cells. hTS cells were treated with bFGF (10 ng/ml) in the conditioned medium. FGF receptor (FGFR) inhibitor PD166866 could block the bFGF-induced activation of phosphatidylinositol 3-kinase (PI3K) by immunoblotting assay (FIG. 10F), suggesting that the inhibitory effect was through the FGFR at the cell membrane. As a result, the downstream effector AKT was phosphorylated evidenced by using PI3K siRNA (FIG. 10G). To clarify which protein kinase B (AKT) subunit was activated, specific siRNA against three AKT subunits: AKT1, AKT2, and AKT3 were examined by immunoblotting assay. The result showed that only AKT1 phosphorylated and activated its downstream effector cAMP response element-binding protein 1 (CREB1) (FIG. 10H). This function was further confirmed by immunoprecipitation (IP) assay (FIG. 10I). Taken together, this indicates that bFGF induces activation of the PI3K/AKT1/CREB1 signaling pathway at 4 hr induction.

microRNA (miR)-124, a small non-coding RNA, is involved in the Foxa2 expression in pancreatic β-cells, a derivative of ventral foregut endoderm. Subsequently, in the nucleus, the activated CREB1 directly targeted at three sites of the promoter of miR-124a to induce miR-124a expression at 4 hr induction by ChIP-qPCR assay (FIG. 10C) and knockdown of CREB1 reduced its expression (FIG. 10J). Expression of CREB1 and miR-124 over time appeared in a parallel correlation by qPCR analysis (FIG. 10D). These results indicate that bFGF-induced PI3K/Akt/CREB1 signaling pathway enables to spatiotemporally upregulate miR-124a at the early differentiation of hTS cells.

3) MiR-124a Directs DE Specification

Figure 11A:
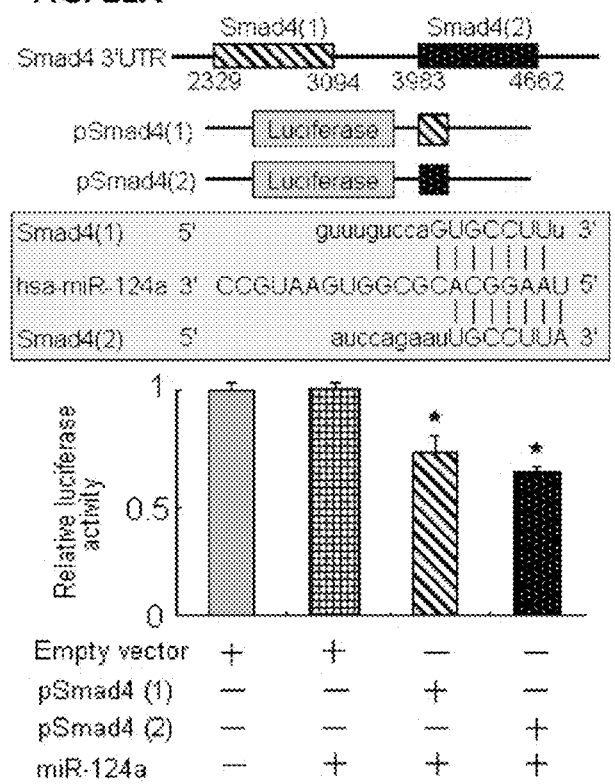
FIGS. 11A to 11I and 11J to 11K illustrate molecular mechanisms for DE specification. (11A, 11B, 11C) Luciferase reporter assays of miR-124a repressing the expressions of Smad4 plasmid (pSmad4) (A), pGSK3β (B), and pCdx2 (C) via targeting the promoter(s) of gene (upper panel). Empty vector: control, Data indicating mean±SD, n=3, *: p<0.05 as statistic significant.
Figure 11B:
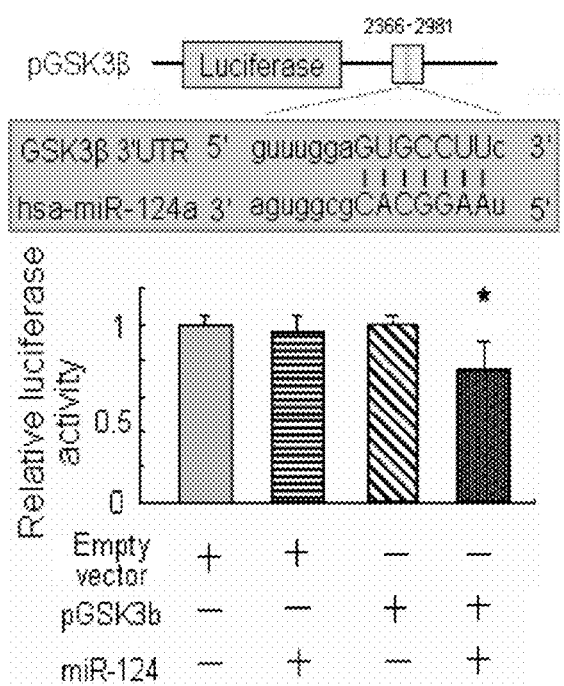
Figure 11C:
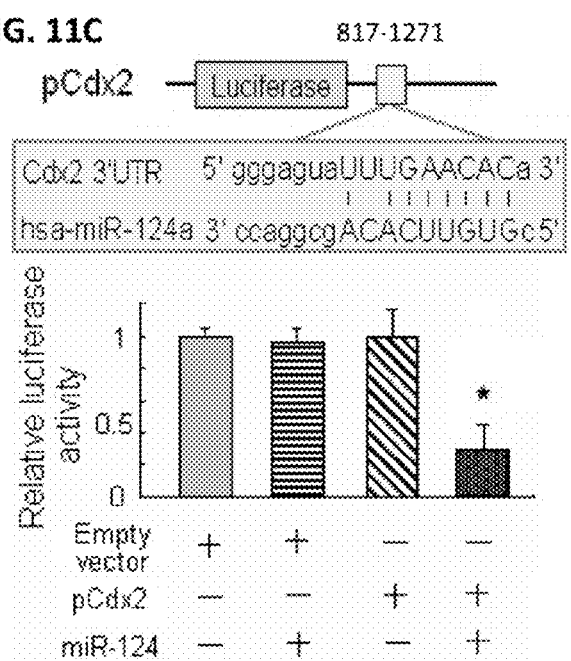
Figure 11D:
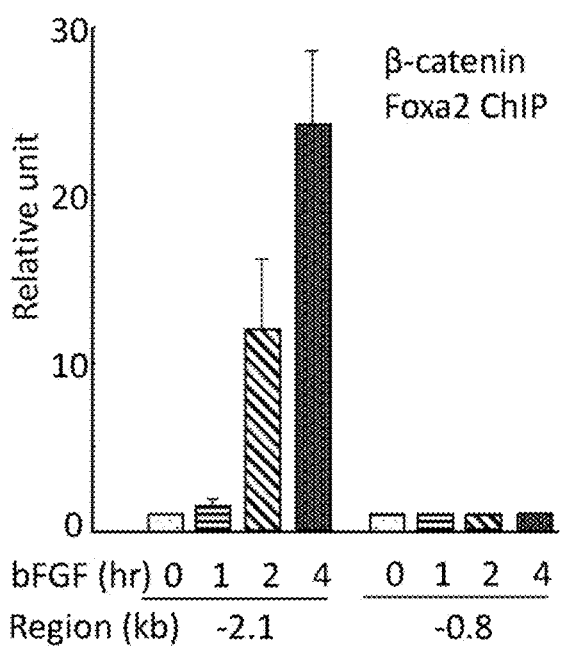
Figure 11E:
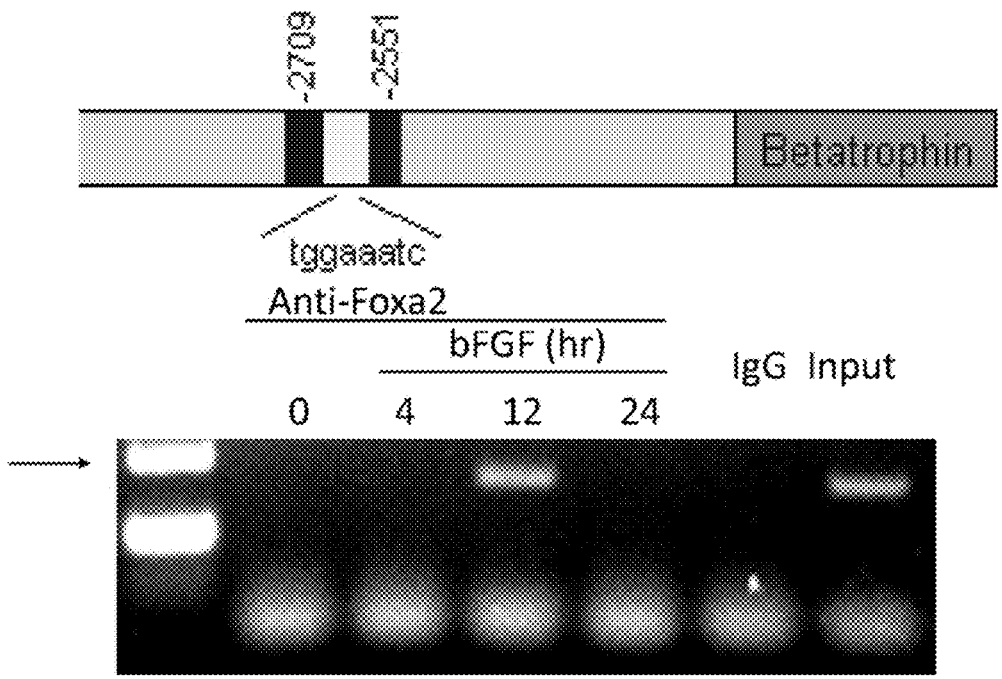
Figure 11F:
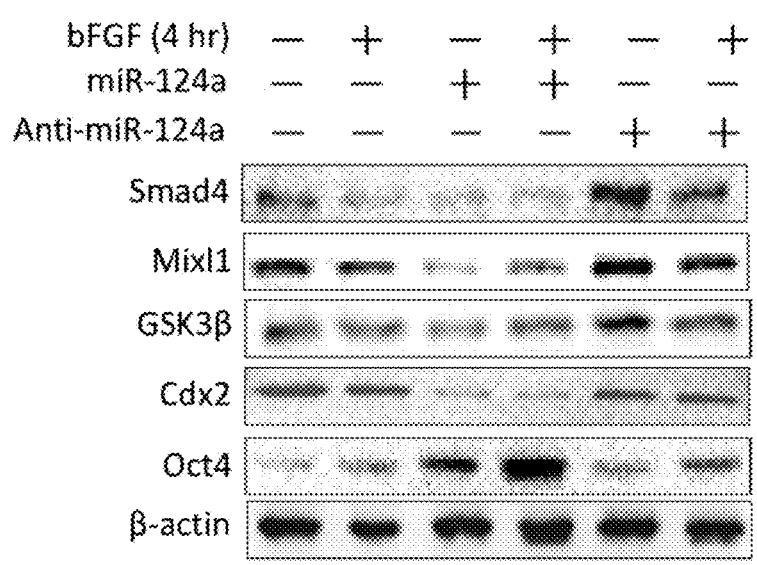

Several genes relevant to hepatogenesis were screened and constructed the luciferase reporter assays, by which several signal transduction proteins were measured, including mothers against decapentaplegic homolog 4 (Smad4) (FIG. 11A), glycogen synthase kinase 3β (GSK3β) (FIG. 11B), and homeobox transcription factor Cdx2 (FIG. 11C). Inhibitory functions of miR-124a include: i) to target at the promoter of Smad4 messenger RNA (Smad4 mRNA) to prevent Smad4 production (FIG. 11A, lower). Consequently, the inhibitory Smad4 caused suppression of Mixl1, which was verified by knockdown of Smad4 (FIG. 11J). This mechanism explained the downregulation of Mixl1 in the DE stage (FIG. 10A) and the migratory cell fate transition during gastrulation; ii) to target at the promoter of GSK3β mRNA to inhibit its translation (FIG. 11B, lower), thereby, resulting in the nuclear translocation of downstream substrate cadherin-associated protein β-1 (β-catenin). In the nucleus, β-catenin targeted the promoter of Foxa2 gene to produce Foxa2 (FIG. 11D), highlighting the differentiation at the stage of DE. Interestingly, this increased Foxa2 in turn induced c19orf80 gene transcription, encoding betatrophin protein expression (FIG. 11E). Betatrophin is a hormone produced in liver, controls pancreatic β cell proliferation; iii) to target at the caudal-related homeobox transcripts Cdx2 mRNA to inhibit its translation to the pluripotent transcription factor Cdx2 (FIG. 11C, lower). All these molecular events occurred at 4 hr induction, which was confirmed by using miR-124a and anti-miR-124a antibody by immunoblotting assay (FIG. 11F).

Figure 11G:
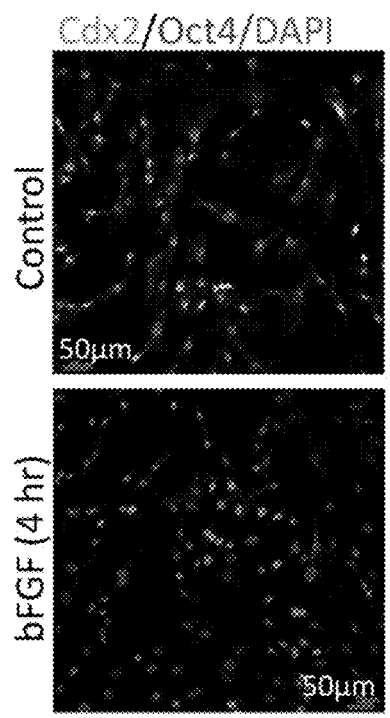
Figure 11H:
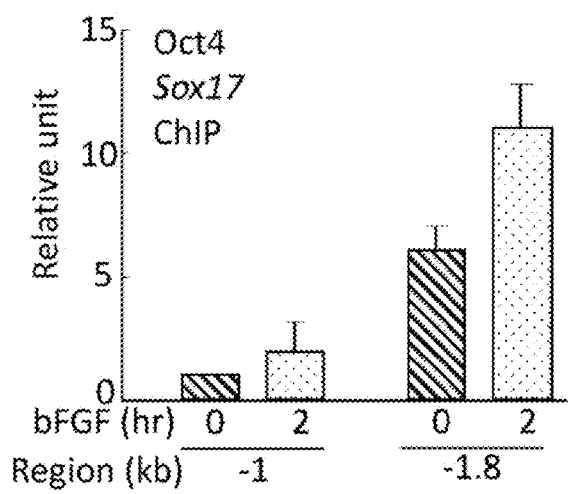
Figure 11I:
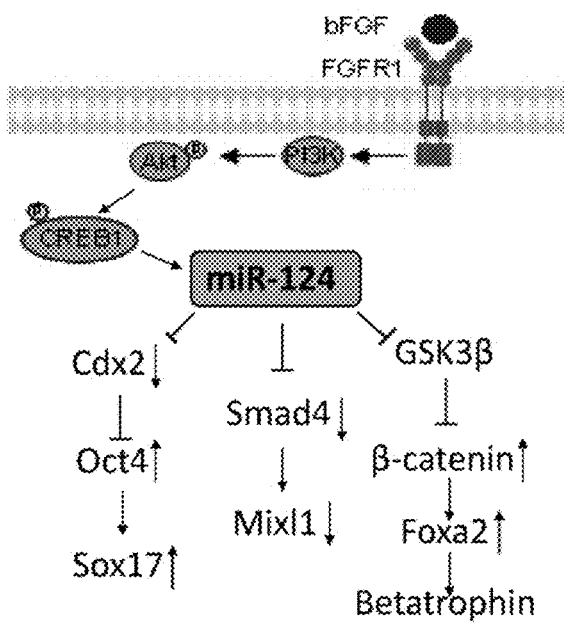
Figure 11J:
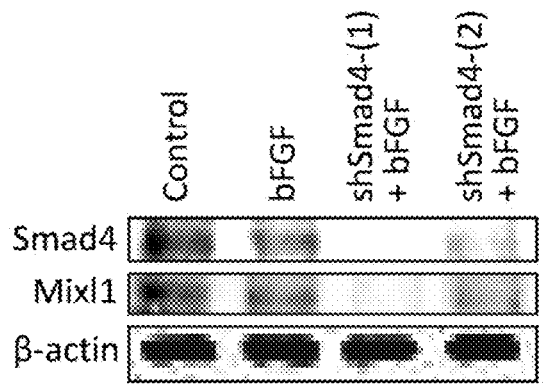
Figure 11K:
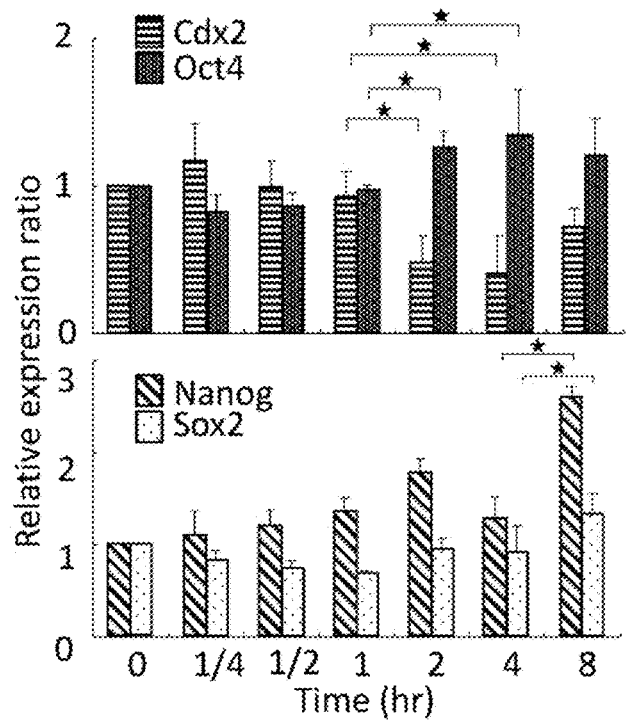

Subsequently, the decreased Cdx2 promoted upregulation of pluripotent transcription factor Oct4 by immunofluorescence imaging study (FIG. 11G). Overexpression of Oct4 was further verified by knockdown of miR-124a using anti-miR-124a antibody by immunoblotting assay (FIG. 11F). This reciprocal inhibitory relationship between Cdx2 and Oct4 is evidenced by immunoblotting assay (FIG. 11K, upper). Furthermore, observed was the significantly gradual elevation of pluripotency transcription factor Nanog at 8 hr induction (FIG. 11K, lower). These results suggested that Oct4 played the main role in maintaining the pluripotent characteristics of DE lineages; while Nanog might play as a supportive role consistent with that in hES cells. Importantly, the activated Oct4 in turn targeted at the promoter of Sox17 gene by ChIP-qPCR assay (FIG. 11H) that promoted Sox17 expression (FIG. 10A). Expression of Sox17 represented another milestone in the DE differentiation. Together, FIG. 11I is a schematic illustration to describe the regulatory molecular mechanisms, by which bFGF induction initiated DE formation mediating miR-124a in hTS cells.

4) Generation of Hepatocyte-Like Cells in 3-D Tissue Structure

Figure 12A:
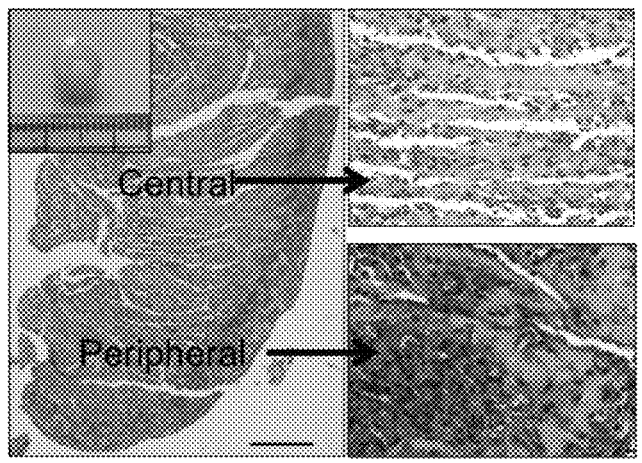
FIGS. 12A to 12D and 12E to 12F illustrate biological characteristics of hepatocyte-like cells. (12A) H&E staining of the crescent cell mass (left panel, insert). Numerous clustered cells distributed irregularly at the outer peripheral layer containing abundant small embryonic progenitor-like cells with condensed nuclei (right lower). Columnar tree-like ECMs along with hepatocyte-like cell linings radiating from the peripheral layer to the central areas (right upper). (12B) Hepatocyte-like cells in the CC14-damaged liver tissues, showing immunoreactive stem-121-positive cells (left upper), C-kit positive cells (right upper, arrow), CK19 (left lower, arrow), and CK18 (right lower, arrow). (12C) A variety of specific immunoreactive markers during liver development observed in the crescent cell mass histologically. Cellular surface markers make up polygonal shape of hepatocyte seen in small insert. (12D) Representative electron micrographs showing: a large cytoplasm/nucleus ratio, plenty of mitochondria (m), endoplasmic reticulum (rer), lipid droplets, space of Disse (SD), extracellular matrix (ecm), nucleus (n), and sinusoid in upper micrograph, glycogen (gly) storage with rosette formation (red circle) in lower left micrograph, and lower right micrographs showing bile canaliculus lumen (bc) and junctional complex (upper) and tight junction (lower). (12E) Immunoreactive albumin (ALB) and AFP expressed in the hepatocyte-like cells. (12F) Morphological changes during hTS cells differentiation to hepatocyte-like cells in time course.
Figure 12B:
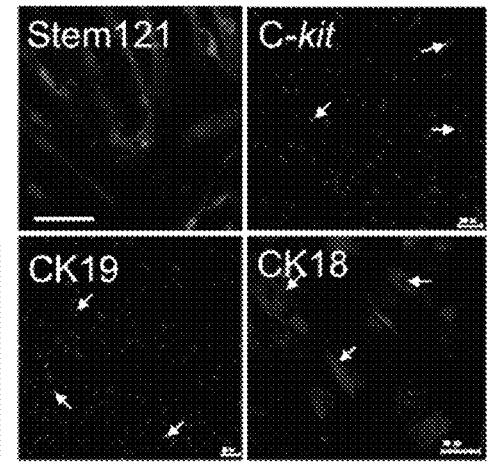

Subsequently, cells were cultured with a combination of bFGF (10 ng/ml), dexamethasone (Dexa; 0.1 μM), oncostatin M (OSM; 10 ng/ml), bone morphogenetic protein 4 (BMP4; 20 ng/ml), and hepatic growth factor (HGF; 5 ng/ml) after DE formation (8 hr). Unexpectedly, cellular morphology might exhibit as dispersed fibroblast-like cells or gradually aggregate to form a crescent cell mass, depending on seeding density in culture (FIG. 12A. insert and FIG. 12F). Histologic examination of the cell mass revealed two distinct peripheral and central compartments, constructing a 3-dimensional (3D) tissue structure. In the peripheral part, numerous clustered small cells distributed irregularly among the extracellular matrix (ECM) beyond the basement membrane. Cells had condensed nuclei, frequently eccentric located, and abundant granular and vacuoles in the eosinophilic cytoplasm similar to the embryonic stem/progenitor cells (FIG. 12F). In the central part, many independent columnar ECMs, by cell linings at both sides, distributed from the basal towards the central areas (FIG. 12A). These cells contained abundant eosinophilic cytoplasm and dispersed chromatin in the single round nucleus with one or two prominent nucleoli mimicking the phenotypic hepatocytes. Several binucleate cells could be seen. This feature is similar to that known as hepatic plates in human liver.

Figure 12C:
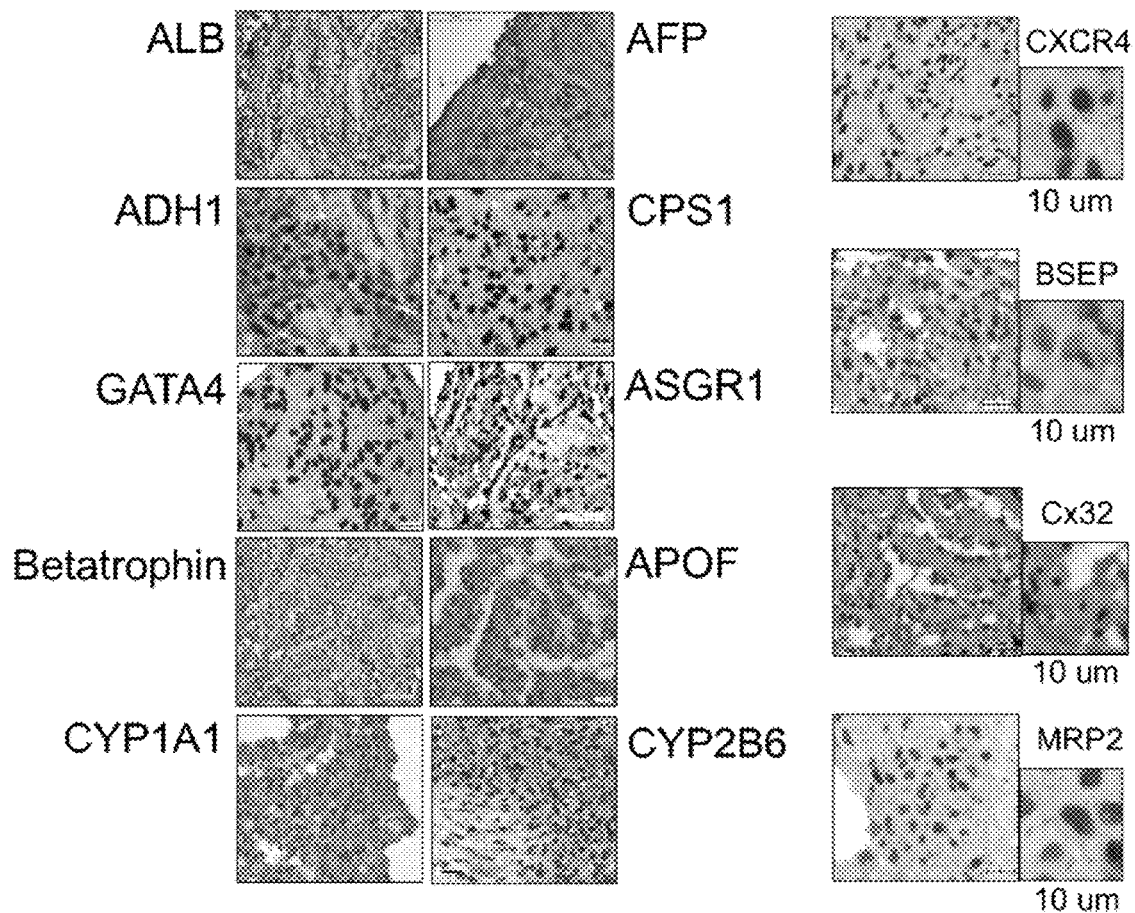
Figure 12D:
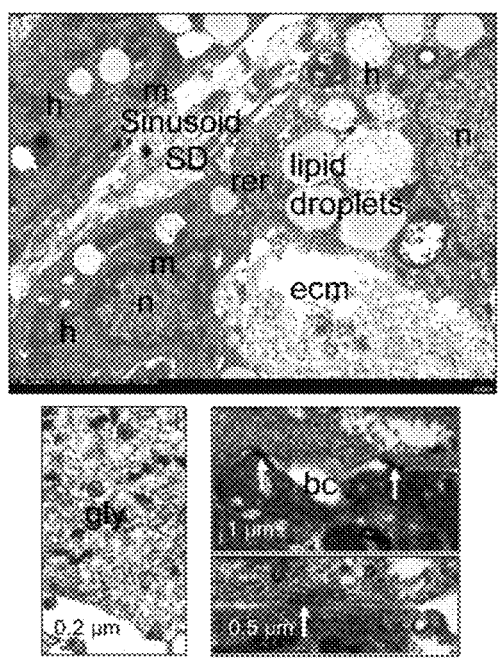
Figure 12E:
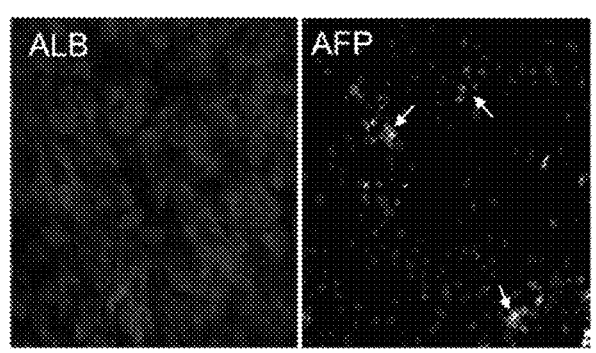
Figure 12F:
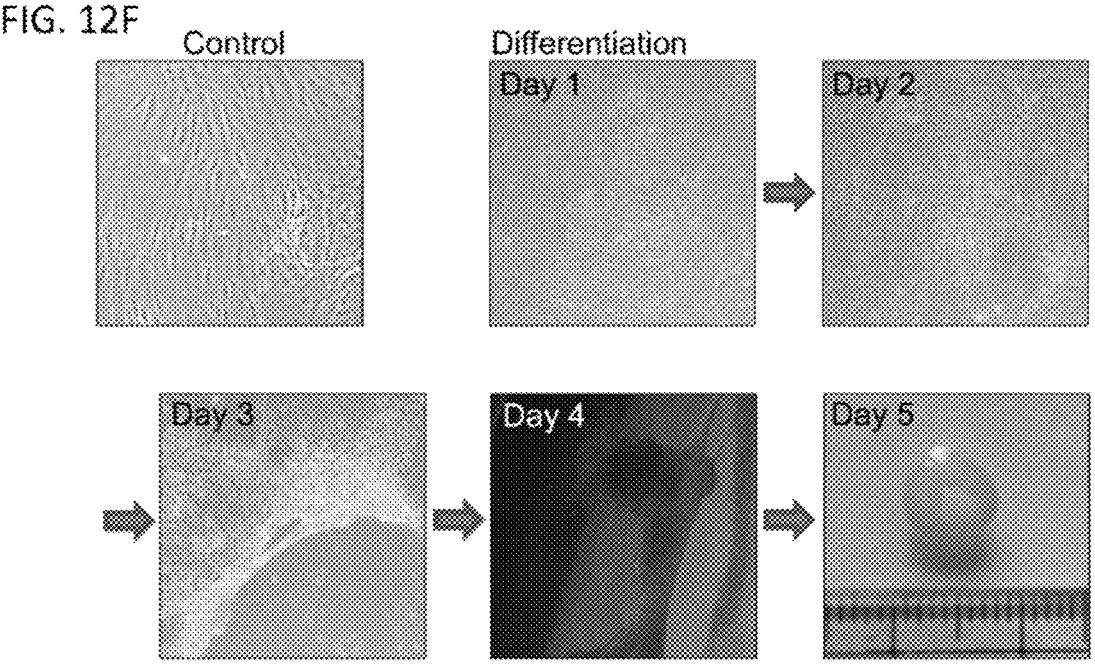

Immunocytochemically, these hepatocyte-like cells exhibited specific marker(s) of: i) human cytoplasmic marker stem 121™ for human cells, mast/stem cell growth factor receptor C-kit for liver intrinsic stem cells, CK19 for cholangiocytes, and CK18 for hepatocytes (FIG. 12B); and ii) albumin (ALB), α-fetoprotein (AFP), Betatrophin, ADH1, APOF, CPS1, GATA4, CYP1A1, and CYP2B6 in the cytoplasm for hepatocytes immunohistochemically (FIG. 12C, and FIG. 12E). Whilst a subset of surface markers including ASGR1, CXCR4, BSEP, MRP2, and Cx32 constructed a polygonal cell shape similar to the primary human hepatocyte (FIG. 12C). Furthermore, electron microscopy revealed a similar ultrastructure to primary hepatocyte, including a large cytoplasm to nucleus ratio, plenty of mitochondoria, well-organized endoplasmic reticulum, tight junction, numerous lipid vacuoles, glycogen storage, enlarged lumen of the bile canaliculus with junctional complexes, and multiplex ECMs (FIG. 12D).

Figure 13A:
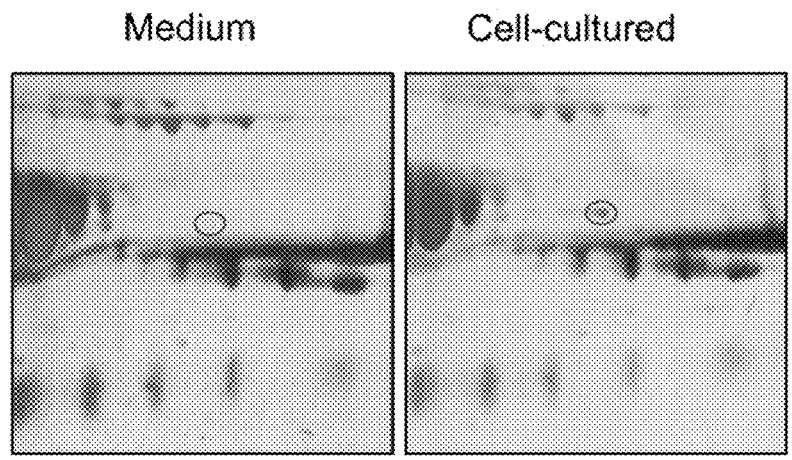
Figure 13B:
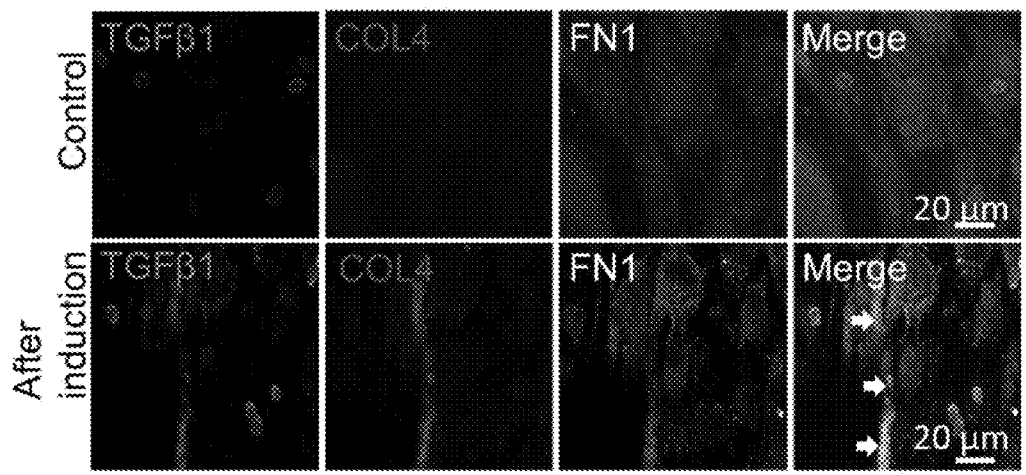

5) TGFβ1 Contributes to the Formation of Fibronectin and Collagen IV Scaffold in Hepatic ECMs Among 9 newly upregulated, secreted proteins in the cell-cultured medium, protein (no. 413) became an attractive target because it significantly predicted, by 46% of peptide sequences matched, to be the transforming growth factor-β (TGF-β)-induced protein ig-h3 precursor (TGFβ1) by Mascot MS/MS ions search system (ESI-QUAD-TOF, Bruker Impact HD, Matrix Science, USA) (FIG. 13A, red arrow; FIG. 13C). TGFβ1 is a major fibrogenic, multifunctional cytokine, acting as both autocrine and paracrine manner to enhance fibronectin and collagen formation in hepatic stellate cells (HSCs). Accordingly, to identify the presence of TGFβ1, immunohistochemistry was used to demonstrate the coexpression of immunoreactive TGFβ1, fibronectin, and collagen IV in the ECMs by immunohistochemistry (FIG. 13B). These results suggest that TGFβ1, fibronectin, and collagen IV constitute, at least partly, the scaffold of ECMs in the 3-D tissue structure of hepatocyte-like cells that may support proliferation and differentiation of hepatocytes in the hepatic plates.

6) Transcriptional Expression Characterizes the Stage-Specific Hepatic Differentiation Forty two hepatic development-associated genes were analyzed, suggesting that differentiating cells might share an overlapping pattern in gene expressions during cellular processes. As mentioned, the transition from pluripotent hTS cells to primitive streak (15 to 30 min) and mesendoderm 1 hr), expressing an elevation of GSC, Brachyury (T), and Sox7 along with a gradual increase of Mixl1, Foxa2 and Sox17 was observed (FIG. 10A). Sox7 is primarily expressed in the primitive streak, visceral endoderm, and parietal endoderm but not DE (Kanai-Azuma et al., 2002). At the DE stage (1 to 8 hr), persistence of high transcriptional expressions sustained, including CXCR4, Foxa2, Sox17, HHEX, and Sox7, and declined thereafter (Table 3). As cell process entered the hepatic endoderm stage (8 hr to 1 day), a core group of endoderm transcription factors including Sox17 and Foxa2, in turn, regulated a cascade of genes committing cells to the endoderm lineage. Shortly after hepatic specification, the epithelium begins to express genes associated with liver bud genes including Albumin, AFP, and Hnf4α. A large number of hepatoblast-associated gene expressions emerged to commit cell differentiation to bipotential hepatoblasts (day 2 to day 4). Wherefrom hepatoblasts expressed specific genes in association with fetal hepatocytes (like AFP), adult hepatocytes (like ALB and Hnf4α), and biliary epithelial cells (like cytokeratin-19), allowing the differentiation to reach the fetal/adult hepatocytic stage (>day 4). Together, these progressive transcriptional expressions are consistent with the cellular processes in liver development as listed in Table 3.

7) Hepatocyte-Like Cells Exhibit Liver Functions

Figure 14A:
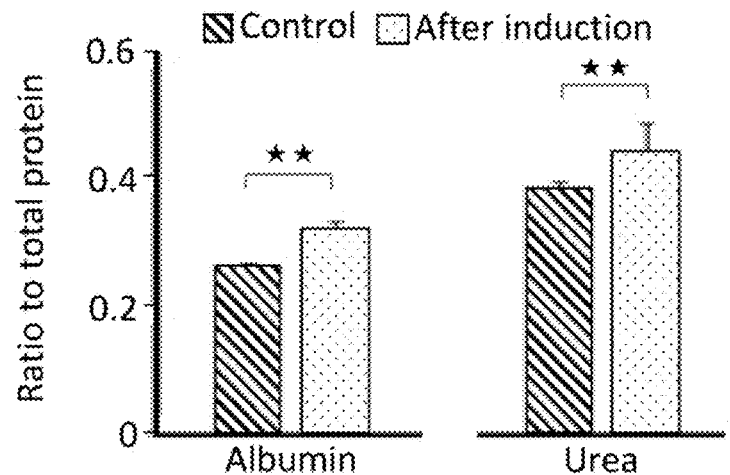
FIGS. 14A to 14E illustrate functional Characteristics of Hepatocyte-Like Cells. (14A) HepatoHepatocyte-like cells secrete albumin (left) and urea (right; by stimulation of 5 mM ammonium chloride for 1-day) into the cultured medium by automatic analyzer (Hitachi 7080; Tokyo, Japan). Error bars indicate SD of 3 replicates. **: p<0.01. (14B) LDL uptake assay shows immunoreactive LDL (red, left), LDL receptor (LDLR, green, middle), and their emerged image (right) in the cells. (14C) Oil-O-Red test shows fat droplets (red) in the cells. (14D) Glycogen storage test identifies the presence of glycogen (pink and red) by periodic acid-Schiff (PAS) staining using diastase treatment (upper panel) and also by fluorescent PAS staining (lower panel). (14E) A variety of phase I-II CYP 450 enzyme activity in response to inducer (green) and inhibitor (pink) at 24 hr treatment in hepatocyte-like cells by qPCR analysis. Abbreviations: Rif, rifampin; Cip, ciprofloxacin; Itra, itraconazole; Phen, phenobarbital; Gem, gemfibrozil; THA, 2,4,6-trihydroxyacetophenone; CDCA, chenodeoxycholic acid; and Tico, ticlopidine.
Figure 14B:
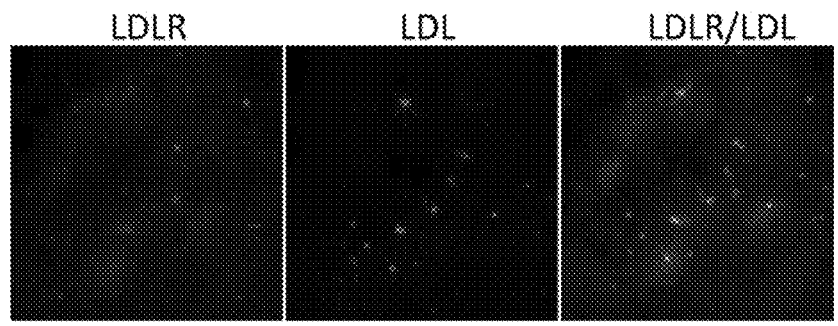
Figure 14C:
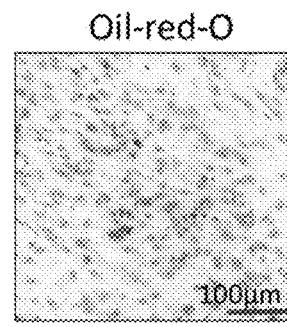
Figure 14D:
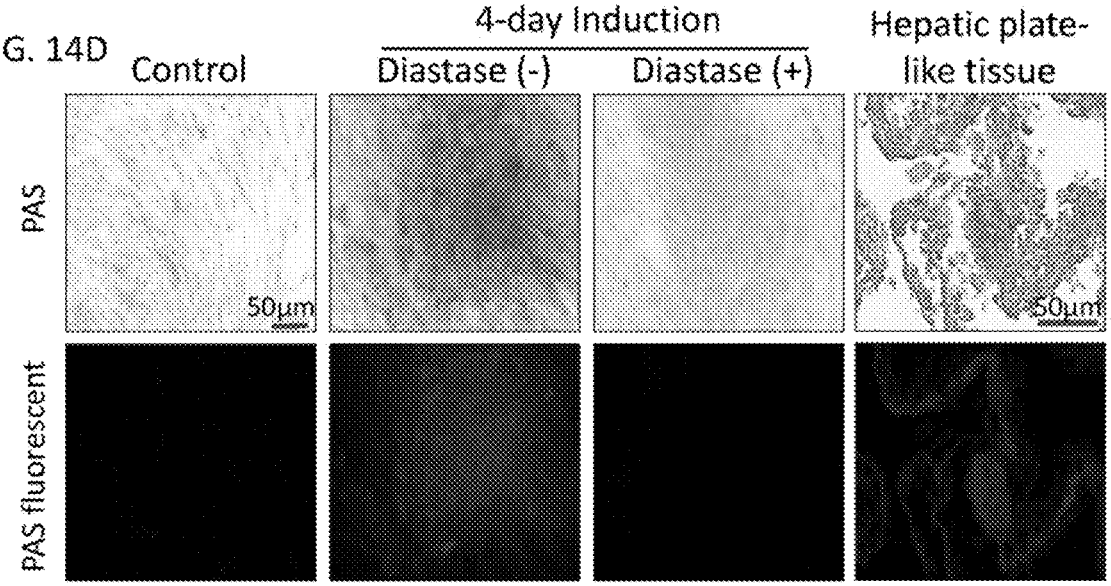
Figure 14E:
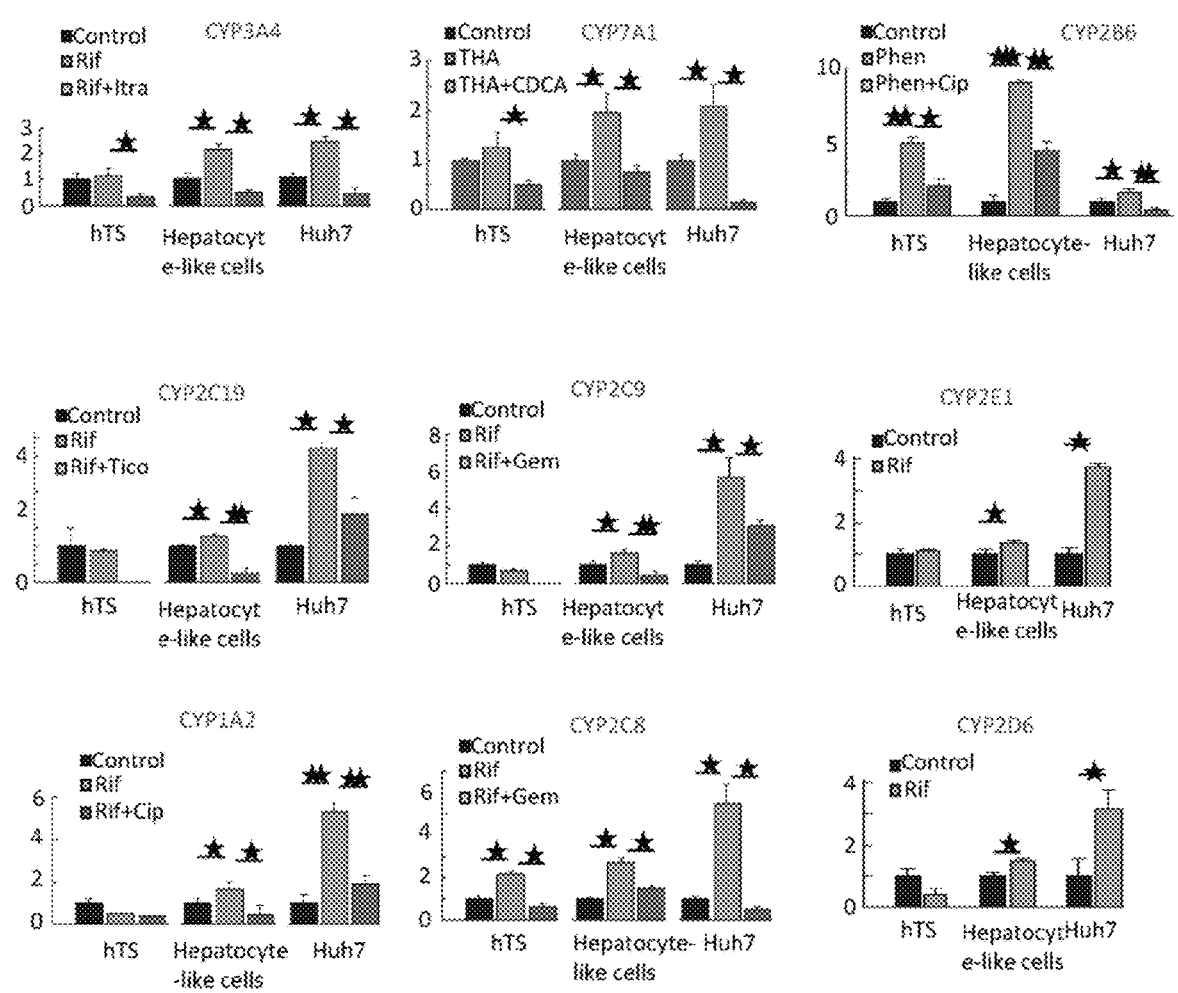

Preservation of liver functions is essential requirement in the pluripotent stem cell-derived hepatocytes. To that, cell culture medium was collected and subjected to the enzyme-linked immunosorbent assay (ELISA). The results demonstrated the elevated levels of albumin, $NHCl_4$-induced urea, and $CCl_4$-induced GOT, GPT, and ALP in the medium after induction (FIG. 14A). LDL uptake assay revealed that these cells contained ability of LDL uptake (FIG. 14B). Oil-O-Red staining revealed the presence of lipid droplets, suggesting the capacity in adipogenesis (FIG. 14C). Furthermore, glycogen storage test revealed a positive periodic acid-Schiff (PAS) staining, which was supported by diastase digestion and PAS fluorescence emission test in either cytology or histology (FIG. 14D). Next, qPCR analysis revealed the capacity of cytochromes P450 (CYPs) enzymes in response to a variety of metabolize specific drugs, including CYP3A4, CYP7A1, CYP2B6, CYP1A2, CyP2C8, CYP2C9, CYP2D6, and CYP2E1 (FIG. 14E). Functionally, for example, the refampin-induced CYP3A4 mRNA was reduced by its inhibitor itraconazole; while the 2,4,6-trihydroxyacetophenone (THA)-induced cholesterol 7α-hydroxylase (CYP7A1) mRNA was reduced by chenodeoxycholic acid (CDCA). These results suggest the capability in oxidation of xenobiotics as well as the bile acid and cholesterol metabolism, respectively.

8) Functional Hepatocyte-Like Cells Posses Characteristic of Stem Cell Homing

Figure 15D:

Animal study was designed to mimic the clinical scenario in acute hepatic failure, by which intraperitoneal infusion of carbon tetrachloride ($CCl_4$) was given in Sprague Dawley rats, followed by intravenous injection (tail vein) of the hTS cell-derived hepatocyte-like cells. The goals were to examine whether these xenografts can be survival by homing in the rat's liver and what role of these cells play. Serum samples were collected at 0, 1, 2, 4, and 7 days to measure AST and ALT levels. Rats were sacrificed at 2, 4, and 7 days to get the liver samples for histopathological studies. Biochemical study revealed that serum AST and ALT levels appeared to be significantly higher in the cell therapy group ($CCl_4$+cells) than the control group ($CCl_4$ only) over time (FIG. 15A). To elucidate this ambiguous observation, the liver tissues were inspected histopathologically.

Using human cytoplasmic marker stem-121™ (Stem Cell Technologies. Inc. WA) as an indicator, a positive immunoreactive stem-121 expression in hTS cells was identified (FIG. 15B), followed by the confirmation of presence of stem-121-positive hepatocyte-like cells in the liver tissues 4-day after implantation (FIG. 15C). This observation indicated that intravenous administration of the hepatocyte-like cells enabled to be homing to the liver tissues. Interestingly, these stem-121$^{positive}$ hepatocytes underwent degeneration as well immunohistochemically (FIG. 15C). This fact explains a much higher elevation of AST and ALT levels in the cell therapy group than the only CCl4-treated group because of an additional effect of $CCl_4$ (24 hr half-live in blood) which caused degeneration of the implanted hepatocyte-like cells. The intravenous infusion of hTS cell-derived hepatocyte-like cells can reach to and reside in the $CCl_4$ injury liver tissues.

9) Hepatocyte-Like Cells Possess Immune Privilege by Expressing HLA-G and TGFβ1 and Recruiting Capacity of CD4$^+$Foxp3$^+$ Treg Cells Implanted hepatocyte-like cells expressed human leukocyte antigen G (HLA-G) because there was a coexpression of stem-121 and HLA-G in the hepatic tissues at 4-days post-implantation immunohistochemically (FIG. 15D), suggesting a characteristic of immune privilege. HLA-G, membrane-bound or soluble, strongly acts on different immune cell types (NK, T, B, monocytes/dendritic cells) to inhibit both innate and adaptive immunity through the interaction with inhibitory receptors that are expressed at the surface of immune cells.

Figure 15E:
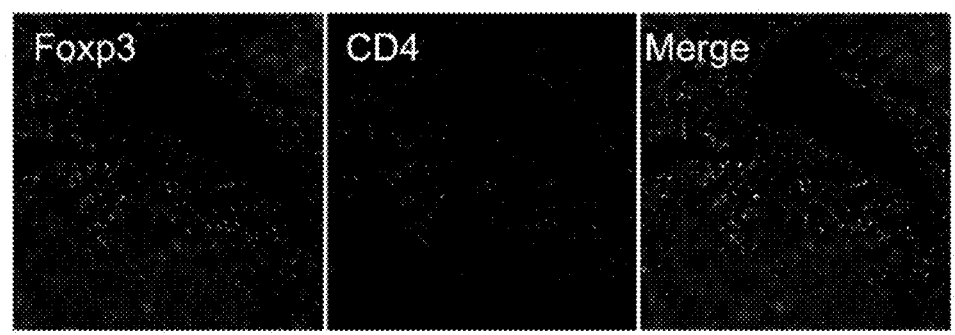
Figure 15F:
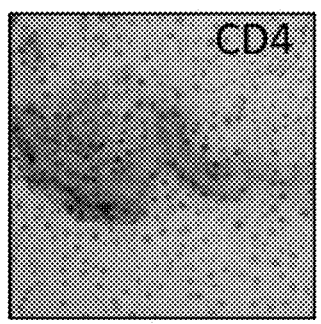

Furthermore, hepatocyte-like cells were able to secrete TGFβ1 into the ECMs (FIG. 13B). TGFβ1 is a critical regulator of thymic T cell development and a crucial player in peripheral T cell homeostasis, tolerance to self antigens, and T cell differentiation during the immune response. Meanwhile, CD4$^+$Foxp3$^+$ T regulatory (Treg) cells were present in the hepatic sinusoids immunocytochemically (FIG. 15E), suggesting the recruitment of the Treg cells to the liver in response to the implanted cells. Active immune suppression by cytokine TGFβ1 or CD4$^+$Foxp3$^+$ Treg cells plays a pivotal mechanism of peripheral T cell tolerance. The implanted hepatocyte-like cells possess immune privilege by expressing HLA-G and TGFβ1, and recruiting CD4$^+$Foxp3$^+$ Treg cells to the liver to control peripheral T cell tolerance.

TABLE 1

| Target | Manufacturer | Code no. | WB | Flow | IF |
|---|---|---|---|---|---|
| FGFR1 | Abcam | ab10646 | 1/400 | | 1/200 |
| MIXL1 | Abcam | ab57854 | 1/1000 | | 1/200 |
| SMAD4 | Santa Cruz Biotechnology | sc-7966 | 1/200 | | |
| CDX2 | Abcam | Ab76541 | 1/1000 | 1/40 | 1/200 |
| | Cell signaling | 3977s | 1/1000 | 1/40 | |
| | BD Pharmingen | 560395 | | | |
| OCT4 | Abcam | Ab19857 | 5 µg/ml | 1/40 | 1 µs/ml |
| | Millpore | MAB4419 | 2 µg/ml | | 1/200 |
| | BD Pharmingen | 560794 (Cy 5.5) | | | |
| NANOG | Chemicon | AB9220 | 1/1000 | 1/40 | 1/200 |
| | Cell signaling | 3580s | 1/1000 | | 1/200 |
| | BD Pharmingen | 560791 | | | |
| SOX2 | Epitomics | 2683s | 1/1000 | 1/40 | 1/200 |
| | Abcam | Ab59776 | 1/1000 | | |
| | BD Pharmingen | 560291 (PE) | | | |
| C-peptide | Abcam | Ab14181 | 1/100 | | 1/50 |
| | Santa Cruz Biotechnology | Sc-51647 | 1/100 | | 1/50 |
| β-actin | Santa Cruz Biotechnology | Sc-130065 | 1/2000 | | |
| Somatostatin | Santa Cruz Biotechnology | Sc-55565 | 1/200 | | 1/100 |
| Glut2 | Chemicon | AB1342 | | | 1/100 |
| Glucagon | Santa Cruz Biotechnology | Sc-13091 | 1/200 | | 1/100 |
| Insulin | Santa Cruz Biotechnology | sc-7839 | 1/100 | | 1/50 |
| Ngn3 | Santa Cruz Biotechnology | sc-25654 | 1/200 | | 1/100 |
| Amylase | Santa Cruz Biotechnology | sc-12821 | 1/200 | | 1/100 |
| Pancreatic polypeptide | Chemicon | sc-80494 | | | 1/100 |
| PDX1 | BD Pharmingen | 562160 | 1/2000 | | 1/200 |
| | Cell signaling | 5679 | 1/1000 | | 1/200 |
| PI3K | Cell signaling | 4249s | 1/1000 | | |
| p-AKT(Ser473) | Cell signaling | 4058 | 1/1000 | | |
| AKT | Cell signaling | 4685 | 1/1000 | | |
| CREB1 | Cell signaling | 9197 | 1/1000 | | |
| p-CREB1(Ser1330) | Cell signaling | 9191 | 1/1000 | | |
| β-Catenin | Cell signaling | 9587 | 1/1000 | | |
| | Epitomics | 1247-1 | 1/2000 | | |
| GSK3β | Cell signaling | 9315 | 1/1000 | | |
| p-GSK3β(Ser9) | Cell signaling | 9336 | 1/500 | | |
| GSK-3α/β (Tyr-279/Tyr-216) | ECM Biosciences | GM1321 | 1/500 | | |
| GSC | Abcam | ab117871 | 1/500 | | 1/100 |
| Brachyury | Abcam | Ab20680 | 1/1000 | | 1/200 |
| SOX17 | Origene | TA502483 | 1/200 | | 1/100 |
| FOXA2 | Abcam | Ab40874 | | | |
| HNF1b | Abcam | ab59118 | 1/1000 | | 1/200 |
| SOX9 | Abcam | ab26414 | 1 µg/ml | | 1/200 |
| PTF1a | Abcam | ab57257 | 1/500 | | 1/200 |
| NKX6.1 | Abcam | ab90716 | 1 µg/ml | | 5 µg/ml |
| GATA4 | Abcam | ab84593 | 1/1000 | | 1/200 |
| NKX2.2 | Abcam | Ab79916 | 1/1000 | | 1/200 |
| FOXA2 | Abcam | Ab40874 | 1/1000 | | 1/200 |
| SOX17 | R&D systems | AF1924 | 1/1000 | | 1/200 |
| CXCR4 | Abcam | Ab124824 | 1/1000 | | 1/200 |
| HNF4a | Santa Cruz Biotechnology | Sc374229 | 1/200 | 1/100 | 1/100 |
| Albumin | Calbiochem | 126584 | 1/500 | 1/100 | 1/100 |
| AFP | Millipore | Mabd78 | 1/1000 | 1/100 | 1/200 |
| BSEP | Santa Cruz Biotechnology | Sc74500 | 1/200 | 1/100 | 1/100 |
| MRP2 | Santa Cruz Biotechnology | Sc5570 | 1/200 | 1/100 | 1/100 |
| Betatrophin | Acris Antibodies GmbH | H00055908-B01P | 1/500 | 1/100 | 1/100 |

TABLE 2

Primers used, e.g., in Example 1

| Target gene | Gene Name | Forward | SEQ ID NO: | Reverse | SEQ ID NO: | NCBI accession numbers |
|---|---|---|---|---|---|---|
| T | Brachyury | acctgggtactcccaatccta | 9 | actgactggagctggtaggt | 58 | NM_001270484.1 |
| SOX7 | Sex determining region Y (SRY)-box 7 | cgaagcgaggcgaccc | 10 | ccacgactttcccagcatct | 59 | NM_031439.3 |
| CXCR4 | C-X-C chemokine receptor type 4 | gaaaccctcagcgtctcagt | 11 | agtagtgggctaagggcaca | 60 | NM_001008540.1 |
| FOXA2 | Forkhead box protein A2 | ctggtcgtttgttgtggctg | 12 | ggaggagtagccctcgg | 61 | NM_021784.4 |
| SOX17 | SRY-box 17 | gatacgccagtgacgaccag | 13 | acgacttgcccagcatcttg | 62 | NM_022454.3 |
| AFP | Alpha-1-fetoprotein | cagccacttgttgccaactc | 14 | ggccaacaccagggtttact | 63 | NM_001134.2 |
| ALB | Albumin | aagccttggtgttgattgcc | 15 | gcacagcatgtcagccatttc | 64 | NM_000477.5 |
| HNF1a | Hepatocyte nuclear factor 1-alpha | caccaagcaggtcttcacctc | 16 | tctcgatgacgctgtggttg | 65 | NM_000545.5 |
| HNF4a | Hepatocyte nuclear factor 4-alpha | tgacgatgggcaatgacacg | 17 | agcccggaagcatttcttga | 66 | NM_178850.2 |
| HNF6 | Hepatocyte nuclear factor 6 | gcttagcagcatgcaaaagga | 18 | ctgacagtgctcagctccaa | 67 | NM_004498.2 |
| TTR | transthyretin | gcctctgggaaaaccagtga | 19 | atcccatccctcgtccttca | 68 | NM_000371.3 |
| KRT8 | Keratin 8 | ggacctgcaggaagggatct | 20 | tctggttgaccgtaactgcg | 69 | NM_001256282.1 |
| KRT18 | Keratin 18 | acatccgggcccaatatgac | 21 | tccaagctggccttcagattt | 70 | NM_199187.1 |
| KRT19 | Keratin 19 | agctgagcatgaaagctgct | 22 | gatcttcctgtccctcgagca | 71 | NM_002276.4 |
| SERPINA1 | Serpin peptidase inhibitor, clade A (alpha-1 antiproteinase, antitrypsin), member 1 | tccgataactggggtgacct | 23 | agacggcattgtcgattcact | 72 | NM_000295.4 |
| TAT | Tyrosine aminotransferase | gatgagcagcaaaggcaacc | 24 | acagtagggtccccaatgga | 73 | NM_000353.2 |
| G6PC | Glucose-6-phosphatase | tcaacctcgtctttaagtggatt | 25 | gtatacacctgctgtgcccat | 74 | NM_000151.3 |
| ADH1C | Alcohol dehydrogenase 1C (class I), gamma polypeptide | gctgcaggaatctgtcgttc | 26 | ccccgaggattgcctagatcat | 75 | NM_000669.4 |

TABLE 2-continued

Primers used, e.g., in Example 1

| Target gene | Gene Name | Forward | SEQ ID NO: | Reverse | SEQ ID NO: | NCBI accession numbers |
|---|---|---|---|---|---|---|
| APOF | Apolipoprotein F | aatgactggactgtgtgggta | 27 | caggacaaggggtctgagga | 76 | NM_001638.2 |
| C/EBPa | CCAAT-enhancer-binding protein alpha | taactcccccatggagtcgg | 28 | atgtcgatggacgtctcgtg | 77 | NM_004364.4 |
| C/EBPb | CCAAT-enhancer-binding protein beta | actttagcgagtcagagccg | 29 | gatttaaaggcaggcggcg | 78 | NM_005194.3 |
| CPS1 | Carbamoyl-phosphate synthase 1, mitochondrial | aggcccatgccacaaatca | 30 | agcaacagaggatggatggc | 79 | NM_001122633.2 |
| PCK2 | Phosphoenolpyruvate carboxykinase 2, mitochondrial | acagtgaaggtcgactccg | 31 | ccgcacataccaggtttcca | 80 | NM_001018073.2 |
| TDO2 | Tryptophan 2,3-dioxygenase | tgggaactacctgcatttgga | 32 | tcggtgcatccgagaaacaa | 81 | NM_005651.3 |
| GYS2 | Glycogen synthase 2 (liver) | ccaagagaagctaccaagcc | 33 | tgcctccaactttattggtcac | 82 | NM_021957.3 |
| HHEX | Hexosaminidase A (alpha polypeptide) | cccctgggcaaacctctact | 34 | tctcctccatttagcgcgtc | 83 | NM_002729.4 |
| PROX1 | Prospero homeobox 1 | agcaaatgactttgaggttcca | 35 | ctcttgtaggcagttcgggg | 84 | NM_001270616.1 |
| CX32 | Connexin 32 | gctccccaaggtgtgaatga | 36 | actaggatgagctgcaggga | 85 | NM_000166.5 |
| BSEP | Bile salt export pump | tattcacagggtcgttggct | 37 | agaagccaactctaacgcca | 86 | NM_003742.2 |
| MRP2 | Multidrug resistance-associated protein 2 | gtgtttccacagagcggcta | 38 | ccaggttcacatctcggact | 87 | NM_000392.4 |
| CYP1A2 | Cytochrome P450 1A2 | aacaagggacacaacgctgaat | 39 | ggaagagaaacaagggctgagt | 88 | NM_000761.4 |
| CYP2B6 | Cytochrome P450 2B6 | atggggcactgaaaaagactga | 40 | agaggcggggacactgaatgac | 89 | NM_000767.4 |
| CYP3A4 | Cytochrome P450 3A4 | ccttacacatacacacccttggaagt | 41 | agctcaatgcatgtacagaatccccggtta | 90 | NM_017460.5 |
| CYP2C8 | Cytochrome P450 2C8 | tatggtcctgtgttcaccgt | 42 | tcaactcctccacaaggcagt | 91 | NM_001198855.1 |
| CYP2C9 | Cytochrome P450 2C9 | ttcatgcctttctcagcagg | 43 | ttgcacagtgaaacatagga | 92 | NM_000769.2 |
| CYP2C19 | Cytochrome P450 2C19 | cgaggtccagagatacatc | 44 | tgtcatgtagcacagaagtg | 93 | NM_000771.3 |
| CYP2D6 | Cytochrome P450 2D6 | ctaagggaacgacactcatcac | 45 | ctcaccaggaaagcaaagacac | 94 | NM_000106.5 |
| CYP2E1 | Cytochrome P450 2E1 | acagagaccaccagcacaact | 46 | atgagcggggaatgacacaga | 95 | NM_000773.3 |

TABLE 2-continued

Primers used, e.g., in Example 1

| Target gene | Gene Name | Forward | SEQ ID NO: | Reverse | SEQ ID NO: | NCBI accession numbers |
|---|---|---|---|---|---|---|
| CYP3A5 | Cytochrome P450 3A5 | gaagaaaagtcgcctcaac | 47 | aagaagtccttgcgtgtcta | 96 | NM_000777.4 |
| CYP7A1 | Cytochrome P450 7A1 | tgctacttctgcgaaggcat | 48 | tccgtgagggaattcaaggc | 97 | NM_000780.3 |
| UGT | UDP glucuronosyl transferase | cccctattttttcaaaaatgtctt | 49 | attgatcccaaagagaaaaccac | 98 | NM_019077.2 |
| Betatrophin | Chromosome 19 Open Reading Frame 80 (Angiopoietin-Like Protein 8, Hepatocellular Carcinoma-Associated Gene TD26, Lipasin,) | acatctccctccccagactc | 50 | tgctctgtgctcagaagtgg | 99 | NM_018687.6 |
|  |  | ctgtcggctgagggtttccat | 51 | gagtctggggagggagatgt | 100 |  |
| miR124-2 ChIP |  | tctgcggctctttggtttca | 52 | tctgccttcagcacaagagg | 101 | NC_000008.11 |
|  |  | gcggctctttggtttcaagg | 53 | ctgccttcagcacaagagga | 102 |  |
| miR124-3 ChIP |  | cccgcagttctcaaggacac | 54 | agaagggagccaggcaagtc | 103 | NC_000020.11 |
| SOX17 ChIP |  | ttgtagattgctctctctcctcc | 55 | gtgaagccttggctagggg | 104 | NC_000008.10 |
| FOXA2 ChIP |  | cccatcattgattcctggat | 56 | ttgggaggctgagatttgtc | 105 | NC_000020.10 |
| Betatrophin ChIP |  | gtcagccctccctgactgat | 57 | catgtggatttccagcctgc | 106 | NC_000019.9 |

TABLE 3

Transcriptional gene profiles throughout hepatic differentiation

| Function\Stage | Gene | DE (8 hr) | Hepatic endoderm (8 hr to 1 D) | Hepatoblast 2 D | Hepatoblast 4 D | Hepatocyte-like cells (>4 D) |
|---|---|---|---|---|---|---|
| DE | CXCR4 | +++ | + | + | + | NA |
|  | Foxa2 | ++++ | + | ++ | + |  |
|  | Sox17 | ++++ | ++ | + | + |  |
|  | HHEX | ++ | + | − | +++ |  |
|  | Brachyury (T) | ++++ | + | − | − |  |
|  | Sox7 | ++++ | ++ | − | + | NA |
| Tyrosine catabolism | TAT | NA | ++ | − | − | − |
| Fetal α-fetoprotein precursor | AFP | NA | + | − | ++++ | +++ |
| Proteins carrier synthesized in the liver | ALB | NA | + | + | ++++ | ++++ |
| Gluconeogenesis | PCK2 | NA | + | + | ++ | +++ |
| Pancreatic β-cell promoter, Lipid regulator | Betatrophin | NA | + | + | ++ | +++ |
| Serine protease inhibitor | SERPINA1 | NA | + | − | ++ | +++ |
| Bile acid biosynthesis | CYP7A1 | NA | + | + | + | +++ |
| Drug and steroid metabolism (phase I) | CYP2B6 | NA | + | − | ++ | +++ |

TABLE 3-continued

Transcriptional gene profiles throughout hepatic differentiation

| Function\Stage | Gene | DE (8 hr) | Hepatic endoderm (8 hr to 1 D) | Hepatoblast 2 D | Hepatoblast 4 D | Hepatocy-like cells (>4 D) |
|---|---|---|---|---|---|---|
| Drug and steroid metabolism (phase I) | CYP3A4 | NA | + | + | ++ | +++ |
| Ethanol catabolism (phase I) | ADH1C | NA | + | + | ++ | ++ |
| Liver glucagon synthase | GYS2 | NA | + | + | ++ | ++ |
|  | PEPCK | NA | + | − | ++ | − |
| Hepatic transcriptional activator | Hnf6 | NA | + | + | + | ++ |
| Secretion of bile salts | BSEP | NA | + | − | + | ++ |
| Cholesterol transport regulator | APOF | NA | + | − | − | ++ |
| Hepatic gap junction | Cx32 (GJB1) | NA | + | − | + | ++ |
| Regulator of several hepatic genes | Hnf4α | NA | + | − | + | + |
| Adipocyte differentiation | C/EBPβ | NA | + | + | − | + |
| Thyroxin- and retinol-binding protein | TTR | NA | + | − | − | + |
| Enzyme of urea cycle | CPS1 | NA | + | − | + | + |
| Enzyme of glucose homeostasis | G6PC | NA | − | − | +++ | +++ |
| Regulator of several hepatic genes | Hnf1α | NA | − | − | ++ | +++ |
| IL-6-mediated barrier protection | CK18 | NA | − | − | ++ | ++ |
| IL-6-mediated barrier protection | CK8 | NA | − | − | ++ | ++ |
| Hepatocyte migration | PROX1 | NA | + | − | + | +++ |
| Organization of bile duct | CK19 | NA | − | − | + | ++ |
| Hepatobiliary excretion | MRP2/ABCC2 | NA | + | − | − | + |
| Tryptophan metabolism | TDO2 | NA | + | ++ | − | + |

Denotation: NA, not available; (−) indicating expression <2-fold, (+) >2-fold, (++) >10-fold, (+++) >100-fold, and (++++) >1,000-fold.

TABLE 4

Antibodies used, e.g., in Example 2

| Target | Manufacturer | Code no. | WB | Flow | IF/IHC |
|---|---|---|---|---|---|
| Stem121 | StemCells | AB-121-U-050 |  |  | 1/1000 |
| Mixl1 | Abcam | ab57854 | 1/1000 |  | 1/200 |
| Smad4 | Santa Cruz Biotechnology | sc-7966 | 1/200 |  |  |
| Cdx2 | Abcam | Ab76541 | 1/1000 |  | 1/200 |
|  | Cell signaling | 3977s | 1/1000 | 1/40 |  |
|  | BD Pharmingen | 560395 |  | 1/40 |  |
| Oct4 | Abcam | Ab19857 | 5 µg/ml |  | 1 µg/ml |
|  | Millipore | MAB4419 | 2 µg/ml | 1/40 | 1/200 |
|  | BD Pharmingen | 560794 (Cy 5.5) |  |  |  |
| c-Kit | Santa Cruz Biotechnology | Sc19983 |  |  | 1/400 |
| CK18 | Abcam | Ab32118 |  | 1/100 | 1/200 |
| CK19 | Cell signaling | 4558 |  |  | 1/200 |
| β-actin | Santa Cruz Biotechnology | Sc-130065 | 1/2000 |  |  |
| ADH | Santa Cruz Biotechnology | Sc137078 |  |  | 1/200 |
| CPS1 | Abcam | Ab110303 |  |  | 1/200 |
| ASGR1 | Thermo Fisher Scientific | MAB0244 |  | 1/100 | 1/200 |
| Cx32 | Santa Cruz Biotechnology | Sc7258 |  |  | 1/100 |
| ApoF | Santa Cruz Biotechnology | Sc107409 |  |  | 1/400 |
| CYP1A1 | Santa Cruz Biotechnology | Sc25304 |  |  | 1/100 |
| CYP2B6 | Santa Cruz Biotechnology | Sc62204 |  |  | 1/100 |

TABLE 4-continued

Antibodies used, e.g., in Example 2

| Target | Manufacturer | Code no. | WB | Flow | IF/IHC |
|---|---|---|---|---|---|
| HLA-G | Abcam | Ab4570 | | | 1/200 |
| CD4 | eBioscience | 14-0040-85 | | | 1/400 |
| Foxp3 | Abcam | Ab22510 | | | 1/400 |
| HNF4A | Santa Cruz Biotechnology | Sc374229 | 1/200 | | 1/100 |
| α-tubulin | GeneTex | GTX112141 | 1/1000 | | |
| CREB1 | Cell signaling | 9197 | 1/1000 | | |
| P-CREB1 (Ser1330) | Cell signaling | 9191 | 1/1000 | | |
| GSK3β | Cell signaling | 9315 | 1/1000 | | |
| TGFβ1 | Santa Cruz Biotechnology | Sc146 | | | 1/500 |
| COL4 | Santa Cruz Biotechnology | Sc59814 | | | 1/500 |
| FN1 | Santa Cruz Biotechnology | Sc6952 | | | 1/500 |
| GSC | Abcam | ab117871 | 1/500 | | 1/100 |
| Brachyury | Abcam | Ab20680 | 1/1000 | | 1/200 |
| Sox17 | Origene R&D | TA502483 MAB1927 | 1/1000 | | 1/100 |
| Sox7 | Santa Cruz Biotechnology | Sc20093 | 1/200 | | |
| Foxa2 | Abcam | Ab40874 | 1/1000 | | 1/200 |
| GATA4 | Abcam | ab84593 | 1/1000 | | 1/200 |
| CXCR4 | Abcam | Ab124824 | 1/1000 | | 1/200 |
| Hnf4a | Santa Cruz Biotechnology | Sc374229 | 1/200 | 1/100 | 1/100 |
| Albumin | Calbiochem | 126584 | 1/500 | 1/100 | 1/100 |
| AFP | Millipore | Mabd78 | 1/1000 | 1/100 | 1/200 |
| BSEP | Santa Cruz Biotechnology | Sc74500 | 1/200 | 1/100 | 1/100 |
| MRP2 | Santa Cruz Biotechnology | Sc5570 | 1/200 | 1/100 | 1/100 |
| Betatrophin | Acris Antibodies GmbH | H00055908-B01P | 1/500 | 1/100 | 1/100 |

TABLE 5

Primers used, e.g., in Example 2

| Target gene | Forward | SEQ ID NO: | Reverse | SEQ ID NO: |
|---|---|---|---|---|
| Brachyury | acctgggtactcccaatccta | 9 | actgactggagctggtaggt | 58 |
| Sox7 | cgaagcgaggcgaccc | 10 | ccacgactttcccagcatct | 59 |
| Cxcr4 | gaaaccctcagcgtctcagt | 11 | agtagtgggctaagggcaca | 60 |
| Foxa2 | ctggtcgtttgttgtggctg | 12 | ggaggagtagccctcgg | 61 |
| Sox17 | gatacgccagtgacgaccag | 13 | acgacttgcccagcatcttg | 62 |
| AFP | cagccacttgttgccaactc | 14 | ggccaacaccagggtttact | 63 |
| Albumin | aagccttggtgttgattgcc | 15 | gcacagcagtcagccatttc | 64 |
| Hnf1a | caccaagcaggtcttcacctc | 16 | tctcgatgacgctgtggttg | 65 |
| Hnf4a | tgacgatgggcaatgacacg | 17 | agcccggaagcatttcttga | 66 |
| Hnf6 | gcttagcagcatgcaaaagga | 18 | ctgacagtgctcagctccaa | 67 |
| Ttr | gcctctgggaaaaccagtga | 19 | atcccatccctcgtccttca | 68 |
| KRT8 | ggacctgcaggaagggatct | 20 | tctggttgaccgtaactgcg | 69 |
| KRT18 | acatccgggcccaatatgac | 21 | tccaagctggccttcagattt | 70 |
| KRT19 | agctgagcatgaaagctgcct | 22 | gatcttcctgtccctcgagca | 71 |
| Serpina1 | tccgataactggggtgacct | 23 | agacggcattgtcgattcact | 72 |

TABLE 5 -continued

Primers used, e.g., in Example 2

| Target gene | Forward | SEQ ID NO: | Reverse | SEQ ID NO: |
|---|---|---|---|---|
| Tat | gatgagcagcaaaggcaacc | 24 | acagtagggtccccaatgga | 73 |
| G6p | tcaacctcgtctttaagtggatt | 25 | gtatacacctgctgtgcccat | 74 |
| Adh1C | gctgcaggaatctgtcgttc | 26 | ccccgaggattgcctagatcat | 75 |
| ApoF | aatgactggactgtgtgggta | 27 | caggacaaggggtctgagga | 76 |
| C/EBPa | taactcccccatggagtcgg | 28 | atgtcgatggacgtctcgtg | 77 |
| C/EBPb | actttagcgagtcagagccg | 29 | gatttaaaggcaggcggcg | 78 |
| Cps1 | aggcccatgccacaaatca | 30 | agcaacagaggatggatggc | 79 |
| Pck2 | acagtgaaggtcgactccg | 31 | ccgcacataccaggtttcca | 80 |
| Tdo2 | tgggaactacctgcatttgga | 32 | tcggtgcatccgagaaacaa | 81 |
| Gys2 | ccaagagaagctaccaaagcc | 33 | tgcctccaactttattggtcac | 82 |
| Hex | cccctgggcaaacctctact | 34 | tctcctccatttagcgcgtc | 83 |
| Prox1 | agcaaatgactttgaggttcca | 35 | ctcttgtaggcagttcgggg | 84 |
| Cx32 | gctccccaaggtgtgaatga | 36 | actaggatgagctgcaggga | 85 |
| BSEP | tattcacagggtcgttggct | 37 | Agaagccaactctaacgcca | 86 |
| MRP2 | gtgtttccacagagcggcta | 38 | Ccaggttcacatctcggact | 87 |
| CYP1A2 | aacaagggacacaacgctgaat | 39 | ggaagagaaacaagggctgagt | 88 |
| CYP2B6 | atggggcactgaaaaagactga | 40 | agaggcggggacactgaatgac | 89 |
| CYP3A4 | ccttacacatacacacccctttggaagt | 41 | agctcaatgcatgtacagaatccccggtta | 90 |
| CYP2C8 | tatggtcctgtgttcaccgt | 42 | tcaactcctccacaaggcagt | 91 |
| CYP2C9 | ttcatgcattctcagcagg | 43 | ttgcacagtgaaacatagga | 92 |
| CYP2C19 | cgaggtccagagatacatc | 44 | tgtcatgtagcacagaagtg | 93 |
| CYP2D6 | ctaagggaacgacactcatcac | 45 | ctcaccaggaaagcaaagacac | 94 |
| CYP2E1 | acagagaccaccagcacaact | 46 | atgagcggggaatgacacaga | 95 |
| CYP3A5 | gaagaaaagtcgcctcaac | 47 | aagaagtccttgcgtgtcta | 96 |
| CYP7A1 | tgctacttctgcgaaggcat | 48 | tccgtgagggaattcaaggc | 97 |
| UGT | cccctattttttcaaaaatgtctt | 49 | attgatcccaaagagaaaaccac | 98 |
| Betatrophin | acatctccctcccccagactc | 50 | tgctctgtgctcagaagtgg | 99 |
|  | ctgtcggctgagggtttccat | 51 | gagtctgggagggagatgt | 100 |
| miR124-2 ChIP | tctgcggctattggtttca | 52 | tctgccttcagcacaagagg | 101 |
|  | gcggctctttggtttcaagg | 53 | ctgccttcagcacaagagga | 102 |
| miR124-3 ChIP | cccgcagttctcaaggacac | 54 | agaagggagccaggcaagtc | 103 |
| Sox17 ChIP | ttgtagattgctctctctcctcc | 55 | gtgaagccttggctagggg | 104 |
| Foxa2 ChIP | cccatcattgattcctggat | 56 | ttgggaggctgagatttgtc | 105 |
| betatrophin ChIP | gtcagccctccctgactgat | 57 | catgtggatttccagcctgc | 106 -2.5 kb |

The examples and embodiments described herein are for illustrative purposes only and various modifications or changes suggested to persons skilled in the art are to be included within the spirit and purview of this application and scope of the appended claims.

What is claimed is:

1. An isolated human hepatocyte, wherein the isolated human hepatocyte endogenously expresses transforming growth factor beta 1 (TGFβ1), fibronectin, and collagen IV.

2. The isolated human hepatocyte of claim 1, wherein the isolated human hepatocyte is a human hepatic progenitor cell.

3. The isolated human hepatocyte of claim 1, wherein the isolated human hepatocyte further expresses human leukocyte antigen G (HLA-G).

4. The isolated human hepatocyte of claim 1, wherein the isolated human hepatocyte recruits CD4$^+$Foxp3$^+$Treg cells.

5. The isolated human hepatocyte of claim 1, wherein a plurality of the isolated human hepatocytes forms a tissue of a 3-dimensional structure.

6. The isolated human hepatocyte of claim 1, wherein a plurality of the isolated human hepatocytes forms a crescent cell mass.

7. A population of isolated human hepatocytes that comprises a plurality of the isolated human hepatocytes of claim 1, wherein the plurality of isolated human hepatocytes are present in a cluster or an aggregate.

8. A kit that comprises the isolated human hepatocyte of claim 1 and a carrier.

9. A pharmaceutical composition that comprises the isolated human hepatocyte of claim 1 and a pharmaceutically acceptable carrier.

10. A method of treating a disorder of liver tissue or liver function in a subject in need thereof, comprising administering to the subject a pharmaceutical composition of claim 9, whereby the disorder is treated.

11. A method of screening a therapeutic compound for use in treatment or prevention of a condition, comprising:
a) contacting the isolated human hepatocyte of claim 1, with the therapeutic compound; and
b) detecting an expression level of a biomarker in the isolated human hepatocyte.

12. A method of producing a therapeutic protein, comprising culturing the isolated human hepatocyte of claim 1 in a medium and extracting the therapeutic protein from the medium.

13. A method of regenerating a liver, comprising applying the isolated human hepatocyte of claim 1 to an ex vivo perfusion system to regenerate the liver.

14. A cell therapy, comprising intravenously administering to a subject in need thereof a composition that comprises the isolated human hepatocyte of claim 1.

15. A method of bioprinting, comprising applying the isolated human hepatocyte of claim 1 to a bioprinting system.

16. A method of generating a tissue scaffold, comprising culturing the isolated human hepatocyte of claim 1 in a medium on a three-dimensional biocompatible substrate to generate the tissue scaffold.

17. An artificial tissue or organ, comprising human hepatocytes that endogenously express human leukocyte antigen G (HLA-G) and one or more biomarkers selected from the group consisting of C—X—C chemokine receptor type 4 (CXCR4), forkhead box protein A2 (FOXA2), hematopoietically expressed homeobox (HHEX), cytochrome P450 7A1 (CYP7A1), bile salt export pump (BSEP), alpha-1-antitrypsin member 1 (SERPINA1), ATP-binding cassette sub-family C member 2 (ABCC2), CCAAT-enhancer-binding protein beta (C/EBPβ), hepatocyte nuclear factor 1-alpha (HNF1α), and any combination thereof.

* * * * *